US011896644B2

United States Patent
Woo et al.

(10) Patent No.: US 11,896,644 B2
(45) Date of Patent: Feb. 13, 2024

(54) INHIBITION OF BETA-ARRESTIN OLIGOMERIZATION IN TAUOPATHY

(71) Applicant: UNIVERSITY OF SOUTH FLORIDA, Tampa, FL (US)

(72) Inventors: Jung A. Woo, Wesley Chapel, FL (US); Stephen Bryant Liggett, Treasure Island, FL (US); David E. Kang, Wesley Chapel, FL (US); Yu Chen, Tampa, FL (US); Eric Lewandowski, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/798,041

(22) PCT Filed: Feb. 8, 2021

(86) PCT No.: PCT/US2021/017114
§ 371 (c)(1),
(2) Date: Aug. 5, 2022

(87) PCT Pub. No.: WO2021/159093
PCT Pub. Date: Aug. 12, 2021

(65) Prior Publication Data
US 2023/0116783 A1   Apr. 13, 2023

Related U.S. Application Data

(60) Provisional application No. 62/971,510, filed on Feb. 7, 2020.

(51) Int. Cl.
*A61K 38/17*   (2006.01)
*A61P 25/28*   (2006.01)
(Continued)

(52) U.S. Cl.
CPC .......... *A61K 38/1709* (2013.01); *A61K 31/42* (2013.01); *A61K 31/437* (2013.01); *A61K 31/496* (2013.01); *A61P 25/28* (2018.01)

(58) Field of Classification Search
CPC combination set(s) only.
See application file for complete search history.

(56) References Cited

U.S. PATENT DOCUMENTS

2018/0193325 A1   7/2018 Vincent et al.

FOREIGN PATENT DOCUMENTS

| CN | 103816540 | * 11/2012 | ............ A61K 38/10 |
| WO | 2008/148349 A1 | 12/2008 | |
| WO | WO-2010058423 A2 | * 5/2010 | ........... C07D 263/20 |

OTHER PUBLICATIONS

Richard-Bildstein S, Aissaoui H, Pothier J, Schäfer G, Gnerre C, Lindenberg E, Lehembre F, Pouzol L, Guerry P. J Med Chem. Dec. 24, 2020;63(24):15864-15882. doi: 10.1021/acs.jmedchem. 0c01588. Epub Dec. 14, 2020. PMID: 33314938. (Year: 2020).*

(Continued)

*Primary Examiner* — Adam Weidner
*Assistant Examiner* — Laura Ann Essex
(74) *Attorney, Agent, or Firm* — Quarles & Brady LLP

(57) ABSTRACT

As disclosed herein, β-arrestin1 and β-arrestin2 levels are highly elevated in brains of FTLD-tau patients suggesting that both β-arrestin1 and β-arrestin2 are elevated in the brains of patients with AD and FLTD. The current work also shows that when β-arrestin2 is overexpressed, tau levels become elevated. The data indicate that β-arrestin2 reduces tau clearance by impairing p62-mediated autophagy, a role carried out by the oligomerized form of β-arrestin2. Therefore, disclosed herein are β-arrestin oligomerization inhibitors that can be used to prevent β-arrestin oligomerization and therefore the accumulation of tau in cells, i.e. tauopathy. Also disclosed are methods of treating a tauopathy in a (Continued)

subject that involve administering to the subject a therapeutically effective amount of a β-arrestin oligomerization inhibitor disclosed herein.

7 Claims, 95 Drawing Sheets

(51) Int. Cl.
    *A61K 31/42*     (2006.01)
    *A61K 31/437*     (2006.01)
    *A61K 31/496*     (2006.01)

(56) References Cited

OTHER PUBLICATIONS

Irwin DJ, Trojanowski JQ, Grossman M. Front Aging Neurosci. Feb. 21, 2013;5:6. doi: 10.3389/fnagi.2013.00006. PMID: 23440936; PMCID: PMC3578350. (Year: 2013).*

Gyombolai P, Boros E, Hunyady L, Turu G. Mol Cell Endocrinol. Jun. 15, 2013;372(1-2):116-27. doi: 10.1016/j.mce.2013.03.013. Epub Mar. 27, 2013. PMID: 23541635. (Year: 2013).*
English translation of Pei et al.(CN103816540) (Year: 2012).*
Hanson SM, Vishnivetskiy SA, Hubbell WL, Gurevich VV. Biochemistry. Jan. 22, 2008;47(3):1070-5. doi: 10.1021/bi7021359. Epub Dec. 28, 2007. PMID: 18161994; PMCID: PMC2562240. (Year: 2008).*
International Search Report of related PCT/US2021/017114, dated Apr. 23, 2021, 2 pages.
Written Opinion of related PCT/US2021/017114, dated Apr. 23, 2021, 3 pages.
Baier "Neuroscientist targets B-arrestins with the aim of arresting Alzheimer's disease" University of South Florida, Sep. 20, 2019, pp. 1-9 (retrieved from https://hscweb3.hsc.usf.edu/blog/2019/09/20/neuroscientist-targets-b-arrestins-with-the-aim-of-arresting-alzheimers-disease/ on Apr. 11, 2021 ).
Boularan et al., "beta-arrestin 2 oligomerization controls the Mdm2-dependent inhibition of p53" Proc Natl Acad Sci U S A. Nov. 13, 2007;104(46):18061-6.
Woo et al., "β-Arrestin2 oligomers impair the clearance of pathological tau and increase tau aggregates" Proc Natl Acad Sci U S A. Mar. 3, 2020;117(9):5006-5015.

\* cited by examiner

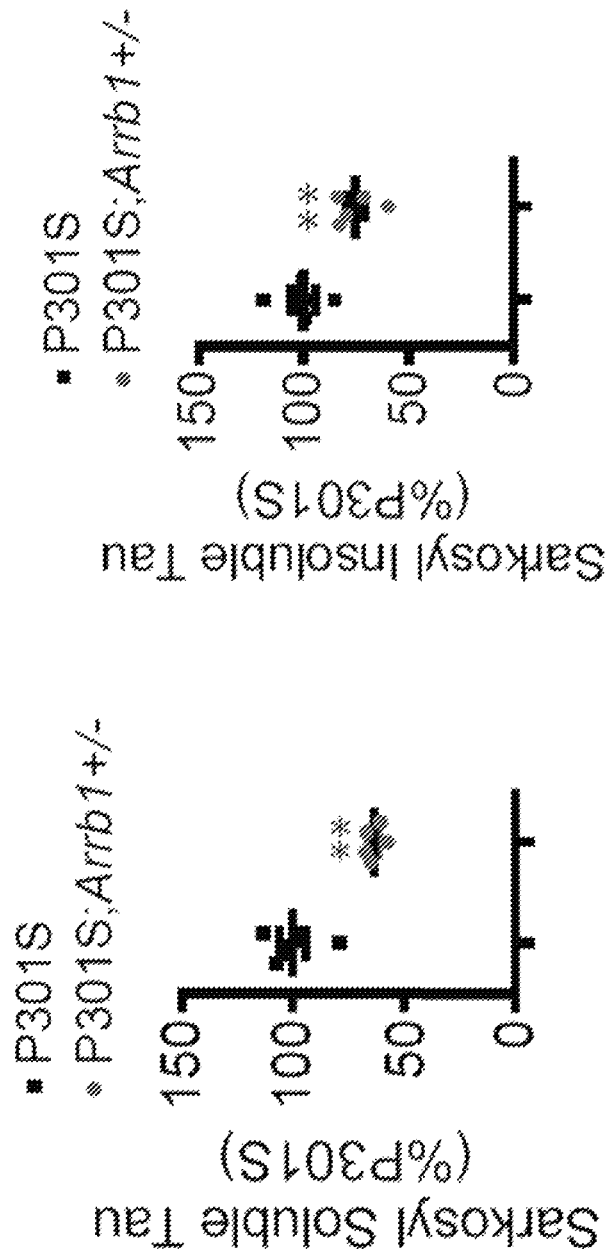

INHIBITION OF BETA-ARRESTIN OLIGOMERIZATION IN TAUOPATHY

CROSS-REFERENCE TO RELATED APPLICATIONS

This application is a 371 U.S. National Phase entry of International Application No. PCT/US2021/017114, filed Feb. 8, 2021, which claims the benefit of U.S. Provisional Patent Application No. 62/971,510, filed Feb. 7, 2020, each of which are incorporated herein by reference in their entirety for all purposes.

STATEMENT REGARDING FEDERALLY SPONSORED RESEARCH OR DEVELOPMENT

This invention was made with Government Support under Grant No. AG059721 awarded by the National Institutes of Health. The Government has certain rights in the invention.

BACKGROUND

Second in prevalence only to Alzheimer's disease as the cause of early onset non-vascular dementia, frontotemporal lobar degeneration (FTLD) is an aggressive neurodegenerative disease whose pathologic basis is ill-defined (Irwin D J, et al. (2015) Acta Neuropathol 129(4):469-491). Like AD, the most common form of FTLD (FTLD-tau) displays an accumulation of hyperphosphorylated tau within inclusion bodies of neurons of the affected regions including the cortex and temporal lobes and some subcortical neurons (Cairns N J, et al. (2007) Acta Neuropathol 114(1):5-22). In contrast to AD, where amyloid β (Aβ) is an integral part of the tangle, there is no accumulation of Aβ in FTLD neurons, but rather in most forms a marked accumulation of tau is observed. Interestingly, even in AD, tau appears to be indispensable for Aβ to transduce neurotoxic signals (Vossel K A, et al. (2010) Science 330(6001):198; Jin M, et al. (2011) Proc Natl Acad Sci USA 108(14):5819-5824). Indeed, tauopathy correlates significantly better than Aβ with cognitive deficits in AD (Nelson P T, et al. (2010) Brain Pathol 20(1):66-79; Tiraboschi P, et al. (2004) Neurology 62(11):1984-1989; Matthews F E, et al. (2009) PLoS Med 6(11):e1000180). This pathogenic role for tau in AD, and several reported observations regarding G protein coupled receptors (GPCRs) in the pathology and treatment of AD reveals the need for a better understanding of how GPCRs and associated proteins integrate into the tauopathy of FTLD, where unique therapeutic strategies are lacking to date.

SUMMARY

As disclosed herein, β-arrestin1 and β-arrestin2 levels are highly elevated in brains of FTLD-tau patients suggesting that both β-arrestin1 and β-arrestin2 are elevated in the brains of patients with AD and FLTD. The current work also shows that when β-arrestin2 is overexpressed, tau levels become elevated. The data indicate that β-arrestin2 reduces tau clearance by impairing p62-mediated autophagy, a role carried out by the oligomerized form of β-arrestin2.

β-arrestin2 can be found as an oligomer in multiple cell types (Milano S K, et al. (2006) J Biol Chem 281(14):9812-9823; Storez H, et al. (2005) J Biol Chem 280(48):40210-40215). Inositol hexakisphosphate (IP6) enhances this self-association of β-arrestin2 by bridging neighboring molecules in a head-to tail configuration. Positively charged arginine and lysine residues within the N-terminus and C-terminus of β-arrestin2 were found to be critical for both IP6 binding and oligomerization. Given the physical overlap of IP6 and GPCR binding sites, β-arrestin2 binding to an activated GPCR and to IP6 is mutually exclusive, indicating that in the oligomeric form β-arrestin2 may serve other purposes apart from GPCR binding Therefore, disclosed herein are β-arrestin oligomerization inhibitors that can be used to prevent β-arrestin oligomerization and therefore the accumulation of tau in cells, i.e. tauopathy. Also disclosed are methods of treating a tauopathy in a subject that involve administering to the subject a therapeutically effective amount of a β-arrestin oligomerization inhibitor disclosed herein.

β-arrestin1 and β-arrestin2 form homo- and hetero-oligomers, and inositol hexakisphosphate (IP6) promotes these oligomers. Therefore, in some embodiments, the β-arrestin oligomerization inhibitor is a molecule, such as a peptide, that blocks IP6 binding, thereby reducing oligomerization of b-arrestin2. In some embodiments, the oligomerization inhibitor is a β-arrestin mutant that acts as dominant negative for homo-hetero oligomerization of β-arrestin1 and/or β-arrestin2.

The provided data also indicated that pharmacological inhibitors for β-arrestin oligomerization can represent a promising therapeutic strategy that can alleviate AD and tauopathies. Therefore, molecular docking screening was performed with FTMap analysis to screen millions of compounds that block the interface between β-arrestin2 and β-arrestin2. Approximately 30 predicted inhibitory compounds were tested using cell-based assays, resulting in a few small molecule compounds and their analogs that reduce pathogenic tau.

Regarding the mutants they are the same size as β-arrestin2, full length. IP6 binding sites are in both C-terminus and N-terminus. (just point mutations). Either blocking IP6 binding to C terminus or N terminus can abolish its oligomerization. So, the initial thought was to screen the compounds that block the IP6 binding sites, but several compounds were found that bind the interface between β-arrestin2 and β-arrestin2. These compounds were confirmed to block the oligomerization by Co-IP, FRET, and PLA assays.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A contains representative immunoblots of β-arrestin2 from the frontal cortex of 12 age-matched unaffected controls and 10 FTLD-tau patients. The numbers above the lanes are sample numbers corresponding to the subjects, with some samples repeated on the second gel. FIGS. 1B and 1C show quantification of β-arrestin2 protein and mRNA levels in the frontal cortex of FTLD-tau patients compared with unaffected controls (N=12 healthy control, N=10 FTLD-tau, **P<0.005, *P<0.05). FIG. 1D shows correlation of insoluble tau and β-arrestin2 expression in FTLD-tau patients (N=10 FTLD-tau). Each data point represents mean results from duplicate determinations from a given subject. The blots are shown in SI Appendix, FIG. 1E contains representative immunoblots of β-arrestin2 in the mouse cortex from 7-month-old WT and tau P301S-transgenic littermates. FIGS. 1F and 1G show quantification of β-arrestin2 protein and mRNA levels in the cortex of WT and tau P301S-transgenic littermates (N=5 WT, N=4 tau P301S, **P<0.005, *P<0.05). FIG. 1H shows representative staining of β-arrestin2 (magenta) and total tau (green) using DIV21 hippocampal primary neurons derived from WT and tau P301S littermates (bar=10 μm). FIG. 1I shows quantification of β-arrestin2 immunoreactivity (N=3 independent experiments, *P<0.05). The box plots show all data points, the median and IQR, and the minimal and maximal values.

FIG. 2A contains representative immunoblots of the indicated proteins in Hela-V5-tau cells transiently transfected with GFP or GFP-β-arrestin2. FIGS. 2B to 2D show quantification of tau, PHF1, and AT8 levels from 6 experiments (*P<0.05, P<0.005 vs GFP). FIG. 2E shows representative immunoblots of the indicated proteins in Hela-V5-tau cells transiently transfected with either control siRNA or β-arrestin2 siRNA. FIG. 2F shows quantification of tau levels from 4 experiments (#P<0.0001). FIG. 2G shows representative staining of tau and AT8 in hippocampal primary neurons from tau P301S-transgenic mice transduced with either control or β-arrestin2 adenovirus (bar=10 μm). FIGS. 2H and 2I show quantification of AT8 and total tau immunoreactivities from 3 independent experiments, #P<0.0001, *P<0.0005). FIG. 1J shows representative staining of tau in hippocampal primary neurons from tau P301S-transgenic mice transduced with either GFP-lenti shRNA or GFP-lenti β-arrestin2 shRNA. FIG. 2K shows quantification of total tau immunoreactivity (N=4 independent experiments, #P<0.0001). FIG. 2L shows representative immunoblots of indicated proteins from Hela-V5-tau cells transfected with GFP or GFP-β-arrestin2 and treated with cycloheximide (100 μg/ml) for indicated times. FIG. 2M shows quantification of tau levels with cycloheximide treatment (N=4; **P<0.005, #P<0.0005, *P<0.05, repeated measures ANOVA, followed by Bonferroni post-hoc test). The box plots show all data points, the median and IQR, and the minimal and maximal values.

FIGS. 3A to 3I show genetic reduction in β-arrestin2 mitigates neuronal tauopathy. FIG. 3A shows representative immunoblots for sarkosyl-soluble and sarkosyl-insoluble tau from brains of 7-month-old tau P301S, tau P301S/Arrb2$^{+/-}$, and tau P301S/Arrb2$^{-/-}$ littermates. FIGS. 3B and 3C shows quantification of 4 experiments performed as shown in a), **P<0.005, #P<0.0001. FIG. 3D shows representative staining of phospho-tau, pS199/202 in hippocampus and cortex of 7-month-old tau P301S, tau P301S/Arrb2$^{+/-}$ and tau P301S/Arrb2$^{-/-}$ mice (bar=20 μm). FIGS. 3E and 3F show quantification of pS199/202 immunoreactivity in cortex and hippocampus (N=4/genotype, #P<0.0001). FIG. 3G shows input/output (I/O) analysis generated by stepping up stimulation amplitude from 1 to 15 mV in WT, tau P301S, tau P301S/Arrb2$^{+/-}$, and tau P301S/Arrb2$^{-/-}$ acute slices. (N=35-46 slices/genotype from 4 mice/genotype). FIG. 3H shows PPF showing fEPSP slope as a function of 30-300 ms interstimulus interval (N=38-49 slices/genotype from 4 mice/genotype). FIG. 3I shows LTP induced by theta burst stimulation showing significant differences in fEPSP slope between tau P301S compared to WT, tau P301S/Arrb2$^{+/-}$ and tau P301S/Arrb2$^{-/-}$ slices (N=25-43 slices/genotype from 4 mice/genotype, #P<0.0001). Data shown are either box plots or mean±SEM.

FIG. 4A shows representative immunoblots of DIV18 cortical primary neurons from tau P301S transduced with GFP, β-arrestin2 ΔIP6C-GFP, or β-arrestin2 ΔIP6N-GFP at DIV5. FIG. 4B shows quantification of tau level (N=4, #P<0.0001, *P<0.0005). FIGS. 4C and 4D contain representative immunoblots of indicated proteins in Hela-V5-tau cells transfected with control vector, β-arrestin2 ΔIP6C, β-arrestin2 ΔIP6N treated with cycloheximide (100 μg/ml) for indicated times. FIG. 4E shows quantification of tau levels with cycloheximide treatment (N=4; P<0.005, ***P<0.0005, #P<0.0001, repeated measures ANOVA, followed by Bonferroni post-hoc). Data are shown as box plots or mean±SEM.

FIG. 5A contains representative images of LC3 positive autophagosomes from Hela-V5-tau cells transiently transfected with control vector or β-arrestin2-myc with/without 100 nM of Bafilomycin A1 (bar=10 μm). FIG. 5N shows quantification of GFP-p62 puncta (N=4 independent experiments, #P<0.0001). Data are shown as box plots or mean±SEM.

FIG. 6A shows representative immunoblots for sarkosyl-soluble and sarkosyl-insoluble tau from brains of 7-month-old tau P301S mice stereotaxically injected with rAAV9 encoding GFP, GFP-β-arrestin2 ΔIP6C or GFP-β-arrestin2 ΔIP6C into the hippocampus at 5-months of age. FIGS. 6B and 6C show quantification of sarkosyl soluble and insoluble tau from tau P301S mice stereotaxically injected as in FIG. 6A, N=4/genotype, P<0.005, *P<0.0005). FIG. 6D shows representative staining of total tau (magenta) of the hippocampus of 7-month-old tau P301S stereotaxically injected as in FIG. 6A (bar=20 μm). FIG. 6A shows quantification of total tau immunoreactivities (N=4/genotype, #P<0.0001). Data are shown as box plots.

FIG. 9A contains representative immunoblots of indicated proteins from DIV18 tau P301S cortical primary neurons transduced with control adenovirus or β-arrestin2 adenovirus on DIV5. FIG. 9B shows quantification of total tau levels (N=4, P<0.005). FIG. 9C contains representative immunoblots of indicated proteins from DIV18 tau P301S cortical primary neurons transduced with control shRNA-lentivirus or β-arrestin2 shRNA-lentivirus on DIV5. FIG. 9D shows quantification of total tau levels (N=4, P<0.005). FIG. 9E shows Hela-V5-tau cells transfected with control vector or β-arrestin2 and subjected to qRT-PCR for tau mRNA and normalized to control (N=6 each). FIG. 9F shows Hela-V5-tau cells transfected with control siRNA or β-arrestin2 siRNA and subjected to qRT-PCR for tau mRNA and normalized to control (N=6 each).

FIG. 10A contains representative immunoblots of sarkosyl soluble and insoluble tau from DIV18 cortical neurons derived from tau P301S and tau P301S; Arrb2$^{-/-}$. FIGS. 9A and 9B show quantification of sarkosyl soluble tau (FIG. 9B) sarkosyl insoluble tau (FIG. 9C) from DIV18 cortical primary neurons derived from tau P301S and tau P301S; Arrb2$^{-/-}$ (N=3; ***P<0.005). FIG. 9D contains representative confocal images of synaptophysin and drebrin in DIV21 hippocampal primary neurons derived from WT and tau P301S littermates transduced with either GFP-lenti shRNA or GFP-lenti β-arrestin2 shRNA on DIV5 (Scale bar=10 μm). FIGS. 9E and 9B show quantification of synaptophysin (FIG. 9E) and drebrin (FIG. 9F) immunoreactivities (N=3 independent experiments, #P<0.005).

FIG. 11A contains representative confocal images of total tau in Hela-V5-tau cells transfected with YFP, YFP-β-arrestin2 ΔIP6C, or YFP-β-arrestin2 ΔIP6N (Scale bar=10 μm). FIG. 11B contains representative confocal images of proximity ligation assay (PLA) in Hela-V5-tau cells transfected with β-arrestin2-flag and β-arrestin2-myc with YFP control, YFP-β-arrestin2 ΔIP6C, or YFP-β-arrestin2 ΔIP6N. FIG. 11C shows quantification of β-arrestin2-flag/β-arrestin2-myc PLA puncta/cell (N=3 independent experiments, P<0.005, *P<0.0005). FIG. 11D contains representative immunblots of filter-trap assay for tau from Hela-V5-tau cells transfected with control vector, β-arrestin2 ΔIP6C-flag, or β-arrestin2 ΔIP6N-flag. FIG. 11E shows quantification of insoluble tau aggregates (N=8/condition, #P<0.0001).

FIG. 12A contains representative confocal images of mCherry and EGFP in Hela-V5-tau cells transfected with mCherry-GFP-p62 together with control vector, β-arrestin2-flag, or β-arrestin2 ΔIP6N-flag (Scale bar=10 μm). FIG. 12B shows quantification of mCherry only particles to total particles normalized to control (N=3 independent experiments, #P<0.0001). The box and whisker plots show all data points, and the box plots show all data points, the median and IQR, and the minimal and maximal values. FIG. 12C contains representative immunoblots of indicated proteins from Hela-V5-tau cells transfected GFP or GFP-β-arrestin2 with/without HA-p62. Note that β-arrestin2 is present in HA immune complexes only in the presence of HA-p62, whereas β-arrestin2 is not detected in control IgG beads. FIG. 12D contains representative immunoblots of indicated proteins from Hela-V5-tau cells transfected with control, β-arrestin2-flag, β-arrestin2 ΔIP6C-flag or β-arrestin2 ΔIP6N-flag together with either HA-p62 and/or GFP-p62. Lysates were subjected to IP for HA. FIG. 12E contains representative confocal images of proximity ligation assay (PLA) of Hela-V5-tau cells transfected with β-arrestin2-flag, β-arrestin2 ΔIP6C-flag, or β-arrestin2 ΔIP6N-flag (Scale bar=20 μm).

FIG. 13A shows Hela-V5-tau cells transfected with control siRNA or β-arrestin1 siRNA. After transfection, cells were treated with either vehicle or 10 μM isoproterenol (Iso), lysed and immunoblotted for indicated proteins. Representative blots are shown. FIG. 13B shows quantification of phospho-tau levels. n=3 independent experiments. *p<0.05. 1-way ANOVA with Dunnett's test. FIG. 13C shows Hela-V5-tau cells transfected with control siRNA or β-arrestin1 siRNA and treated with either vehicle, 1 μM or 10 μM LY-379,268, lysed and immunoblotted for indicated proteins. Representative blots are shown. FIG. 13D shows quantification of phospho-tau levels. n=4 independent experiments. *p<0.05, **0<0.005. 1-way ANOVA with Dunnett's test. FIG. 13E shows Hela-V5-tau cells transfected with control siRNA or β-arrestin2 siRNA and treated with either vehicle, 10 μM Iso, or 10 μM LY-379,268, lysed and immunoblotted for indicated proteins. FIG. 13F shows quantification of phospho-tau levels. n=4 independent experiments. *p<0.05, **p<0.005. 1-way ANOVA with Dunnett's test.

FIG. 14A shows RIPA soluble extracts from the frontal cortex of healthy controls and FTLD-tau patients were immunoblotted for β-arrestin1 and actin. Representative blots are shown. FIG. 14B show quantification of RIPA soluble β-arrestin1 levels. healthy control (n=12), FTLD-tau patients (n=10). *p<0.0005. Unpaired t-test. FIG. 14C shows RIPA insoluble extracts from the frontal cortex of healthy controls and FTLD-tau patients were immunoblotted for β-arrestin1 and actin. Representative blots are shown. FIG. 14D shows quantification of RIPA insoluble β-arrestin1 levels. healthy control (n=12), FTLD-tau patients (n=10). *p<0.0005. Unpaired t-test. FIG. 14E shows RIPA insoluble extracts from the frontal cortex of FTLD-tau patients were immunoblotted for β-arrestin1, tau and actin. FIG. 14F shows correlation between RIPA insoluble tau and β-arrestin1 in FTLD-tau patients (n=10 FTLD-tau; $R^2$=0.4874, P=0.0248, linear regression). FIG. 14G shows representative Z-stack images of FTLD-tau brains showing that β-arrestin1 and AT8+(pS202/pT205) tau pathology are colocalized (Scale bar=20 μm). White boxes are magnified below.

FIG. 15A shows DIV5 hippocampal primary neurons derived from P0 tauP301S mice were transduced with GFP or β-arrestin1-shRNA-GFP lentivirus and immunostained for tau on DIV21. Representative images are shown (Scale bar=10 μm). FIG. 15B shows quantification of tau intensity. n=4 independent experiments. #p<0.0001. Unpaired t-test. FIG. 15C shows DIV5 cortical primary neurons derived from P0 tauP301S pups were transduced with control or β-arrestin1 shRNA lentivirus. Cortical neurons were lysed at DIV18 and immunoblotted for β-arrestin1, tau, and actin. Representative blots are shown. FIG. 15D shows quantification of total tau levels. n=4 independent experiments. **p<0.005. Unpaired t-test. FIG. 15E shows Hela-V5-tau cells transfected with control vector or β-arrestin1, lysed and immunoblotted for β-arrestin1, tau, phospho-tau, and actin. Representative blots are shown. FIGS. 15F and 15G show quantification of total tau (FIG. 15F) and phospho-tau (FIG. 15G) levels. n=6 independent experiments. *p<0.05, #p<0.0001. Unpaired t-test.

FIGS. 16A to 16J show genetic reduction in β-arrestin1 alleviates tauopathy in vivo. FIG. 16A contains confocal images of 7-month-old tauP301S and tauP301S; Arrb1$^{+/-}$ littermates hippocampus stained for pS199/pS202 tau (Scale bar=10 μm). White boxes are magnified below. Representative images are shown. FIG. 16B shows quantification of pS199/pS202 tau intensity. n=4/genotype. #p<0.0001. Unpaired t-test. FIG. 16C shows sarkosyl-soluble and insoluble extracts from 7-month-old tauP301S and tauP301S; Arrb1$^{+/-}$ brains were immunoblotted for β-arrestin1, tau, and actin. Representative blots are shown. FIGS. 16D and 16E show quantification of sarkosyl-soluble and insoluble tau levels. n=5/genotype. p<0.005. Unpaired t-test. FIG. 16F shows input-output analysis from 4-month-old WT, tauP301S, and tauP301S; Arrb1$^{+/-}$ acute slices. (WT: 33 slices, 5 mice; tauP301S: 32 slices, 5 mice; tauP301S; Arrb1$^{+/-}$:30 slices, 4 mice). No significant differences observed. FIG. 16G shows paired pulse facilitation (PPF) analysis from 4-month-old WT, tauP301S, and tauP301S; Arrb1$^{+/-}$ acute slices. (WT: 33 slices, 5 mice; tauP301S: 40 slices, 5 mice; tauP301S; Arrb1$^{+/-}$:35 slices, 4 mice). 2-way ANOVA with Dunnett posthoc test. #p<0.0001: 20-180 ms, WT vs. tauP301S. *p<0.0005: 20 ms, tauP301S vs. tauP301S; Arrb1$^{+/-}$. **p<0.005: 200-260 ms, WT vs. tauP301S. *p<0.05: 280-300 ms, WT vs. tauP301S; 40,100, & 120 ms, tauP301S vs. tauP301S; Arrb1$^{+/-}$. FIG. 16H shows long-term potentiation (LTP) induced by theta burst stimulation. (WT: 31 slices, 5 mice; tauP301S: 29 slices, 5 mice; tauP301S; Arrb1+/-:31 slices, 4 mice). 2-way ANOVA with Dunnett posthoc test. *p<0.0001 in all time points, WT vs. tauP301S and tauP301S Arrb1$^{+/-}$ vs. tauP301S. All data are presented as mean±SEM. FIG. 16I shows hippocampal primary neurons derived from WT and tauP301S P0 pups were transduced with either GFP or β-arrestin1-shRNA-GFP lentivirus on DIV5. Neurons were stained with synaptophysin on DIV21 (Scale bar=10 μm). Representative images are shown. FIG. 16J shows quantification of synaptophysin intensity. n=4 independent experiments, #p<0.0001. 1-way ANOVA with Dunnett's test.

FIG. 17A shows microtubule-binding sedimentation assay was performed using 1 μg recombinant tau incubated with either 2 μg BSA or 2 μg recombinant β-arrestin1. Indicated amounts of β-arrestin1 or BSA were incubated with or without 0.4 nM pre-polymerized microtubules in the presence of tau, and microtubule-bound tau was monitored by co-sedimentation and subsequent immunoblotting for tau. Representative blots are shown. FIG. 17B shows quantification of microtubule bound tau. n=5 independent experiments. *p<0.005. Unpaired t-test. FIG. 17C shows microtubule-binding sedimentation assay with indicated amount of recombinant β-arrestin1, 1 μg of tau, and 0.4 nM pre-polymerized microtubules. Tau and β-arrestin1 in the microtubule-bound pellet and unbound supernatant were monitored by co-sedimentation and subsequent immunoblotting. FIG. 17D shows tubulin polymerization measured by turbidity at 340 nm in the presence of 2 μg of indicated recombinant proteins. n=4 independent experiments. #p<0.0001. 2-way repeated measures ANOVA. FIG. 17E shows confocal images of Hela-V5-tau cells transfected with either control siRNA or β-arrestin1 siRNA and treated with 20 μM of nocodazole for 30 min and recovered for another 1 h. Cells were fixed and immunostained for tubulin and β-arrestin1 (Scale bar=10 μm). White boxes magnified to the right. FIG. 17F shows quantification of transfected cells with tubulin intensity normalized to control siRNA transfected cells. n=4 independent experiments. #p<0.0001. Unpaired t-test.

FIG. 18A shows quantification of β-arrestin1 mRNA levels by qRT-PCR in Hela-V5-tau cells transfected with control vector or β-arrestin1. n=6 independent experiments.

FIG. 18N shows quantification of GFP-p62 and HA-p62 interaction n=3 independent experiments. p<0.005. Unpaired t-test.

FIG. 20A shows DIV18 cortical primary neurons derived from PS19 P0 pups treated with either vehicle or 10 μM isoproterenol (ISO) for 24 hours, lysed and immunoblotted for tau, pS396/pS404-tau (PHF1), and actin. Representative blots are shown. FIG. 20B shows quantification of PHF1 levels. n=4 independent experiments. *p<0.05. Unpaired t-test. All data are presented as mean±SEM. FIG. 21C shows DIV18 cortical primary neurons derived from PS19 P0 pups treated with vehicle, 1 μM or 10 μM LY-379,268, lysed and immunoblotted for tau, PHF1, and actin. Representative blots are shown. FIG. 20D shows quantification of PHF1 levels. n=4 independent experiments. ***p<0.0005. Unpaired t-test. All data are presented as mean±SEM. FIG. 20E shows DIV11 cortical primary neurons derived from Arrb2$^{-/-}$ P0 pups were treated with vehicle, 10 μM ISO, or 10 μM LY-379,268 for 24 hours, lysed and immunoblotted for tau, PHF1, and actin. Representative blots are shown.

FIG. 21A contains confocal images of healthy control brain stained with β-arrestin1 and AT8 (Scale bar=20 μm). FIG. 21B shows secondary antibody-only staining shows no immunoreactivities in FTLD-tau brain.

FIG. 22A shows HeLa-V5-tau cells transfected with control siRNA or β-arrestin1 siRNA, lysed and immunoblotted for β-arrestin1, tau, and actin. Representative blots are shown. FIG. 22B shows quantification of tau. n=4 independent experiments. #p<0.0001. Unpaired t-test. All data are presented as mean±SEM.

FIG. 23A shows HeLa-V5-tau cells transfected with control vector or β-arrestin1-myc and treated with vehicle or 100 nM of Bafilomycin A1 for 4 hours. Cells were fixed and immunostained for myc and LC3 (Scale bar=10 μm). Representative images are shown. FIG. 23B shows quantification of LC3 puncta area normalized to vector control vehicle condition. n=4 independent experiments. #p<0.0001. 1-way ANOVA with Dunnett post hoc test. All data are presented as mean±SEM. FIG. 23C shows HeLa-V5-tau cells transfected with GFP or GFP-β-arrestin1 and/or HA-p62, subjected to co-IP for HA, and immunoblotting for GFP, HA, and actin.

FIG. 27A shows HeLa-V5-tau cells treated with 20 μM of 01, C1, or C2 compounds for 6 hours, and subjected to sarkosylsoluble and insoluble fractionation. C1 and C2 significantly decreased sarkosyl-insoluble tau levels in HeLa-V5-tau cells. (n=4, one-way ANOVA, post hoc Dunnett's, P<0.005, *P<0.0005). FIG. 27B shows DIV21 hippocampal primary neurons derived from Tau-P301S mice treated with 20 μM of 01, C1, or C2 compounds for 6 hours, and stained for HT 7 (total human tau). C1 and C2 significantly decreased HT7 immunoreactivity (n=3, one-way ANOVA, post hoc Dunnett's, *P<0.05, ***P<0.0005.

FIG. 28A shows proximity ligation assay (PLA) using antibodies against GFP and Flag (M2) to detect GFP-βarrestin2/Flag-βarrestin2 complexes show significant reduction in βarrestin2 oligomerization (n=3, one-way ANOVA, post hoc Dunnett's, *P<0.05, ***P<0.0005). Inclusion of only 1 PLA probe as negative control shows no PLA red puncta. FIG. 28B shows cells subjected to lysis and co-immunoprecipitation (co-IP) for GFP-βarrestin2/Flag-βarrestin2 complexes, demonstrating that C1 and C2 compounds reduce βarrestin2 self-interaction to background levels similar to anti-mouse IgG beads alone.

DETAILED DESCRIPTION

Figure 1A:
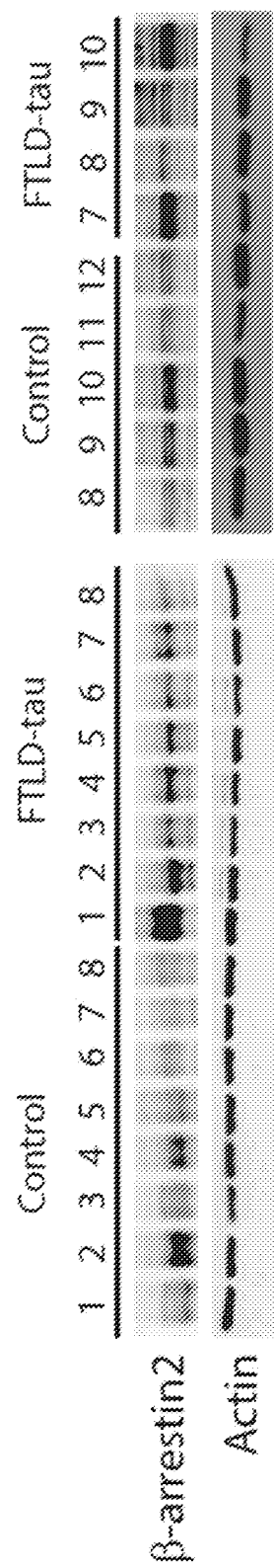
FIGS. 1A to 1I show β-arrestin2 is increased in brains of FTLD-tau patients and tau P301S transgenic mice.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

Definitions

It must be noted that, as used in the specification and the appended claims, the singular forms "a," "an," and "the" include plural referents unless the context clearly dictates otherwise.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino, acids.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to a reference sequence.

"Positively charged," in reference to an amino acid, refers to those amino acids, amino acid derivatives, amino acid mimetics and chemical moieties that are positively charged at physiological pH. Positively charged amino acids include, for example, lysine and arginine.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half-life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

A "vector" or "expression vector" is a replicon, such as plasmid, phage, virus, or cosmid, to which another DNA segment, i.e. an "insert", may be attached so as to bring about the replication of the attached segment.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function. A "therapeutically effective amount" as used herein, is intended to mean an amount sufficient to reduce by at least 10%, preferably at least 25%, more preferably at least 50%, and most preferably an amount that is sufficient to cause an improvement in one or more clinically significant symptoms in the subject.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl. Fused aryl groups including, but not limited to, indene and naphthalene groups are also contemplated. The aryl group can also be fused with a cycloalkyl group. For example, a cyclopentyl group can be fused with a phenyl group.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "halo," "halogen" or "halide," as used herein can be used interchangeably and refer to F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. The terms "substantially R" and "substantially S" are defined herein having at least 70% enantiomeric purity, at least 70% enantiomeric purity, at least 70% enantiomeric purity, at least 75% enantiomeric purity, at least 80% enantiomeric purity, at least 85% enantiomeric purity, at least 90% enantiomeric purity, at least 95% enantiomeric purity, at least 99% enantiomeric purity, or 100% enantiomeric purity of either the R or S enantiomer.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

Beta-Arrestin Oligomerization Inhibitors

Dominant Negative Peptides

In some embodiments, the β-arrestin oligomerization inhibitor is a dominant negative peptide comprising a mutated β-arrestin protein, or fragment thereof, that can block the binding of endogenous β-arrestin1 and/or β-arrestin2 from binding inositol hexakisphosphate (IP6). Mutant forms of β-arrestin protein are described in Milano S K, et al. (2006) J Biol Chem 281(14):9812-9823, which is incorporated by reference in its entirety for the teaching of these mutants. Milano S K, et al. solved the crystal structure of arrestin2 in complex with IP6, identifying two domains involved in IP6-dependent oligomerization. In some embodiments, the mutated β-arrestin protein has a mutation in one or more lysine and/or argine residues in the N-domain and/or C-domain described in Milano S K, et al. For example, in some embodiments, the mutated β-arrestin has least one amino acid substitution corresponding to residue K158, K161, R162, K232, R234, K252, K326, or K328 of a wildtype arrestin2.

Pharmacological Inhibitors

In some embodiments, the β-Arrestin oligomerization inhibitor is a compound having the structure below or the pharmaceutically-acceptable salt thereof

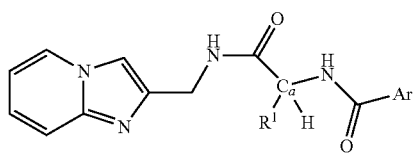

wherein $R^1$ is hydrogen or an alkyl group;
Ar is an aryl group; and
when $R^1$ is an alkyl group, the stereochemistry at $C_a$ is racemic, substantially R, or substantially S.

In one embodiment, $R^1$ is hydrogen. In one embodiment, Ar is an unsubstituted or substituted phenyl group. In another embodiment, Ar is a phenyl group substituted with one or more halogen atoms. In one embodiment, $R^1$ is a $C_1$ to $C_{10}$ alkyl group such as, for example, methyl, ethyl, propyl isopropyl, or butyl. In one embodiment, the stereochemistry at $C_a$ is substantially R. In another embodiment, the stereochemistry at $C_a$ is substantially S. In another embodiment, the stereochemistry at $C_a$ is racemic. In one embodiment, Ar is an unsubstituted or substituted phenyl group. In one embodiment, Ar is a phenyl group substituted with one or more alkyl groups or halogen atoms. In one embodiment, the phenyl group is substituted with 1 to 3 halogen atoms. The position of the halogen atoms on the phenyl ring can vary. In another embodiment, Ar is a phenyl group with a fused with a cycloalkyl group. The cycloalkyl group can have from 4 to 7 carbon atoms. In one aspect, the phenyl group with a fused with a cycloalkyl group has the structure below

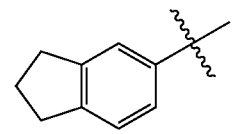 [SMILES: *c1ccc2c(c1)CCC2]

In some embodiments, the β-Arrestin oligomerization inhibitor is a compound having the structure below or the pharmaceutically-acceptable salt thereof

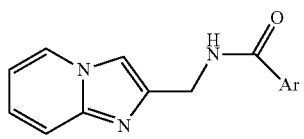

wherein Ar is an aryl group.

In one embodiment, Ar is an unsubstituted or substituted phenyl group. In another embodiment, Ar is a phenyl group substituted with an alkyl group or a cycloalkyl group.

In some embodiments, the β-Arrestin oligomerization inhibitor is a compound having the structure below or the pharmaceutically-acceptable salt thereof

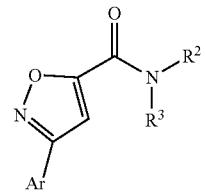

wherein $R^2$ and $R^3$ are, independently, hydrogen or an alkyl group; and
Ar is an aryl group.

In one embodiment, $R^2$ is hydrogen. In another embodiment, $R^3$ is a $C_1$ to $C_{10}$ alkyl group such as, for example, methyl, ethyl, propyl isopropyl, or butyl. In one embodiment, Ar is an unsubstituted or substituted phenyl group. In another embodiment, Ar is a phenyl group substituted with an alkyl group or a halogen atom.

In some embodiments, the β-Arrestin oligomerization inhibitor is a compound having the structure below or the pharmaceutically-acceptable salt thereof

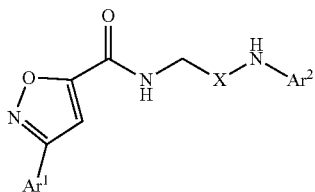

wherein Ar¹ and Ar² are, independently, an aryl group; and

X is CH$_2$ or C=O.

In one embodiment, Ar¹ is an unsubstituted or substituted phenyl group. In another embodiment, Ar¹ is a phenyl group substituted with an alkyl group or a halogen atom. In one embodiment, Ar¹ is an unsubstituted or substituted heteroaryl group. In another embodiment, Ar¹ is an unsubstituted or substituted piperidinyl group or pyridazinyl group. In one embodiment, Ar² is an unsubstituted or substituted phenyl group. In another embodiment, Ar² is a phenyl group substituted with an alkyl group or a halogen atom. In one embodiment, Ar² is an unsubstituted or substituted piperidinyl group. In another embodiment, Ar² is a piperidinyl group substituted with an alkyl group or a halogen atom.

In some embodiments, the β-Arrestin oligomerization inhibitor is a compound having the structure below or the pharmaceutically-acceptable salt thereof

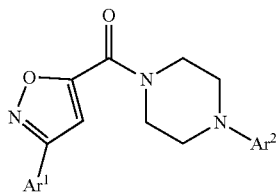

wherein Ar¹ and Ar² are, independently, an aryl group.

In one embodiment, Ar¹ is an unsubstituted or substituted phenyl group. In another embodiment, Ar¹ is a phenyl group substituted with an alkyl group or a halogen atom. In one embodiment, Ar² is an unsubstituted or substituted phenyl group. In another embodiment, Ar² is a phenyl group substituted with an alkyl group or a halogen atom.

In some embodiments, the β-Arrestin oligomerization inhibitor is a compound selected from the group consisting of (2-[(2,3-dihydro-1H-inden-5-yl)formamido]-N-({imidazo[1,2-a]pyridin-2-yl}methyl)acetamide), N-{2-[(6-methylpyridazin-3-yl)amino]ethyl}-3-phenyl-1,2-oxazole-5-carboxamide, 2-[(2,4-difluorophenyl)formamido]-N-({imidazo[1,2-a]pyridin-2-yl}methyl)acetamide, (2S)—N-({imidazo[1,2-a]pyridin-2-yl}methyl)-3-methyl-2-[(3-methylphenyl)formamido]butanamide, 2-[(3-bromophenyl)formamido]-N-({imidazo[1,2-a]pyridin-2-yl}methyl)acetamide, N-({imidazo[1,2-a]pyridin-2-yl}methyl)-3-[(piperidin-4-yl)methyl]benzamide, 2-[(3-chlorophenyl)formamido]-N-({imidazo[1,2-a]pyridin-2-yl}methyl)acetamide, N-{2-[(3-methylpyridin-4-yl)amino]ethyl}-3-phenyl-1,2-oxazole-5-carboxamide, 1-(4-fluorophenyl)-4-[3-(4-fluorophenyl)-1,2-oxazole-5-carbonyl]piperazine, 2-{[3-(4-methylphenyl)-1,2-oxazol-5-yl]formamido}-N-(2,4,6-trimethylphenyl)acetamide, N-(2-bromophenyl)-2-{[3-(4-methylphenyl)-1,2-oxazol-5-yl]formamido}acetamide, and 3-phenyl-N-(propan-2-yl)-1,2-oxazole-5-carboxamide.

In some embodiments, the β-Arrestin oligomerization inhibitor is a compound having a structure represented by a formula:

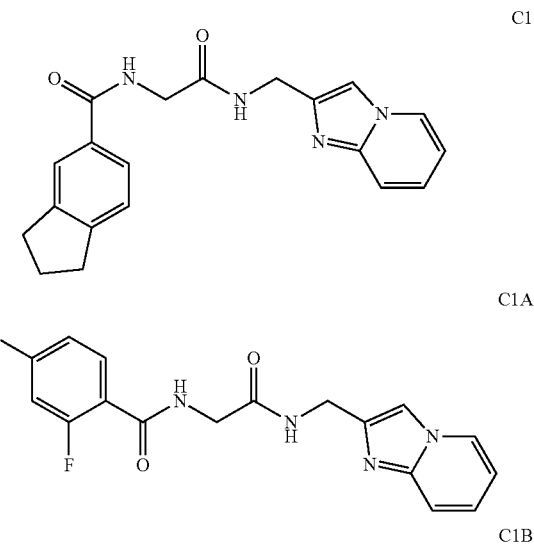

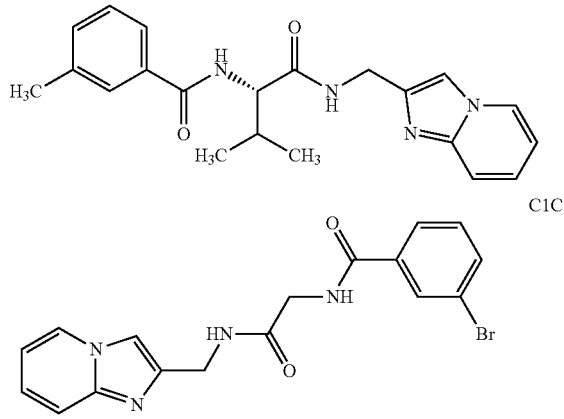

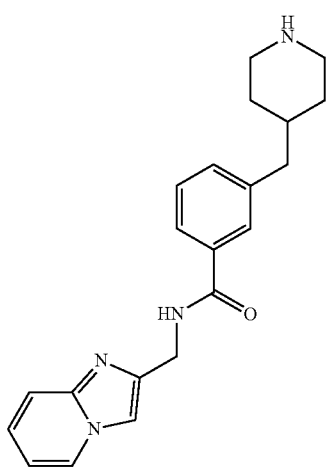

C1E

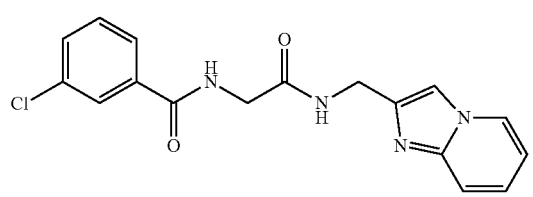

C1E

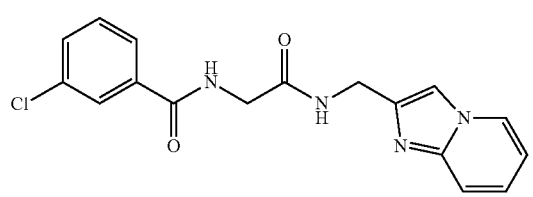

C2

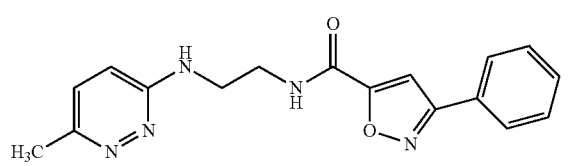

C2A

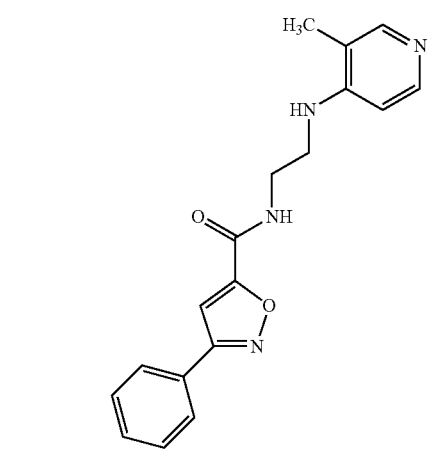

C2B

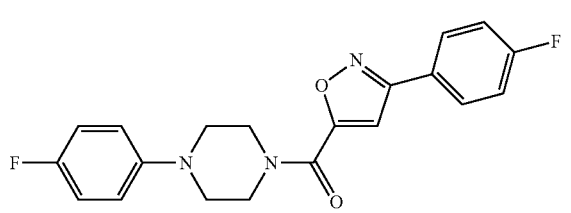

C2C

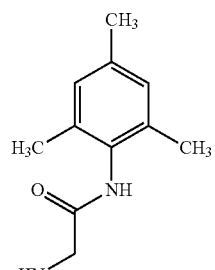

C2D

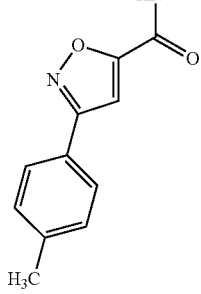

C2E

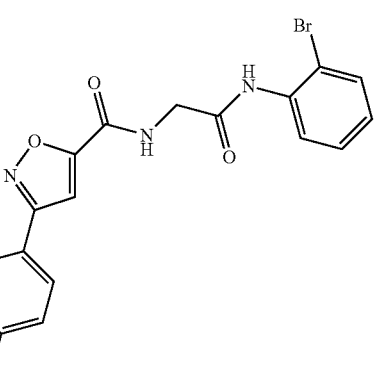

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitoneally, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with an basoc reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multilayer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions disclosed herein, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for treating a tauopathy in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, or a polymorph thereof. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using the Compounds

In a further aspect, the present disclosure provides methods of treating a tauopathy that involve administration of a therapeutically effective amount of a β-arrestin oligomerization inhibitor disclosed herein to a subject in need thereof.

A tauopathy is a disorder characterized by an abnormal level of tau in a cell, a tissue, or a fluid in an individual. In some cases, a tauopathy is characterized by the presence in a cell, a tissue, or a fluid of elevated (higher than normal) levels of tau or tau polypeptides and/or pathological forms of tau. For example, in some cases, a tauopathy is characterized by the presence in brain tissue and/or cerebrospinal fluid of elevated levels of tau or tau polypeptides and/or pathological forms of tau. A "higher than normal" level of tau in a cell, a tissue, or a fluid indicates that the level of tau in the tissue or fluid is higher than a normal, control level, e.g., higher than a normal, control level for an individual or population of individuals of the same age group. See, e.g., Blomberg et al. (2001) "Cerebrospinal fluid tau levels increase with age in healthy individuals" Dement. Geriatr. Cogn. Disord. 12:127. In some cases, an individual having a tauopathy exhibits one or more additional symptoms of a tauopathy (e.g., cognitive decline).

In other cases, a tauopathy is characterized by the presence in a cell, a tissue, or a fluid of lower than normal levels of tau. A "lower than normal" level of tau in a tissue or a fluid indicates that the level of tau in the cell, tissue, or fluid is lower than a normal, control level, e.g., lower than a normal, control level for an individual or population of individuals of the same age group.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. The present disclosure provides a treatment method as described above, wherein the tauopathy is Alzheimer's, Pick's disease, sporadic Frontotemporal dementia and Frontotemporal dementia with Parkinsonism linked to chromosome 17. Other tauopathies include, but are not limited to, Progressive supranuclear palsy (PSP), Corticobasal degeneration (CBD) and Subacute sclerosing panencephalitis.

A neurodegenerative tauopathy includes Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia (FTD), frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

Aspects of the Disclosure

The disclosure will be better understood upon reading the following numbered aspects which should not be confused with the claims. Each of the numbered aspects described below can in some instances be combined with additional aspects described above.

Aspect 1. A method of treating a tauopathy in a subject, the method comprising administering to the human subject a therapeutically effective amount of a β-arrestin oligomerization inhibitor.

Aspect 2. The method of Aspect 1, wherein the tauopathy is selected from the group consisting of Alzheimer's disease, Pick's disease, Frontotemporal dementia, Frontotemporal dementia with Parkinsonism linked to chromosome 17, progressive supranuclear palsy, Corticobasal degeneration, subacute sclerosing panencephalitis, amyotrophic lateral sclerosis/parkinsonism-dementia complex, argyrophilic grain dementia, British type amyloid angiopathy, cerebral amyloid angiopathy, Creutzfeldt-Jakob disease, dementia pugilistica, diffuse neurofibrillary tangles with calcification, Down's syndrome, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non- Guamanian motor neuron disease with neurofibrillary tangles, postencephalitic parkinsonism, prion protein cerebral amyloid angiopathy, progressive subcortical gliosis, Tangle only dementia, multi-infarct dementia, ischemic stroke, chronic traumatic encephalopathy, traumatic brain injury, and stroke.

Aspect 3. The method of Aspect 2, wherein the tauopathy is frontotemporal lobar degeneration.

Aspect 4. The method of any one of Aspects 1 to 3, wherein the β-arrestin oligomerization inhibitor is a dominant negative mutant of β-arrestin1 or β-arrestin2 that blocks endogenous β-arrestin1 and/or β-arrestin2 from binding inositol hexakisphosphate (IP6).

Aspect 5. The method of any one of Aspects 1 to 3, wherein the β-arrestin oligomerization inhibitor is a compound having a structure below or the pharmaceutically-acceptable salt thereof:

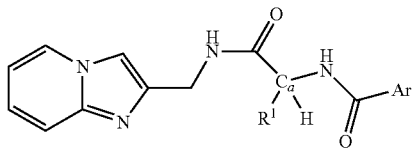

wherein $R^1$ is hydrogen or an alkyl group;
Ar is an aryl group; and
when $R^1$ is an alkyl group, the stereochemistry at $C_a$ is racemic, substantially R, or substantially S.

Aspect 6. The method of Aspect 5, wherein $R^1$ is hydrogen.

Aspect 7. The method of Aspect 5 or 6, wherein Ar is an unsubstituted or substituted phenyl group.

Aspect 8. The method of Aspect 5 or 6, wherein Ar is a phenyl group substituted with one or more halogen atoms.

Aspect 9. The method of Aspect 5, wherein $R^1$ is a $C_1$ to $C_{10}$ alkyl group.

Aspect 10. The method of Aspect 9, wherein the stereochemistry at $C_a$ is substantially R.

Aspect 11. The method of Aspect 9, wherein the stereochemistry at $C_a$ is substantially S.

Aspect 12. The method of Aspect 9, wherein the stereochemistry at $C_a$ is racemic.

Aspect 13. The method of any one of Aspects 9 to 12, wherein Ar is an unsubstituted or substituted phenyl group.

Aspect 14. The method of any one of Aspects 9 to 12, wherein Ar is a phenyl group substituted with one or more halogen atoms.

Aspect 15. The method of any one of Aspects 9 to 12, wherein Ar is a phenyl group with a fused with a cycloalkyl group.

Aspect 16. The method of any one of Aspects 1 to 3, wherein the compound is C1, C1A, C1B, C1C, or C1E.

Aspect 17. The method of any one of Aspects 1 to 3, wherein the β-arrestin oligomerization inhibitor is a compound having a structure below or the pharmaceutically-acceptable salt thereof:

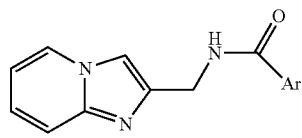

wherein Ar is an aryl group.

Aspect 18. The method of Aspect 17, wherein Ar is an unsubstituted or substituted phenyl group.

Aspect 19. The method of Aspect 17, wherein Ar is a phenyl group substituted with an alkyl group or a cycloalkyl group.

Aspect 20. The method of any one of Aspects 1 to 3, wherein the compound is C1D.

Aspect 21. The method of any one of Aspects 1 to 3, wherein the β-arrestin oligomerization inhibitor is a compound having a structure below or the pharmaceutically-acceptable salt thereof:

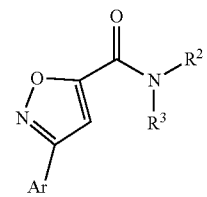

wherein $R^2$ and $R^3$ are, independently, hydrogen or an alkyl group; and
Ar is an aryl group.

Aspect 22. The method of Aspect 121, wherein $R^2$ is hydrogen.

Aspect 23. The method of Aspect 21 or 22, wherein $R^3$ is a $C_1$ to $C_{10}$ alkyl group.

Aspect 24. The method of any one of Aspects 21 to 23, wherein Ar is an unsubstituted or substituted phenyl group.

Aspect 25. The method of any one of Aspects 21 to 23, wherein Ar is a phenyl group substituted with an alkyl group or a halogen atom.

Aspect 26. The method of any one of Aspects 1 to 3, wherein the compound is C2E.

Aspect 27. The method of any one of Aspects 1 to 3, wherein the β-arrestin oligomerization inhibitor is a compound having a structure below or the pharmaceutically-acceptable salt thereof:

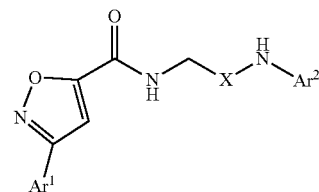

wherein $Ar^1$ and $Ar^2$ are, independently, an aryl group; and
X is $CH_2$ or $C=O$.

Aspect 28. The method of Aspect 27, wherein $Ar^1$ is an unsubstituted or substituted phenyl group.

Aspect 29. The method of Aspect 27, wherein $Ar^1$ is a phenyl group substituted with an alkyl group or a halogen atom.

Aspect 30. The method of Aspect 27, wherein $Ar^1$ is an unsubstituted or substituted heteroaryl group.

Aspect 31. The method of Aspect 27, wherein $Ar^1$ is an unsubstituted or substituted piperidinyl group or pyridazinyl group.

Aspect 32. The method of any one of Aspects 27 to 31, wherein $Ar^2$ is an unsubstituted or substituted phenyl group.

Aspect 33. The method of any one of Aspects 27 to 31, wherein $Ar^2$ is a phenyl group substituted with an alkyl group or a halogen atom.

Aspect 34. The method of any one of Aspects 27 to 31, wherein $Ar^2$ is an unsubstituted or substituted piperidinyl group.

Aspect 35. The method of any one of Aspects 27 to 31, wherein $Ar^2$ is a piperidinyl group substituted with an alkyl group or a halogen atom.

Aspect 36. The method of any one of Aspects 27 to 35, wherein X is $CH_2$.

Aspect 37. The method of any one of Aspects 27 to 35, wherein X is C=O.

Aspect 38. The method of any one of Aspects 1 to 3, wherein the compound is C2, C2A, C2C, or C2D.

Aspect 39. The method of any one of Aspects 1 to 3, wherein the β-arrestin oligomerization inhibitor is a compound having a structure below or the pharmaceutically-acceptable salt thereof:

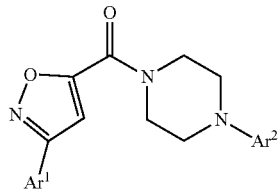

wherein $Ar^1$ and $Ar^2$ are, independently, an aryl group.

Aspect 40. The method of Aspect 39, wherein $Ar^1$ is an unsubstituted or substituted phenyl group.

Aspect 41. The method of Aspect 39, wherein $Ar^1$ is a phenyl group substituted with an alkyl group or a halogen atom.

Aspect 42. The method of any one of Aspects 39 to 41, wherein $Ar^2$ is an unsubstituted or substituted phenyl group.

Aspect 43. The method of any one of Aspects 39 to 41, wherein $Ar^2$ is a phenyl group substituted with an alkyl group or a halogen atom.

Aspect 44. The method of any one of Aspects 1 to 3, wherein the compound is C2B.

A number of embodiments of the invention have been described. Nevertheless, it will be understood that various modifications may be made without departing from the spirit and scope of the invention. Accordingly, other embodiments are within the scope of the following claims.

EXAMPLES

Example 1: β-Arrestin2 Oligomers Impair the Clearance of Pathological Tau and Increase Tau Aggregates Introduction GPCRs initiate a wide range of physiological processes, and several GPCRs have been shown to potentially play roles in AD pathogenesis (Ni Y, et al. (2006) Nat Med 12(12):1390-1396; AbdAlla S, et al. (2009) J Biol Chem 284(10):6566-6574; Thathiah A, et al. (2009) Science 323 (5916):946-951; Bakshi P, et al (2008) ACS Chem Biol 3(12):777-789; Ray B, et al. (2010) Neurosci Lett 470(1): 1-5; Alley G M, et al. (2010) J Neurosci Res 88(1):143-154; Minkeviciene R, et al. (2004) J Pharmacol Exp Ther 311 (2):677-682; Scholtzova H, et al. (2008) J Neurosci Res 86(12):2784-2791). Genetic and pharmacological studies indicate that neuronal expression and/or activation of several GPCRs with diverse structures, endogenous agonists, and cell signaling effects positively contribute to Aβ and/or tau pathogenesis in animal model. However, it is not clear how this heterologous array of GPCRs can impinge on Aβ and tau pathogenesis and neurodegeneration in AD. One potential commonality among these receptors is their interaction with arrestins. Upon agonist binding (Wilden U, et al. (1986) Proc Natl Acad Sci USA 83(5):1174-1178), most GPCRs become phosphorylated by G protein coupled receptor kinases, and the phosphorylated receptors are substrates for the binding of arrestins. These proteins physically interdict between receptor and G protein, partially uncoupling activated receptor from its functional transducer. This phenomenon is thought to be a mechanism to regulate function within the complex signaling environment of the cell. Agonist activation also induces receptor internalization and promotes additional signals, which have been shown to be due to arrestins acting as multifunctional adapter and scaffolding proteins. Arrestins constitute a small family of 4 homologous proteins, known as Arrestin1, Arrestin2 (β-arrestin1), Arrestin3 (β-arrestin2), and Arrestin4 (Wilden U, et al. (1986) Proc Natl Acad Sci USA 83(5):1174-1178; Moore C A, et al. (2007) Annu Rev Physiol 69:451-482; Gurevich V V & Gurevich E V (2006) Pharmacol Ther 110(3):465-502). While Arrestin1 and Arrestin4 bind to only few receptors (rhodopsin and the color opsins) and are expressed in specific cell types (Shinohara T, et al. (1987) Proc Natl Acad Sci USA 84(20):6975-6979; Yamaki K, et al. (1987) Biochem Biophys Res Commun 142(3):904-910), β-arrestin1 and β-arrestin2 are ubiquitously expressed and show the highest levels of expression in the brain and spleen. β-arrestins exist in three distinct states in cells: (1) free unbound, (2) GPCR-bound, and (3) microtubule-bound, each with the potential for different signaling capabilities (Hanson S M, et al. (2006) J Biol Chem 281(14):9765-9772; Hanson S M, et al. (2007) J Mol Biol 368(2):375-387; Nair K S, et al. (2004) J Biol Chem 279(39):41240-41248; Gao H, et al. (2004) Mol Cell 14(3):303-317; Song X, et al. (2007) J Neurochem 103(3):1053-1062; Wu N, et al. (2006) J Mol Biol 364(5): 955-96). Previous studies have shown that β-arrestin2 is increased in AD brains (Thathiah A, et al. (2013) Nat Med 19(1):43-49). In addition, genetic studies have demonstrated that endogenous β-arrestin2 promotes Aβ production and deposition by physically interacting with the Aph-1 subunit of the γ-secretase complex (27) linking β-arrestin2 to Aβ pathogenesis (Thathiah A, et al. (2013) Nat Med 19(1):43-49). Prior to the current work, however, it was not known whether, or how, β-arrestin2 pathogenically impinges on tauopathy and neurodegeneration in AD, or in FTLD where there is no accumulation of Aβ.

Methods

Mice $Arrb2^{-/-}$, tau P301S, and WT mice were all bred in the C57BL6 background for at least three generations prior to interbreeding with each other. The $Arrb2^{-/-}$ mice (Bohn L M, et al. (1999) Science 286(5449):2495-24980) and tau P301S mice (Yoshiyama Y, et al. (2007) Neuron 53(3):337-351) have previously been characterized. All experiments involving mice were performed in accordance with approved protocols by the Institutional Animal Care and Use Committee (IACUC) at USF Health.

Patients Samples

Frozen frontal cortex tissue samples were obtained from the Alzheimer's Disease Research Center at Emory University. Samples from FTLD-tau diagnosed patients (pathologically confirmed) and samples from non-affected (control)

patients who were otherwise matched as closely as possible for sex, age, and APOE genotype were used.

Primary Neuronal Cultures

Primary mouse hippocampal and cortical neuronal cultures were previously described (Woo J A, et al. (2019) Commun Biol 2:112; Woo J A, et al. (2017) Hum Mol Genet 26(20):3973-3988; Woo J A, et al. (2015) Cell Death Differ 22(6):1069-1070). Briefly, primary neurons were prepared from P0 mice. Both hippocampus and cortex were dissected separately in HBSS and digested with trypsin. Neurons were plated on glass coverslips coated with poly-D-lysine (Sigma-Aldrich, St Louis, MO, USA) and maintained in neurobasal medium with glutamax (Invitrogen, Carlsbad, CA, USA) and B27 supplement (Invitrogen, Carlsbad, CA, USA).

Antibodies and Reagents

Antibodies to total tau (Tau A10, 1:1000 for Western blotting, 1:200 for cell/tissue staining, Santa Cruz Biotechnology, Dallas, TX, USA), PHF1 (kind gift from Dr. Peter Davies, 1:20, Albert Einstein College of Medicine), Tau-pS199/pS202 (1:1000 for Western blotting, 1:200 for tissue staining, Invitrogen, Carlsbad, CA, USA), HT7 (1:200 for cell/tissue staining, Invitrogen, Carlsbad, CA, USA), synaptophysin (1:200, Invitrogen, Carlsbad, CA, USA), drebrin (1:400, Abcam, Cambridge, MA, USA), actin (1:5000, Sigma-Aldrich, St. Louis, MO, USA), Flag-M2 (1:1000 for Western blotting, 1:200 for cell staining, Sigma-Aldrich, St. Louis, MO, USA), Myc (1:1000, cell signaling, Danvers, MA, USA), HA (1:1000, cell signaling, Danvers, MA, USA), GFP (1:1000, cell signaling, Danvers, MA, USA).

DNA Constructs, siRNA, shRNA Lentivirus

β-arrestin2, β-arrestin2 ΔIP6C, and β-arrestin2 ΔIP6N constructs were kind gift from S. Marullo (Institut cochin, Paris, France). pCDNA-β-arrestin2-HA was from X. Xin (Shanghai Institute of Materia Medica, Shanghai, China). The following were obtained from Addgene: β-arrestin2 GFP WT plasmid #35411 (68), HA-p62 plasmid #28027 (69), pMXs-puro GFP-p62 plasmid #38277 (Itakura E & Mizushima N (2011) J Cell Biol 192(1):17-27), pmRFP-LC3 plasmid #21075 (Kimura S, Noda T, & Yoshimori T (2007) Autophagy 3(5):452-460). β-arrestin2 ON-TARGET plus SMART pool siRNA was purchased from Dharmacon (Lafayette, CO, USA). β-arrestin2 shRNA plasmid was obtained from Abm (Richmond, BC, Canada). Lenti-virus vectors were co-transfected with pVSVG and Pax2 using polyethylenimine (PEI) in HEK293T cells for overnight. The media was removed and replaced with serum free media next day. After 72 hrs incubation, the media was collected and centrifuged to remove cell debris. Virus was filtered through syringe filter (0.2-0.45 um).

Proximity Ligation Assay (PLA)

The assay was performed using commercially available reagents (Duolink, Sigma-Aldrich, St Louis, MO), with transfection of Hela V5-tau cells with WT β-arrestin2-flag and β-arrestin2-myc, without and with the mutant β-arrestin2 ΔIP6C or β-arrestin2 ΔIP6N constructs. Cells were fixed with 4% paraformaldehyde for 15 min at room temperature and washed with 0.2% triton in TBS. After washing, cells were blocked with 0.2% Triton in 3% Normal goat serum for 1 hour at room temperature. After applying primary antibodies overnight at 4° C., cells were washed and incubated with the PLA probes at 37° C. (1 h), washed with buffer A, incubated with ligation solution at 37° C. (30 min), washed with washing buffer A, incubated with amplification solution at 37° C. (100 min), and washed with washing buffer B before mounting.

Immunocytochemistry and Immunohistochemistry

Cells were fixed with 4% paraformaldehyde for 15 min at room temperature and washed with 0.2% triton in TBS and blocked using 3% BSA with 0.1% triton x-100 for 1 hr, incubated with primary antibodies for overnight at 4° C. and fluorescently labeled secondary antibodies for 45 min at room temperature. For immunohistochemistry, mice were perfused with PBS and fixed with 4% paraformaldehyde. 25-micron sections were blocked using normal goat serum for 1 h and incubated with primary antibodies at 4° C. overnight, followed by secondary antibody incubation for 1 h at room temperature prior to mounting. Images were captured with the Olympus FV10i confocal microscope (Tokyo, Japan), and the immunoreactivities were quantified using the Image J software (National Institutes of Health, Bethesda, MD). Immunoreactivities were quantitated from every 12th serial section through an entire hippocampus. In ICC and IHC experiments, all comparison images were acquired with identical laser intensity, exposure time, and filter. Adjustments to the brightness/contrast were applied equally to all comparison images. Regions of interest were chosen randomly, and investigators were blinded to experimental conditions during image acquisition and quantification.

Cell Lysis, Immunoblotting, and Sarkosyl Extraction

Brain homogenates and cultured cells were lysed with RIPA buffer (50 mM Tris pH 7.4, 150 mM NaCl, 2 mM ethlenediaminetetraacetic acid, 1% NP-40, 0.1% sodium dodecyl sulfate) plus protease and phosphatase inhibitors. Proteins were extracted and centrifuged at 15000 rpm for 15 min at 4° C., and RIPA insoluble fractions were lysed with 5% SDS with 1% β-mercaptoethanol, 50 mM Tris-HCl pH 6.8, 12.5 mM EDTA, 10% glycerol, and 0.02% bromophenol blue. Supernatants were used for western blot analysis. supernatants were used for western blot analysis. co-IP experiments were carried out from NP40 lysates or indicated buffers with preclearing with IgG beads followed by IP with IgG beads alone or IgG beads+indicated antibodies, extensive washing (5×) with the original buffer, and Western blotting on SDS-PAGE. Sarkosyl extraction was performed as previously described (Hasegawa M, et al. (2007) Brain 130(Pt 5):1386-1394). Briefly, brain homogenates were lysed with A68 buffer containing 10 mM Tris-HCl, pH 7.4, 0.8M NaCl, 10% Sucrose, 1 mM EGTA). Samples were centrifuged at 400 g for 20 min at 4° C., and 1% sarkosyl was added to the collected supernatants. The samples were incubated for 1.5 h and centrifuged at 80,000 g for 30 min at room temperature. The pellets were resuspended in 100 ul of 50 mM Tris-HCl, pH 7.4.

Quantitative Real-Time RT-PCR

Quantitative real-time RT-PCR was performed using Roche LightCycler® 96 System (Life Science, San Francisco, CA, USA). Total RNA was isolated from human brains or cell lines using Trizol reagent (Invitrogen, CA, USA), reverse transcribed (Superscript III, Invitrogen, CA, USA), and subjected to quantitative PCR analysis using Syber green master mix (Invitrogen, CA, USA). The comparative threshold cycle (Ct) value was used to calculate the amplification factor, and the relative amount of β-arrestin2 was normalized to GAPDH.

Generation of rAAV9 and Stereotaxic Injections

Recombinant rAAV9 viruses were generated by co-transfection of serotype vector expressing the interest gene with pAAV9 and pXX6 in HEK293 cells and subjected to purification as previously described (Carty N, et al. (2010) J Neurosci Methods 194(1):144-153). For brain injections, isoflurane anesthetized mice were bilaterally injected with a 26-gauge needle attached to a 10-□l syringe (Hamilton, Reno, NV, USA) at the following coordinates: anteroposterior 2.7 mm, lateral 2.7 mm, and vertical 3.0 mm. A total volume of 2 □l purified rAAV9 (1×10$^{12}$ vg/ml) was injected over a 2 min period using the convection enhanced delivery method. Mice were sacrificed 2 month post injection.

Electrophysiology

Electrophysiological recording was performed as previously described (67). Briefly, hippocampus slices were prepared from 3-month-old WT, tauP301S, tauP301S/Arrb2$^{+/-}$, and tauP301S/Arrb2$^{-/-}$ mice and subjected to input/output (IO) curve, paired pulse facilitation (PPF), and long-term potentiation (LTP) recordings. The stimulating electrode was placed in the Schaffer collaterals of the hippocampus. The recording glass electrode loaded with ACSF was positioned at the CA1 stratum radiatum below the pyramidal cell layer.

Atomic Force Microscopy Imaging

Recombinant p62 (4 μg) of with/without recombinant β-arrestin2 (0.2 μg) was prepared in aqueous solution. Samples were incubated for 2 hrs at RT in 30 μl of aqueous solution. 10 μl of solution was drop-casted on freshly cleaved mica surfaces. After 20 min adsorption, filtered distilled water was used to gently wash excessive solutions from the mica surface. The mica was left at room temperature until it was thoroughly dry followed by AFM imaging. Commercial PPP-NCHAuD cantilever (Nanosensors, Switzerland) with a nominal spring constant of 42 N/m and a resonant frequency of 330 kHz were used for AFM imaging.

Recombinant Proteins

His-tau BL21 was provided by L. Blair. Tau WT (4R0N) was subcloned into pET28a vector and transformed into BL21 competent cells. His-β-arrestin2 was transformed into Rosetta competent cells. Cells were resuspended in ice cold lysis buffer (Tris 20 mM, pH8.0, NaCl 150 mM, imidazole 10 mM) with protease inhibitors. pFast-p62-his construct was transformed into DH10Bac competent cells. After blue-white screening, DH10Bac strains were chosen to express and amplify recombinant Bacmids. Sf9 insect cells transfected with Bacmid (midiprep from DH10Bac competent cells) were cultured for 3 days with Sf900 II SFM medium, then P1 generation virus in medium was collected and added to new Sf9 cells. After 2 days culture, Sf9 cells were harvested and lysed with lysis buffer (Tris 20 mM, pH7.4, NaCl 150 mM, Triton-X100 1%, 10 mM imidazole, with protease inhibitors). After sonicating the cells, centrifuge the cells at 14,000 g for 15 min and incubate the supernatants with Ni Sepharose. Recombinant proteins were eluted with ice-cold elution buffer (Tris 20 mM, NaCl 150 mM, 200 mM imidazole), after which proteins were dialyzed in dialysis buffer (Tris 20 mM, NaCl 150 mM, DTT 1 mM) at 4 degree overnight.

Statistical Analysis and Graphs

Statistical analyses were performed by Prism 6.0 software (GraphPad Software, San Diego, CA, USA) using paired or unpaired Student's t-tests, and one- or two-way ANOVA. ANOVA was followed by the indicated post hoc tests. Data are shown as representative experiments, graphs of mean±standard error of the mean (SEM), or box plots showing each data point, the median, the interquartile range (IQR), and the maximal and minimal values.

Results

Figure 1D:
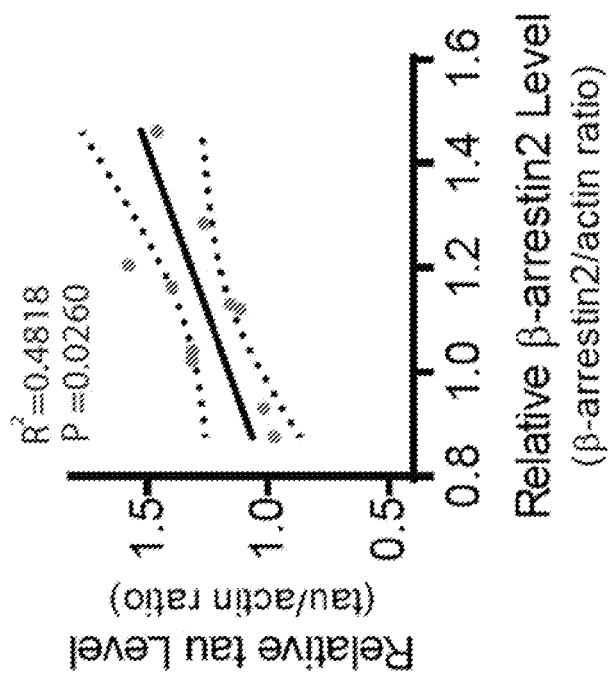
Figure 1C:
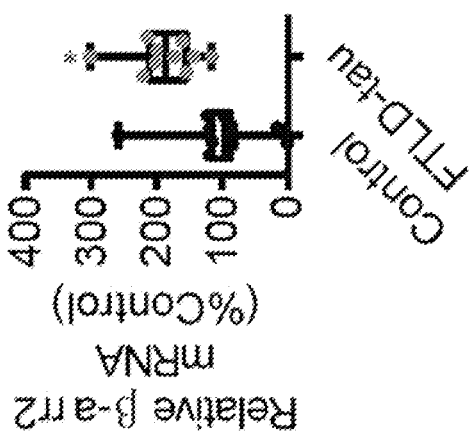
Figure 1B:
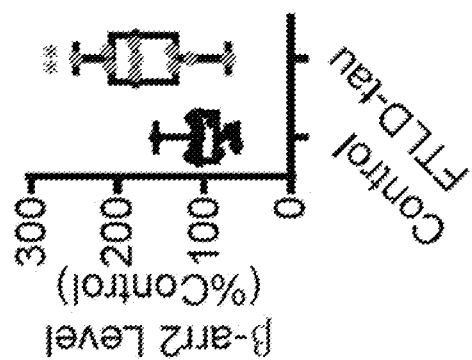
Figure 1E:
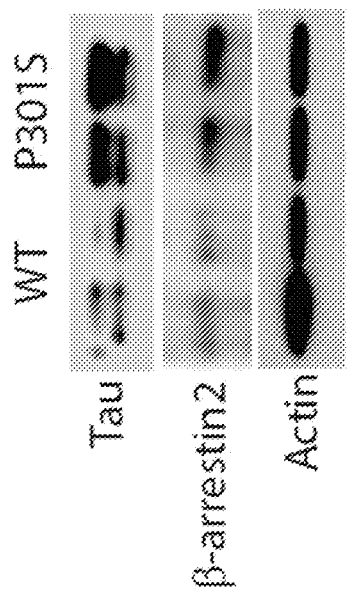
Figure 1F:
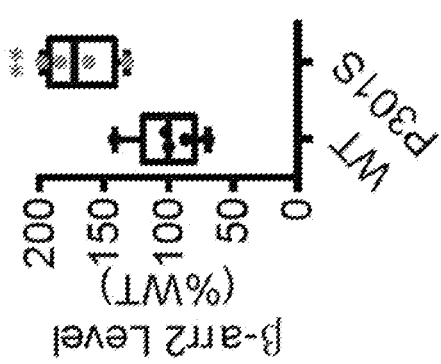
Figure 1G:
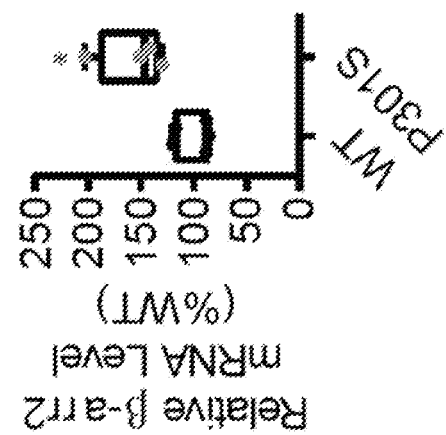
Figures 1H, 1I:
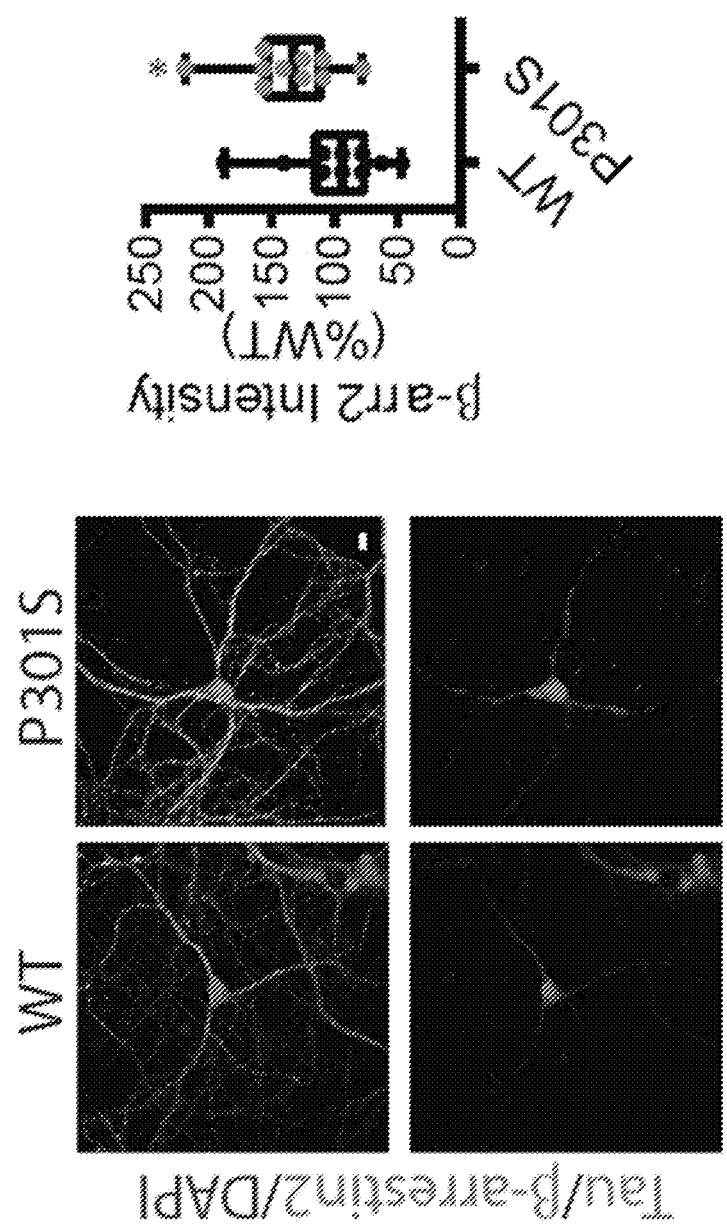
Figure 8:
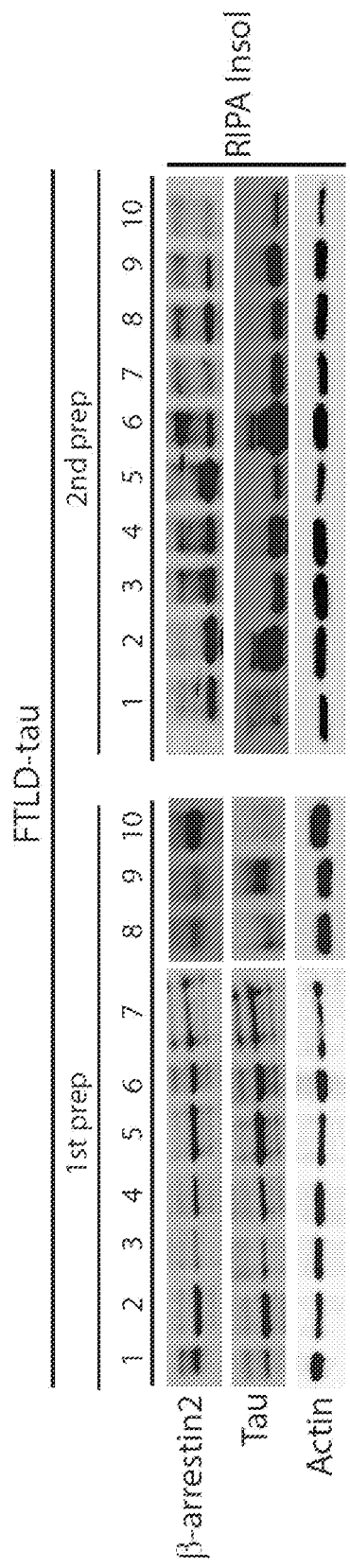
FIG. 8 shows β-arrestin2 levels correlate with tau levels in FTLD-tau brains. RIPA insoluble immunoblots of indicated proteins from the frontal cortex of 10 FTLD-tau patients.
Figure 9B:
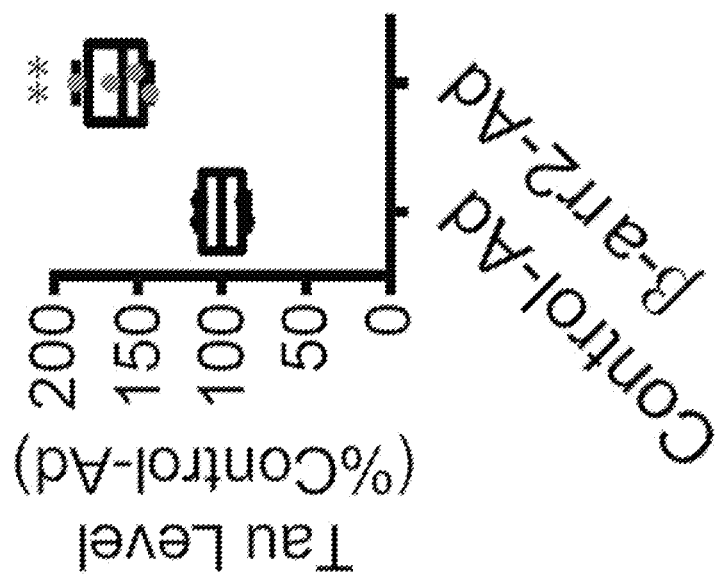
FIGS. 9A to 9F show β-arrestin2 increases tau level without altering mRNA.
Figure 9A:
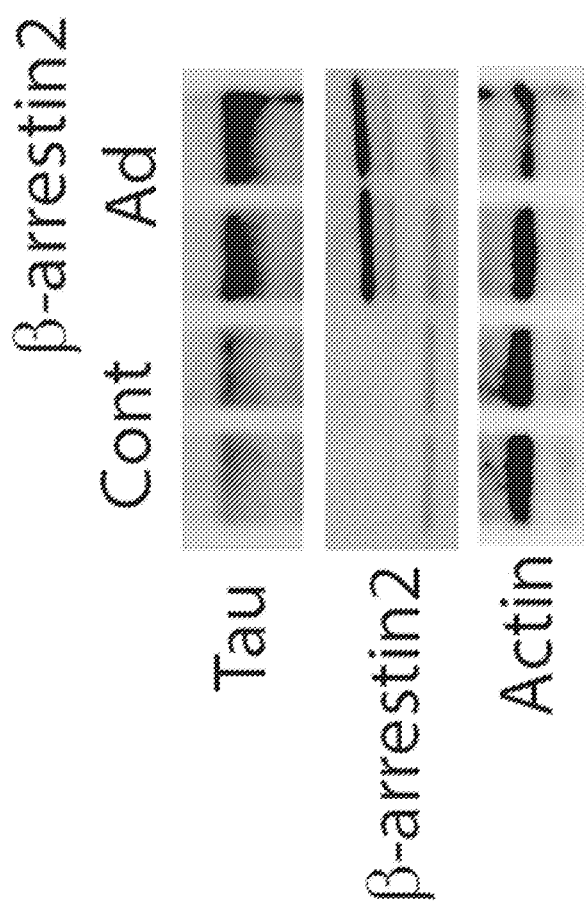
Figure 9D:
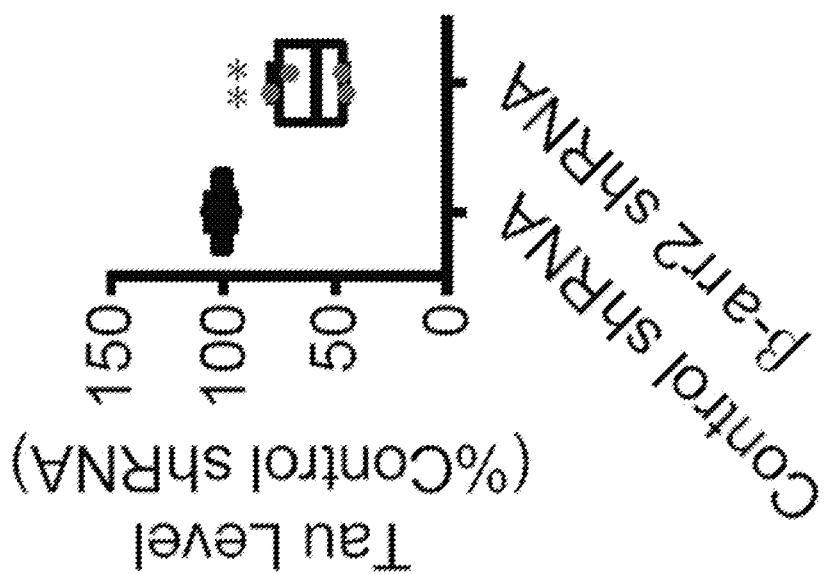
Figure 9C:
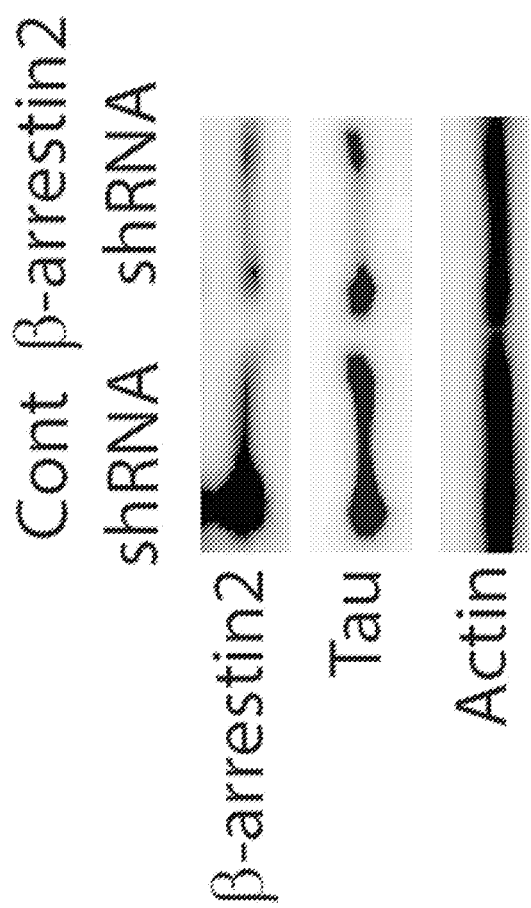
Figure 9F:
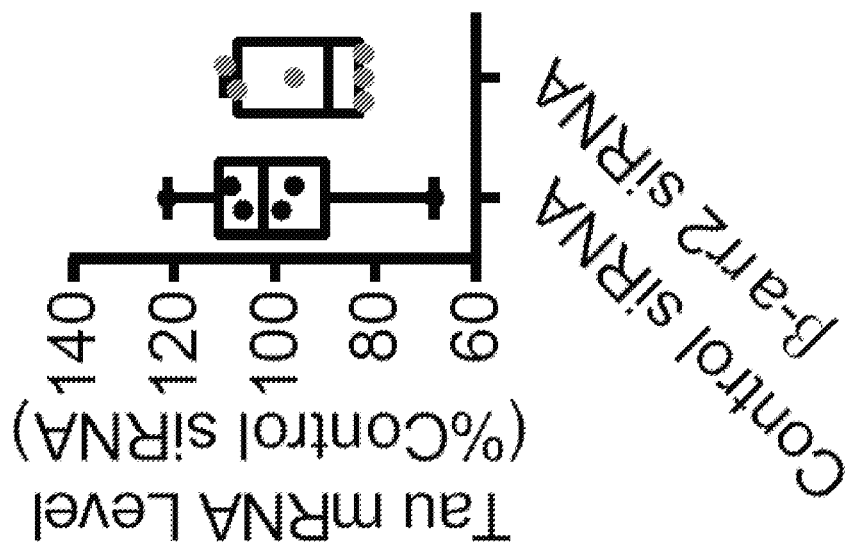
Figure 9E:
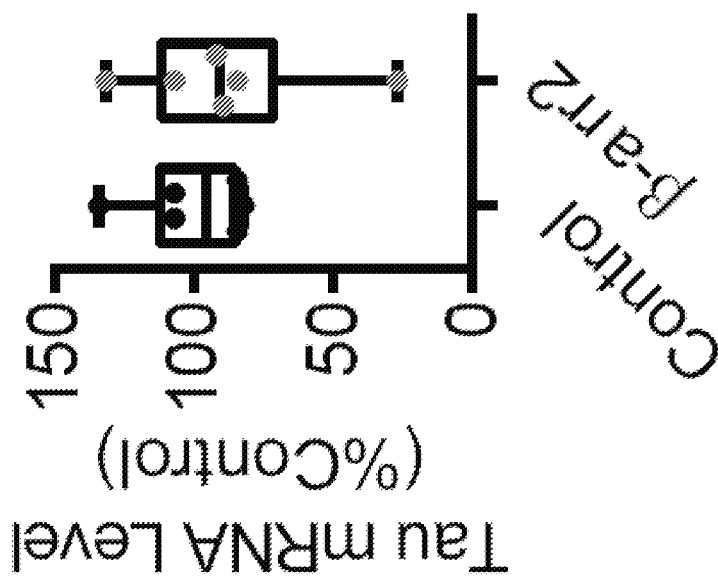

Increased β-Arrestin2 Levels in Brains of FTLD-Tau Patients and Tau P301S Transgenic Mice The expression of β-arrestin2 from the frontal cortex of aged-matched control subjects (N=12) and patients with FTLD and tauopathy (FTLD-tau, N=10) was compared. Western blotting for RIPA soluble β-arrestin2 demonstrated a ~1.8-fold increase in β-arrestin2 protein in the frontal cortex of FTLD-tau patients compared to healthy controls (FIG. 1A-1B). Likewise, qRT-PCR showed a similar increase in β-arrestin2 mRNA in FTLD-tau brain samples compared to the non FTLD-tau controls (FIG. 1C). It was also confirmed that RIPA insoluble β-arrestin2 protein levels positively correlate with tau levels in FTLD-tau brains (FIGS. 1D and 8). Next, the expression of β-arrestin2 in the tau P301S transgenic mouse was assessed. This mouse overexpresses the disease-associated P301S tau in neurons and displays FTLD-like pathophysiology and behavior without Aβ accumulation (Yoshiyama Y, et al. (2007) Neuron 53(3):337-351). β-arrestin2 protein and mRNA were significantly elevated in tau P301S transgenic mouse brains compared to non-transgenic littermates (FIG. 1E-1G). To confirm these results in a different way, cultured DIV 21 primary hippocampal neurons derived from tau P301S and wild type littermates were stained for β-arrestin2 (FIG. 1H). Quantification of β-arrestin2 confirmed in the cell type of interest what was observed in the homogeneous brain tissue (FIG. 1I).

β-Arrestin2 Increases Tau Stability

Figures 2A, 2B, 2C, 2D:
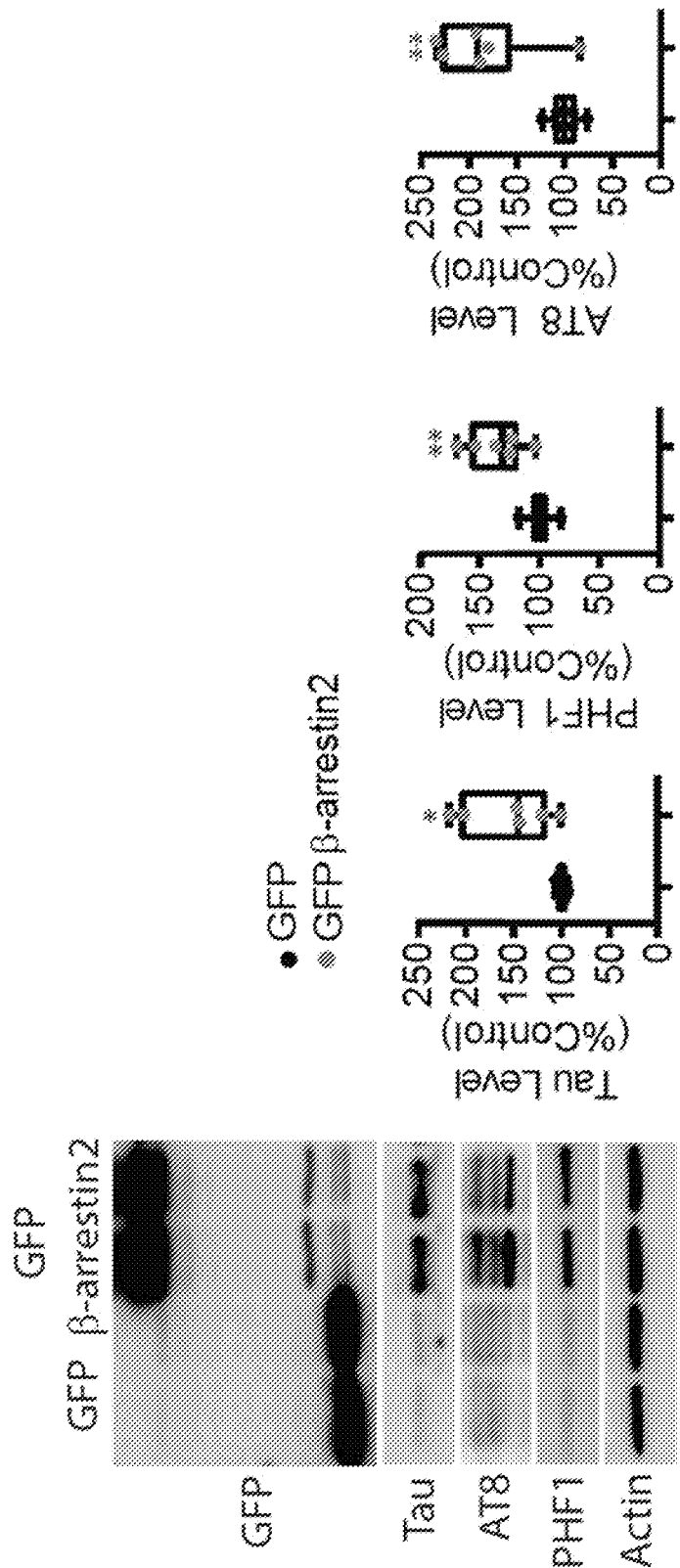
FIGS. 2A to 2M show overexpression and knock-down of β-arrestin2 modulates tau levels.
Figure 2E:
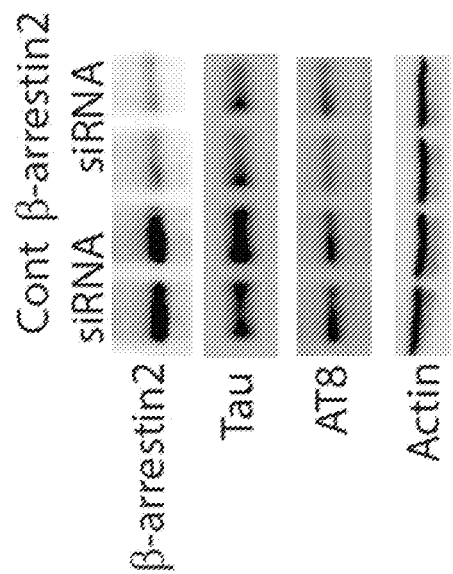
Figure 2F:
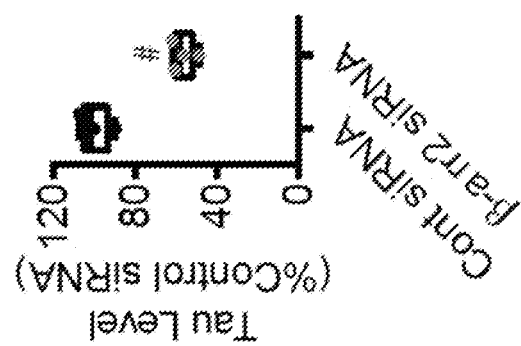
Figure 2G:
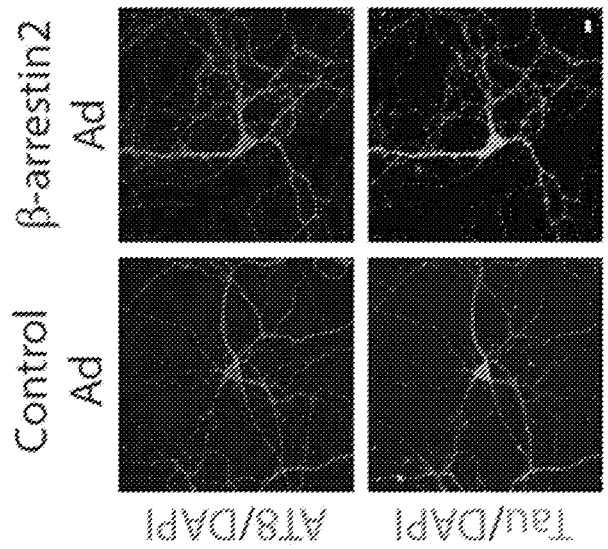
Figure 2J:
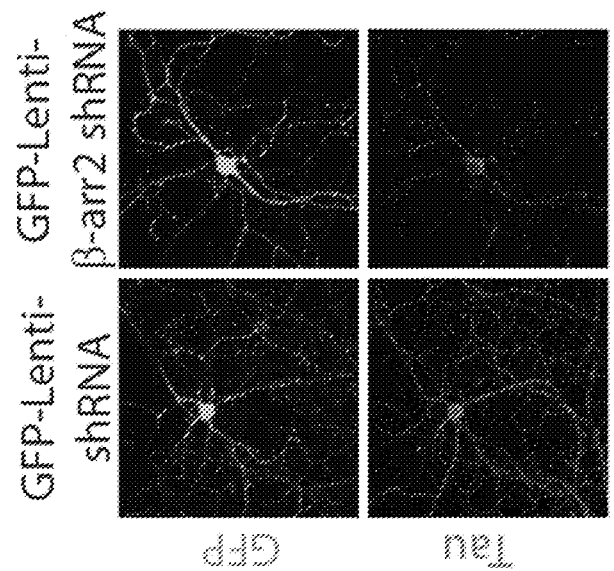
Figure 2I:
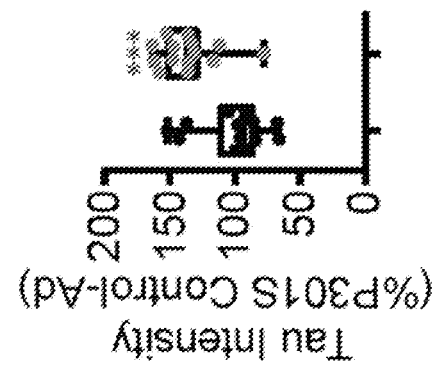
Figure 2H:
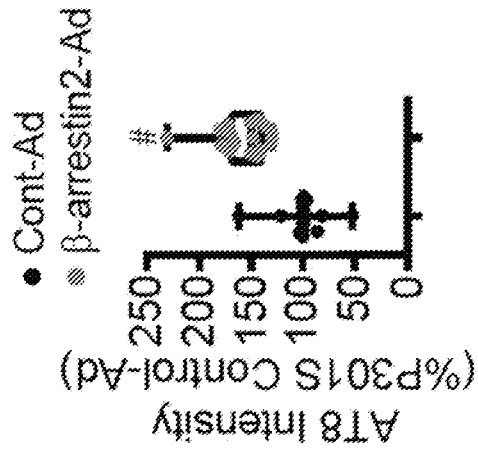
Figures 2K, 2L, 2M:
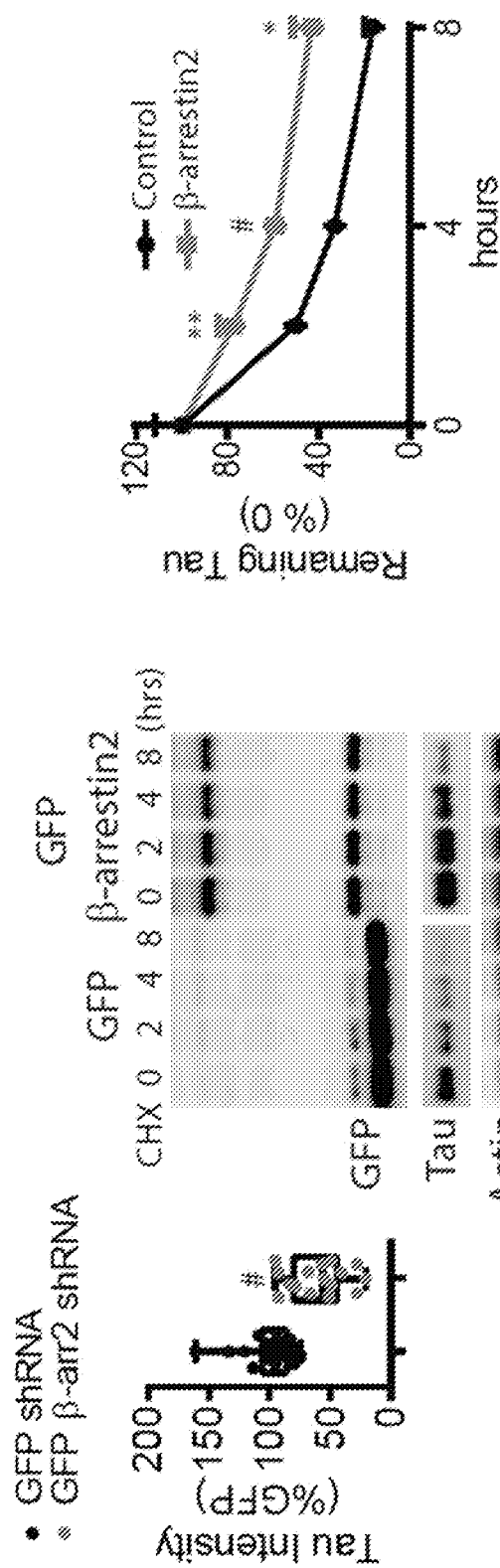

Next determined was whether the observed increase in β-arrestin2 in these tauopathy models can act to regulate tau in a negative (compensatory) or positive (disease enhancing) manner. In Hela cells stably expressing tau (V5-tagged 4R0N tau, termed Hela-V5-tau cells), transfected β-arrestin2 significantly increased total tau and phosphorylated tau (FIGS. 2A-2D), and β-arrestin2 siRNA transfection significantly reduced total tau and phospho-tau (FIGS. 2E,2F). Similarly, infection of tau P301S cortical primary neurons with β-arrestin2 packaged adenovirus also increased total tau and phospho-tau intensities compared to the control adenovirus condition as assessed by immunocytochemical imaging (FIGS. 2G-2I) and immunoblotting (FIGS. 8A,8B). Conversely, lentivirus-mediated shRNA knockdown of β-arrestin2 reduced total tau as assessed by imaging (FIGS. 2J,2K) and immunoblotting (FIGS. 8C,8D) No significant differences in tau mRNA levels were seen by β-arrestin2 overexpression or knockdown (FIGS. 8E,8F). The aforementioned studies were conducted in the absence of any GPCR agonists, which focused attention on non-receptor mechanisms by which β-arrestin2 interacts with tau or other partners to evoke the phenotype. Tau turnover was then examined as a potential mechanism by which increased β-arrestin2 increases the effective levels of tau at steady state. Treatment of Hela-V5-tau cells with cycloheximide to block protein translation showed that transfected β-arrestin2 significantly delays the turnover of tau (FIGS. 2L,2M), consistent with β-arrestin2 stabilizing tau via scaffolding protein: protein interactions.

Figure 3B:
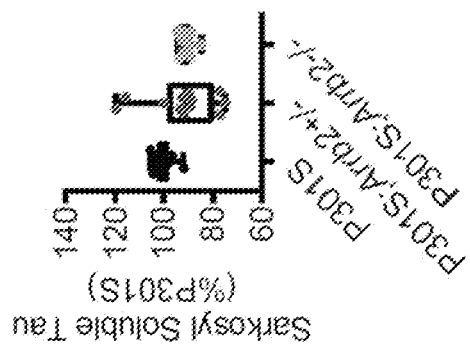
Figure 3C:
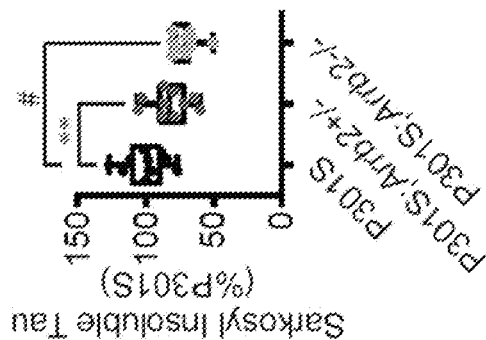
Figure 3A:
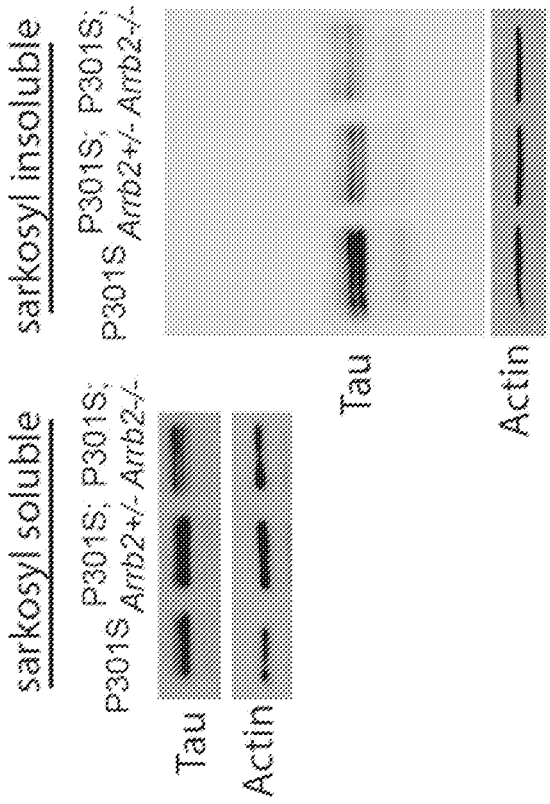
Figure 3D:
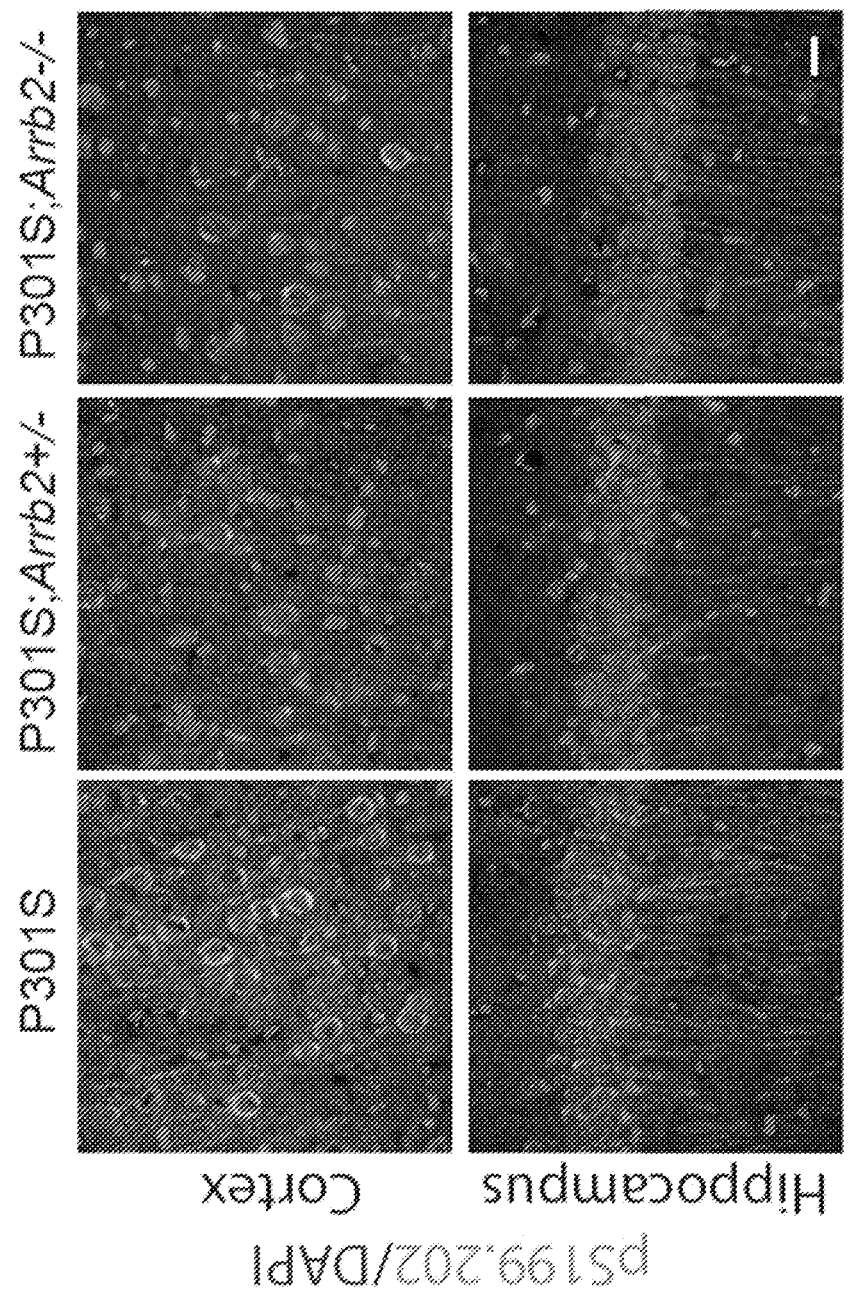
Figure 3E:
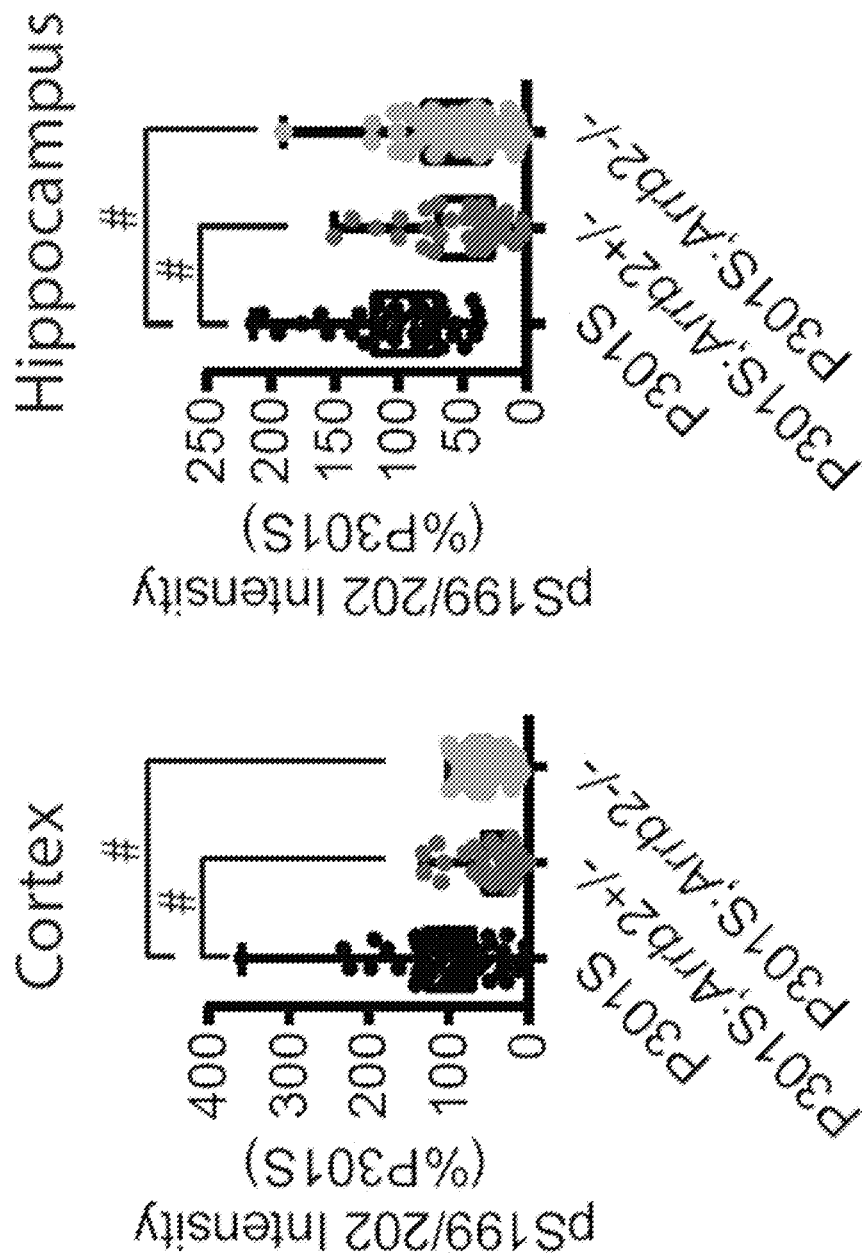
Figure 3G:
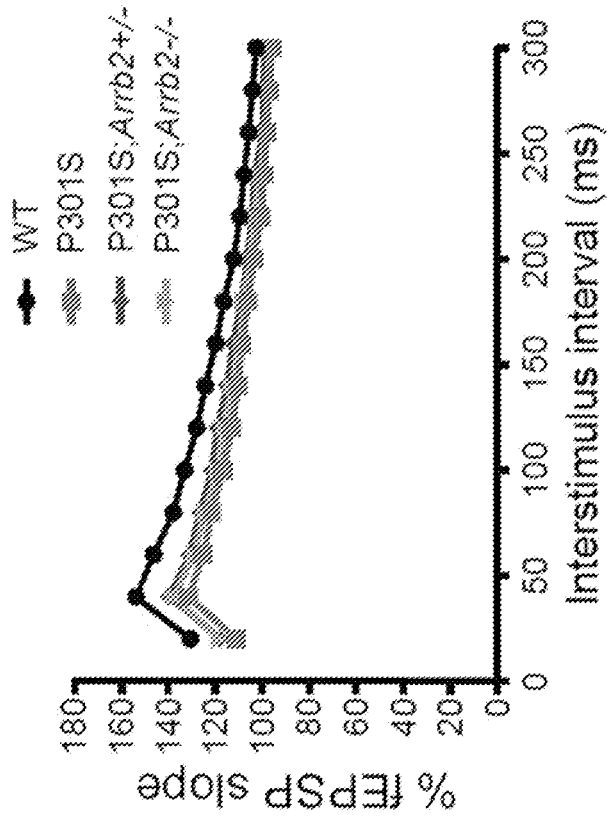
Figure 3F:
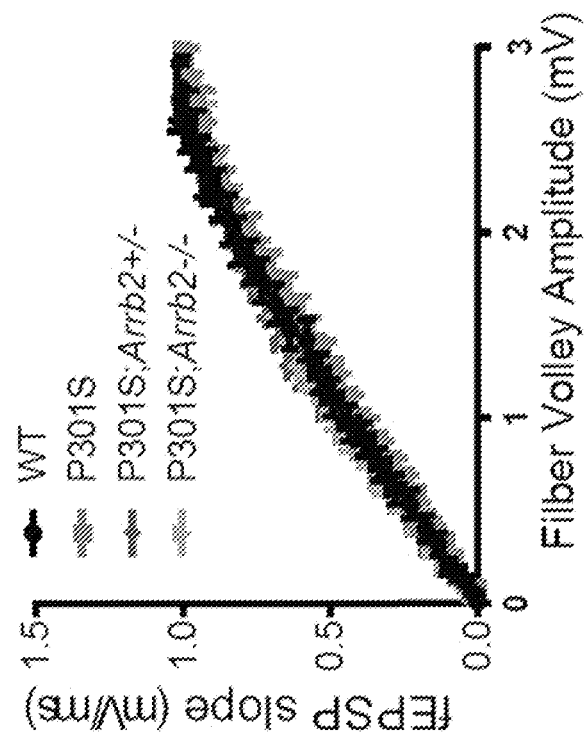
Figures 10A, 10B, 10C:
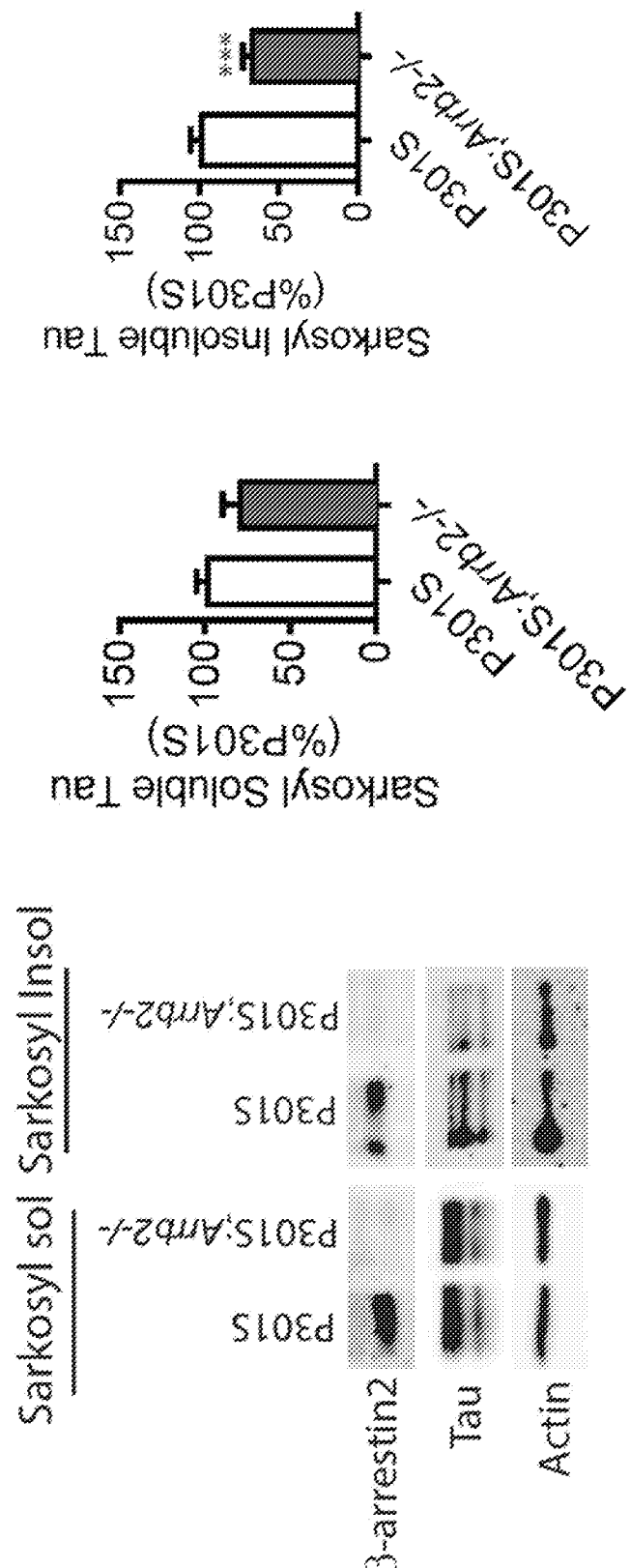
FIGS. 10A to 10F show genetic reduction of β-arrestin2 decreases sarkosyl insoluble tau and mitigates synaptic dysfunction in tau P301S primary neurons.

Genetic Reduction of β-Arrestin2 Mitigates Tauopathy and Synaptic Dysfunction in Tau P301S Mice The above data suggested that increased tau increases β-arrestin2, which in turn acts to further potentiate tau-mediated events by stabilizing the protein, thus indicative of a vicious positive pathogenic feedback cycle. This suggested a therapeutic attack point, should mice display the expected pathologic phenotypes when β-arrestin2 is genetically reduced. Thus, to assesses the physiological relevance of endogenous β-arrestin2 in tau regulation in vivo, the tau P301S transgenic mice was crossed to β-arrestin2$^{-/-}$ (Arrb2$^{-/-}$) mice. 7-month-old tau P301S, tau P301S/Arrb2$^{+/-}$, and tau P301S/Arrb2$^{-/-}$ littermate mouse brains were first fractionated for sarkosyl soluble versus insoluble tau. While there were no significant changes in sarkosyl-soluble tau, sarkosyl-insoluble tau was significantly decreased in tau P301S/Arrb2$^{+/-}$ and tau P301S/Arrb2$^{-/-}$ mice compared to control tau P301S transgenic mice (FIG. 3A-3C). Immunohistochemistry for phospho-tau (pS199/pS202) was performed with cortex (FIGS. 3D,3E) and hippocampus (FIGS. 3D,3F) of 7-month-old WT, tau P301S, tau P301S/Arrb2$^{+/-}$, and tau P301S/Arrb2$^{-/-}$ littermates. Brain sections from tau P301S/Arrb2$^{+/-}$ and tau P301S/Arrb2$^{-/-}$ mice exhibited approximately 50% less phospho-tau immunoreactivity compared to those from tau P301S mice (FIG. 3D-3F). It was confirmed that knockout of β-arrestin2 decreases sarkosyl-insoluble tau in cultured primary neurons derived from brains of the tau P301S/Arrb2$^{-/-}$ mice compared to those from tau P301S mice (FIG. 10A-10C).

Figure 3H:
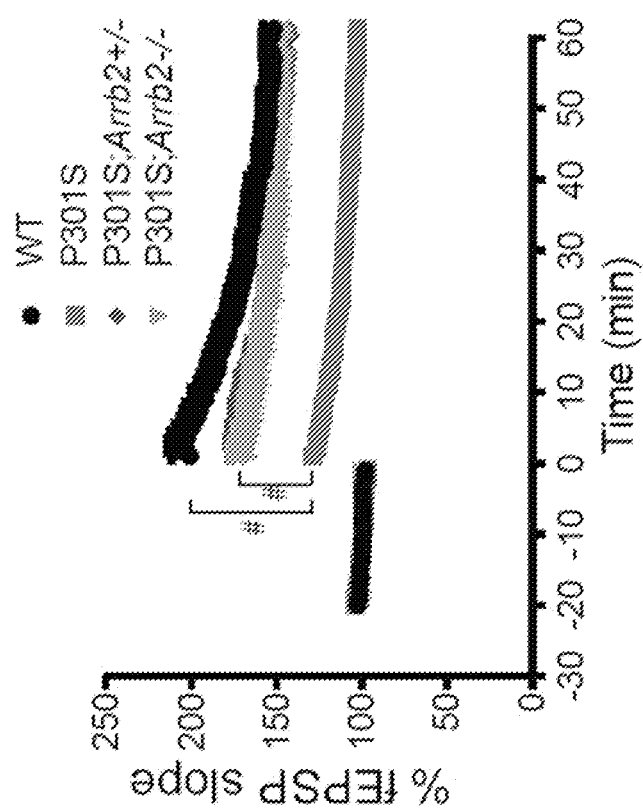
Figure 10D:
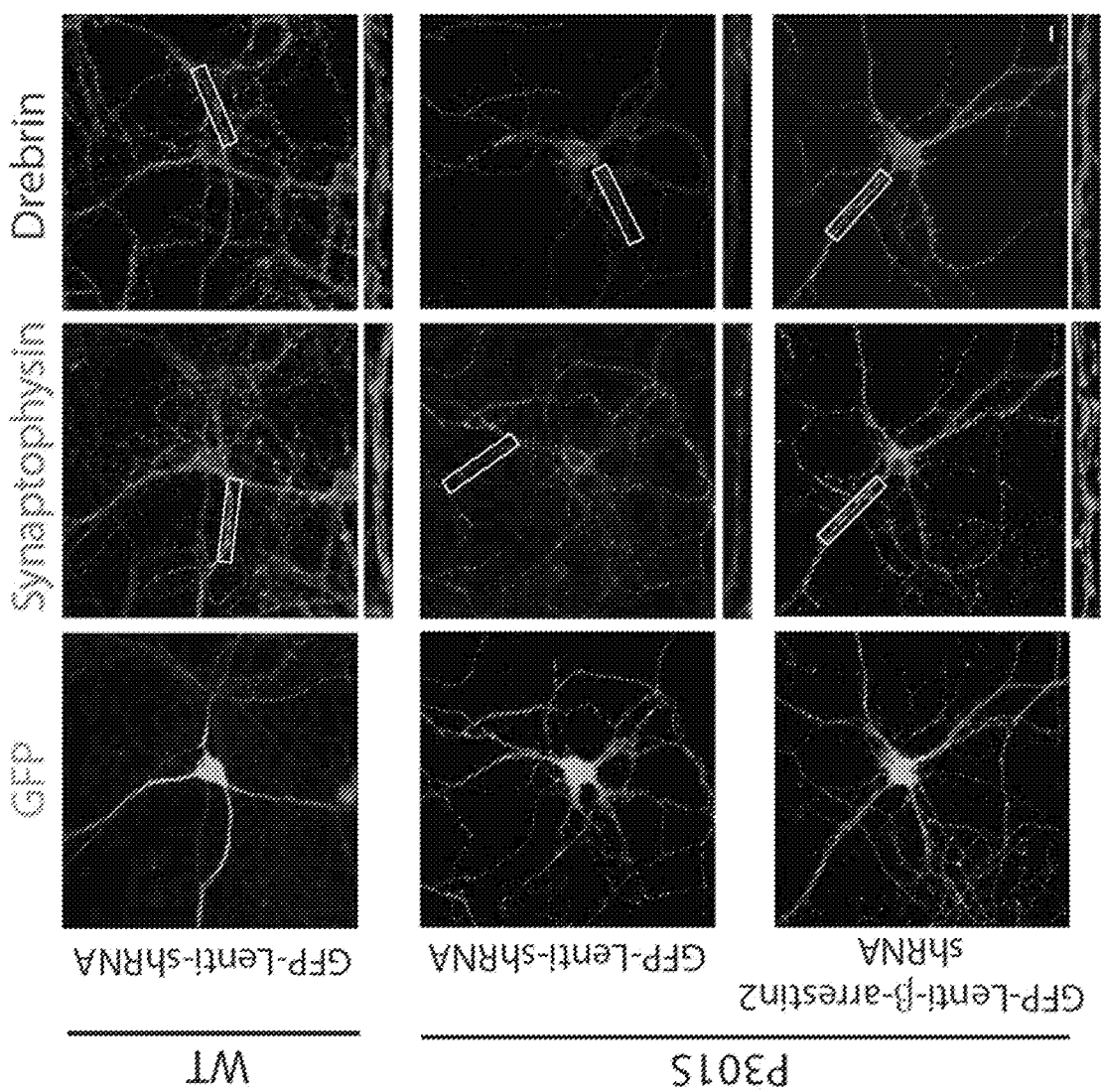
Figures 10E, 10F:
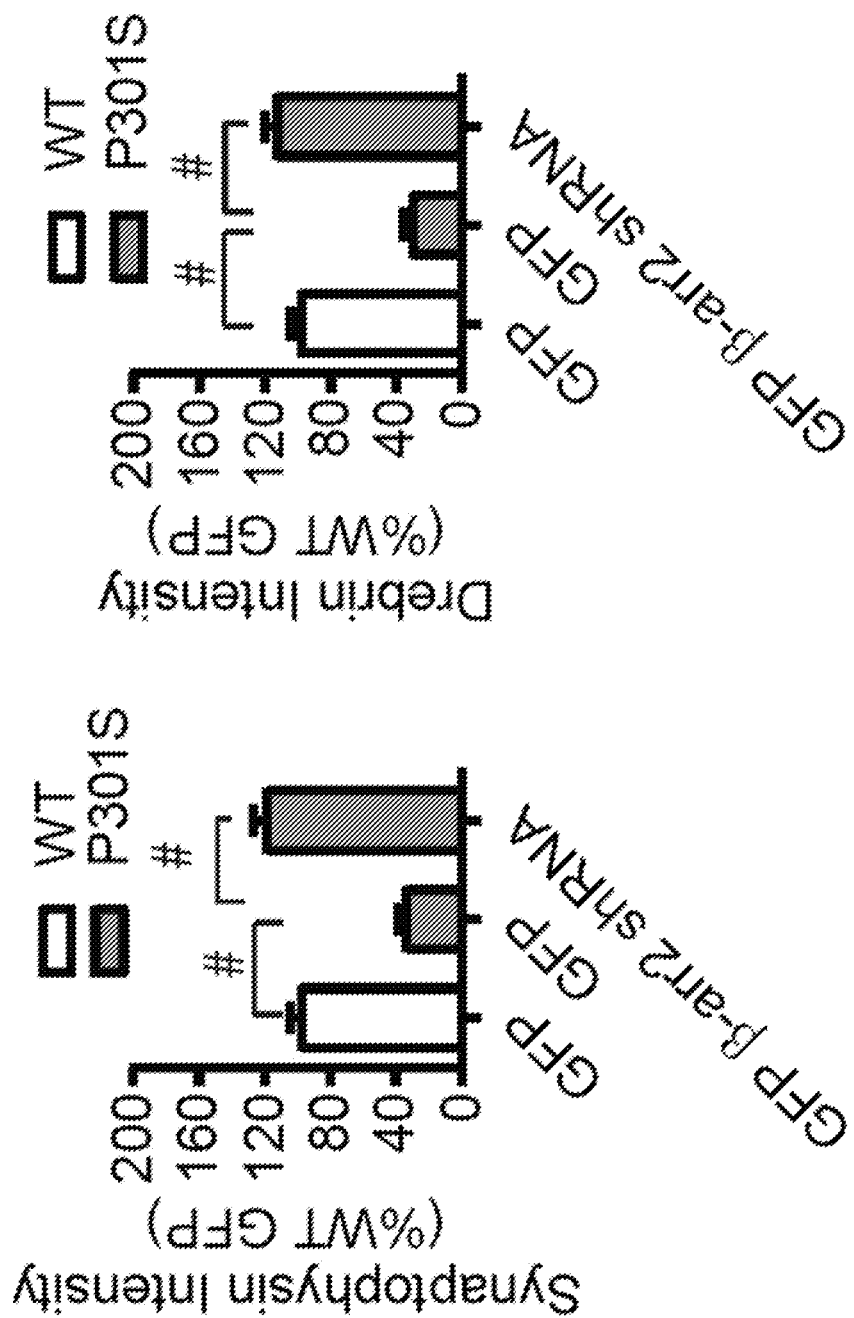

To determine functional changes in synaptic plasticity, electrophysiological recordings of the CA3-CA1 Schaffer collateral pathway of acute brain slices was performed. Input-output (IO) analysis indicated no significant differences among WT, tau P301S, tau P301S/Arrb2$^{+/-}$, and tau P301S/Arrb2$^{-/-}$ littermate slices (FIG. 3G), as expected from previous electrophysiological studies of tau P301S mice (Yoshiyama Y, et al. (2007) Neuron 53(3):337-351; Woo J A, et al. (2019) Commun Biol 2:112; Woo J A, et al. (2017) Hum Mol Genet 26(20):3973-3988). In paired pulse facilitation (PPF) experiments, slight but significant reductions in fEPSP slope in tau P301S slices was detected in all interstimulus intervals (except 260-280 ms) compared to WT slices (FIG. 3H), with tau P301S/Arrb2$^{+/-}$ as well as tau P301S/Arrb2$^{-/-}$ slices being not appreciably different from tau P301S slices (FIG. 3H). In long-term potentiation (LTP) recordings using theta burst stimulation, tau P301S slices were markedly impaired in the induction and maintenance of LTP compared to WT slices. However, LTP in tau P301S/Arrb2$^{+/-}$ and tau P301S/Arrb2$^{-/-}$ slices was significantly restored to levels very similar to those of WT slices (FIG. 3I). These results suggest that the cycle can be broken at the β-arrestin2 interface. As further evidence for a salutary effect of lowering β-arrestin2 and consistent with the LTP data, silencing of β-arrestin2 by shRNA lentivirus significantly rescued the depletion of synaptophysin (presynaptic; FIGS. 10D,10E) and drebrin (postsynaptic; FIGS. 10D,10F) compared to tau P301S primary neurons transduced with control shRNA lentivirus.

β-Arrestin2 Oligomerization is Required for Tau Stability

It has been shown that β-arrestin2 can be found as an oligomer in multiple cell types (Milano S K, et al. (2006) J Biol Chem 281(14):9812-9823; Storez H, et al. (2005) J Biol Chem 280(48):40210-40215). Inositol hexakisphosphate (IP6) enhances this self-association of β-arrestin2 by bridging neighboring molecules in a head-to tail configuration. Positively charged arginine and lysine residues within the N-terminus and C-terminus of β-arrestin2 were found to be critical for both IP6 binding and oligomerization. Given the physical overlap of IP6 and GPCR binding sites, β-arrestin2 binding to an activated GPCR and to IP6 is mutually exclusive, indicating that in the oligomeric form β-arrestin2 may serve other purposes apart from GPCR binding (Dinculescu A, et al. (2002) J Biol Chem 277(14):11703-11708; Breitman M, et al. (2012) J Biol Chem 287(23):19653-19664; Gurevich W & Benovic J L (1993) J Biol Chem 268(16):11628-11638; Gurevich V V, et al. (1995) J Biol Chem 270(2):720-731; Hanson S M, et al. (2007) Proc Natl Acad Sci USA 104(9):3125-3128; Kim M, et al. (2012) Proc Natl Acad Sci USA 109(45):18407-18412; Palczewski K, et al. (1994) Protein Sci 3(2):314-324; Pulvermuller A, et al. (2000) J Biol Chem 275(48):37679-37685; Vishnivetskiy S A, et al. (2011) J Biol Chem 286(27):24288-24299; Zhuang T, et al. (2013) Proc Natl Acad Sci USA 110(3):942-947; Boularan C, et al. (2007) Proc Natl Acad Sci USA 104(46):18061-1806).

The hypothesis that β-arrestin2 self-oligomerization affects tau stability and tauopathy was tested using a β-arrestin2 N-terminal domain mutant (K158A, K161A, and R162A, referred to as β-arrestin2 ΔIP6N), and a C-terminal domain mutant (K232A, R234A, K252A, K326A, and K328A, referred to as β-arrestin2 ΔIP6C); these mutants are incapable of forming oligomers as determined by BRET and co-immunoprecipitation assays (Milano S K, et al. (2006) J Biol Chem 281(14):9812-9823; Storez H, et al. (2005) J Biol Chem 280(48):40210-40215), but nevertheless bind to activated GPCRs with WT affinity (Gaidarov I, et al. (1999) EMBO J 18(4):871-881).

Figures 4A, 4B, 4C:
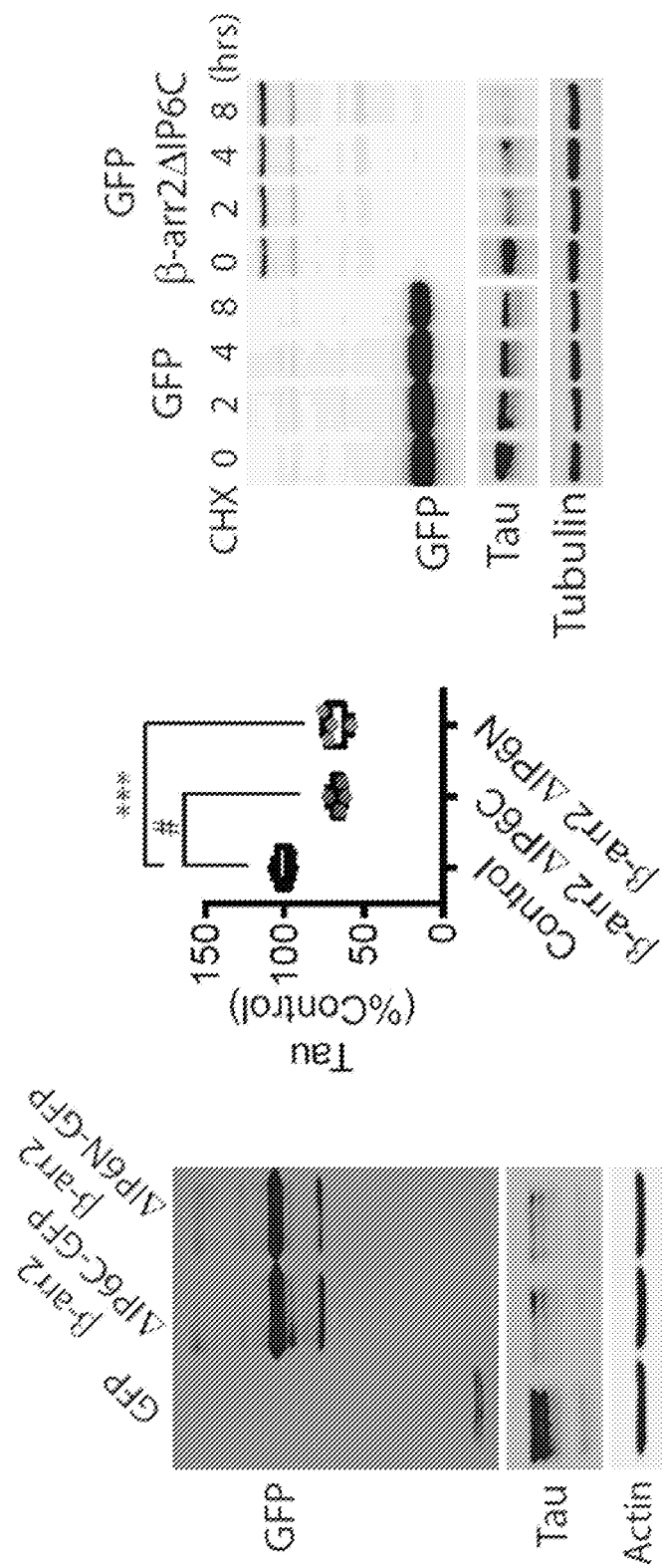
FIGS. 4A to 4E show β-arrestin2 oligomerization is required for suppressing tau turnover.
Figure 4E:
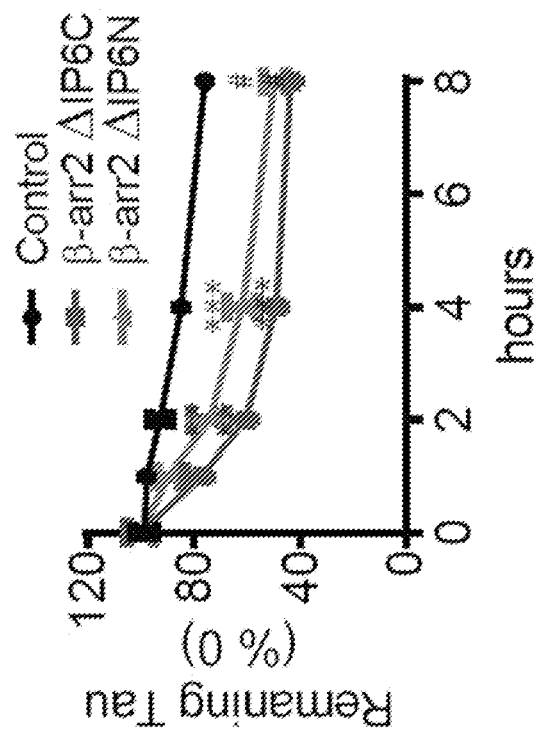
Figure 4D:
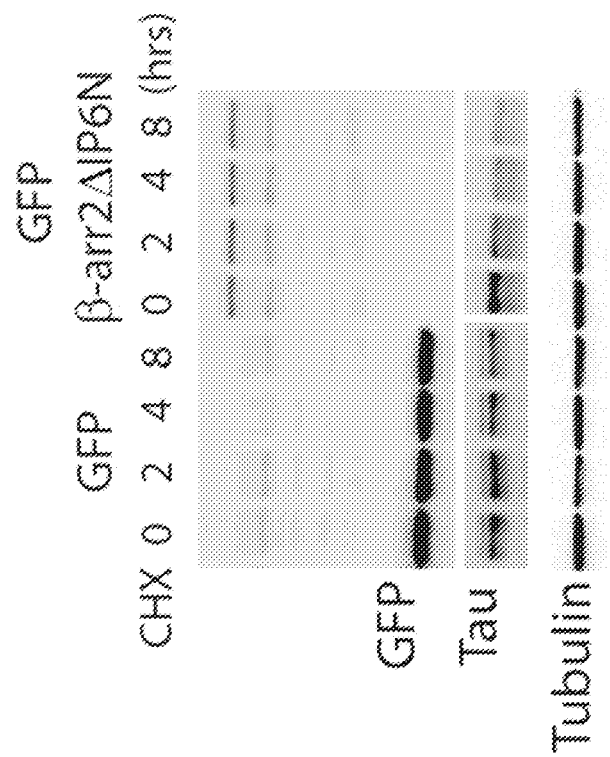
Figure 11A:
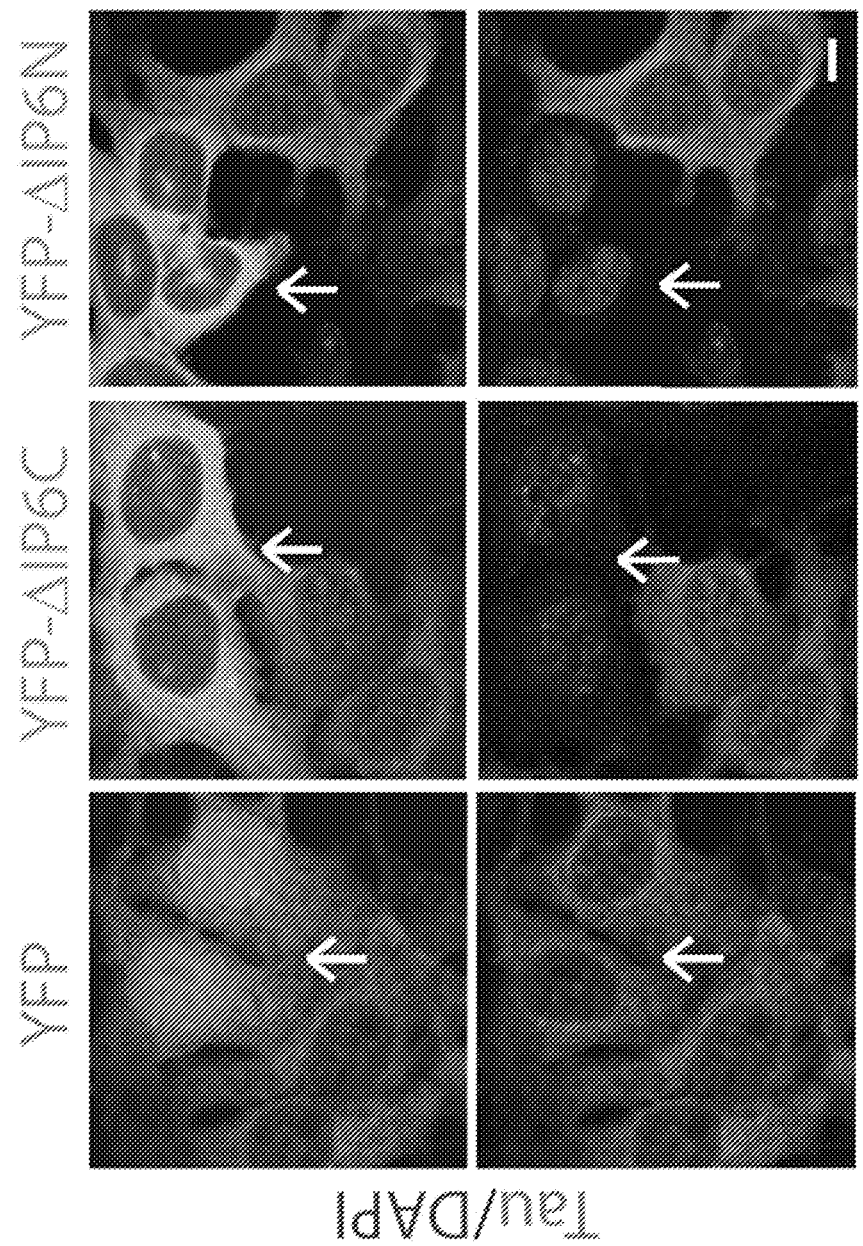
FIGS. 11A to 11E show β-arrestin2 oligomerization mutants reduce tau aggregates.
Figure 11B:
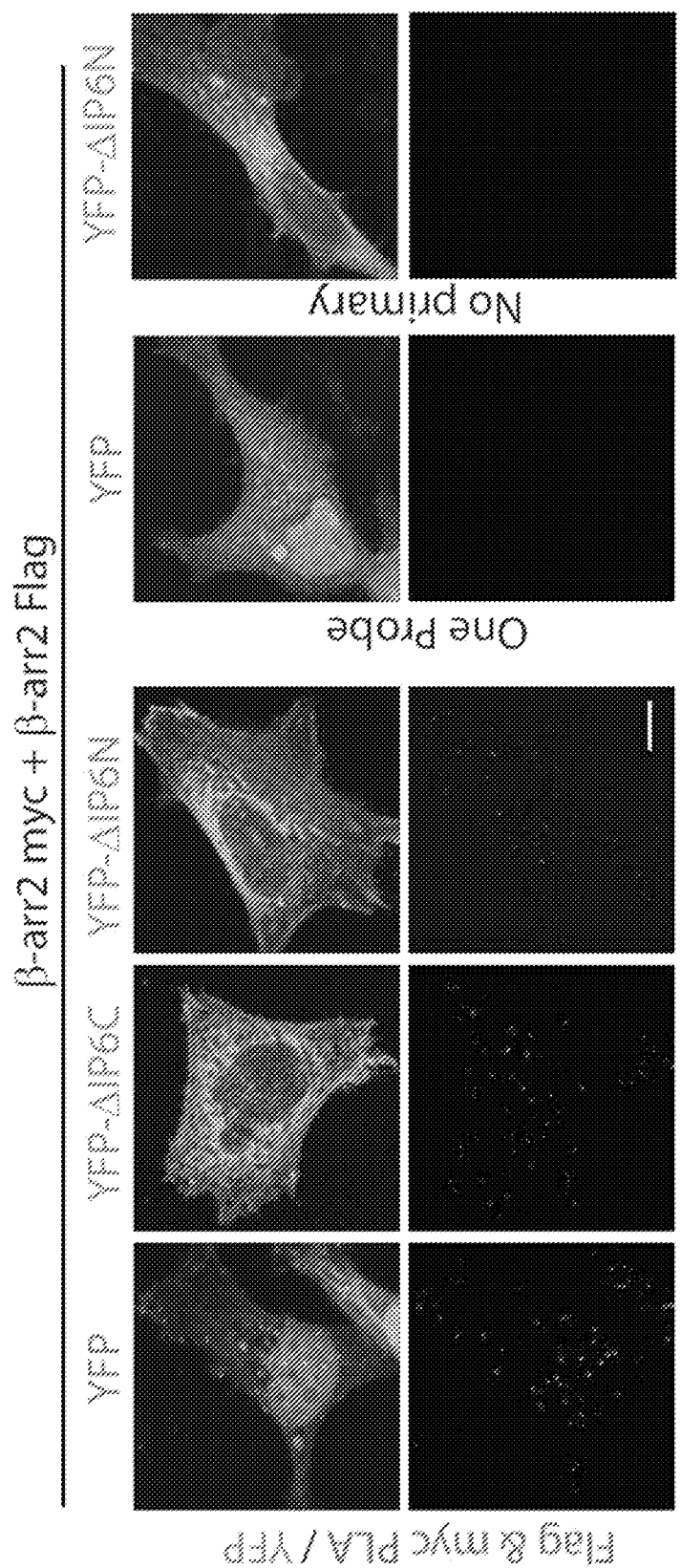
Figures 11C, 11E:
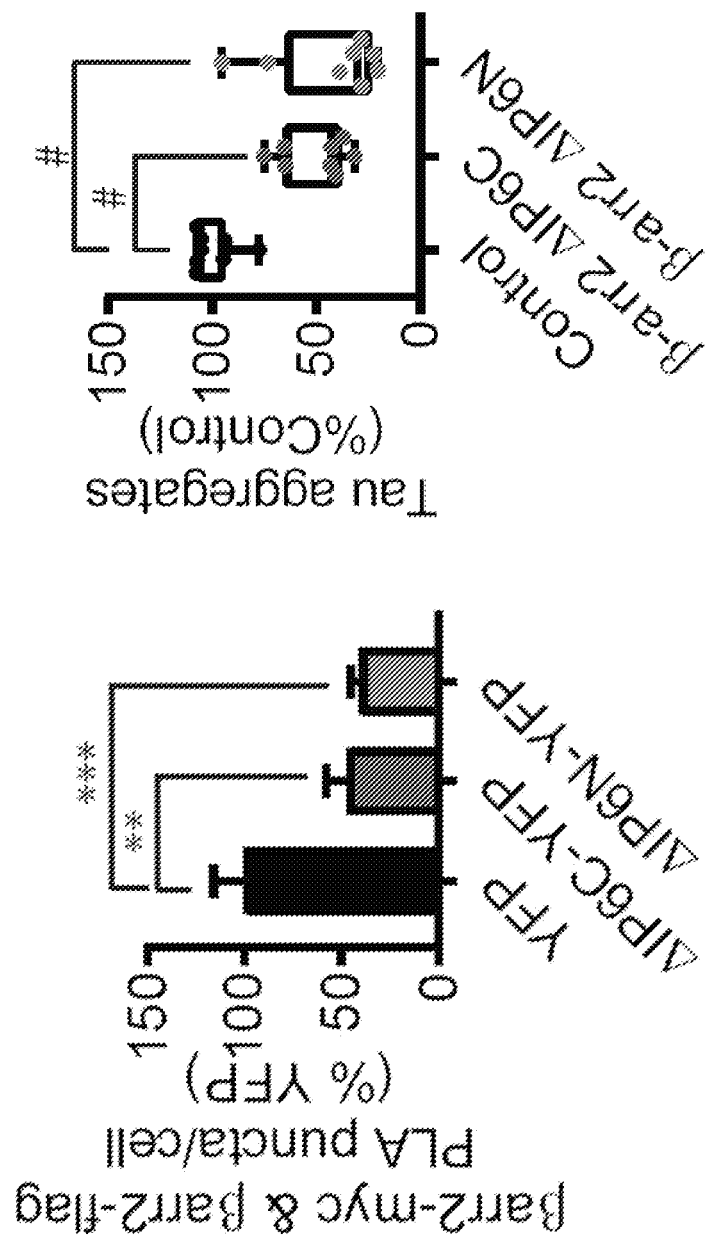
Figure 11D:
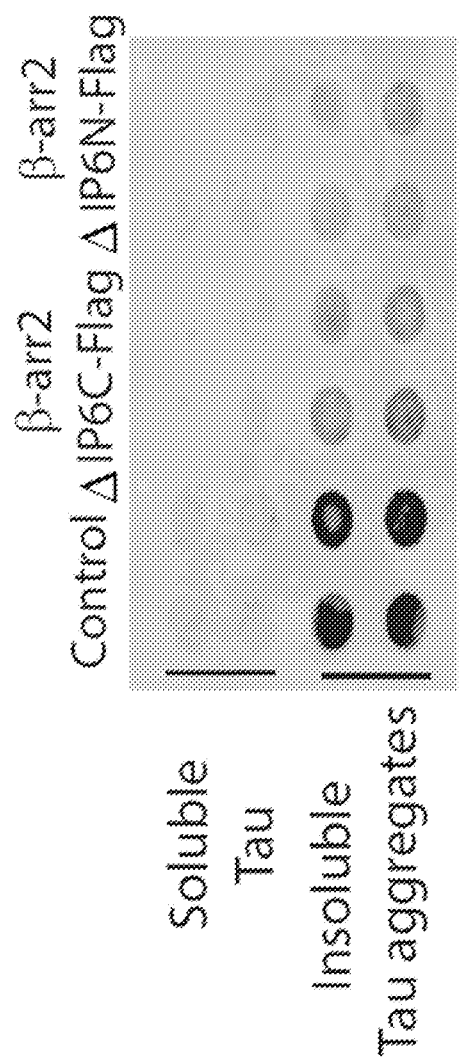

When DIV 18 tau P301S cortical primary neurons were transduced with either β-arrestin2 ΔIP6C or ΔIP6N lentivirus, an approximately 50% reduction in tau compared to control was evident (FIGS. 4A,4B), which represents a key finding relevant to both mechanism of action and potential therapeutic strategies. Consistent with these findings, YFP-β-arrestin2 ΔIP6C and YFP-β-arrestin2 ΔIP6N expression in Hela-V5-tau cells also caused significant reductions in tau as assessed by immunocytochemistry (FIG. 11A). To show that these mutants act as dominant negatives for oligomerization, proximity ligation assays (PLA) were performed examining the interaction between β-arrestin2-flag and β-arrestin2-myc in presence of control vector, or β-arrestin2 ΔIP6C or β-arrestin2 ΔIP6N. Indeed, β-arrestin2 ΔIP6C and β-arrestin2 ΔIP6N significantly reduced β-arrestin2-flag and β-arrestin2-myc interaction (FIGS. 11B,11C). These results confirmed the oligomerization of WT β-arrestin2 in the control setting, and, showed displacement of WT β-arrestin2 from the oligomer by expression of either the ΔIP6C or the ΔIP6N mutants (FIGS. 11B,11C). Also investigated was whether β-arrestin2 oligomerization is required for slowing tau turnover by disrupting oligomerization using these mutants in several models. Studies with the β-arrestin2 ΔIP6C and β-arrestin2 ΔIP6N mutants showed enhancement of tau turnover in the cycloheximide chase experiments (FIG. 4C-4E). To determine whether β-arrestin2 oligomerization status alters tau aggregation itself, filter-trap assays were performed from Hela-V5-tau cells transfected with β-arrestin2 variants, in which tau aggregates from detergent-soluble and-insoluble lysates were captured by cellulose acetate membranes and assessed by immunoblotting. While detergent-soluble lysates showed little to no aggregates, detergent-insoluble lysates derived from β-arrestin2 ΔIP6C or ΔIP6N transfected cells showed significantly reduced tau aggregates compared to control vector transfected cells (FIG. 11D,11E).

β-Arrestin2 Oligomers Interact with p62 and Inhibit p62 Self-Association

Figures 5A, 5B:
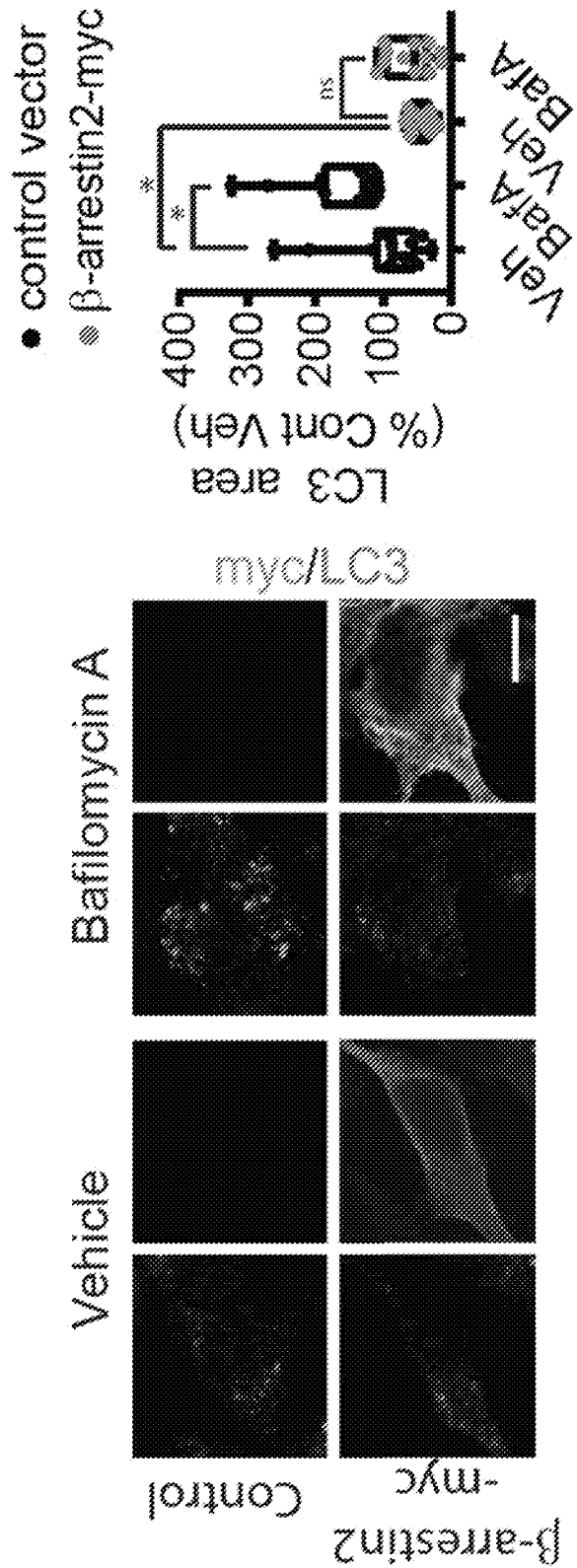
FIGS. 5A to 5N show β-arrestin2 oligomerization inhibits p62-mediated tau degradation.
FIG. 5B shows quantification of LC3 puncta (N=4 independent experiments, *P<0.05).

Hyperphosphorylated (and thus more "ordered") tau is thought to undergo clearance by an autophagy-lysosome pathway (Dolan P J & Johnson G V (2010) J Biol Chem 285(29):21978-21987; Wong E S, et al. (2008) Hum Mol Genet 17(16):2570-2582; Kim S, et al. (2016) Sci Rep 6:24933; Kruger U, et al. (2012) Neurobiol Aging 33(10): 2291-2305; Wang Y, et al. (2010) Neurodegener Dis 7(1-3):103-107). To understand the mechanistic basis of β-arrestin2 in tau stabilization and accumulation, bafilomycin A, a lysosome inhibitor known to activate autophagy and promote the accumulation of LC3-positive autophagosomes, was used to test whether β-arrestin2 affects autophagy. Interestingly, overexpression of β-arrestin2 in Hela-V5-tau cells significantly inhibited bafilomycin A-induced increase in LC3-positive puncta (FIGS. 5A,5B), suggesting that β-arrestin2 inhibits autophagy at, or upstream of LC3.

P62/SQSTM1 is a key autophagy cargo receptor that regulates autophagosome formation by linking its cargo (i.e. misfolded tau or Aβ) to LC3-positive autophagosomes. Indeed, p62 is associated with neurofibrillary tangles (Caccamo A, et al. (2017) Mol Psychiatry 22(6):865-873; King A, et al. (2013) Acta Neuropathol 125(2):303-310; Kuusisto E, et al. (2002) Neuropathol Appl Neurobiol 28(3):228-237; Terni B, et al. (2007) Acta Neuropathol 113(4):403-416), and soluble cytoplasmic p62 levels are significantly reduced in AD brains (Caccamo A, et al. (2017) Mol Psychiatry 22(6):865-873; Zheng X, et al. (2012) Neural Regen Res 7(17):1304-1311). Increased p62 expression improves cognitive impairments in AD animal models by enhancing autophagy induction, and genetic loss of p62 leads to dramatic accumulation of tau and neurodegeneration (Caccamo A, et al. (2017) Mol Psychiatry 22(6):865-873; Zheng X, et al. (2012) Neural Regen Res 7(17):1304-1311; Ramesh Babu J, et al. (2008) J Neurochem 106(1):107-120). Moreover, a recent study showed that p62 expression is associated with clearance of insoluble tau (Xu Y, et al. (2019) Autophagy 15(4):583-598).

Figure 5D:
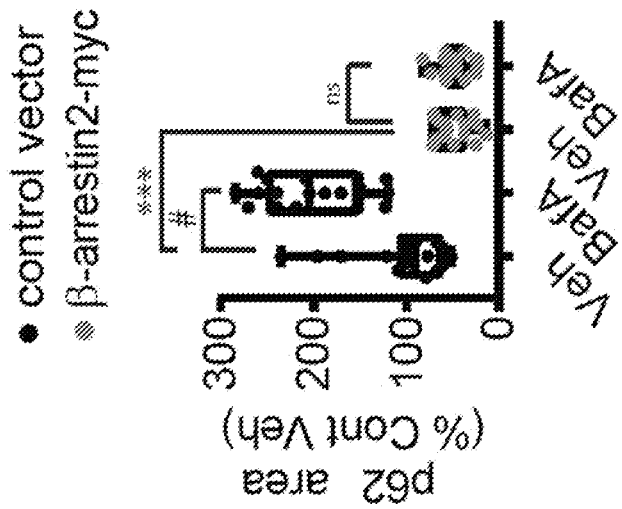
FIG. 5D shows quantification of GFP-p62 puncta (N=4 independent experiments, #P<0.0001, *P<0.0005).
Figure 5C:
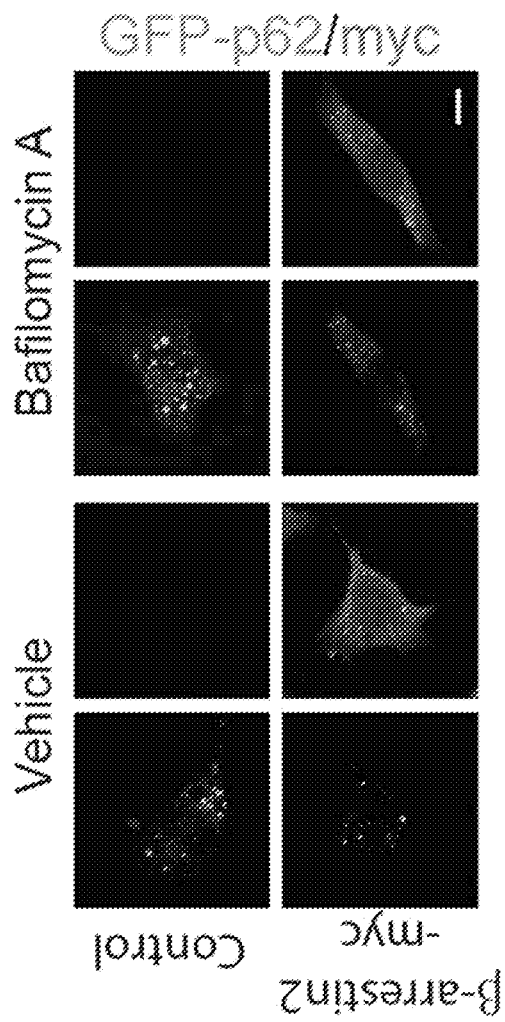
FIG. 5C contains representative images of GFP-p62 positive autophagosomes from Hela-V5-tau cells transiently transfected with control vector or β-arrestin2-myc with/without 100 nM of Bafilomycin A1 (bar=10 μm).
Figure 5E:
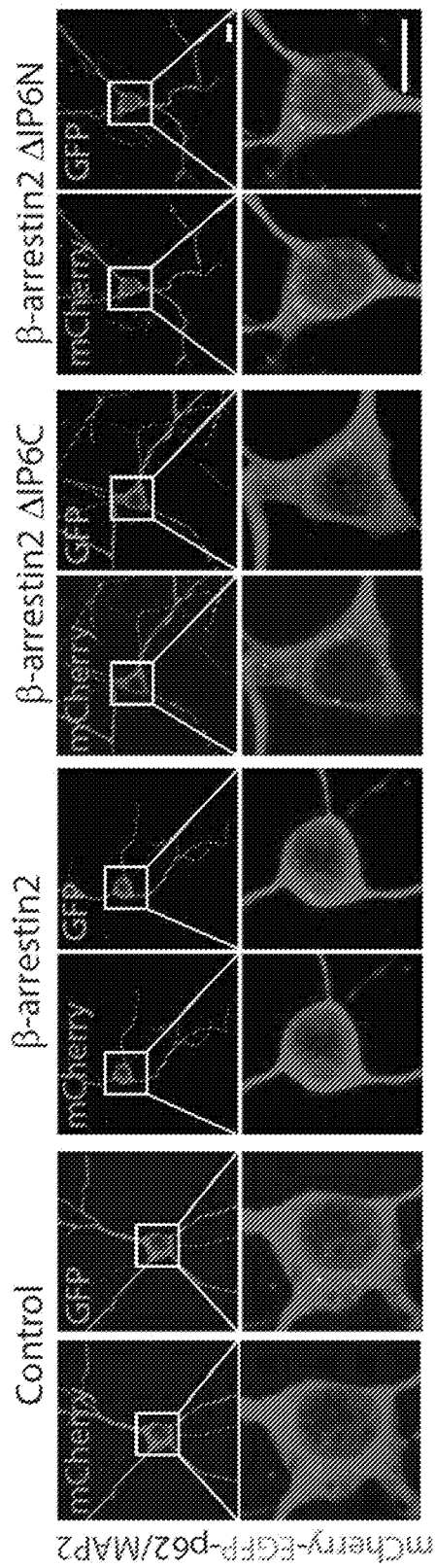
FIG. 5E contains representative images of DIV21 tau P301S hippocampal primary neurons transduced with mcherry-GFP-p62 AAV9 with control, β-arrestin2, β-arrestin2 ΔIP6C, or β-arrestin2 ΔIP6N lentivirus at DIV5.
Figures 5F, 5H:
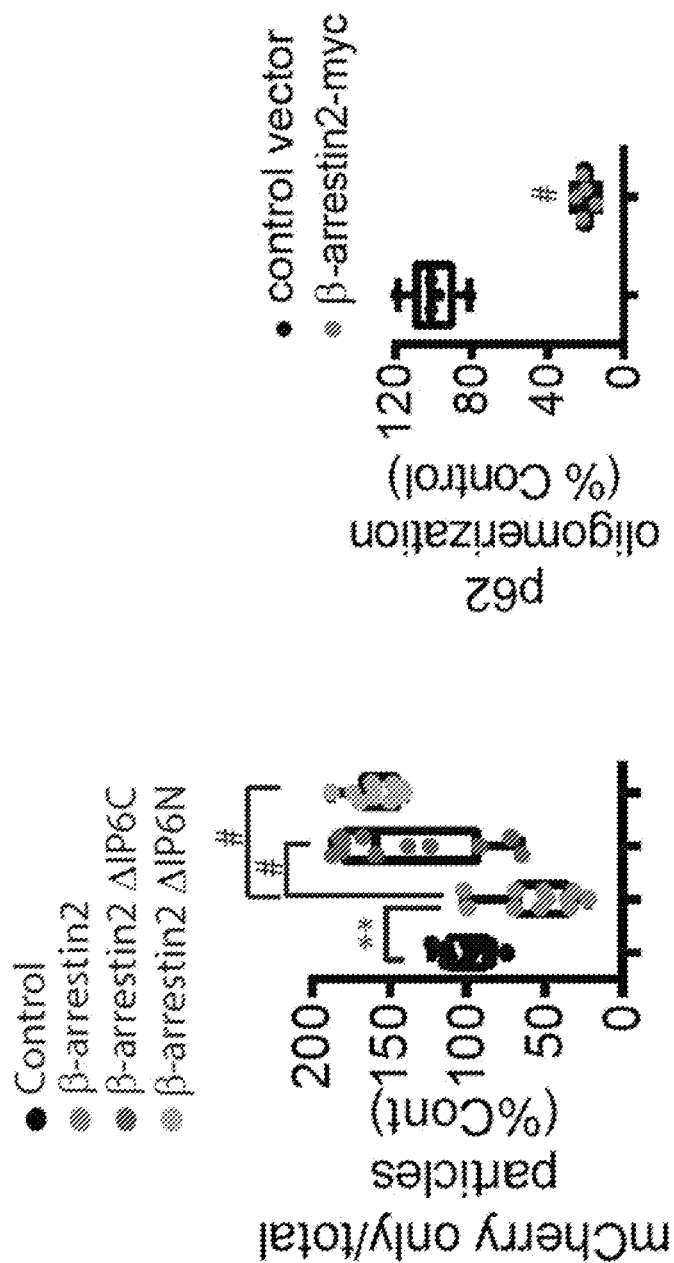
FIG. 5F shows quantification of mCherry only particles (N=3 independent experiments, P<0.005, #P<0.0001).
FIG. 5H shows quantification of GFP-p62 and HA-p62 interaction by co-IP (N=5 independent experiments, #P<0.0001).
Figure 12A:
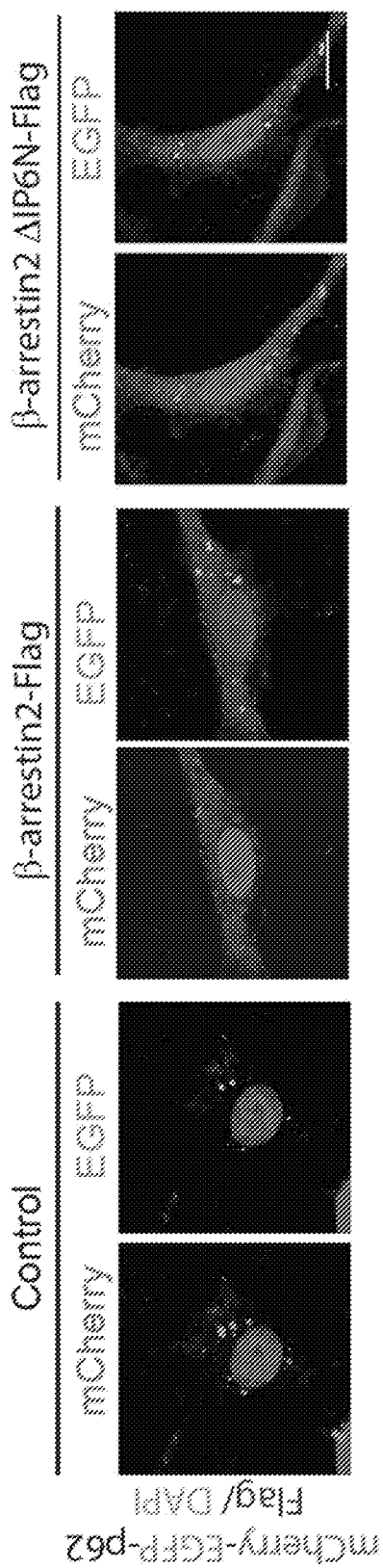
FIGS. 12A to 12E show β-arrestin2 interacts with p62, and β-arrestin2 oligomerization inhibits p62 self-interaction.
Figures 12B, 12C:
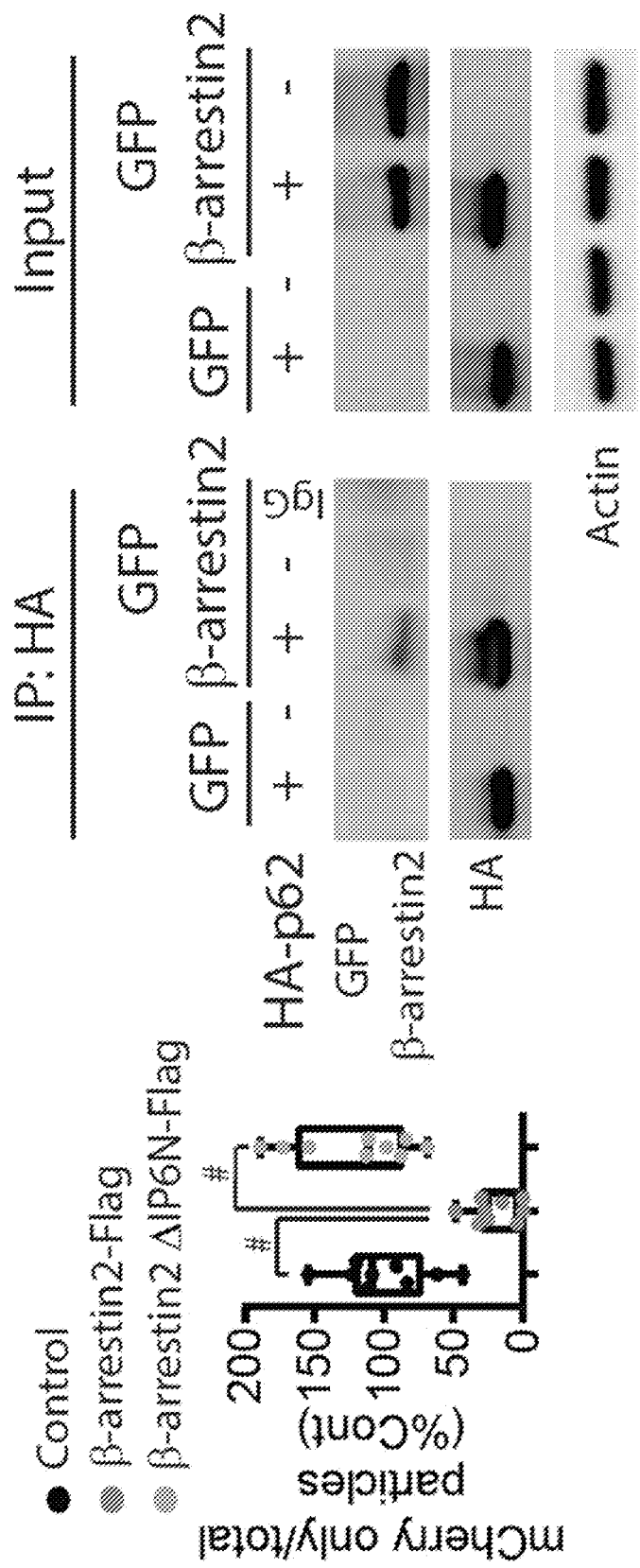

P62 forms particles by self-interaction via its N-terminal PB1 domain, which is essential for its activity and is seen as puncta of different sizes in cells (Wurzer B, et al. (2015) Elife 4:e08941; Itakura E & Mizushima N (2011) J Cell Biol 192(1):17-27). In Hela V5-tau cells transfected with GFP-p62, there was an expected increase in GFP-p62 puncta upon bafilomycin A treatment (FIGS. 5C,5D), However, overexpression of β-arrestin2 significantly reduced GFP-p62 puncta at both steady-state and after bafilomycin, such that bafilomycin A no longer increased GFP-p62 puncta (FIGS. 5C,5D). This suggested that β-arrestin2 inhibits the flux of p62 particles from their target substrates to lysosomes. To directly test this hypothesis, the mCherry-EGFP-p62 autophagy flux reporter was used. This reporter takes advantage of the sensitivity of GFP to low pH (which quenches the signal) and the insensitivity of mCherry to low pH. Therefore, colocalized red and green puncta are indicative of non-lysosomal p62 at steady-state. However, upon fusion with lysosomes (autolysosomes), red puncta persist while green puncta dim and disappear (Larsen K B, et al. (2010) Autophagy 6(6):784-793; Pankiv S, et al. (2007) J Biol Chem 282(33):24131-24145). In primary neurons transduced with control or β-arrestin variant lentiviruses and with high-titer rAAV9 mCherry-EGFP-p62, the ratio of mCherry only to total puncta was significantly reduced by β-arrestin2 expression (FIGS. 5E,5F). Importantly, β-arrestin2 ΔIP6C and ΔIP6N mutants, acting as dominant-negatives to WT β-arrestin2 oligomerization, significantly increased this measure (FIGS. 5E,5F). Thus, these β-arrestin2 mutants which cannot self-oligomerize (and inhibit WT-β-arrestin2 oligomerization), failed to reduce flux, confirming the notion that it is the oligomerized, non-GPCR bound, β-arrestin2 that is acting to fuel the tauopathy. Similar results of p62 autophagy flux with β-arrestin2, and β-arrestin2 ΔIP6N, were seen in Hela-V5-Tau cells (FIGS. 12A,12B).

Figure 5G:
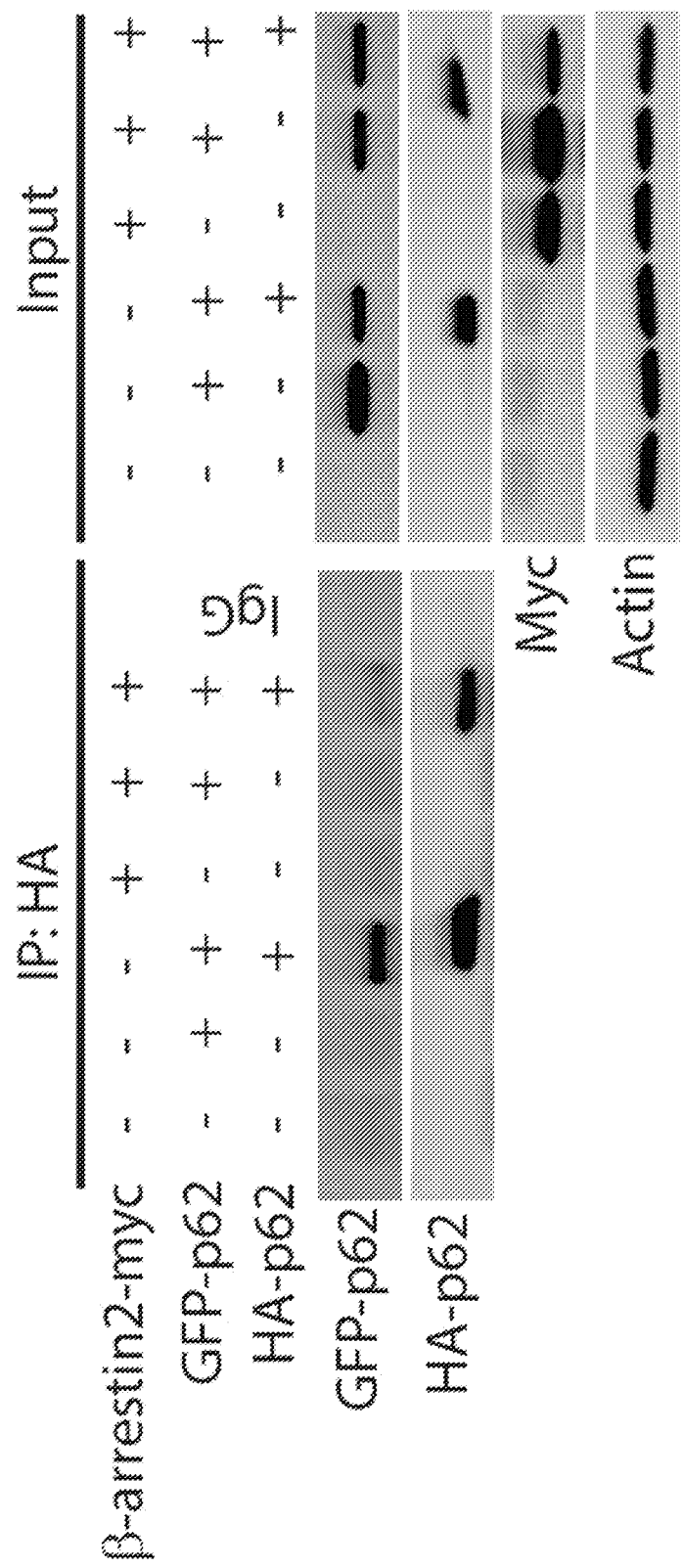
FIG. 5G contains representative immunoblots of Hela-V5-tau cells transiently transfected with control vector or β-arrestin2-myc with either GFP-p62 and/or HA-p62 and subjected to lysis followed by co-IP.
Figure 5I:
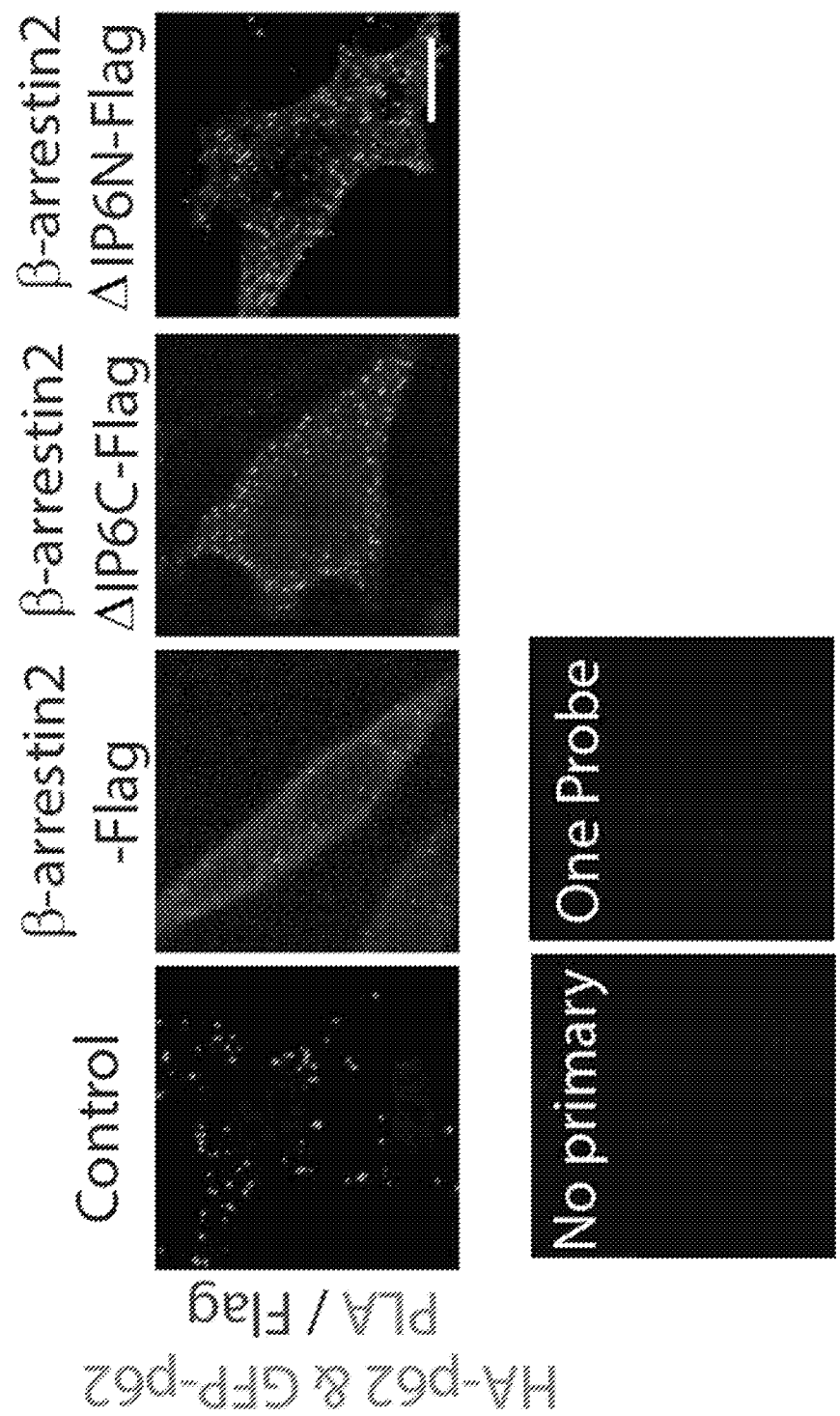
FIG. 5I contains representative images of proximity ligation assay (PLA) of Hela-V5-tau cells transfected with control vector, β-arrestin2, β-arrestin2 ΔIP6C, or β-arrestin2 ΔIP6N (bar=10 μm).
Figure 5L:
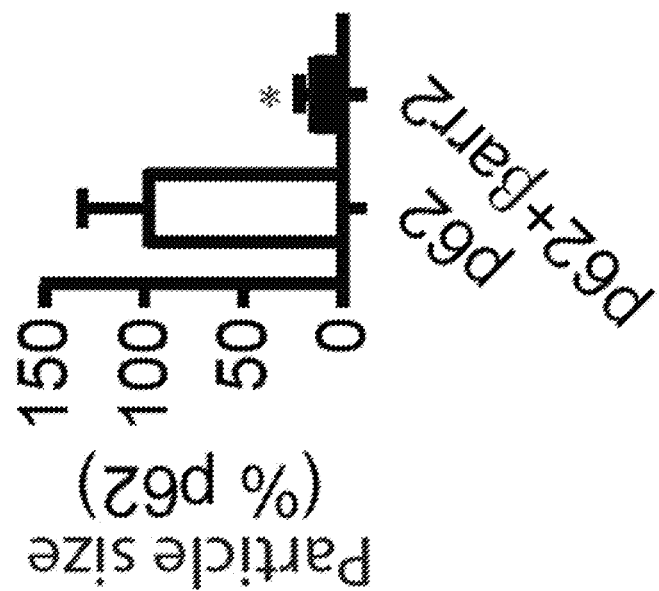
FIG. 5L shows quantification of p62 particle size (N=3 independent experiments, *p<0.05).
Figure 5J:
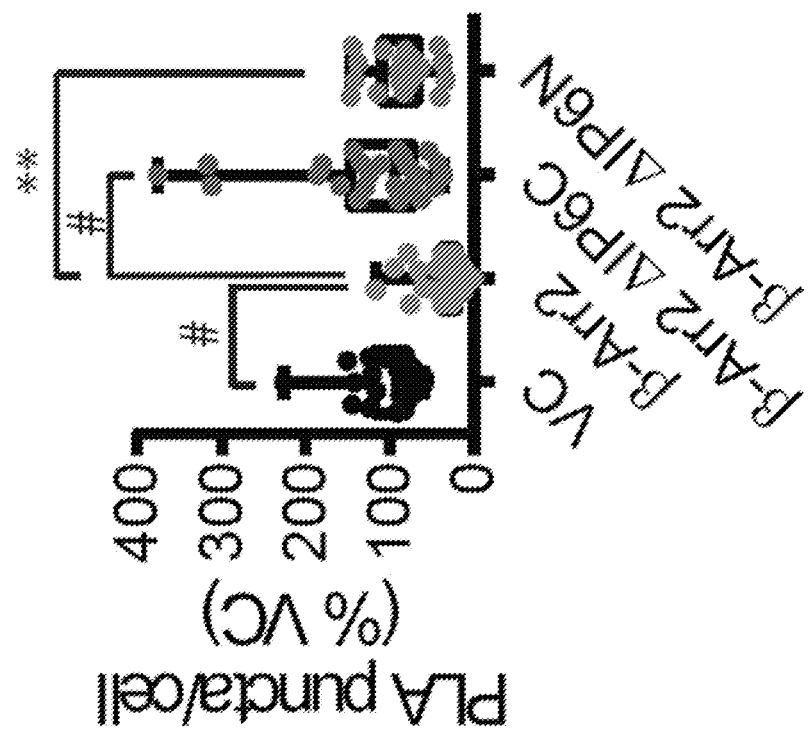
FIG. 5J shows quantification of PLA puncta (N=4 independent experiments, #P<0.0001, **P<0.005).
Figure 5K:
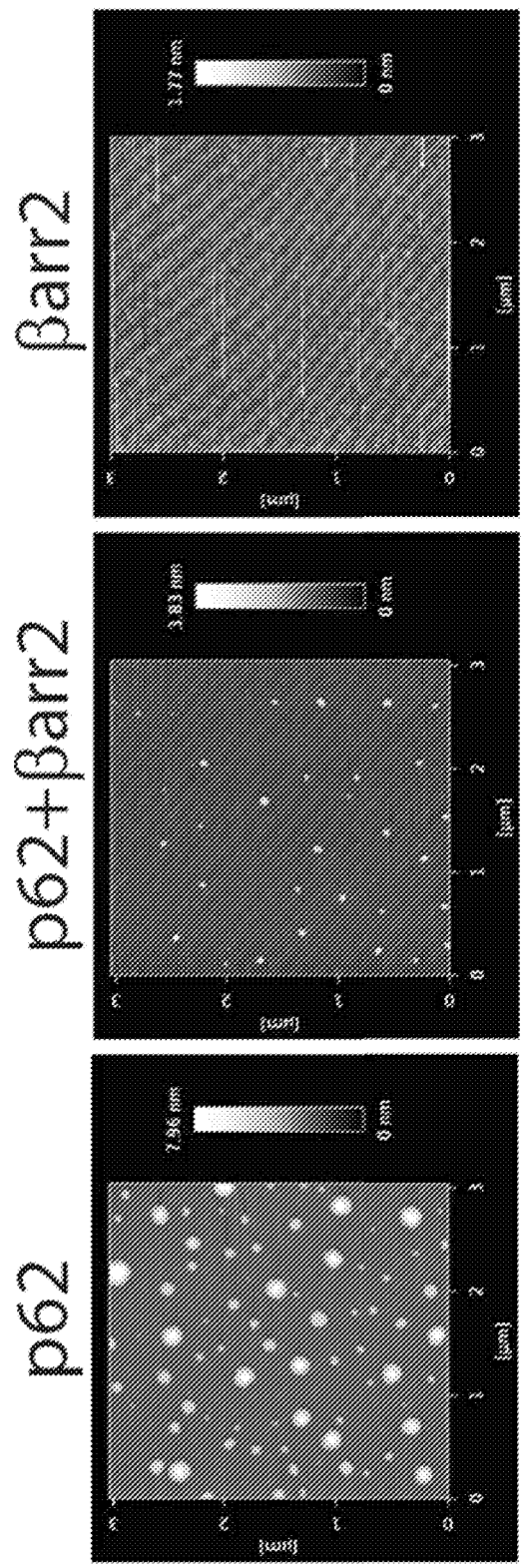
FIG. 5K shows 0.4 μg of p62 incubated with/without 0.2 μg of β-arrestin2 for 2 hrs at RT prior to AFM imaging.
Figure 5M:
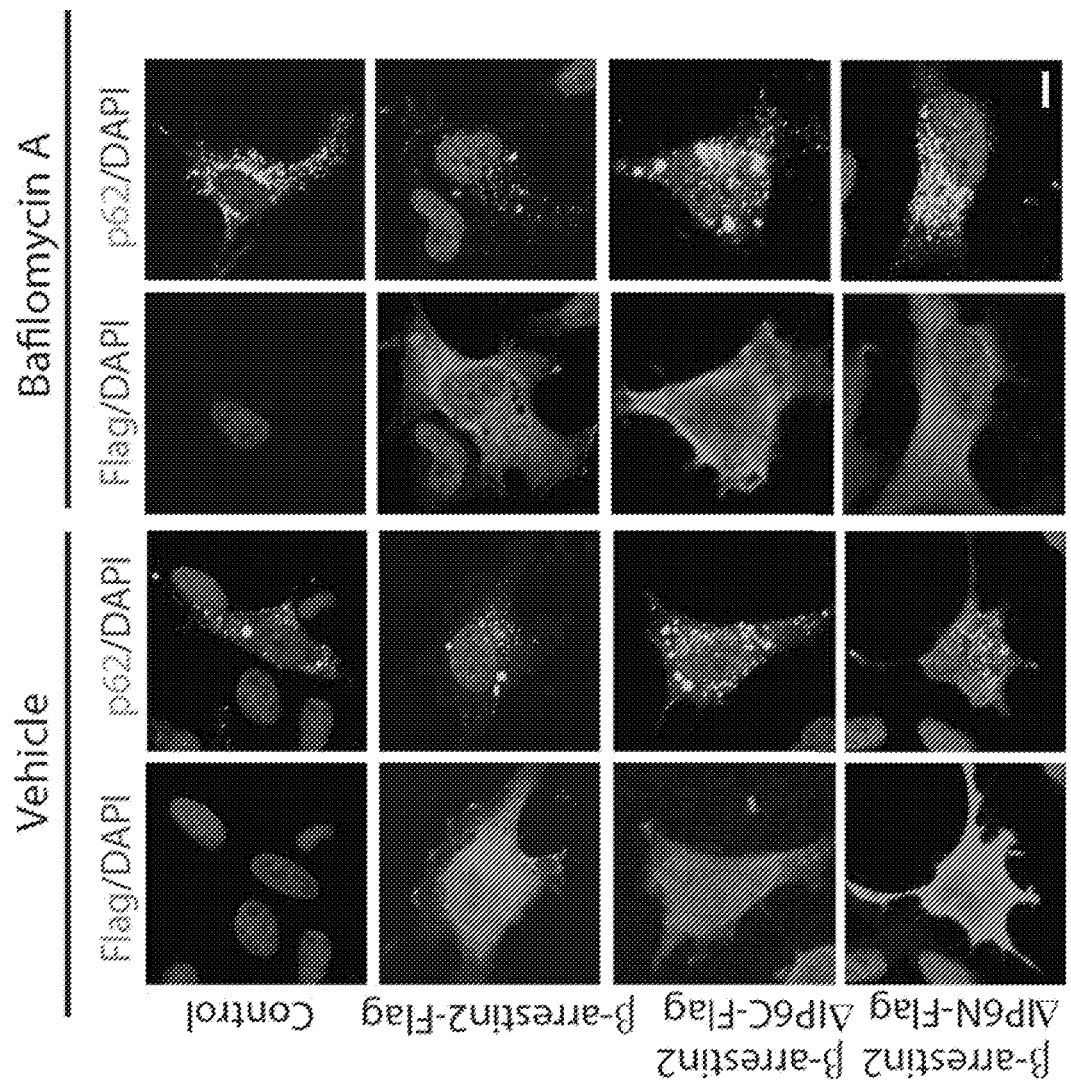
FIG. 5M shows representative staining of flag in Hela-V5-tau cells transfected with control vector, β-arrestin2-flag, β-arrestin2 ΔIP6C-flag or β-arrestin2 ΔIP6N-flag with GFP-p62 with/without 100 nM of Bafilomycin A treatment (bar=10 μm).
Figure 5N:
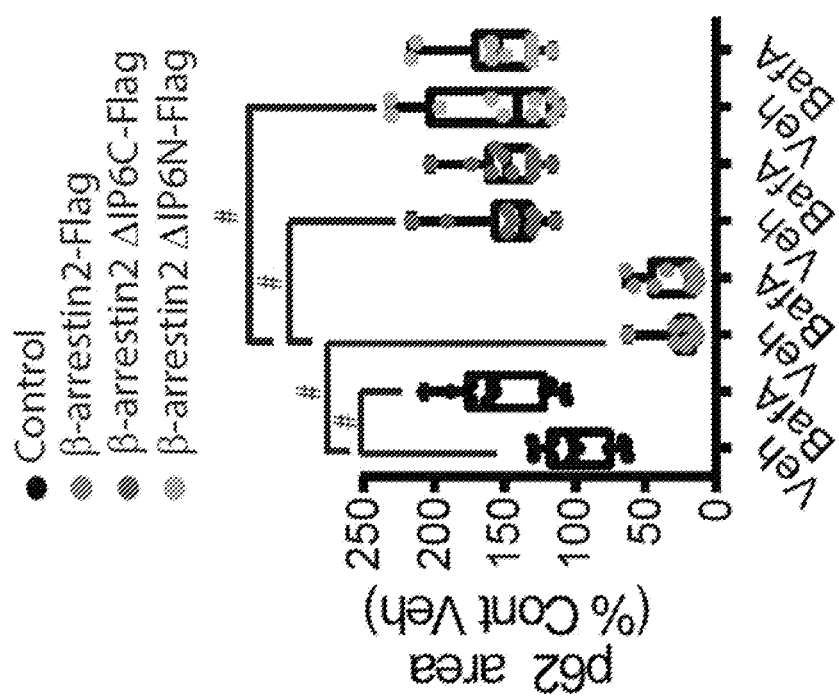
Figure 12D:
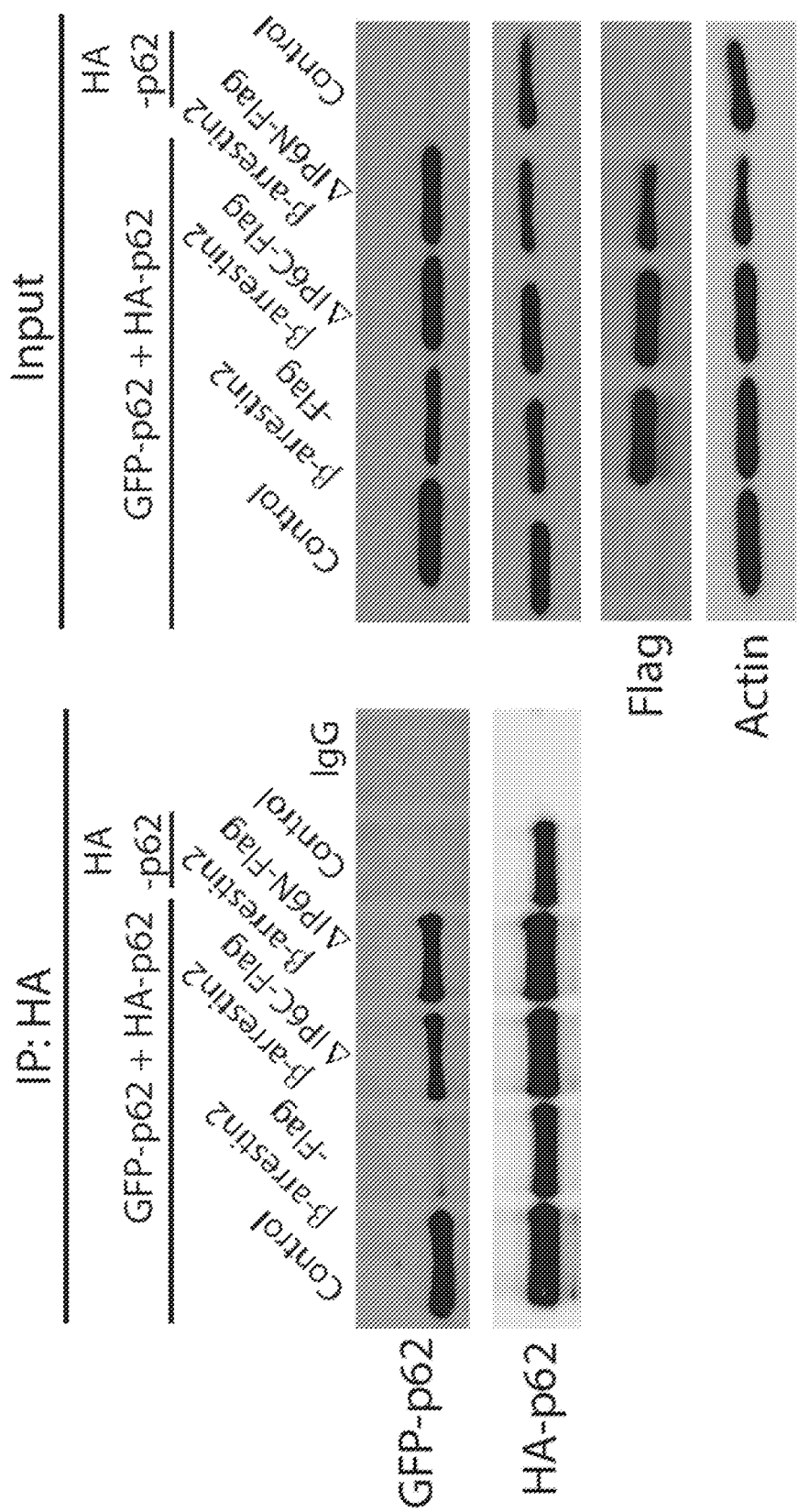
Figure 12E:
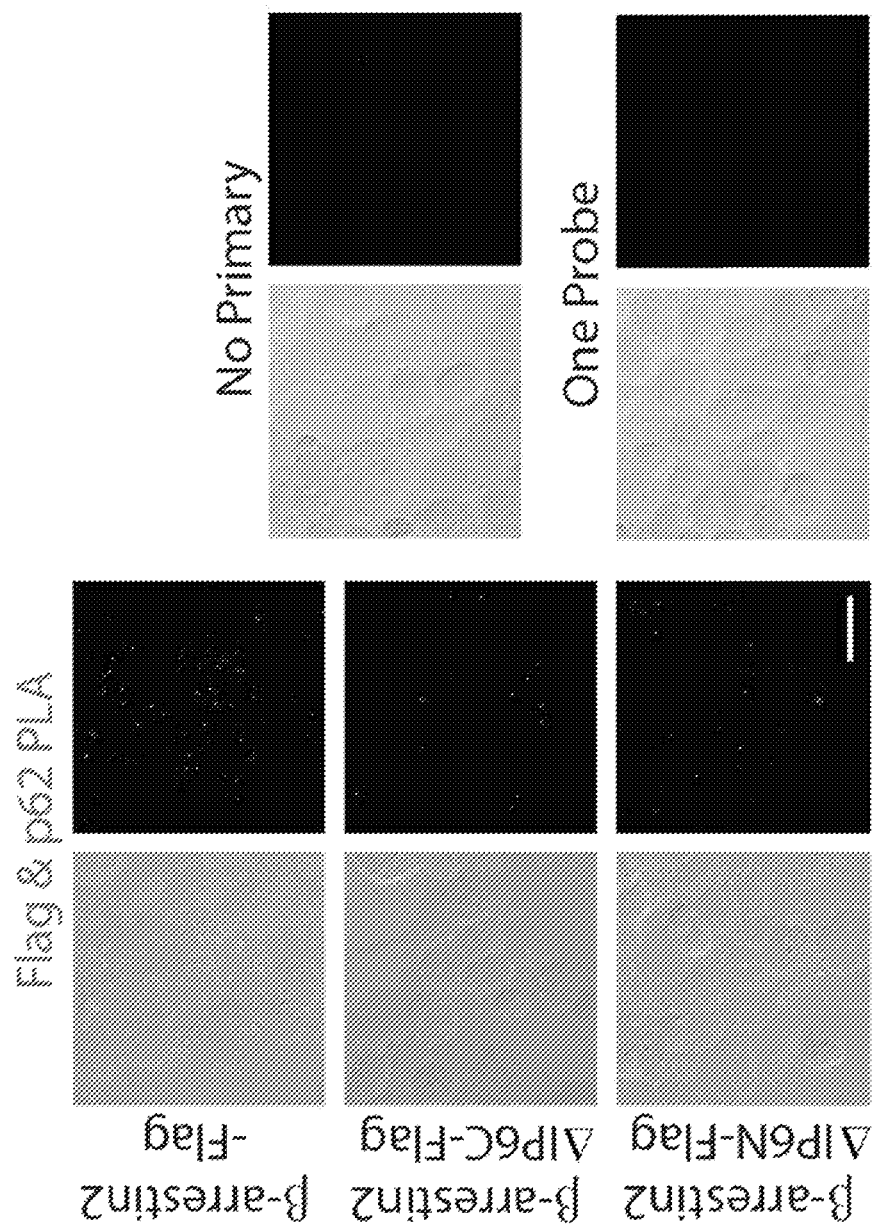
Figure 12F:
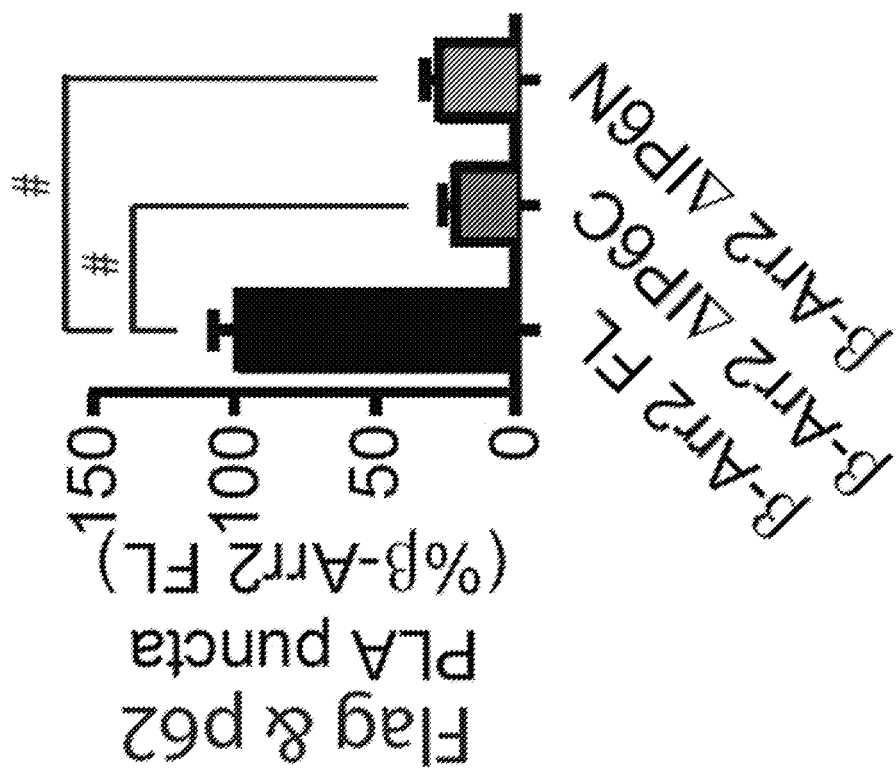
FIG. 12F show quantification of flag/p62 PLA puncta/cell (N=4 independent experiments, #P<0.0001).

Given the effects on p62 autophagy flux, whether β-arrestin2 physically interacts with p62 was tested. Co-immunoprecipitation (co-IP) experiments indeed showed that β-arrestin2 forms a complex with p62 (FIG. 12C). Self-association of p62 via its N-terminal PB1 domain is essential for its cargo receptor activity by enabling more interaction sites (multiple binding) to its ubiquitinated cargo as well as simultaneous binding to multiple LC3 proteins (Wurzer B, et al. (2015) Elife 4:e08941; Itakura E & Mizushima N (2011) J Cell Biol 192(1):17-27). Hence, whether β-arrestin2 affects p62 self-interaction was tested by co-IP experiments using HA-p62 and GFP-p62 constructs. β-arrestin2 reduced p62 self-association as detected by co-IP of GFP-p62 and HA-p62 (FIGS. 5G,5H). Given that β-arrestin2 oligomeric mutants, ΔIP6C and ΔIP6N, reduced tau aggregates by slowing tau turnover, next tested was whether β-arrestin2 ΔIP6C and ΔIP6N mutants affect p62 self-association by a proximity ligation assays (PLA) as well as co-IP. While β-arrestin2 significantly reduced the HA-p62/GFP-p62 complex PLA signal (p62 self-interaction), neither β-arrestin2 ΔIP6C nor β-arrestin2 ΔIP6N reduced HA-p62/GFP-p62 PLA puncta (FIGS. 5I,5J). It was also confirmed that while β-arrestin2 significantly reduced HA-p62 and GFP-p62 interaction, neither β-arrestin2 ΔIP6C nor β-arrestin2 ΔIP6N alone were capable of reducing HA-p62 and GFP-p62 interaction by co-IP (FIG. 12D). In fact, both β-arrestin2 ΔIP6C and β-arrestin2 ΔIP6N show much less interaction with p62 compare to β-arrestin2 (FIGS. 12E,12F). Recent studies have shown that purified recombinant p62 spontaneously forms globular oligomers (Zaffagnini G, et al. (2018) EMBO J 37(5)). To test whether β-arrestin2 can directly affect p62 oligomerization in vitro, purified recombinant p62, β-arrestin2, and p62 mixed with β-arrestin2 with atomic force microscopy were visualized. Recombinant p62 spontaneously formed visible globular particles between 5-100 nm in diameter (FIG. 5K), whereas only very few small β-arrestin2 particles were visible under identical conditions (FIG. 5K). When p62 was mixed together with β-arrestin2, the size of the particles was substantially reduced (FIG. 5k,l), indicating that the inhibition of p62 self-association by β-arrestin2 reduces the size of p62 particles. Next tested was whether β-arrestin2 oligomerization is required for bafilomycin A-induced p62 puncta formation. As expected, GFP-p62 puncta were increased upon bafilomycin A treatment in control vector transfected cells (FIGS. 5M,5N). However, β-arrestin2 significantly reduced GFP-p62 puncta at both steady-state and after bafilomycin A (FIGS. 5M,5N). Interestingly, both β-arrestin2 ΔIP6C and β-arrestin2 ΔIP6N transfected cells showed increased GFP-p62 puncta at steady-state, indicating that β-arrestin2 ΔIP6C and β-arrestin2 ΔIP6N increases the flux of p62 particles thereby increasing autophagy flux (FIGS. 5M,5N).

Mutant β-Arrestin2 Viral Therapy Inhibits Tauopathy In Vivo

Figure 6A:
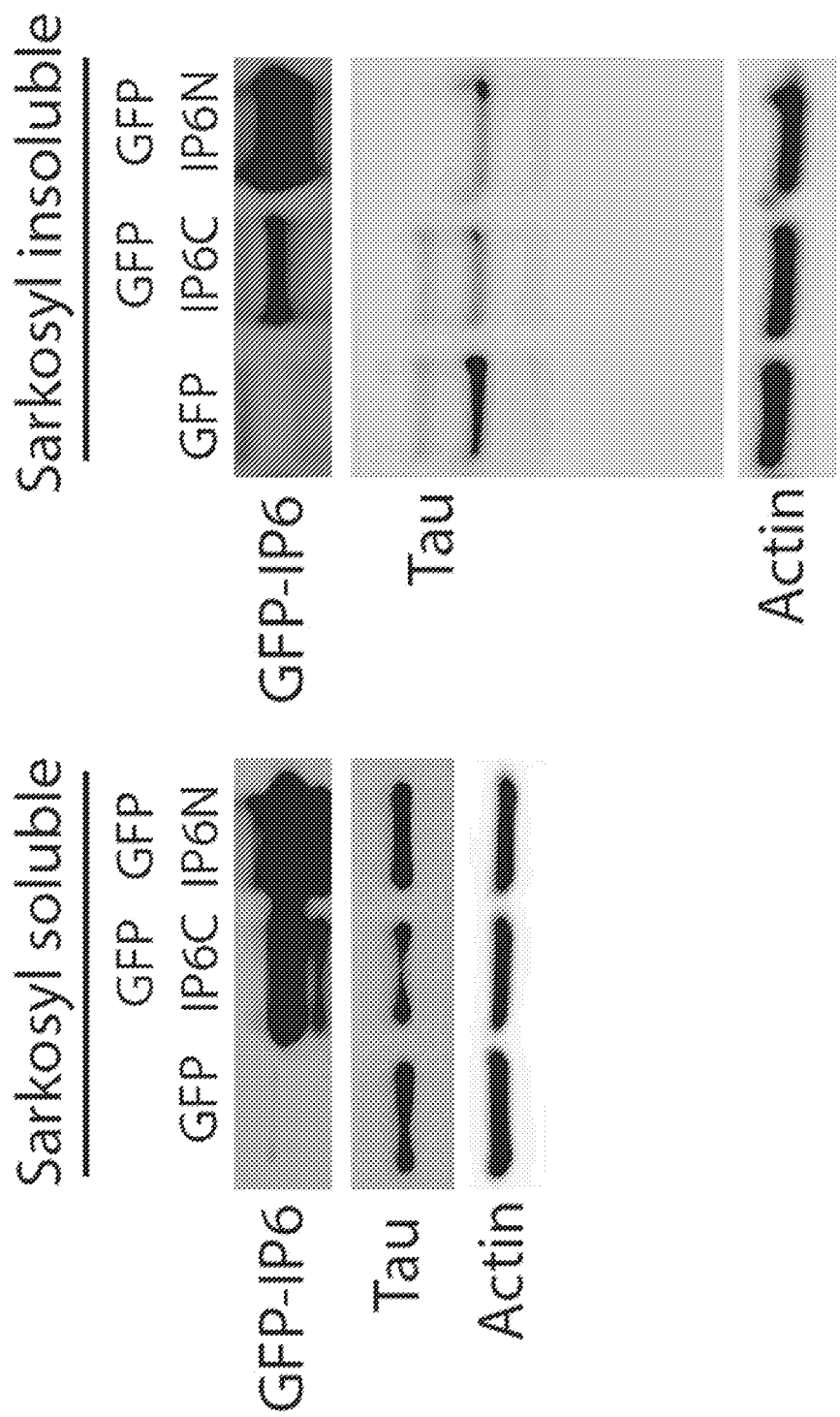
FIGS. 6A to 6E show oligomerization-deficient β-arrestin2 mitigates tauopathy in vivo.
Figures 6B, 6C:
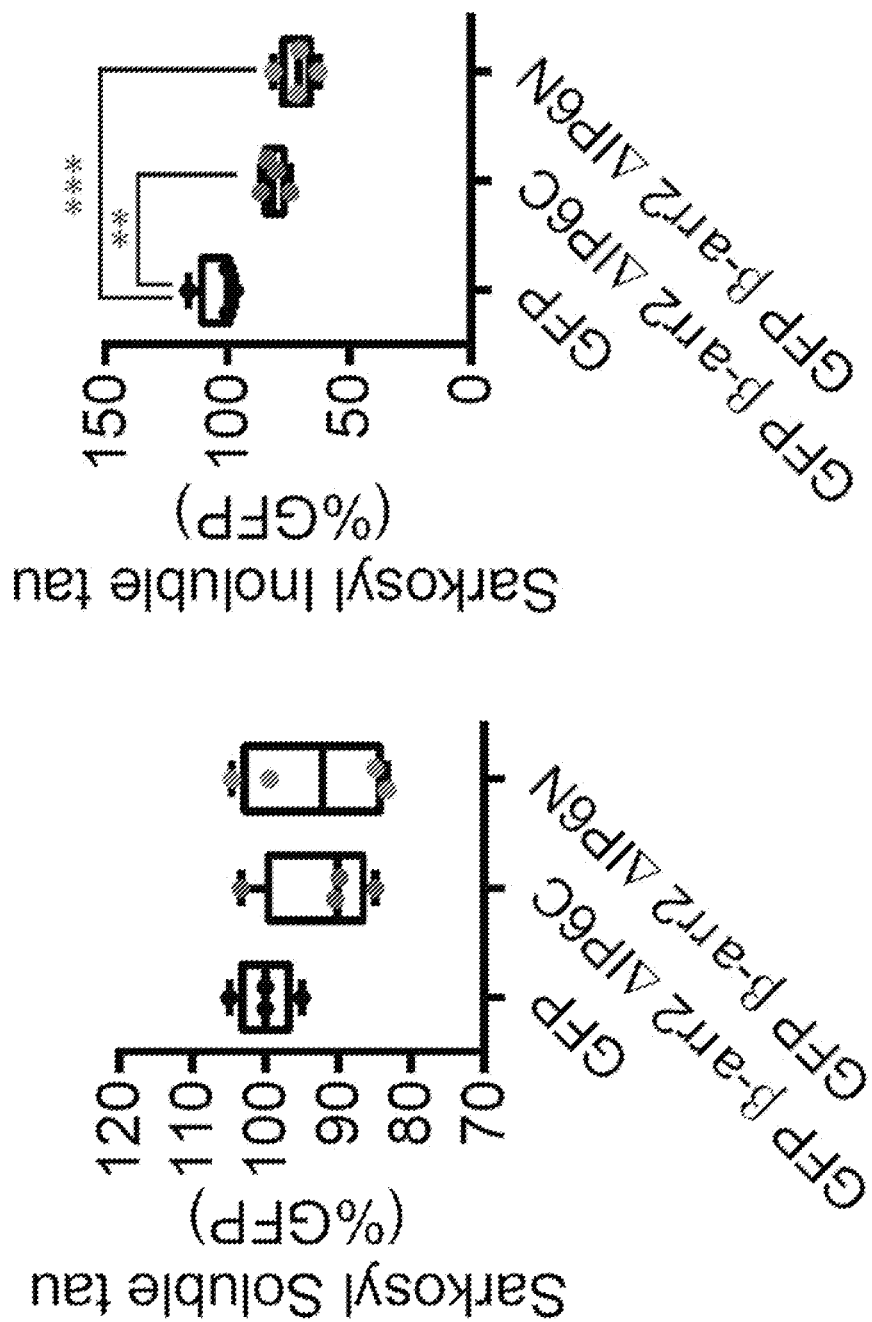
Figure 6D:
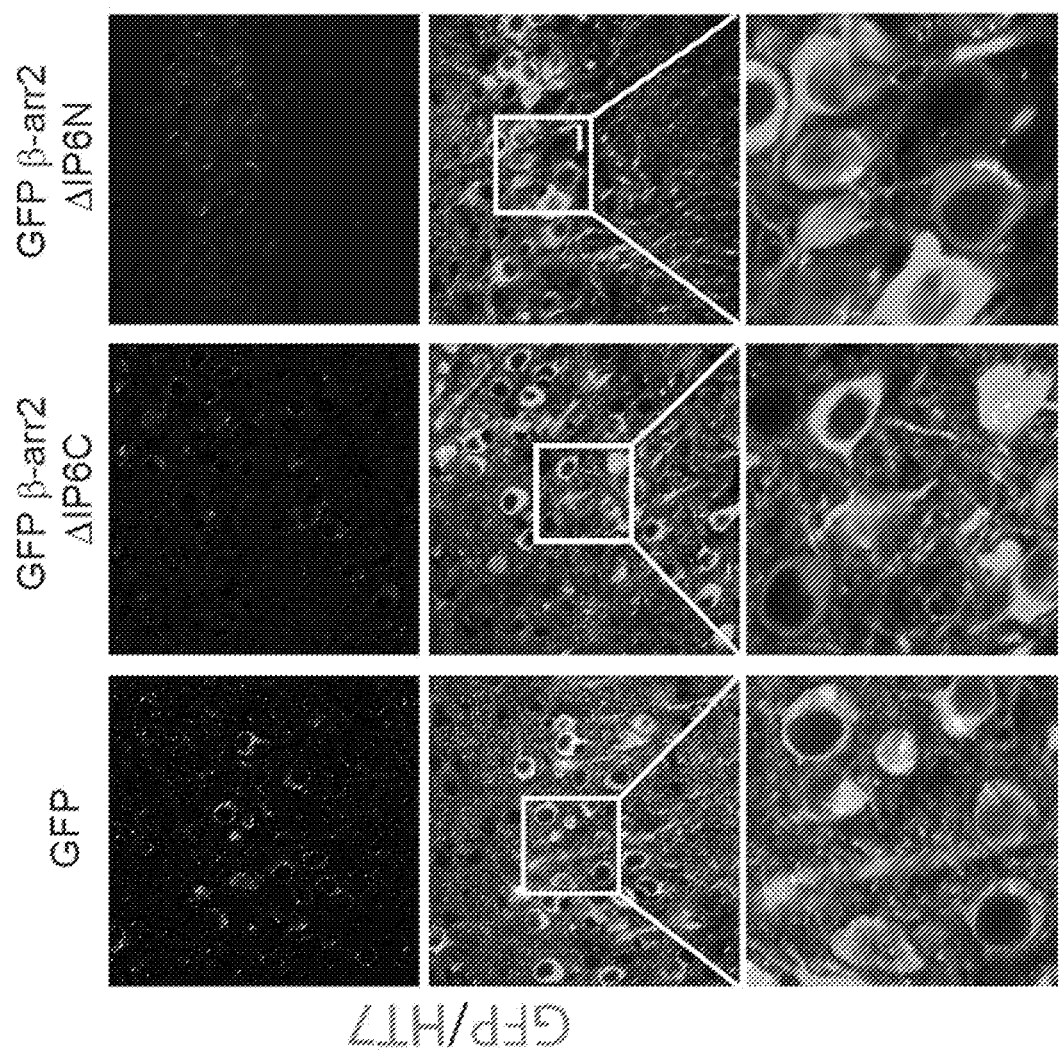
Figure 6E:
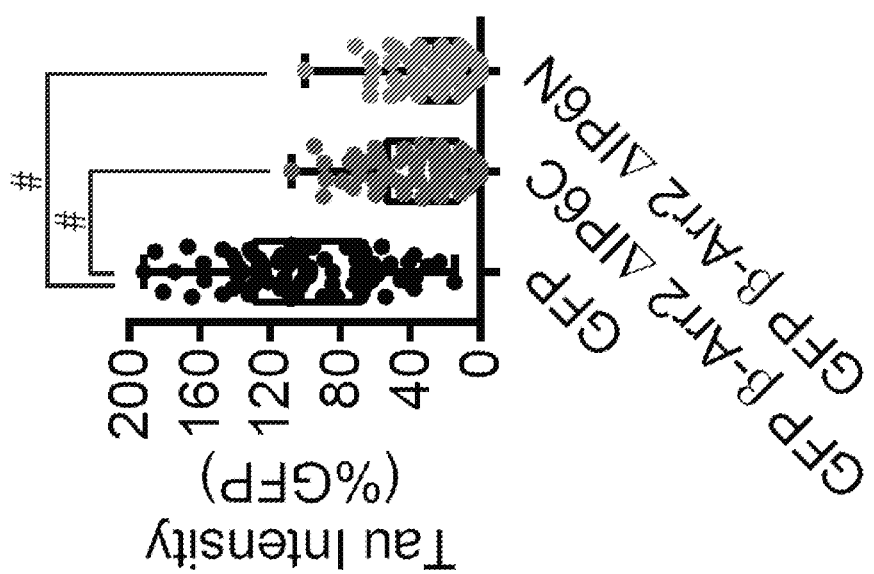

Given the above results, which indicate the requirement for the oligomerized forms of β-arrestin2 in tauopathy, and the dominant-negative effects of mutant β-arrestin2s that fail to oligomerize, whether β-arrestin2 ΔIP6C and β-arrestin2 ΔIP6N mutants reduce tauopathy in the in vivo setting was tested, as a potential therapeutic strategy. High-titer (>1× $10^{12}$ vg ml$^{-1}$) rAAV9 expressing GFP control, GFP-β-arrestin2 ΔIP6N, and GFP-β-arrestin2 ΔIP6C were generated and purified. AAVs were then stereotaxically injected bilaterally into the hippocampus of 5-month old tau P301S mice. Two months post injection, mouse brains were probed for detection of GFP and tau. These studies showed that GFP-β-arrestin2 ΔIP6N or GFP-β-arrestin2 ΔIP6C injection markedly reduced sarkosyl-insoluble tau compared to GFP control (FIGS. 6A,6C). However, sarkosyl soluble tau was not significantly altered by β-arrestin2 mutants (FIGS. 6A,6B). Furthermore, GFP-β-arrestin2 ΔIP6N and GFP-β-arrestin2 ΔIP6C expressing neurons showed significant reductions in HT7-immunoreactive tau compared to GFP-expressing control, or neighboring non-infected, neurons (FIGS. 6D,6E). Given the dominant-negative effects of these mutants (FIGS. 4A,4B, 11B,11C), these results are consistent with their therapeutic mechanism being from effective reduction of oligomerization of the increased endogenous neuronal β-arrestin2 in the tau P301S mice. And, since the injections were given at 5 months of age, when tau accumulation is well underway, it is apparent that that this approach can reduce preexisting tau-tangle pathology.

Discussion

Figure 7:
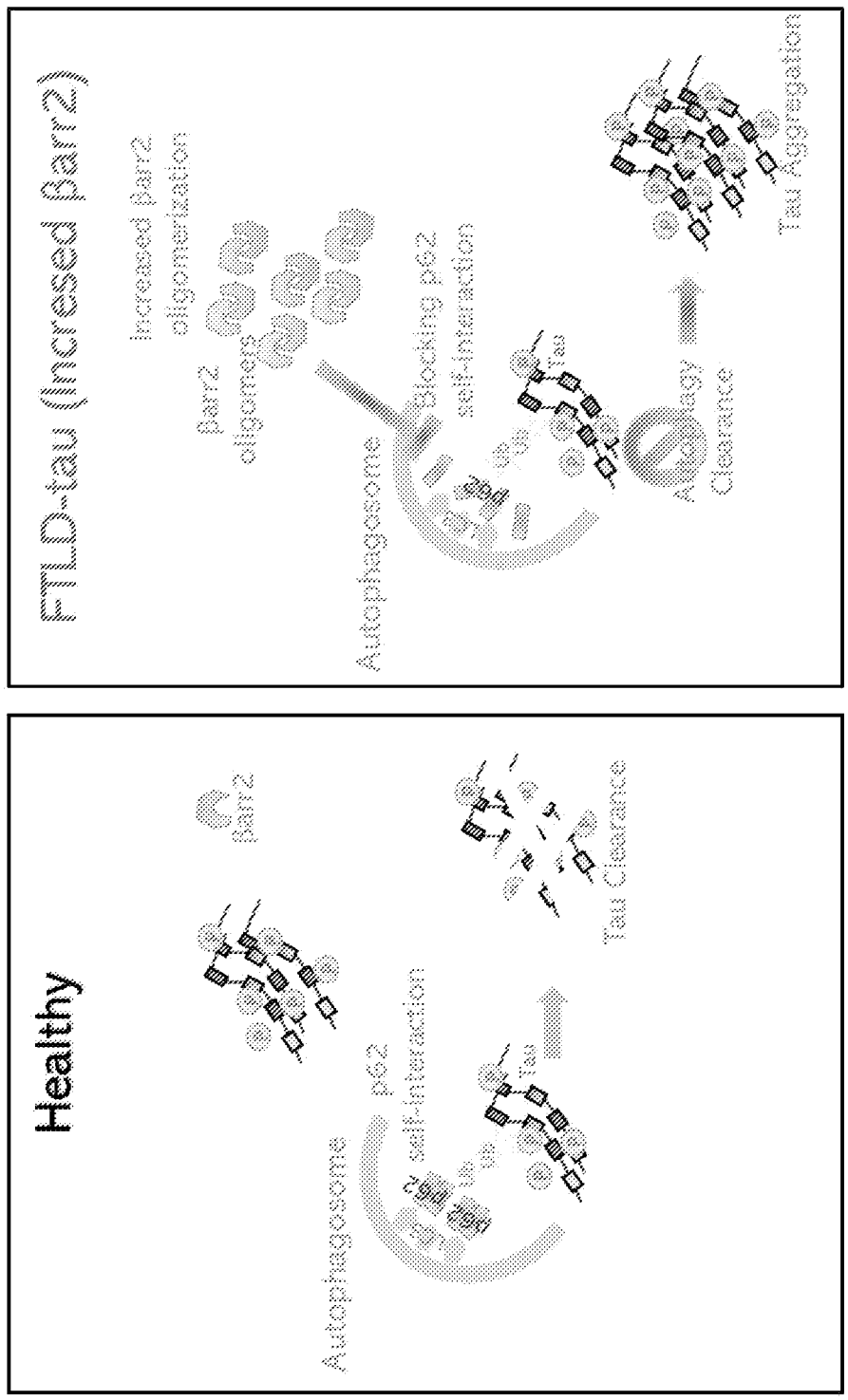
FIG. 7 is a schematic model of how β-arrestin2 promotes tauopathy in FTLD. In healthy brains, monomeric β-arrestin2 regulates GPCR trafficking, and there is no excess of oligomeric β-arrestin2 and thus misfolded tau is efficiently ubiquitylated and targeted for autophagy clearance. However, in FTLD-tau brains, β-arrestin2 oligomers are increased, inhibiting p62-mediated autophagy, leading to failure of misfolded/aggregated tau to be efficiently cleared. In AD, the increased β-arrestin2 also results in an increase in Aβ amyloid (not illustrated)

FTLD represents a distinct clinical and pathological dementia, yet is often misdiagnosed as, or treated in a similar manner to, AD. The most obvious difference between the pathology of AD and FTLD is the absence of Aβ accumulation in FTLD. In its most common form, FTLD-tau has an accumulation of tau as a poignant feature. Given that tau levels (in AD) appear to be a better predictor of cognitive deficits, the tau accumulation in FTLD is presumed to also be a key factor in neurodegeneration in this disease. Agonists and antagonists to several GPCRs have been proposed as potential therapy for AD (Ni Y, et al. (2006) Nat Med 12(12):1390-1396; Melancon B J, et al. (2013) Drug Discov Today 18(23-24):1185-1199; Angulo E, et al. (2003) Brain Pathol 13(4):440-451; Mogi M & Horiuchi M (2009) Hypertens Res 32(9):738-740), and given that tau participates in both AD and FTLD, ways to modulate GPCR signaling through the two β-arrestins that associate with most GPCRs were considered. The increase in β-arrestin2 in human FTLD brains, and in the tau-overexpressing cells, indicated that this might be a fruitful approach for understanding pathogenesis and localizing a point for therapeutic interdiction. Further studies revealed several unexpected findings. First, it became apparent that β-arrestin2 can upregulate tau, and that tau can upregulate β-arrestin2. This suggested that the upregulation of β-arrestin2 in human FTLD brains is maladaptive, rather than a compensatory or salutary event that might abrogate tau accumulation. Hence, this effect is a positive feedback loop, which once initiated serves to fuel further deleterious effects. In addition, it became clear that the oligomerized β-arrestin2 (which does not interact with GPCRs) was responsible for tau accumulation, which led us to examine non-receptor functions of β-arrestin2 in the context of FTLD. Of note, β-arrestin2 has previously been shown to regulate the γ-secretase processing of APP by interacting with Aph-1, thereby positively regulating Aβ generation (Thathiah A, et al. (2013) Nat Med 19(1):43-49). The same studies showed that β-arrestin2 is significantly increased in AD brains and APP transgenic mice (Thathiah A, et al. (2013) Nat Med 19(1):43-49). The current work shows that in cells and mice with elevated tau, β-arrestin2 is elevated. And, when β-arrestin2 is overexpressed, tau levels become elevated. Based on tau mRNA levels being unchanged, tau protein clearance was considered as a mechanism by which β-arrestin2 modulates its levels. The data indicate that β-arrestin2 reduces tau clearance by impairing p62-mediated autophagy, a role carried out by the oligomerized form of β-arrestin2. Specifically, the results indicate that β-arrestin2 oligomers increase tau levels by blocking the self-interaction of p62, an initial step essential in p62-mediated autophagy flux. Genetic reduction or ablation of β-arrestin2 significantly decreased sarkosyl insoluble tau and mitigated tauopathy in vivo. Furthermore, β-arrestin2 mutants incapable of forming oligomers actually reduced insoluble tau. Such actions, which were shown to be due to the dominant-negative 'anti-oligomer' properties of these mutants, reduced tauopathy in cultured model cells and neurons, and a FTLD-tau mouse model in vivo. These data highlight a novel mechanism of tau regulation by β-arrestin2 and provide a proof-of-concept strategy to mitigate tauopathy by targeting β-arrestin2 oligomerization (FIG. 7).

Boularan and colleagues found that the β-arrestin2 ΔIP6N and ΔIP6C mutants do not form oligomers but are otherwise normal in terms of localization and binding to (and mediating internalization of) GPCRs and other partners such as AP2, Filamin A, and MAPK. To date, no previous study has implicated oligomeric β-arrestin2 in p62-mediated autophagy. These findings indicated that β-arrestin2 reduces p62 self-interaction, number of p62 particles, and alters tau clearance. And, expression of β-arrestin2 ΔIP6N and ΔIP6C mutants increase p62 self-interaction and the number of p62 particles by impairing oligomerization of WT (endogenous) β-arrestin2. Such changes were directly related to the turnover of tau and accumulation of insoluble tau, consistent with the role of p62 in preferentially lowering insoluble tau (Xu Y, et al. (2019) Autophagy 15(4):583-598). Moreover, insoluble p62 itself is associated with neurofibrillary tangles (Caccamo A, et al. (2017) Mol Psychiatry 22(6):865-873; King A, et al. (2013) Acta Neuropathol 125(2):303-310; Kuusisto E, et al. (2002) Neuropathol Appl Neurobiol 28(3): 228-237; Terni B, et al. (2007) Acta Neuropathol 113(4): 403-416), while soluble cytoplasmic p62 levels are significantly reduced in AD brains (Caccamo A, et al. (2017) Mol Psychiatry 22(6):865-873; Zheng X, et al. (2012) Neural Regen Res 7(17):1304-1311). Increased p62 expression improves cognitive impairments in AD animal models by enhancing autophagy induction, and genetic loss of SQSTM1/p62 leads to tau accumulation and neurodegeneration brains (Caccamo A, et al. (2017) Mol Psychiatry 22(6):865-873; Zheng X, et al. (2012) Neural Regen Res 7(17):1304-1311; Ramesh Babu J, et al. (2008) J Neurochem 106(1):107-120). P62 self-interaction represents the first step in p62 particle formation, which is essential for p62-mediated autophagy. The regulation of p62 at this step by β-arrestin2 offers an opportunity for therapeutic intervention. The observation that both IP6-binding mutants enhanced p62 self-interaction and reduced insoluble tau indicated that while β-arrestin2 oligomers block p62-mediated autophagy, β-arrestin2 monomers promote p62-mediated autophagy. If so, β-arrestin2 oligomer to monomer transition and vice versa may function as a regulatable molecular switch to toggle p62-mediated autophagy.

In the current experiments, the mutant β-arrestin2 proteins were highly effective at reducing tau in neurons. In individual cells of the brain where expression of ΔIP6N OR ΔIP6C was verified (by their GFP tags), tau levels were essentially undetectable, which was in contrast to the remaining cells with high levels of tau. For gene therapy of human FTLD-tau, mutants with a somewhat decreased capacity for such inhibition might be desirable, so that some levels of the oligomer are present to carry-out other functions. Indeed, oligomeric β-arrestin2 has been shown to facilitate nucleocytoplasmic shuttling of proteins (Boularan C, et al. (2007) Proc Natl Acad Sci USA 104(46):18061-18066) Similarly, small molecule inhibitors of β-arrestin2 oligomerization, given for treatment or prevention of FTLD-tau, could be designed to spare complete loss of the oligomer in the cell. Importantly, these strategies are not expected to alter neuronal GPCR signaling pathways, since the monomeric form of β-arrestin2 would be preserved. Based on these findings, the effects of inhibiting β-arrestin2 oligomerization would be expected to not only inhibit the development of new tau tangles, but also to clear existing tau accumulations due to this mechanism of enhancing tau clearance. Thus, this treatment strategy could be preventative for those at risk or with mild cognitive impairment, and also therapeutic in those with overt FTLD-tau, by decreasing the existing tau tangles. Beyond tauopathy, it is conceivable that this strategy could also prove to be beneficial in other neurodegenerative diseases bearing proteinopathies that are cleared via p62.

Example 2: β-Arrestin1 Drives Tauopathy by Disrupting Microtubule Stability and Impairing p62/SQSTM1-Mediated Tau Clearance Introduction The defining pathological hallmarks of Alzheimer's disease (AD) are the accumulation of amyloid β (Aβ) and hyperphosphorylated tau in brain. Multiple G-protein coupled receptors (GPCRs) have been shown to play integral roles in AD pathogenesis (Ni, Y. et al. Nat Med (2006) 12:1390-1396; AbdAlla, S. et al. J Biol Chem (2009) 284: 6566-6574; AbdAlla, S. et al. J Biol Chem (2009) 284:6554-6565; Thathiah, A. et al. Science (2009) 323:946-951; Bakshi, P., et al. ACS Chem Biol (2008) 3:777-789; Alley, G. M. et al. J Neurosci Res (2010) 88:143-154; Minkeviciene, R., et al. J Pharmacol Exp Ther (2004) 311:677-682; Dobarro, M., et al. Int J Neuropsychopharmacol (2013) 16:2245-2257; Wisely, E. V., et al. Hum Mol Genet (2014) 23:4024-4034; Luong, K. & Nguyen, L. T. Am J Alzheimers Dis Other Demen (2013) 28:427-439; Lee, H. G. et al. Acta Neuropathol (2004) 107:365-371; Lee, H. G. et al. Brain Res (2009) 1249:244-250; Sun, L. et al. FEBS Lett (2005) 579:251-258). However, it is unclear how diverse GPCRs similarly impinge on Aβ and tau pathogenesis. GPCRs share a common mechanism of action via the arrestins scaffolding signaling complexes, which serve to desensitize GPCRs by internalization and degradation in the endo-lysosomal pathway (Lohse, M. J., et al. Science (1990) 248:1547-1550). In addition, arrestins (arrestin1, arrestin2, arrestin3 and arrestin 4) (Wilden, U., et al. Proc Natl Acad Sci USA (1986) 83:1174-1178; Moore, C. A., et al. Annu Rev Physiol (2007) 69:451-482; Gurevich, V. V. & Gurevich, E. V. Pharmacol Ther (2006) 110:465-502) act as multifunctional adapter proteins that regulate various different signaling pathways (Lefkowitz, R. J., et al. Mol Cell (2006) 24:643-652; Lefkowitz, R. J Prog Mol Biol Transl Sci (2013) 118:3-18). While Arrestin1 and Arrestin4 bind to only few receptors (rhodopsin and the color opsins) and are expressed in specific cell types (Shinohara, T. et al. Proc Natl Acad Sci USA (1987) 84:6975-6979; Yamaki, K., et al. Biochem Biophys Res Commun (1987) 142:904-910), Arrestin2 (β-arrestin1) and Arrestin 3 (β-arrestin2) show the highest expression in brain and spleen but are ubiquitously expressed (Lohse, M. J., et al. Science (1990) 248:1547-1550; Attramadal, H. et al. J Biol Chem (1992) 267:17882-17890).

The microtubule-associated protein tau (MAP7) plays an essential role in numerous neurodegenerative diseases (Goedert, M., et al. Proc Natl Acad Sci USA (1988) 85:4051-4055; von Bergen, M. et al. J Biol Chem (2001) 276:48165-48174; Lashley, T., et al. Neuropathol Appl Neurobiol (2015) 41:858-881), and pathogenic species of tau form neurotoxic aggregates, which correlate with cognitive deficits and neurodegeneration in humans and animal models of tauopathy (Wang, Y. & Mandelkow, E. Nat Rev Neurosci (2016) 17:5-21; Ward, S. M., et al. Biochem Soc Trans (2012) 40:667-671; Patterson, K. R. et al. J Biol Chem (2011) 286:23063-23076). Hence, reducing pathogenic tau represents an attractive therapeutic strategy.

Interestingly, β-arrestin1 (Liu, X. et al. Cell Res (2013) 23:351-3650) and β-arrestin2 (Thathiah, A. et al. Nat Med (2013) 19:43-49) are dramatically increased in AD brains and plays a significant role in promoting Aβ production by interacting with the β-secretase subunit Aph-1 (Liu, X. et al. Cell Res (2013) 23:351-365; Thathiah, A. et al. Nat Med (2013) 19:43-49), thereby linking β-arrestin1 and β-arrestin2 to Aβ pathogenesis. A recent study has shown that β-arrestin2 is also increased in Frontotemporal lobar degeneration (FTLD-tau) patients, and genetic reduction in β-arrestin2 significantly mitigates tauopathy in vivo.

However, it is unknown whether and how β-arrestin1 contributes to pathological progression of tauopathy. Furthermore, it is unclear whether β-arrestin1 and/or β-arrestin2 is required for the effects of GPCR stimulation on tauopathy. In this study, β-arrestin1 was found to be significantly increased in Frontotemporal lobar degeneration-tau (FTLD-tau) patients, a degenerative condition defined by tauopathy in the absence of Aβ deposits, and elevated β-arrestin1 promotes tau accumulation and tauopathy in vitro and in vivo by two distinct mechanisms. Furthermore, it was confirmed that both β-arrestin1 and β-arrestin2 mediate GPCR stimulation effects on tauopathy. Therefore, reducing β-arrestin1 or β-arrestin2 is sufficient to block the effects of GPCR stimulation on tauopathy. β-arrestin2 increases pathogenic tau by impairing autophagic flux. Here, the molecular mechanistic basis of β-arrestin1 in tauopathy was further define by demonstrating that β-arrestin1 not only induces the dissociation of tau from microtubules but also inhibits tau-induced microtubule assembly. Moreover, it was found that β-arrestin1 and β-arrestin2 share a common mechanism to promote aggregation of pathogenic tau by blocking autophagy cargo receptor p62. Indeed, Genetic reduction in β-arrestin1 markedly restores synaptic dysfunction and significantly alleviates tauopathy in tauP301S transgenic mice in vivo.

Results

β-Arrestin1 and β-Arrestin2 are Required for mGluR2 and β2AR Mediated Increase in Pathogenic Tau Thus far, two GPCRs have been implicated in tau phosphorylation and accumulation: β2-adrenergic receptor (β2AR) (Dobarro, M., et al. Int J Neuropsychopharmacol (2013) 16:2245-2257; Wisely, E. V., et al. Hum Mol Genet (2014) 23:4024-4034; Luong, K. & Nguyen, L. T. Am J Alzheimers Dis Other Demen (2013) 28:427-439) and metabotropic glutamate receptor 2 (mGluR2) (Lee, H. G. et al. Acta Neuropathol (2004) 107:365-371; Lee, H. G. et al. Brain Res (2009) 1249:244-250). β2AR is significantly increased in the frontal cortex and hippocampus in AD brains compared to controls (Kalaria, R. N. et al. J Neurochem (1989) 53:1772-1781; Kalaria, R. N. & Harik, S. I. Neurosci Lett (1989) 106:233-238). Genetic studies have shown that polymorphisms in β2AR are associated with higher risk for developing sporadic AD (Rosenberg, P. B. et al. Am J Geriatr Psychiatry (2008) 16:883-892; Yu, J. T. et al. Brain Res (2008) 1210:216-222), and genetic reduction in β2AR significantly mitigates tauopathy in vivo (Wisely, E. V., et al. Hum Mol Genet (2014) 23:4024-4034). Isoproterenol, the classical β2AR agonist, markedly increases tau phosphorylation thereby inducing memory deficits in rats (Sun, L. et al. FEBS Lett (2005) 579:251-258). mGluR2 is also significantly increased in AD, and mGluR2s expression closely correlates with hyperphosphorylated tau deposition (Lee, H. G. et al. Acta Neuropathol (2004) 107:365-371; Lee, H. G. et al. Brain Res (2009) 1249:244-250). The mGluR2s agonist LY-379,628 has been reported to increase tau phosphorylation via ERK activation (Lee, H. G. et al.

Figure 21A:
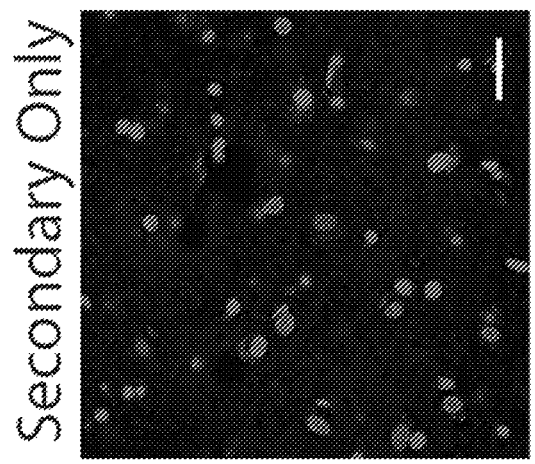
FIGS. 21A and 21B show β-arrestin1 colocalized with phospho-tau AT8 in FTLD-tau patients.
Figure 21A:
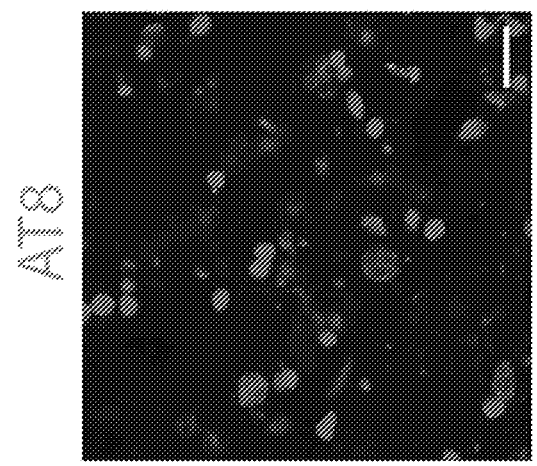
Figure 21B:
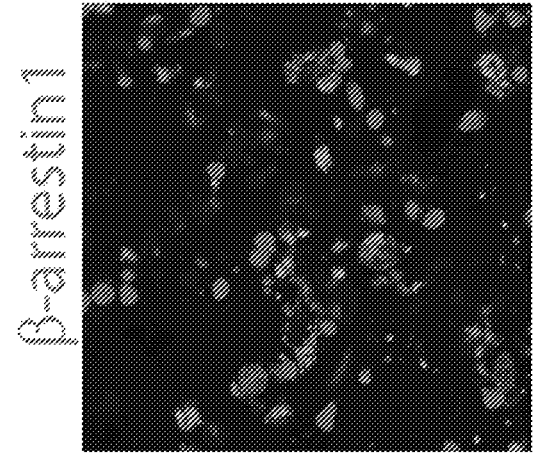

Brain Res (2009) 1249:244-250). Based on these prior observations, the goal was to confirm these findings in tauP301S transgenic primary neurons and Hela cells stably expressing tau (V5-tagged 4R0N tau, Hela-V5-tau cells). As expected 10 µM Isoproterenol (Iso) treatment significantly increased phospho-tau in tauP301S cortical primary neurons (FIGS. 21A,21B). 10 µM LY-379,628 treamtnet also increased phospho-tau in tauP301S cortical neurons (FIGS. 21C,21D).

Figure 13B:
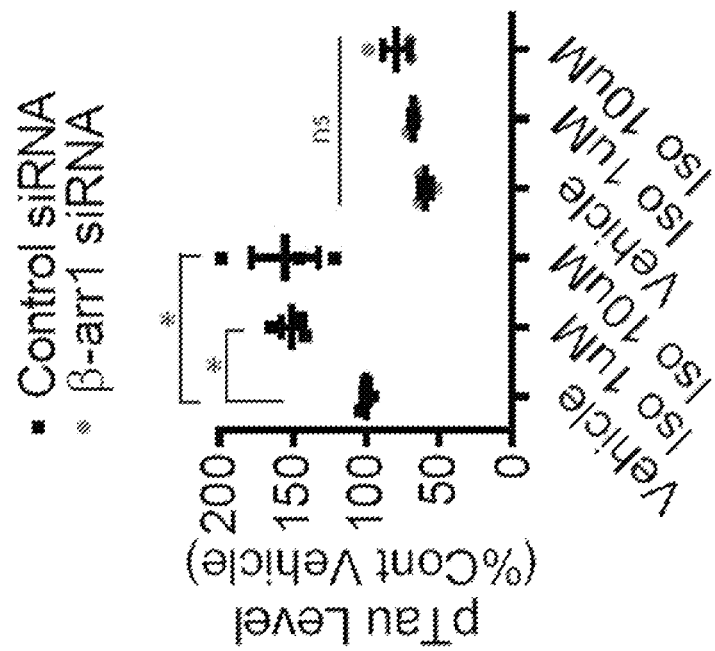
FIGS. 13A to 13F show β-arrestin1 is required for mGluR2 and β2AR mediated increase in pathogenic tau.
Figure 13A:
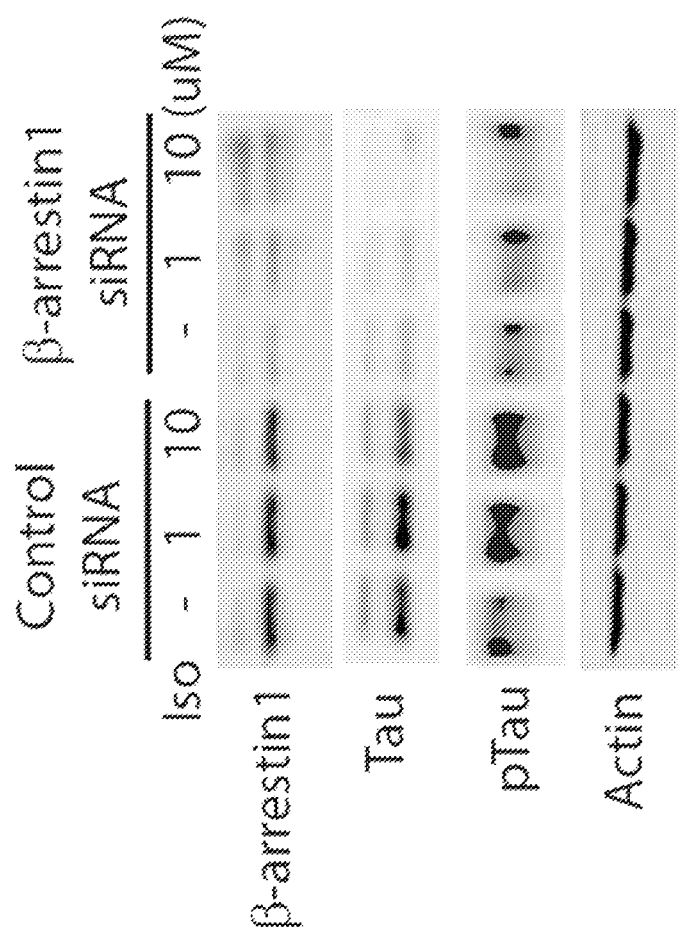
Figures 13C, 13D:
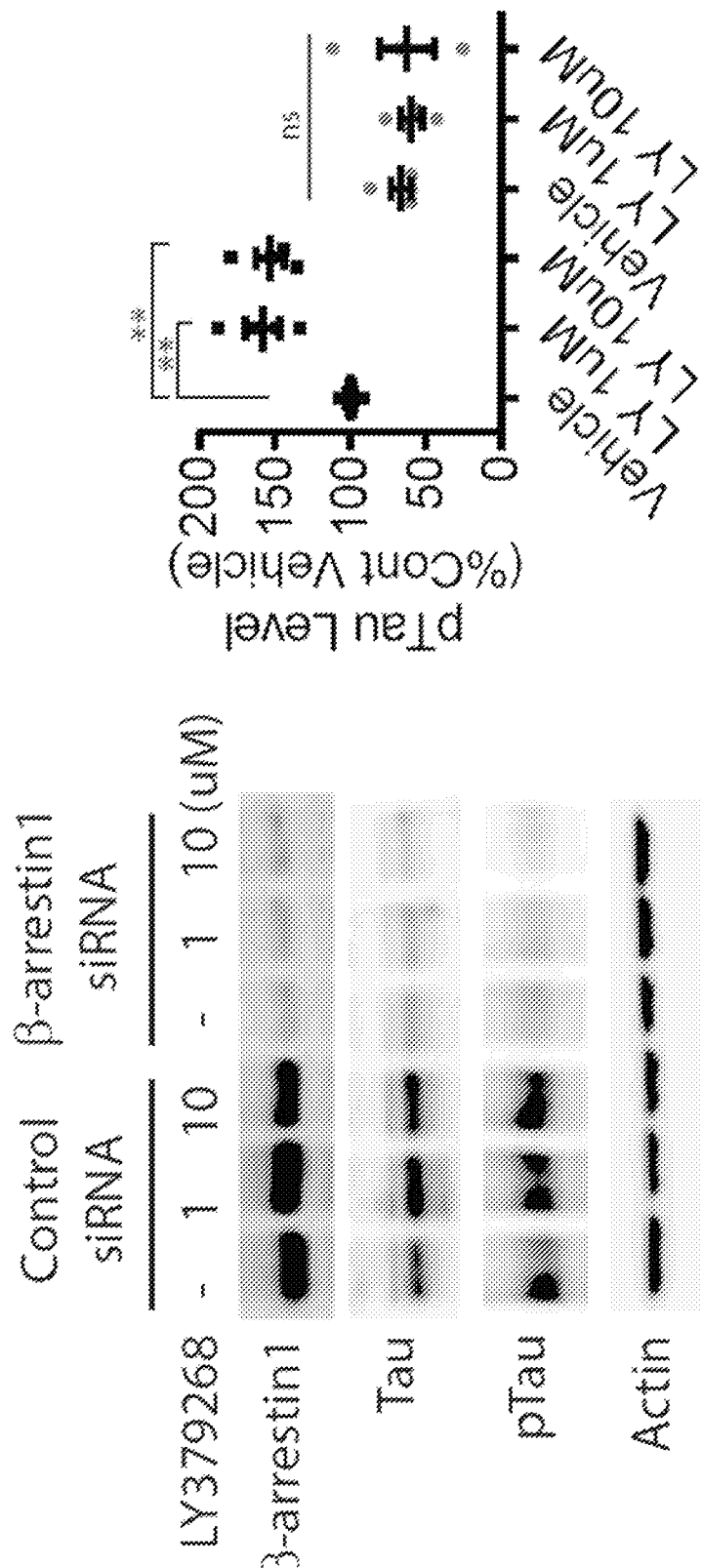
Figures 13E, 13F:
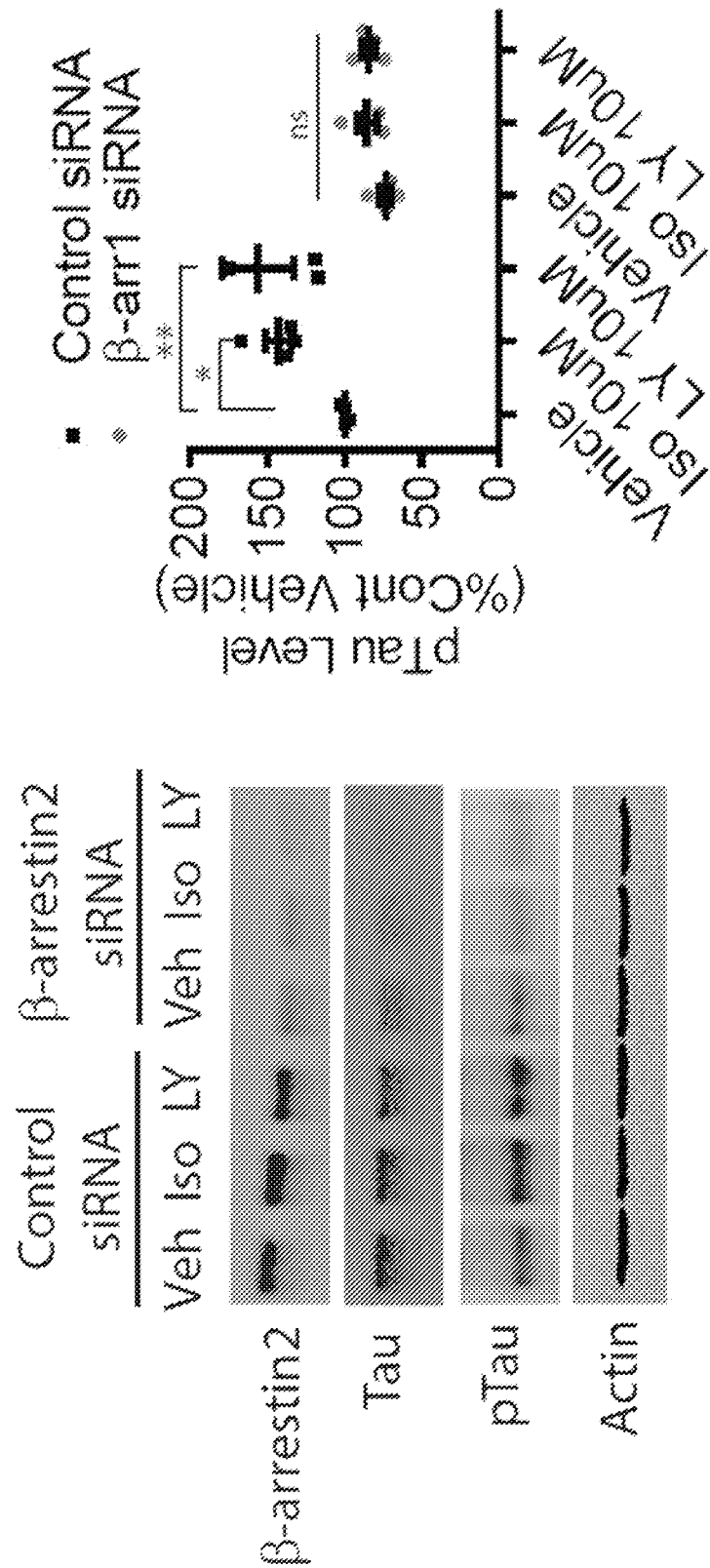

At present, it is not clear how different GPCRs, such as β2AR and mGluR2, and their agonists alter tau phosphorylation. One commonality of downstream signaling between these GPCRs is β-arrestin1 and β-arrestin2, which were initially identified and characterized based on its function to internalize and desensitize GPCRs, including β2AR (Lohse, M. J. et al. J Biol Chem (1992) 267:8558-8564) and mGluR2 (Iacovelli, L. et al. Mol Pharmacol (2009) 75:991-1003). To test whether β-arrestin1 and/or β-arrestin2 is required for β2AR-mediated regulation of tau, Hela-V5-tau cells were transfected with control siRNA or β-arrestin1 siRNA and treated either vehicle or 10 µM Iso. While Iso expectedly increased tau phosphorylation in control siRNA transfected cells, β-arrestin1 siRNA transfected cells failed to respond to Iso, indicating that β-arrestin1 is required for Iso-induced increase in phospho-tau (FIGS. 13A,13B). Interestingly, it was also found β-arrestin1 siRNA significantly reduced total tau levels (FIGS. 13A,13B). Next, assessed was whether β-arrestin1 is required for mGluR2-mediated tau phosphorylation. LY-379,268 treatment increased phospho-tau; however, siRNA-mediated knockdown of β-arrestin1 again resulted in a failure to respond to LY-379,268 such that both total and phospho-tau levels were equally reduced with or without LY-379,268 treatment (FIGS. 13C,13D). Next, Hela-V5-tau cells were transfected with control siRNA or β-arrestin2 siRNA and treated vehicle, 10 µM Iso or LY-379, 268. As expected, both Iso and LY-379,268 treatment increased tau phosphorylation; however, siRNA-mediated knockdown of β-arrestin1 failed to increase tau phosphorylation (FIGS. 13E,13F). These data indicate that both β-arrestin1 and β-arrestin2 is required for mGluR2 and β2AR-mediated increase in pathogenic tau.

Elevated β-Arrestin1 and Colocalization with Pathogenic Tau (AT8) in FTLD-Tau

Figure 14A:
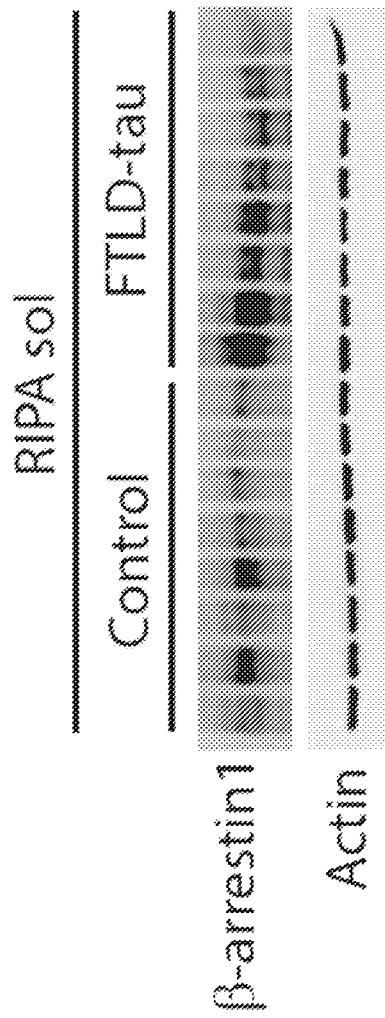
FIGS. 14A to 14G show increased β-arrestin1 in FTLD-tau patient brains.
Figure 14B:
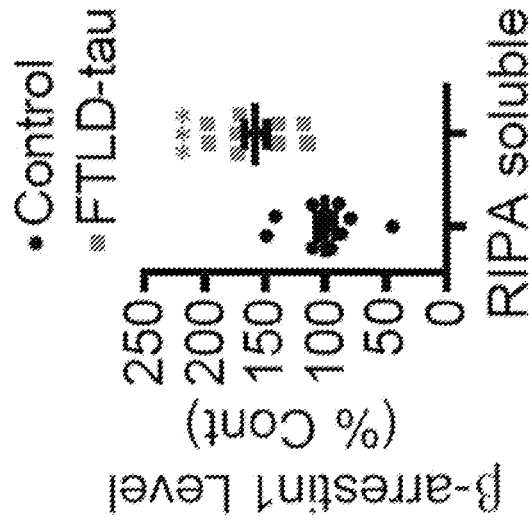
Figure 14C:
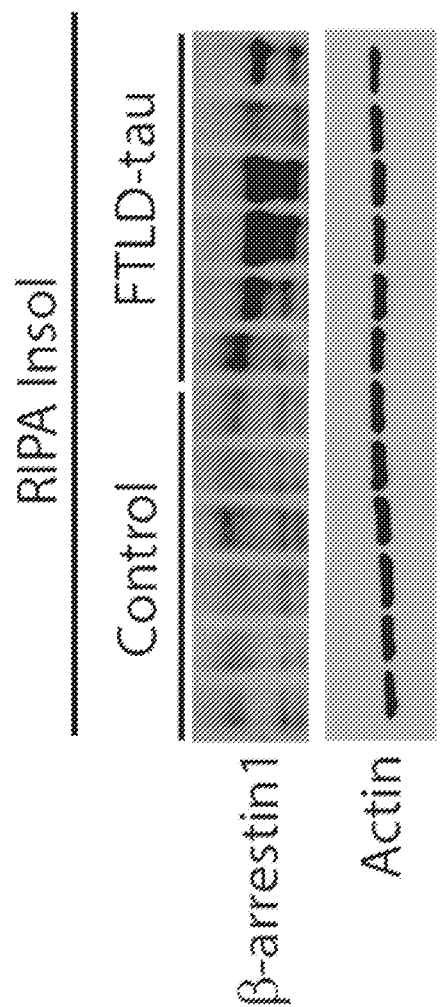
Figure 14D:
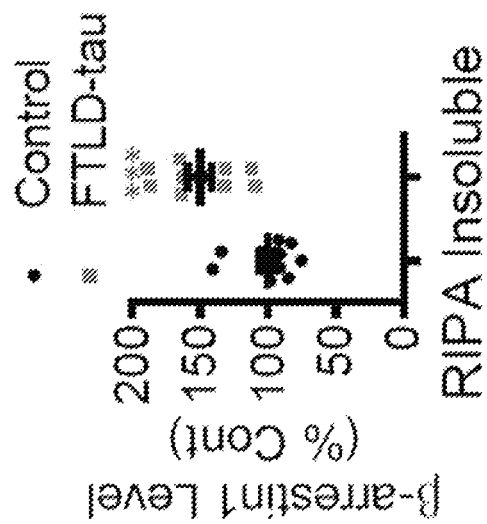
Figure 14F:
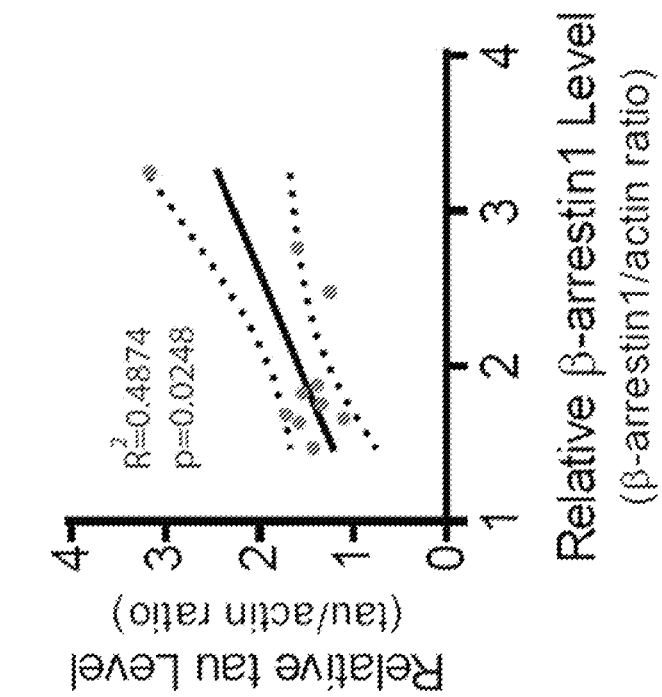
Figure 14E:
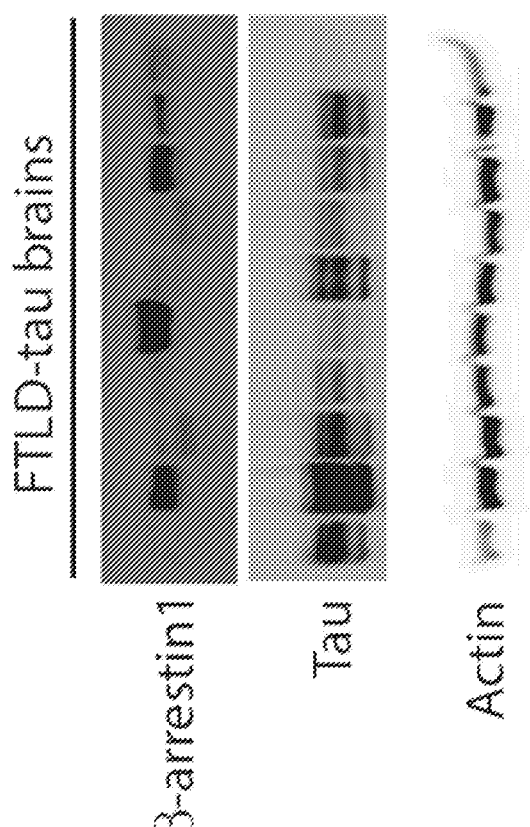
Figure 14G:
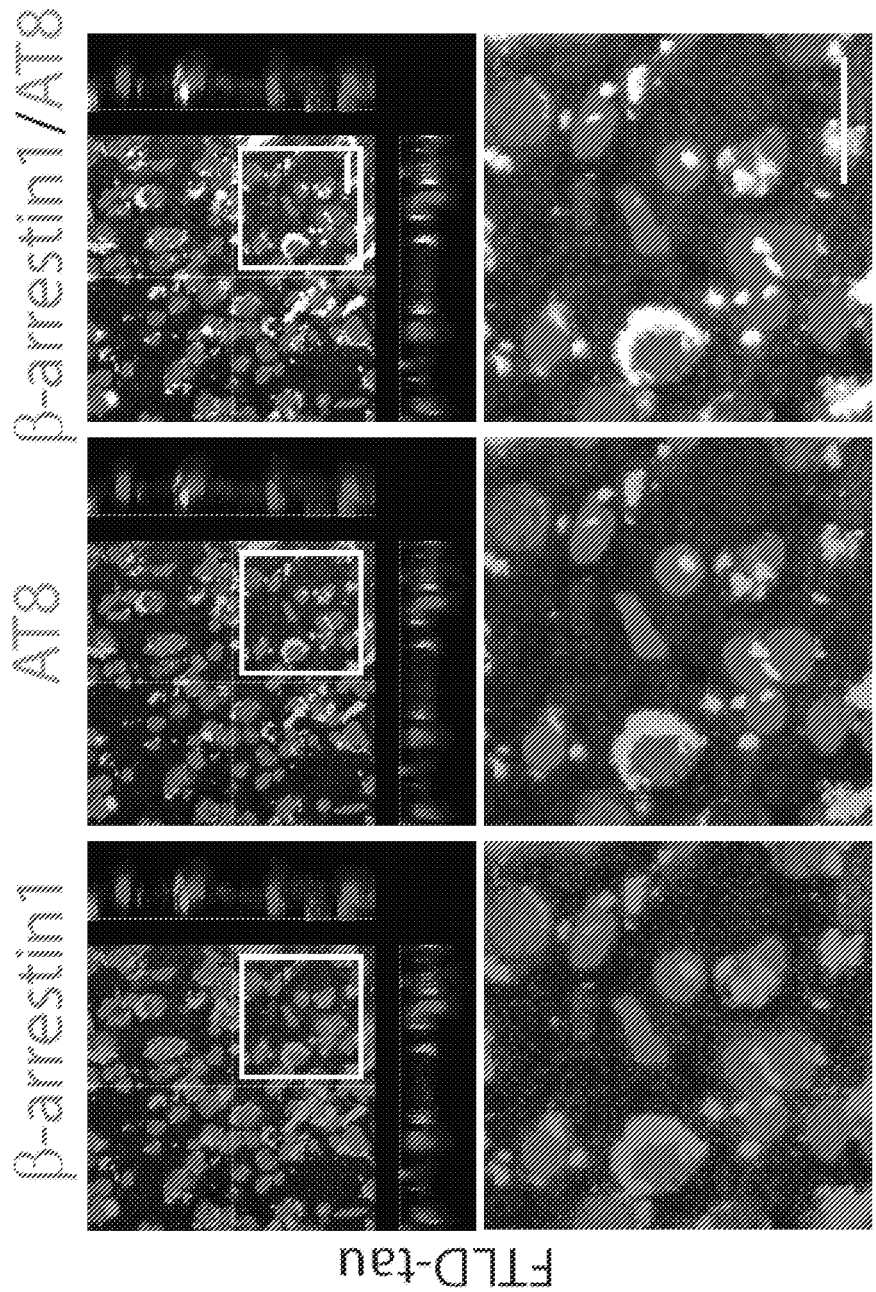
Figures 22A, 22B:
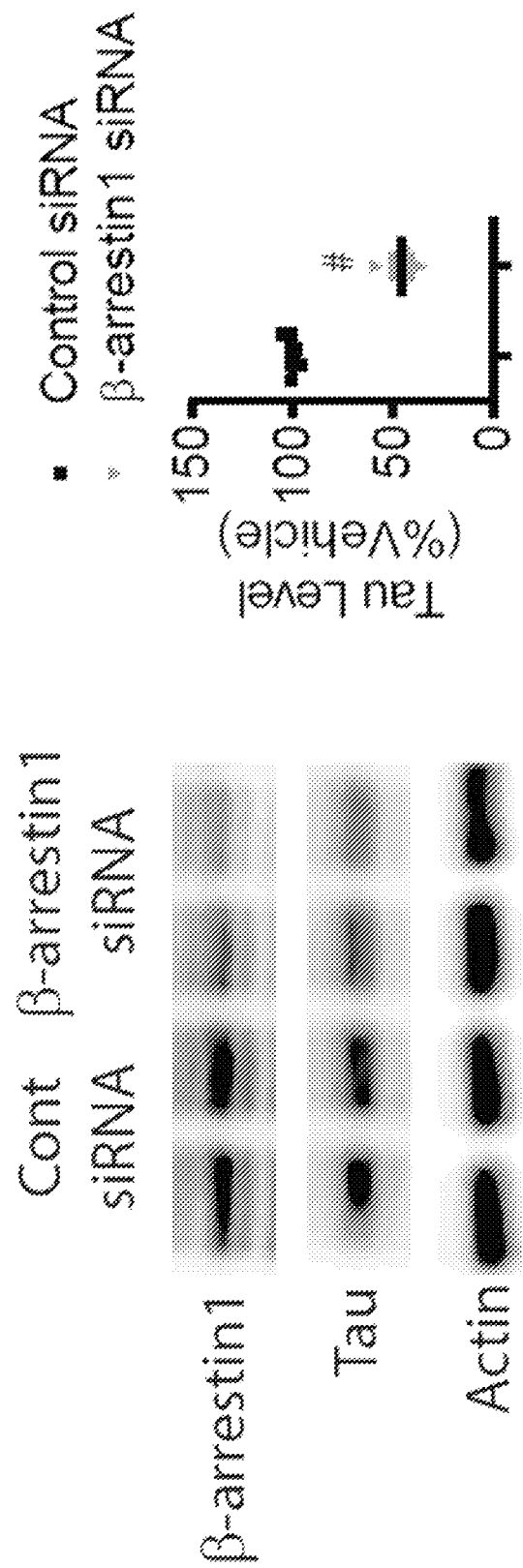
FIGS. 22A and 22B show reduced β-arrestin1 decreases tau levels.
Figure 23A:
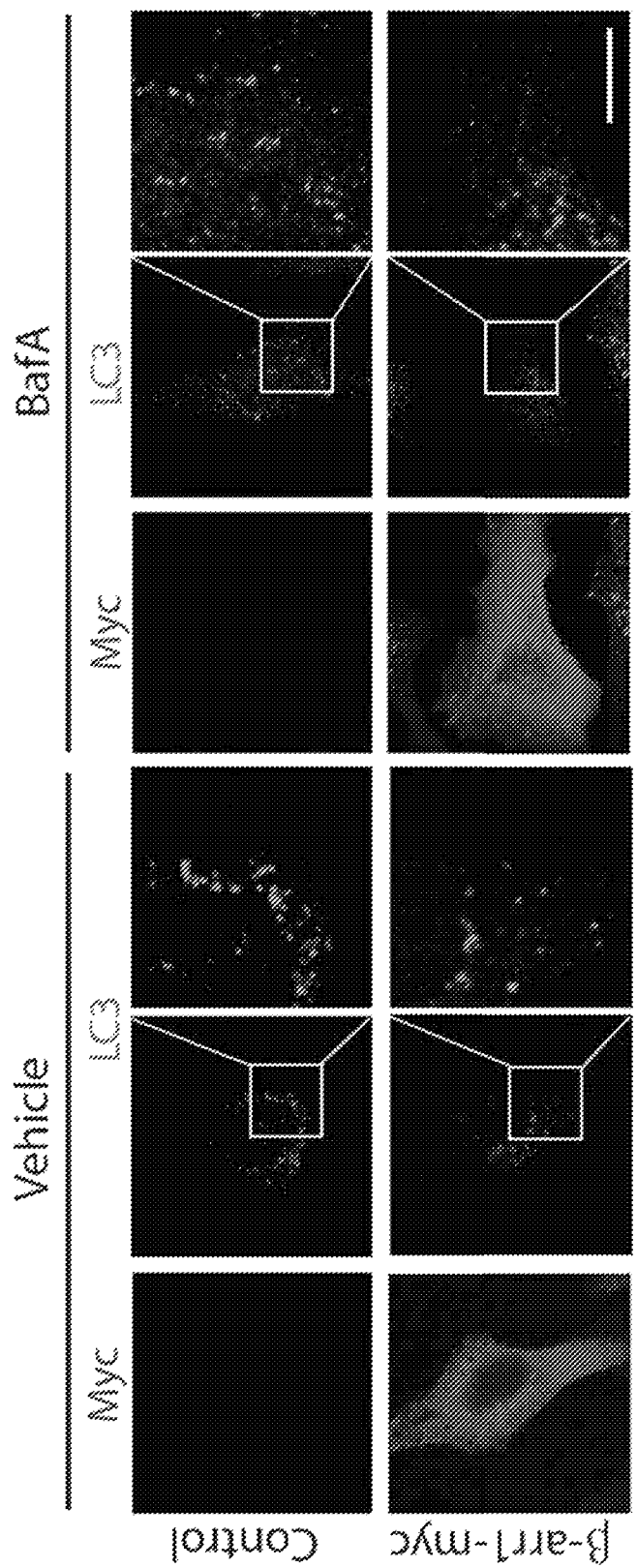
FIGS. 23A to 23C show increased β-arrestin1 impairs LC3-mediated autophagy.
Figure 23B:
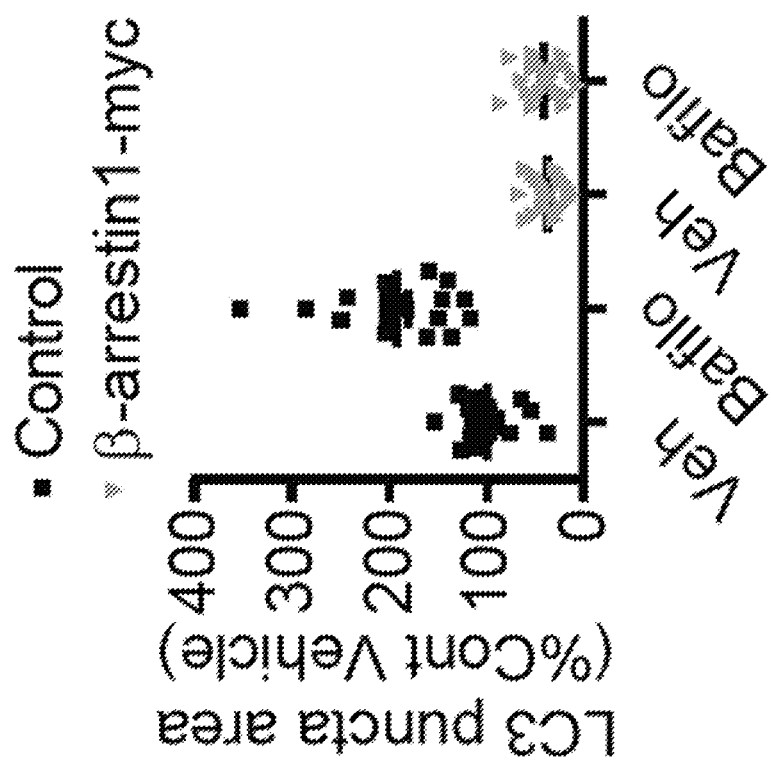
Figure 23C:
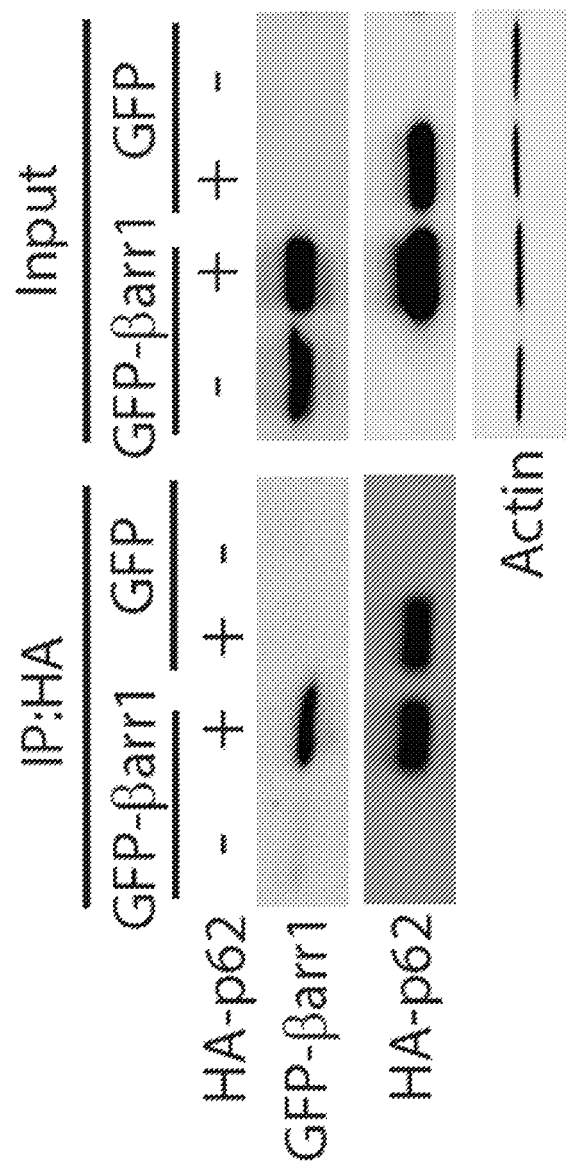

The finding that β-arrestin1 and β-arrestin2 mediate the increase in pathogenic tau in response to GPCR stimulation prompted us to assess β-arrestin1 levels in FTLD-tau patients. β-arrestin2 levels in the frontal cortex of FTLD-tau patients were significantly increased compare to control subjects. However, β-arrestin1 levels has not been examined. Therefore, β-arrestin1 levels were assess in FTLD-tau patients (n=10) compare to the frontal cortex of control subjects (n=12). Interestingly, compared to control subjects (n=12), FTLD-tau brains (n=10) showed >50% increase in β-arrestin1 protein in RIPA-soluble extracts (FIGS. 14A, 14B) and RIPA-insoluble extracts (FIGS. 14C,14D). Interestingly, the levels of insoluble β-arrestin1 closely mirrored those of insoluble tau in FTLD-tau, such that insoluble β-arrestin1 and tau levels significantly correlated with a coefficient of $R^2=0.4874$ by linear regression analysis (FIGS. 14E,14F), suggesting a functional connection between β-arrestin1 and tau in brain. To assess the spatial relationship between β-arrestin1 and tau, FTLD-tau frontal gyrus were next stained for phospho-tau (AT8 antibody: pS202/pT205-tau) and β-arrestin1. Surprisingly, confocal images of AT8+ tau aggregates and β-arrestin1 nearly perfectly colocalized (FIG. 14G) as confirmed by Z-stacked images in 1 micron increments (FIG. 14G). The absence of AT8+ tau pathology in control brains was confirmed, despite the salient presence of β-arrestin1 staining in the same sections (FIG. 22A), while secondary antibody only staining failed to show any immunoreactivity (FIG. 22B).

β-Arrestin1 Promotes the Accumulation of Pathogenic Tau in Primary Neurons

Figures 15A, 15B:
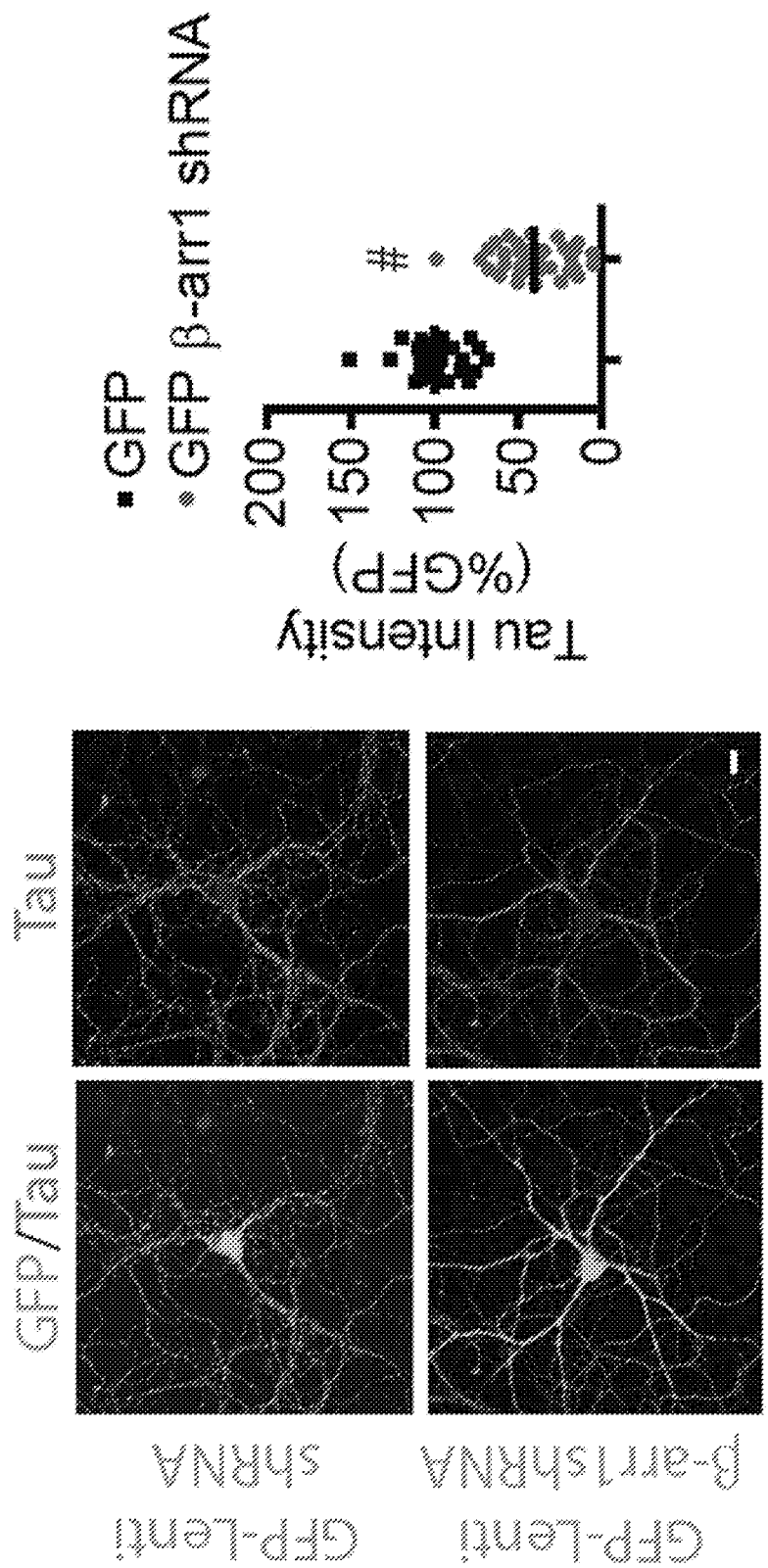
FIGS. 15A to 15G show β-arrestin1 increases tau levels.
Figures 15C, 15D:
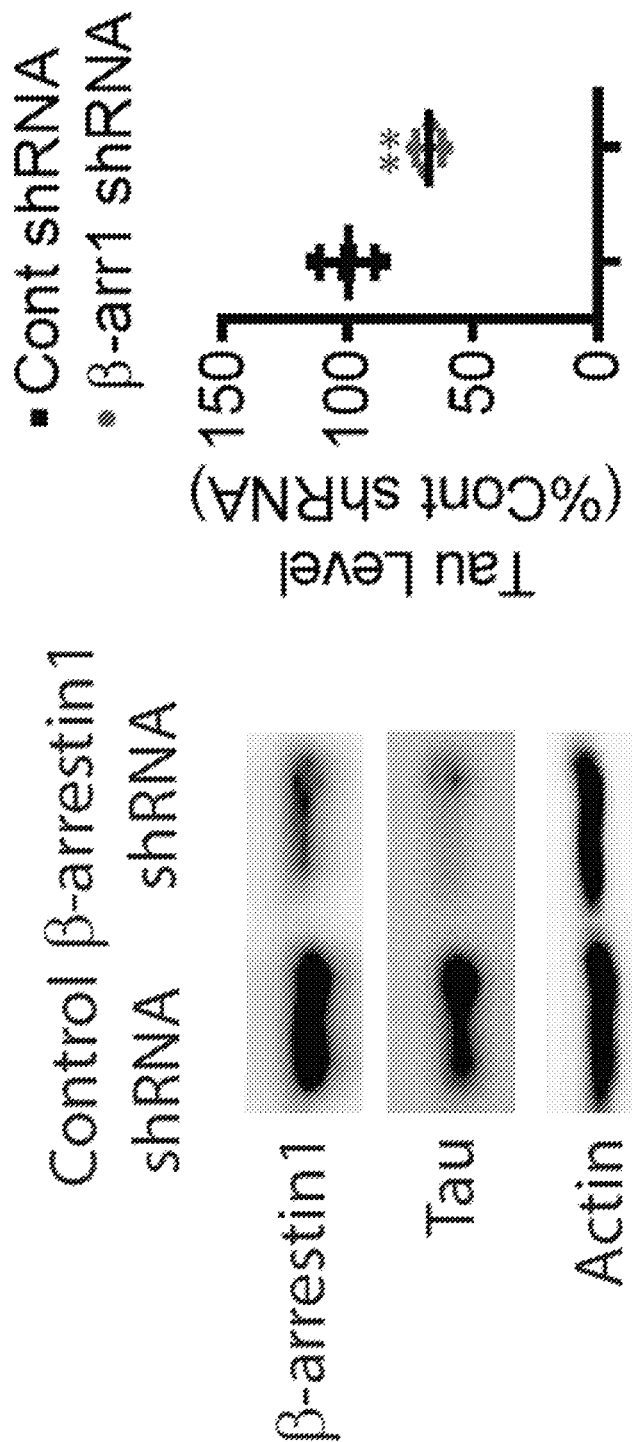
Figure 15G:
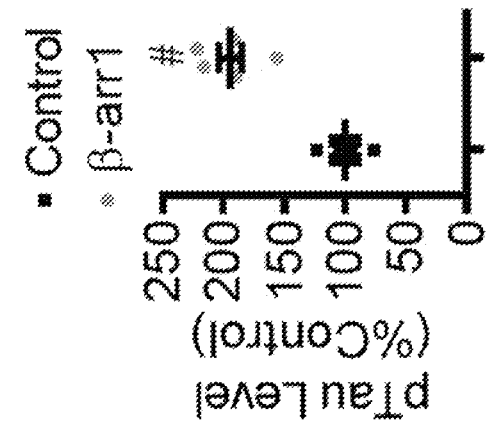
Figure 15F:
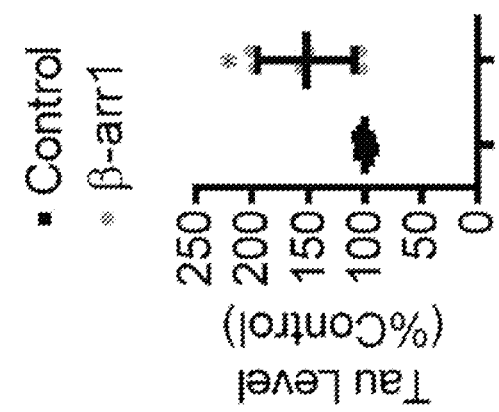
Figure 15E:
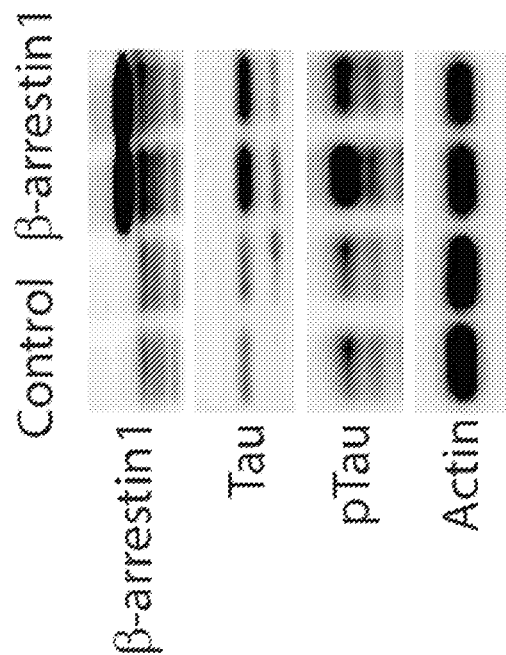

Given that β-arrestin1 was significantly increased in FTLD-tau patients, the next thing assessed was whether endogenous β-arrestin1 increases tau levels. Hela-V5-tau cells were transfected with either control siRNA or β-arrestin1 siRNA. As shown by immunoblotting, β-arrestin1 depletion significantly decreased tau (FIGS. 13A,13C, 23A, 23B). To confirm the relevance of these results in neurons, lentivirus-mediated shRNA knockdown of β-arrestin1 in tauP301S hippocampal primary neurons was used. β-arrestin1 shRNA transduced tauP301S neurons showed a significant approximately 50% decrease in immunoreactivity for tau in neuronal cell bodies and processes compared to control shRNA transduced neurons (FIGS. 15A,15B). It was also confirmed that β-arrestin1 shRNA transduced tauP301S cortical primary neurons exhibit significantly reduced tau levels by Western blotting (FIGS. 15C,15D). As β-arrestin1 levels were increased in FTLD-tau, the next thing determined was whether increased β-arrestin1 conversely enhances tau levels. Transient transfection of β-arrestin1 in Hela-V5-tau cells significantly increased total tau by ~50% (FIGS. 15E,15F) and phospho-tau by nearly 2-fold (FIGS. 15E,15G). These results collectively show that β-arrestin1 is not only increased and colocalized with pathogenic tau in FTLD-tau brains but that β-arrestin1-mediated tau regulation underlies both steady-state and GPCR (β2AR & mGluR2) agonist-induced increased in tau.

Genetic Reduction of β-Arrestin1 Ameliorates Tauopathy In Vivo

Figure 16B:
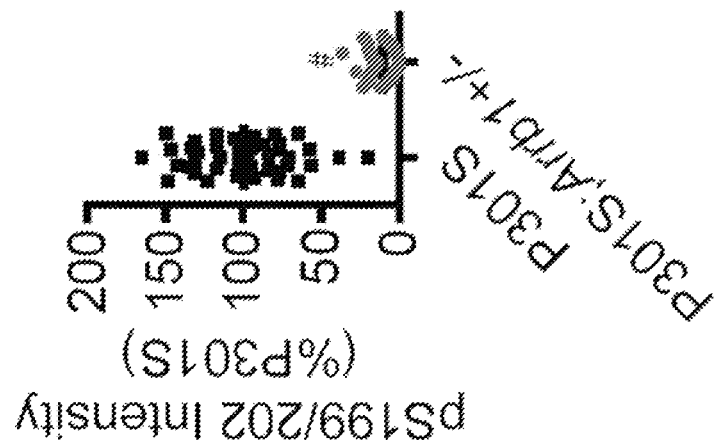
Figure 16A:
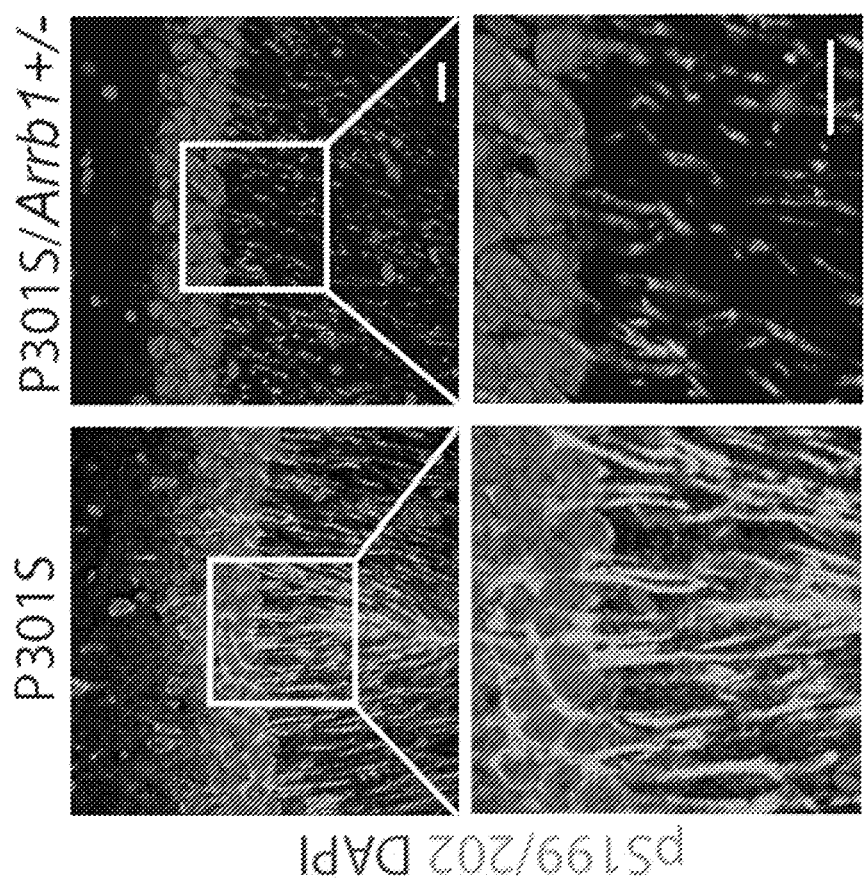
Figure 16E:
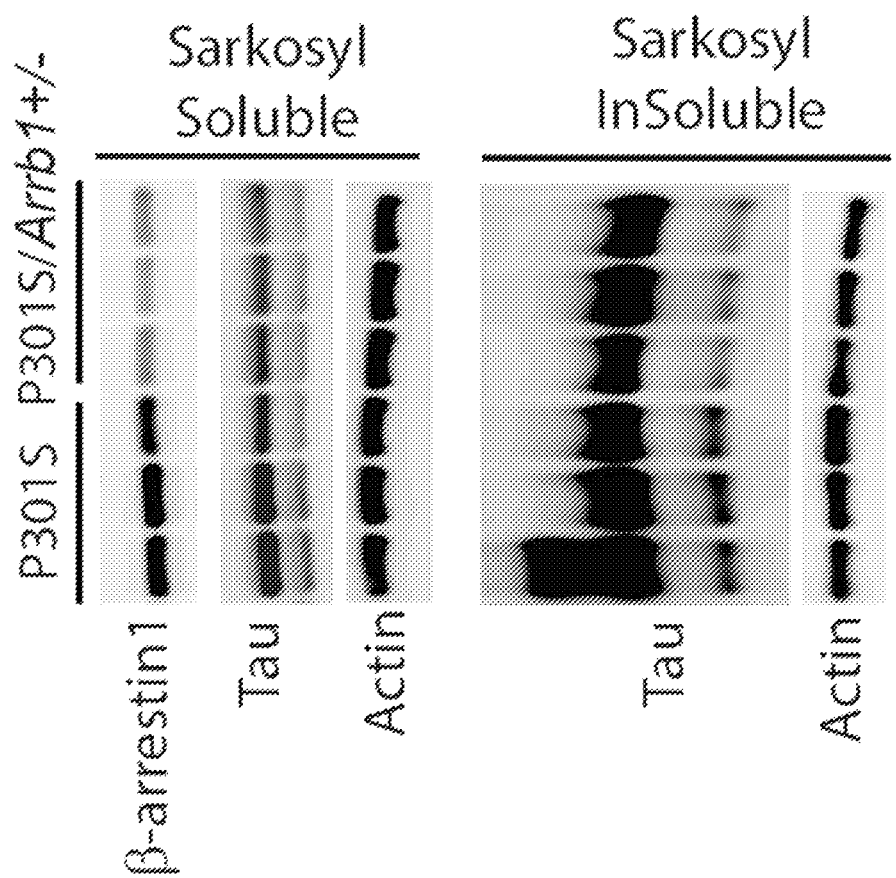

The above data showed that increased β-arrestin1 increases tau and decreased β-arrestin1 reduces tau. Therefore, next assessed was the physiological effects of reducing endogenous β-arrestin1 on tauopathy in vivo. Hemizygous tauP301S transgenic mice were crossed with β-arrestin1$^{+/-}$ (Arrb1$^{+/-}$) mice to generate tauP301S and tauP301S; Arrb1$^{+/-}$ mice. TauP301S mice show tauopathy starting at 4 months of age, which progressively worsens (Yoshiyama, Y. et al. Neuron (2007) 53:337-351). Immunohistochemistry was first performed to detect phospho-tau (pS199/202) from hippocampus of 7-month-old tauP301S and tauP301S; Arrb1$^{+/-}$ littermates. Indeed, tauP301S/Arrb1$^{+/-}$ mice exhibited approximately 60% reduction in phospho-tau immunoreactivity compared to tauP301S littermates (FIGS. 16A, 16B). This finding was further confirmed using sarkosyl extraction. Consistent with immunohistochemistical results, sarkosyl-insoluble tau was significantly reduced by approximately 40% in tauP301S/Arrb1$^{-/-}$ compared to tauP301S littermates (FIGS. 16C,16E). Sarkosyl-soluble tau was also significantly reduced by approximately 40% in tauP301S/ Arrb1$^{+/-}$ compared to tauP301S littermates (FIGS. 16C, 16D).

Figure 16G:
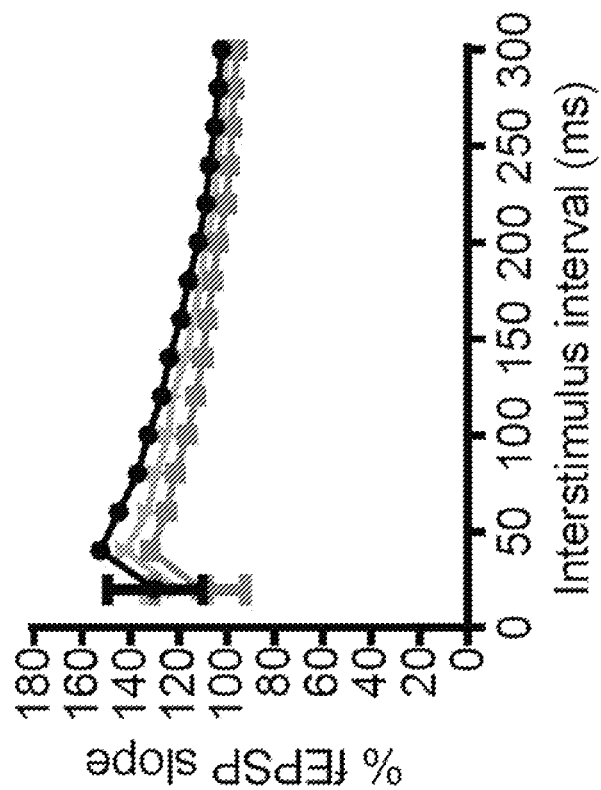
Figure 16F:
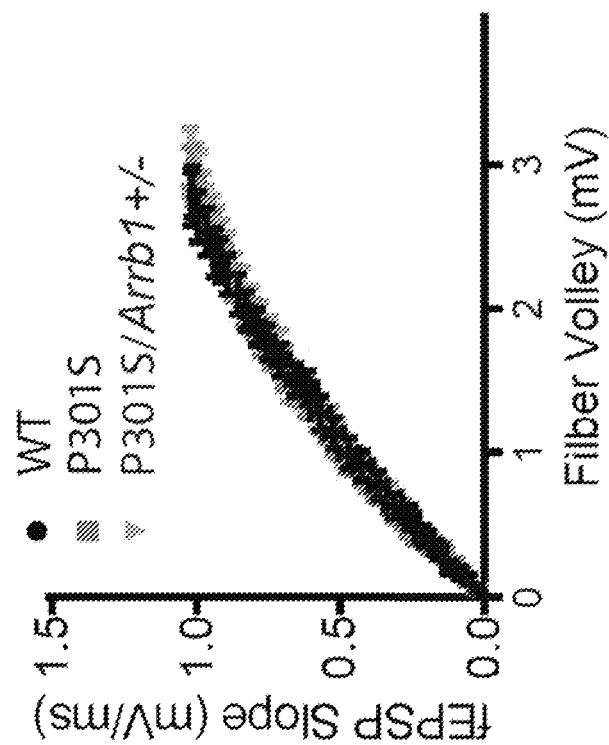
Figure 16H:
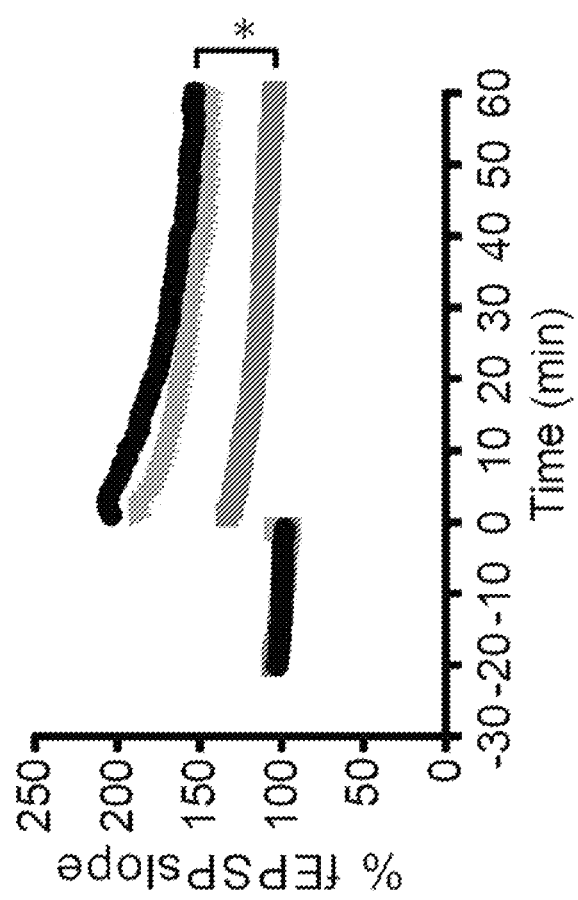
Figure 16I:
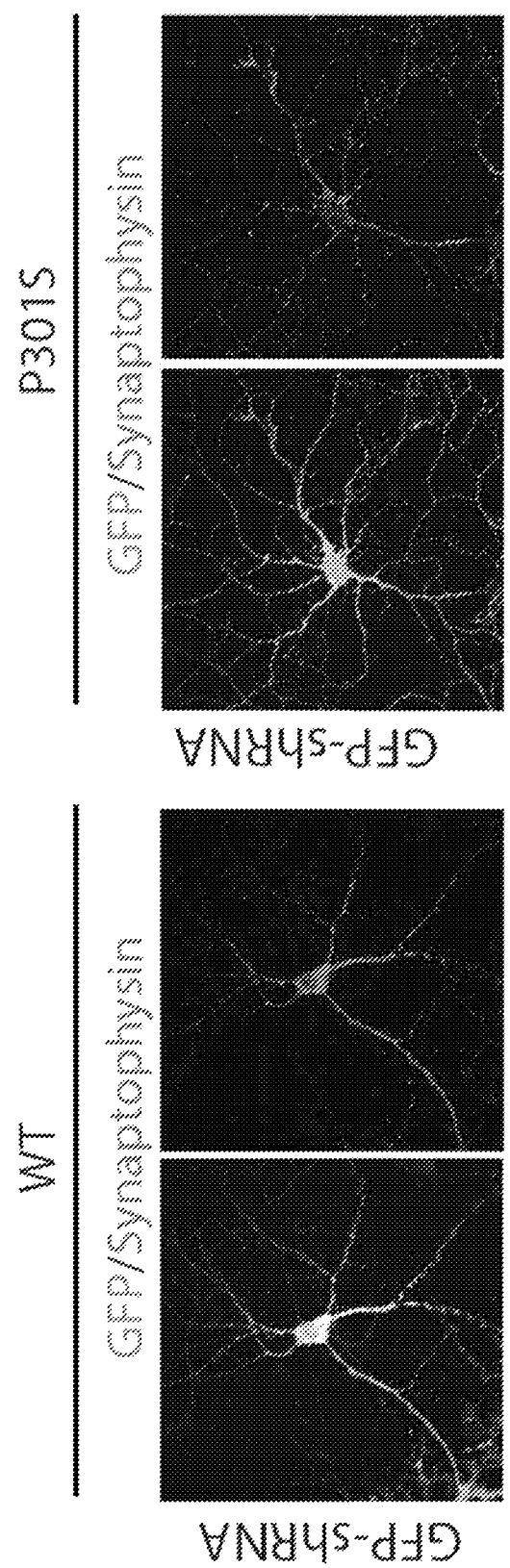
Figure 16J:
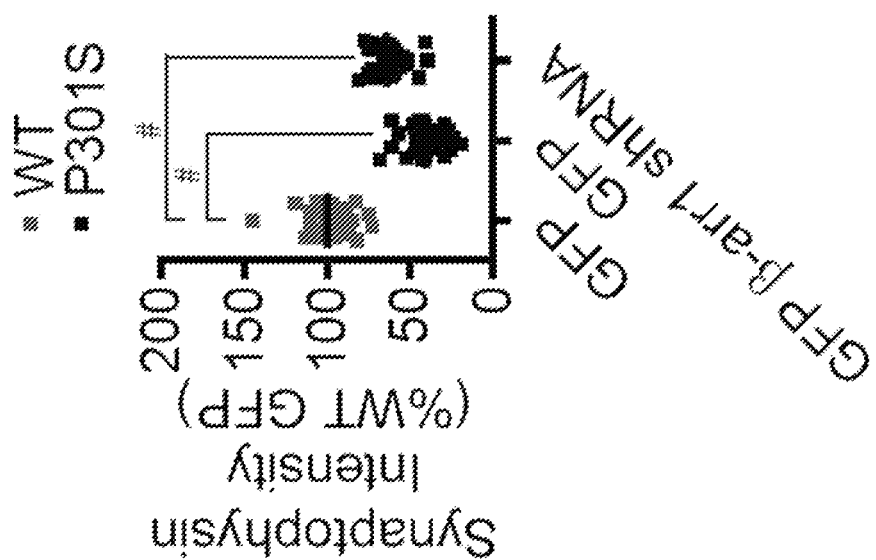
Figures 17A, 17B:
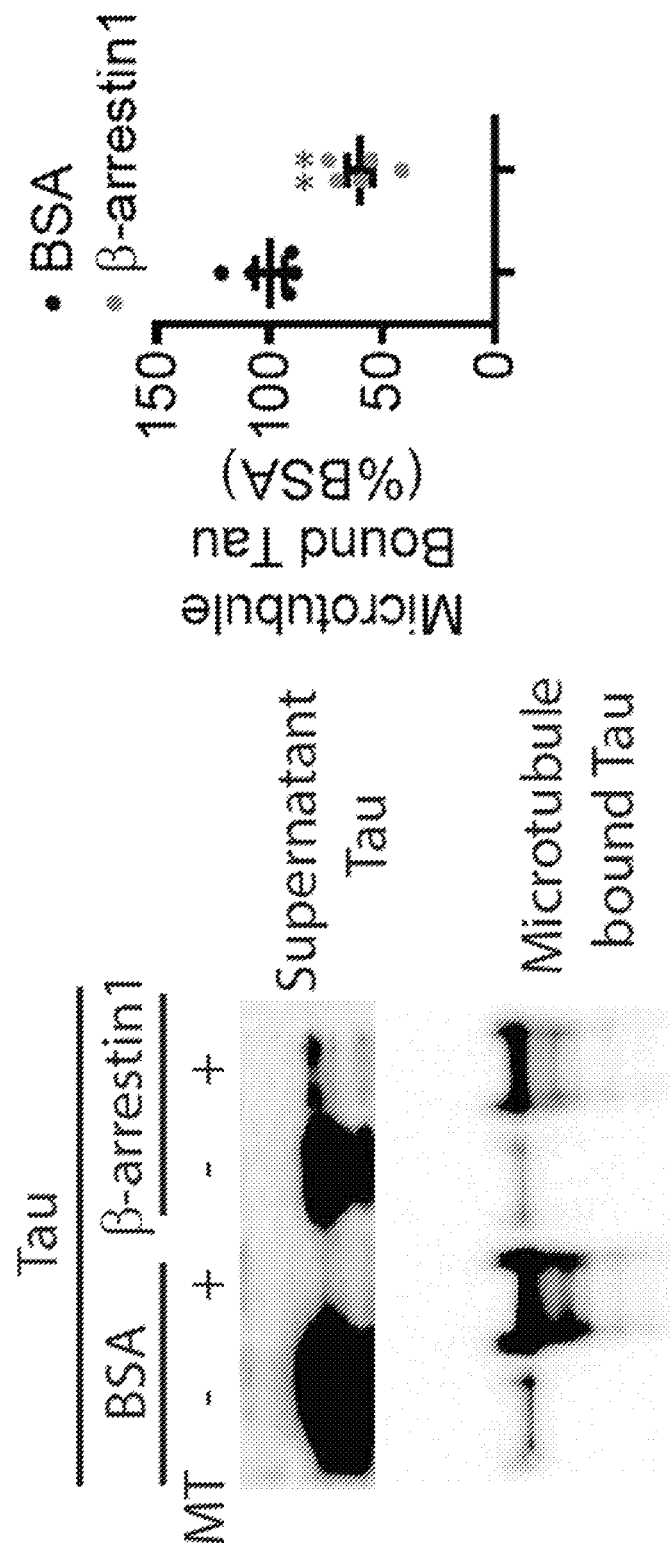
FIGS. 17A to 17F show β-arrestin1 inhibits tau-induced tubulin polymerization and disrupts microtubule stability.
Figure 17D:
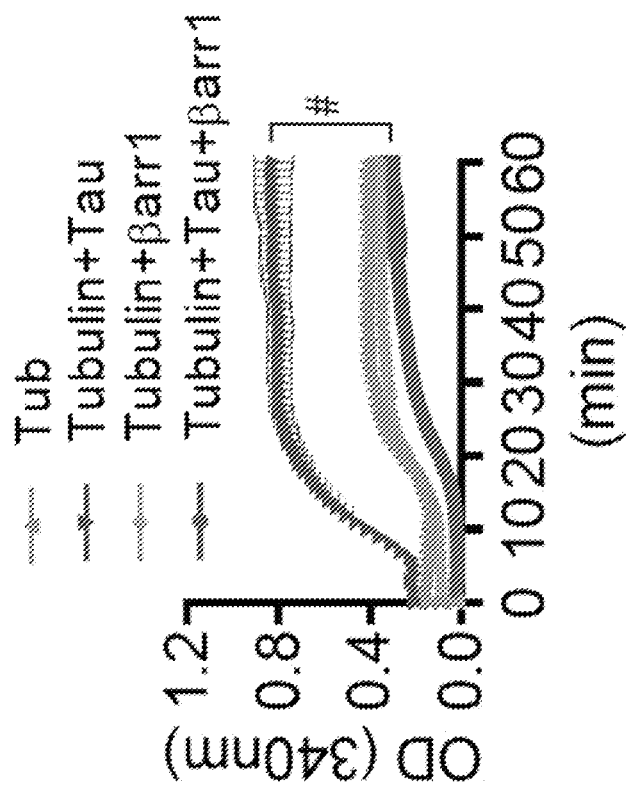
Figure 17C:
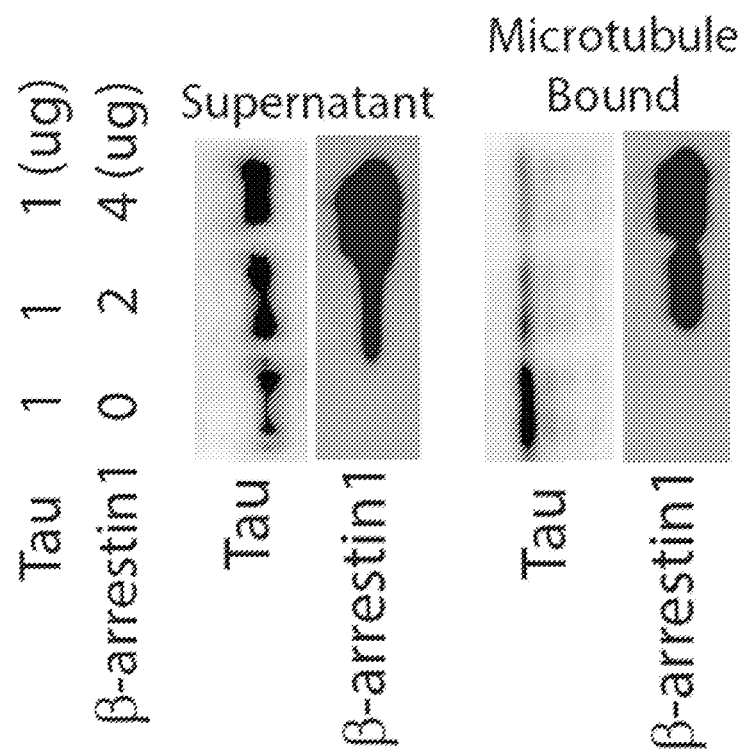

Genetic Reduction of β-Arrestin1 Rescues Functional Synaptic Deficits in tauP301S Mice The initial characterization of the tauP301S mice demonstrated impaired paired-pulse facilitation (PPF) and long-term potentiation (LTP) at 6 months of age (Yoshiyama, Y. et al. Neuron (2007) 53:337-351). Studies later showed that tauP301S mice exhibit pronounced LTP defects even at 3 months of age (Woo, J. A. et al. Hum Mol Genet (2017) 26:3973-3988; Woo, J. A. et al. Commun Biol (2019) 2:112). To assess functional changes in synaptic plasticity, electrophysiological recordings of the CA3-CA1 Schaffer collateral pathway of acute brain slices of 4-month old wild type, tauP301S, and tauP301; Arrb1$^{+/-}$ mice was performed. Initial input-output (IO) analysis indicated no significant differences among WT, tauP301S, tauP301S/Arrb1$^{+/-}$ littermate slices (FIG. 16F). In PPF experiments, significant reductions in fEPSP slope in tauP301S slices was observed in all interstimulus intervals compared to wild type slices, which was accentuated in earlier interstimulus intervals (FIG. 16G) similar to that previously reported (Woo, J. A. et al. Hum Mol Genet (2017) 26:3973-3988; Woo, J. A. et al. Commun Biol (2019) 2:112). In tauP301S; Arrb1$^{+/-}$ slices, there was significantly stronger PFF at interstimulus intervals ranging from 20-120 ms compared to tauP301S, indicating a partial rescue. Long-term potentiation (LTP) recordings using theta burst stimulation showed tauP301S slices to be strongly impaired in both induction and maintenance of LTP compared to wild type slices (FIG. 16H). However, tauP301S/Arrb1$^{+/-}$ slices showed significantly restored LTP compared to tauP301S litter mates, nearly to the level of wild type slices (FIG. 16H). These functional synaptic plasticity results were corroborated in mature DIV21 primary hippocampal neurons stained for synaptophysin. Specifically, tauP301S hippocampal primary neurons (control GFP transduced) exhibited significantly reduced synaptophysin immunoreactivity in primary neurites compared to that in wild type neurites (control GFP transduced). In contrast, tauP301S neurons transduced with β-arrestin1-shRNA-GFP significantly restored synaptophysin immunoreactivity nearly to wild type control levels (FIGS. 16I, 16J)

β-Arrestin1 Promotes the Dissociation of Tau from Microtubules and Inhibits Tau-Induced Microtubule Assembly Tau is a microtubule associated protein that stabilizes microtubules (Cleveland, D. W., et al. J Mol Biol (1977) 116:207-225). However, in tauopathies including AD, tau first dissociates from microtubules, mislocalizes from somatoaxonal to somatodendritic compartments (Ballatore, C., et al. Nat Rev Neurosci (2007) 8:663-672; Biernat, J. & Mandelkow, E. M. Mol Biol Cell (1999) 10:727-740) and becomes progressively insoluble to ultimately form filamentous aggregates (Alonso, A. D., et al. Proc Natl Acad Sci USA (1997) 94:298-303). Arrestins exist in three distinct states in cells: (1) free unbound, (2) GPCR-bound, and (3) microtubule-bound, each with the potential for different signaling capabilities (Hanson, S. M. et al. J Mol Biol (2007) 368:375-387; Gao, H. et al. Mol Cell (2004) 14:303-317; Song, X., et al. J Neurochem (2007) 103:1053-1062). Specifically, β-arrestin1 binds directly to microtubules and recruits Mdm2 and ERK2 (Hanson, S. M. et al. J Mol Biol (2007) 368:375-387; Gurevich, V. V. & Gurevich, E. V. Curr Protoc Pharmacol (2014) 67, Unit 2 10 11-19). Hence, whether the binding of β-arrestin1 to microtubules alters the binding of tau to microtubules was first assessed. Thus, recombinant proteins to perform microtuble binding experiments was used. 1 μg of recombinant His-tau (4R) was incubated with purified microtubules plus BSA control or recombinant β-arrestin1 for 30 minutes. After incubation, the sample was subjected to centrifugation at 100,000 g. Supernatant contains microtubule-unbound proteins and pellet contains microtubule-bound proteins. Remarkably, β-arrestin1 significantly reduced the amount of tau bound to the microtubule pellet by approximately 45%, while increasing the amount of free tau in the supernatant (FIG. 17A,17B). The inhibitory effect of β-arrestin1 on tau binding to microtubules was dose-dependent, as increasing amounts of β-arrestin1 progressively reduced tau bound to microtubules (FIG. 17C). Next, assessed was whether β-arrestin1 alters tau-induced microtubule assembly in vitro. As expected, tubulin alone exhibited time-dependent polymerization into microtubules, which greatly accelerated with the addition of recombinant tau (FIG. 17D). However, addition of β-arrestin1 together with tau completely inhibited tau-induced acceleration of microtubule assembly (FIG. 17D). Addition of β-arrestin1 alone with tubulin also weakly reduced tubulin polymerization compared to tubulin alone, suggesting that β-arrestin1/tubulin binding may have a minor inhibitory role in microtubule assembly.

Figure 17E:
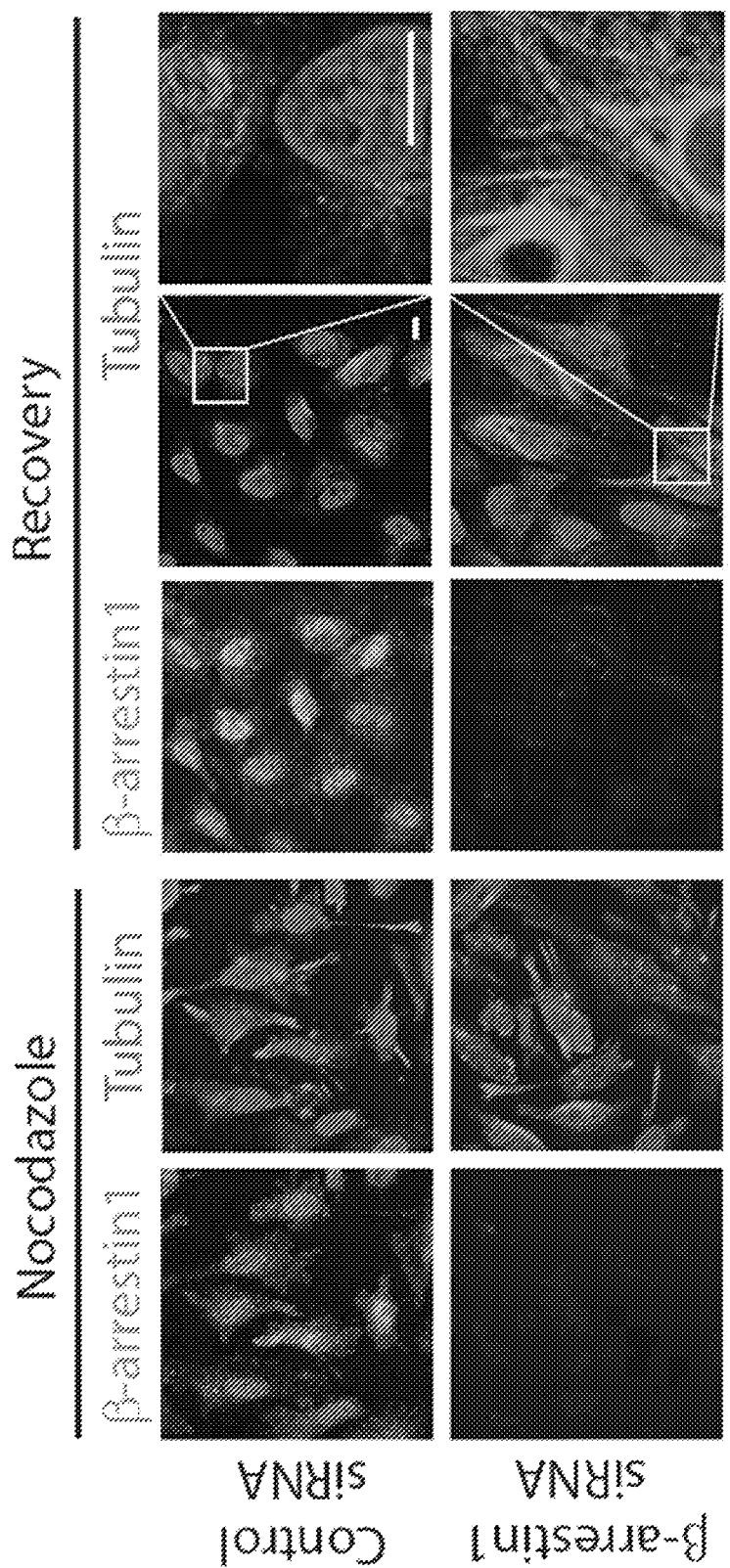
Figure 17F:
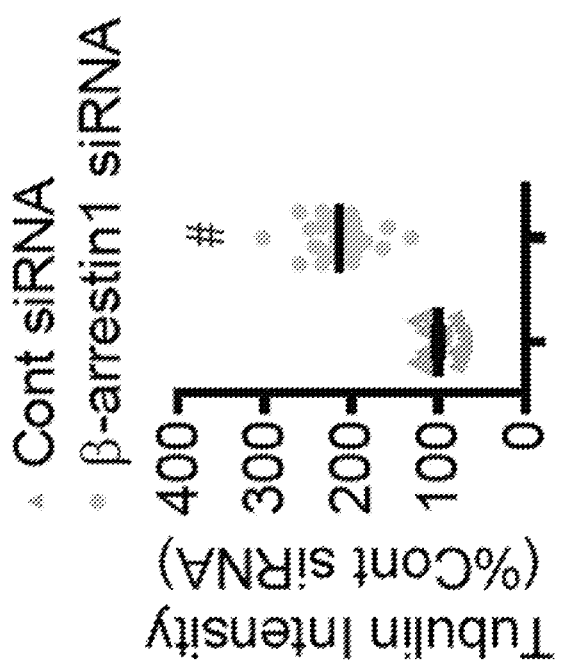
Figures 18A, 18B:
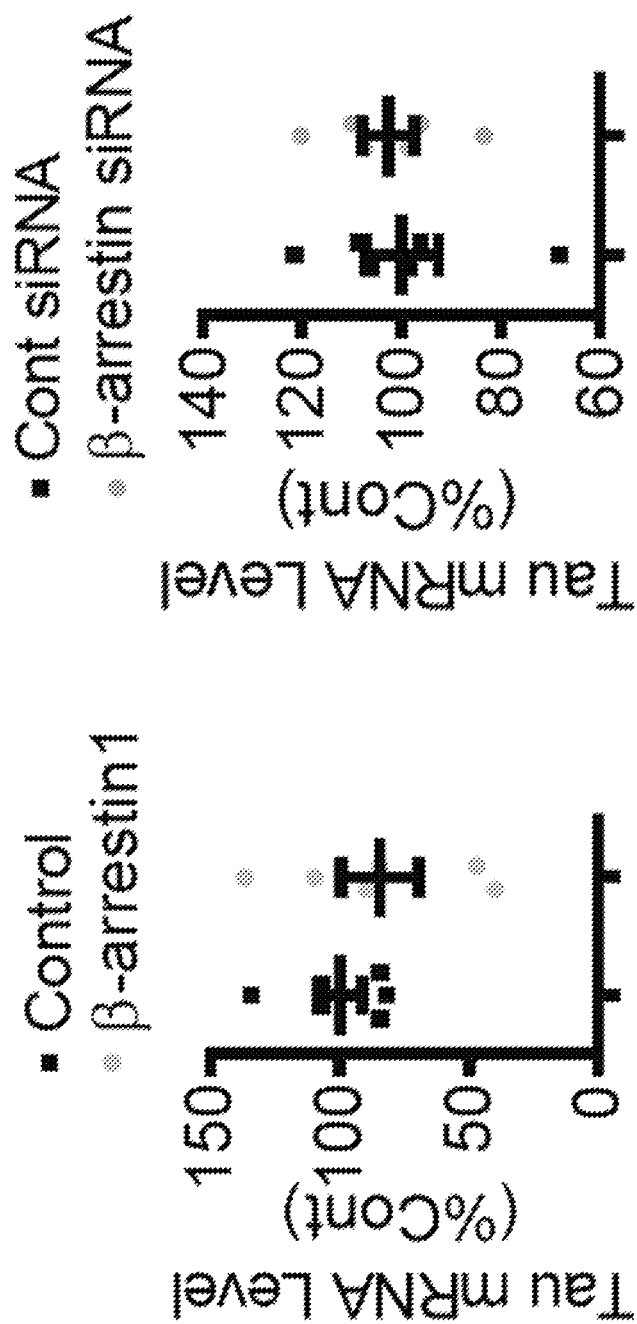
FIGS. 18A to 18N show β-arrestin1 inhibits autophagy-mediated tau clearance.
FIG. 18B shows quantification of β-arrestin1 mRNA levels by qRT-PCR in Hela-V5-tau cells transfected with either control siRNA or β-arrestin1 siRNA. n=6 independent experiments.
Figure 18D:
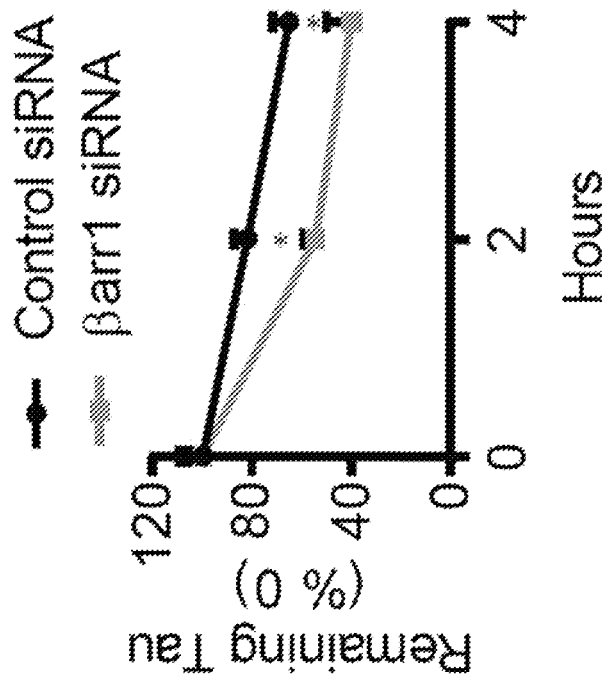
FIG. 18D shows quantification of tau remaining after cycloheximide treatment. n=3 independent experiments. *p<0.05. 2-way repeated measures ANOVA.
Figure 18C:
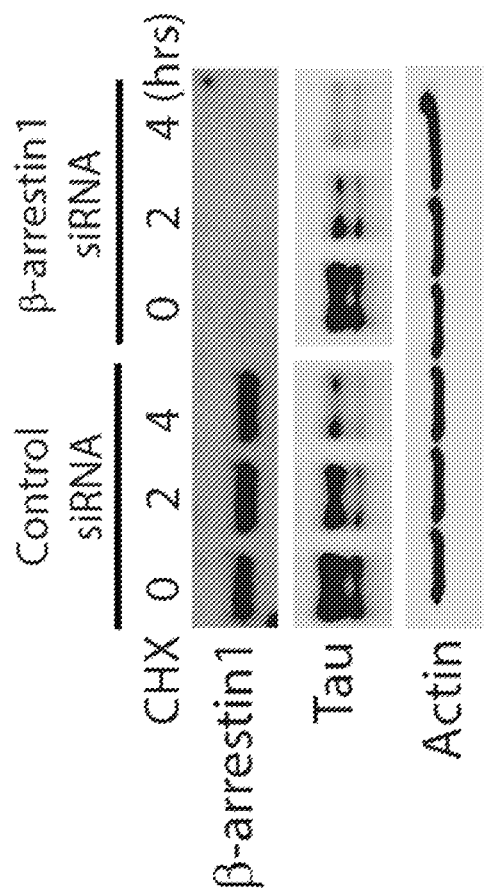
FIG. 18C shows Hela-V5-tau cells transfected with control siRNA or β-arrestin1 siRNA and treated with cycloheximide (100 μg/ml) for 2 hours and 4 hours. Cells were subjected to immunoblotting for β-arrestin1, tau, and actin. Representative blots are shown.

To determine whether such inhibitory action of β-arrestin1 in tau-dependent microtubule assembly in vitro can be seen in cells, Hela-V5-tau cells were transfected with control siRNA or β-arrestin1 siRNA. After transfection, cells were treated with nocodazole for 30 min, which induces the rapid disassembly of microtubules (Woo, J. A. et al. Commun Biol (2019) 2:112). After 30 minutes, the media containing nocodazole was washed out and the cells allowed to recover for 1 hour. Upon nocodazole treatment, staining for tubulin appeared highly disorganized in both control or β-arrestin1 siRNA transfected conditions (FIG. 17E). Upon washout of nocodazole for 1 h, reassembly of microtubules was readily visible as seen by salient filamentous microtubule staining in perinuclear regions, which was significantly increased by nearly 3-fold in β-arrestin1 siRNA transfected cells compared to control siRNA transfected cells (FIGS. 17E,17F). These results in transfected cells and in vitro therefore indicate that β-arrestin1 promotes the dissociation of tau from microtubules, which both inhibits microtubule assembly and enables tau missorting.

β-Arrestin1 does not Alter Tau mRNA but Increases Tau Stability by Disrupting p62 Self-Interaction and Impeding p62 Flux Although tau dissociation from microtubules deregulates microtubule dynamics and is necessary for tau missorting and aggregation (Wang, Y. & Mandelkow, E. Nat Rev Neurosci (2016) 17:5-21), such mechanism nevertheless does not readily explain the increase in total tau secondary to increased β-arrestin1. Hence, whether β-arrestin1 alters tau mRNA levels by qRT-PCR for tau mRNA was tested. However, no changes in tau mRNA were observed either after β-arrestin1 overexpression or knockdown (FIGS. 18A, 18B). Next assessed was whether endogenous β-arrestin1 alters tau turnover. Indeed, cycloheximide (CHX) chase experiments showed that β-arrestin1 siRNA significantly facilitates the turnover of tau (FIGS. 18C,18D), indicating that endogenous β-arrestin1 enhances tau levels by increasing its stability.

Figure 18E:
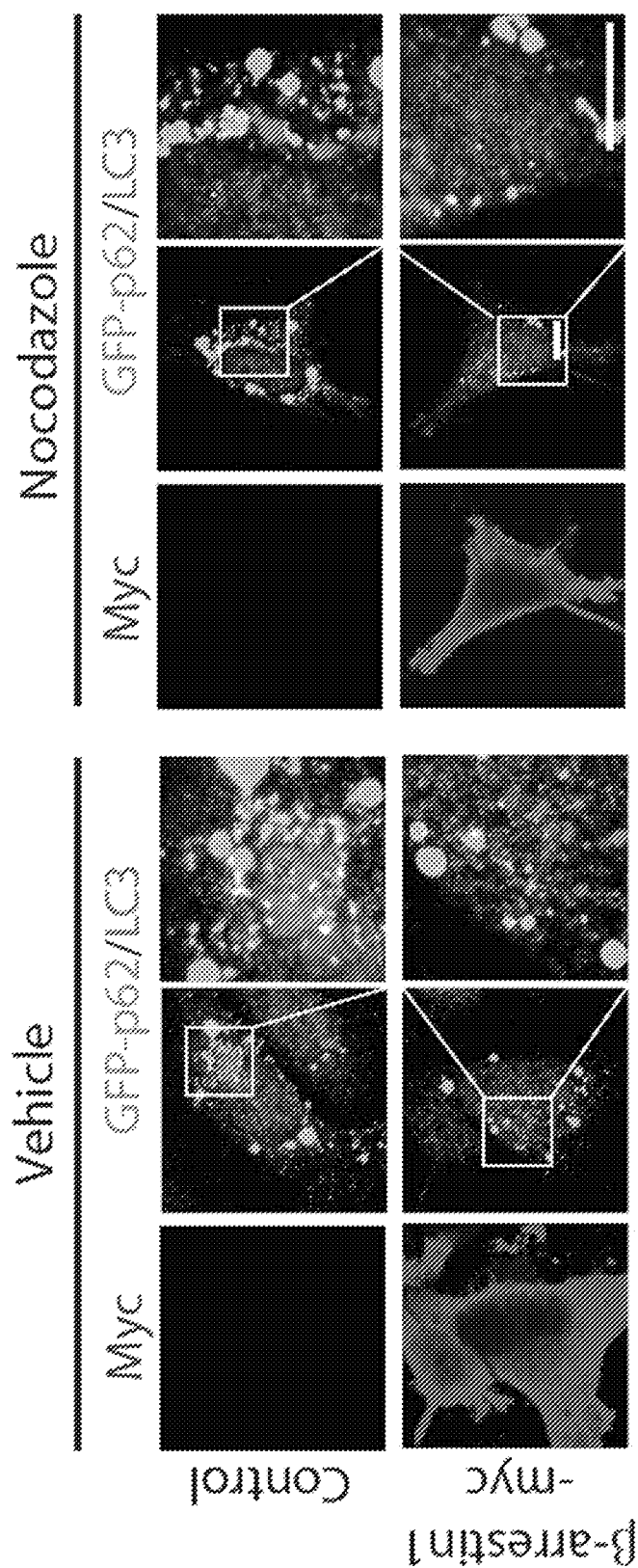
FIG. 18E contains confocal images of Hela-V5-tau cells transfected with GFP-p62 with either control vector or β-arrestin1-myc and treated with vehicle or 20 μM of nocodazole for 30 min. Cells were fixed and immunostained for myc and LC3 (Scale bar=10 μm). Representative images are shown.
Figure 18F:
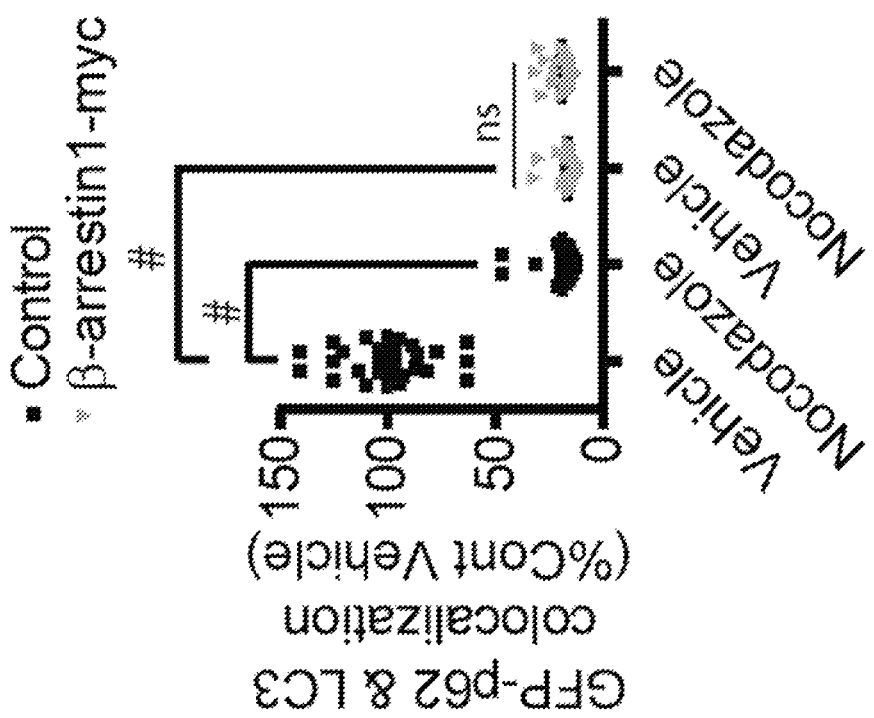
FIG. 18F shows quantification of GFP-p62 and LC3 colocalization. n=4 independent experiments. #p<0.0001. 1-way ANOVA with Dunnett posthoc test.
Figure 18G:
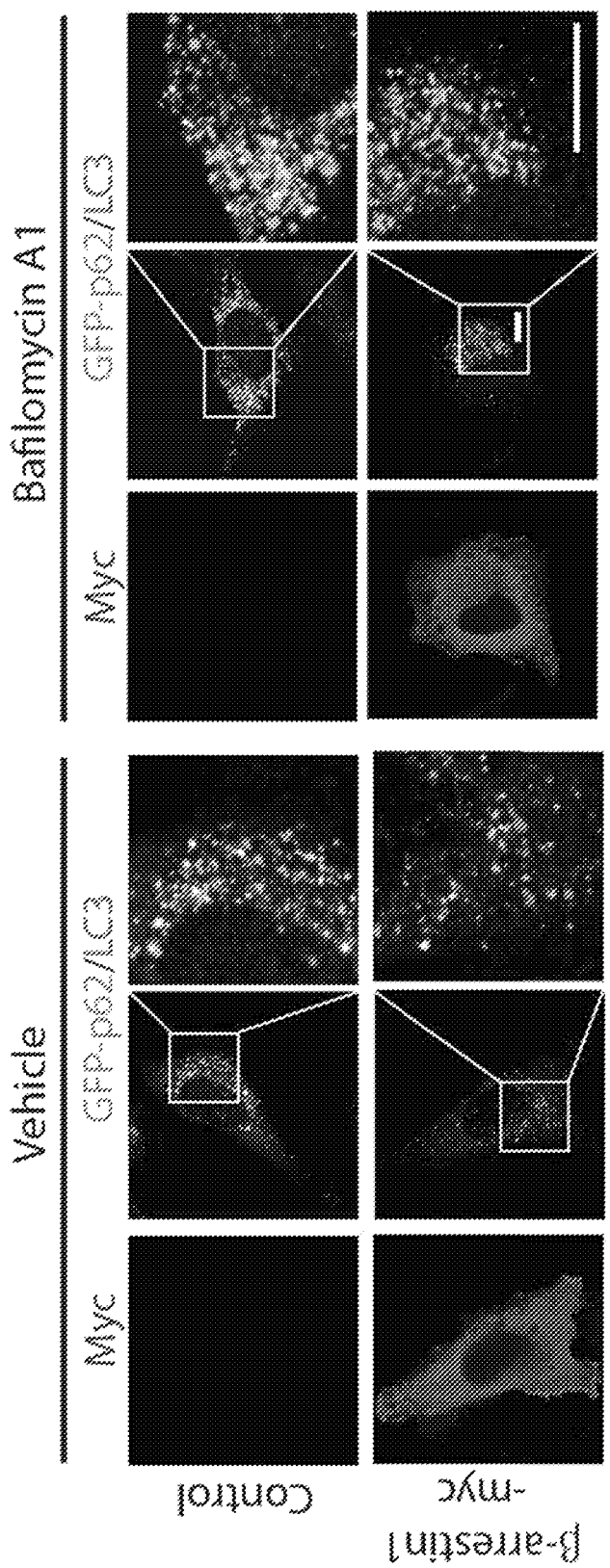
FIG. 18G contains confocal images of Hela-V5-tau cells transfected with GFP-p62 and either vector control or β-arrestin1-myc and treated with vehicle or 100 nM of Bafilomycin A1 for 4 hours. Cells were fixed and immunostained for myc and LC3 (Scale bar=10 μm). Representative images are shown.
Figure 18I:
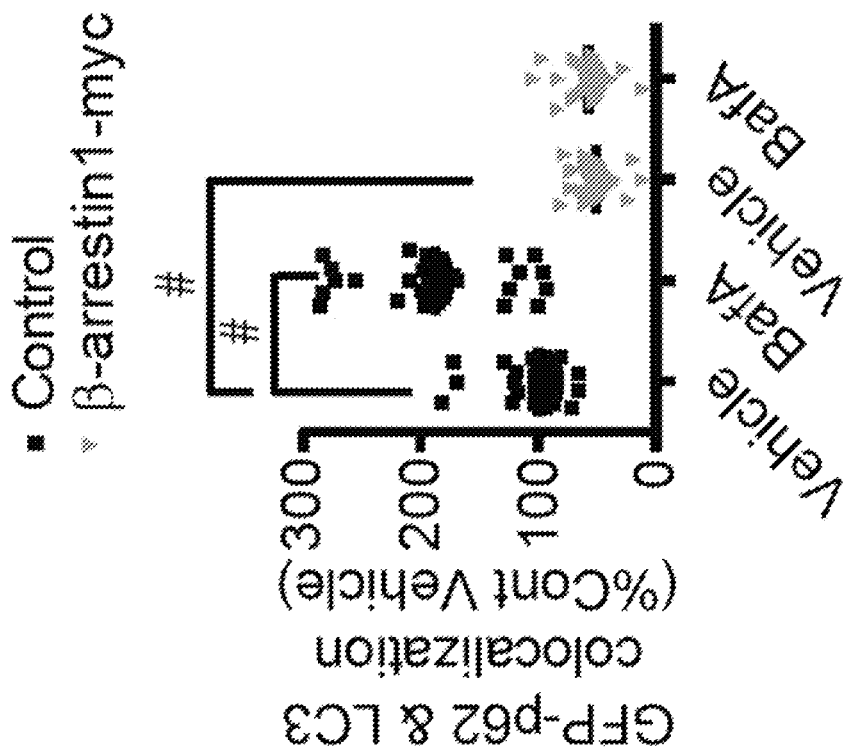
FIG. 18I shows quantification of GFP-p62 and LC3 colocalization. n=4 independent experiments. *p<0.0005, p<0.005, #p<0.0001. 1-way ANOVA with Dunnett posthoc test.
Figure 18H:
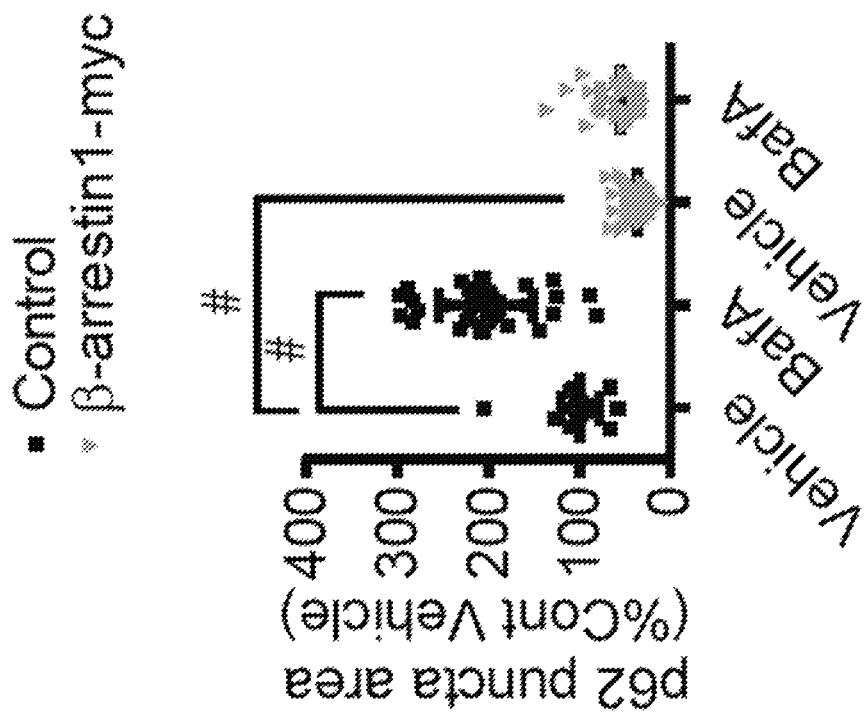
FIG. 18H shows quantification of GFP-p62 puncta area. n=4 independent experiments. *p<0.0005, p<0.005, #p<0.0001. 1-way ANOVA with Dunnett posthoc test.
Figure 24A:
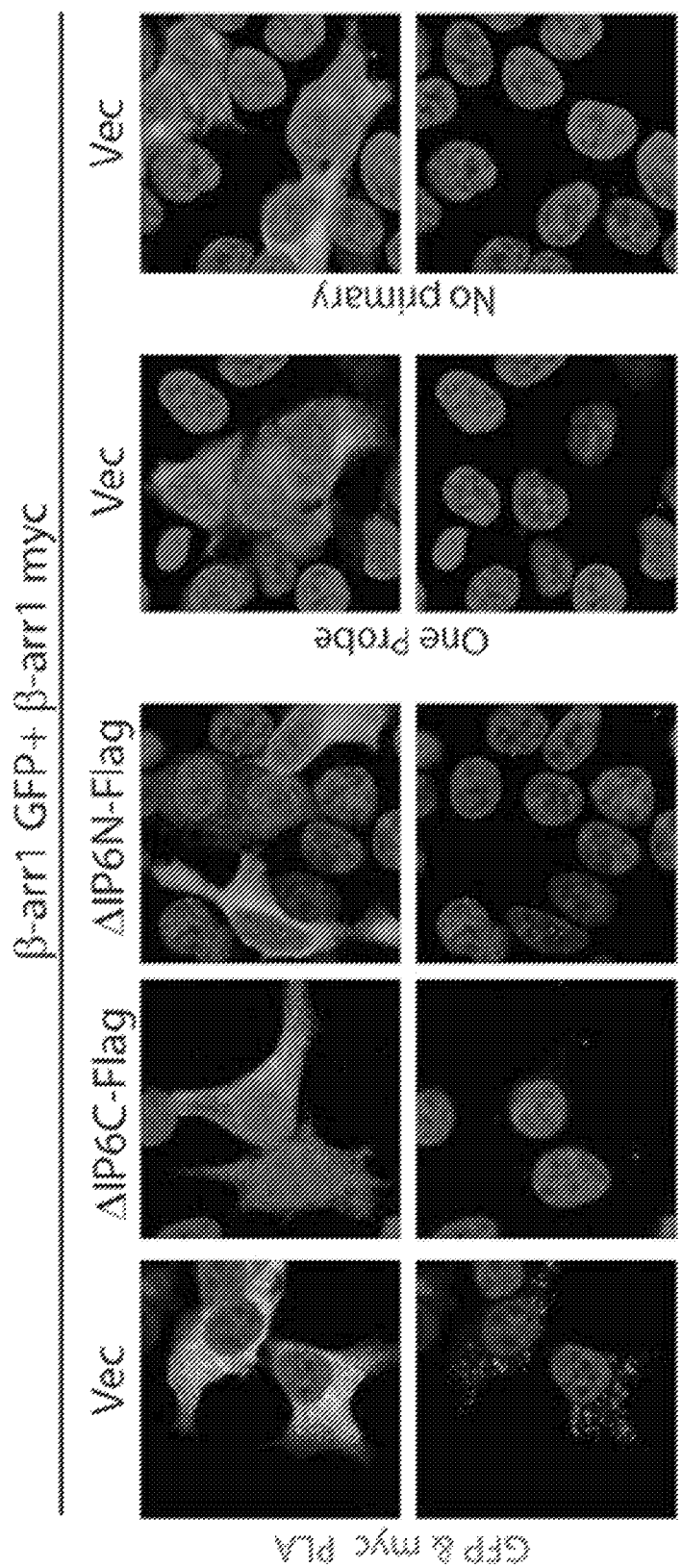
FIGS. 24A to 24D show β-arrestin2 oligomerization mutants impair β-arrestin1 homo-oligomers and β-arrestin1/β-arrestin2 hetero-oligomers. HeLa-V5-tau cells were co-transfected with vector control or β-arrestin2 oligomerization mutants (ΔIP6C or ΔIP6N) together with βarrestin1-GFP+βarrestin1-myc or βarrestin2-myc. Cells were then subjected to proximity ligation assay (PLA) using antibodies against GFP and mycto detect βarrestin1 homo-oligomers (FIGS. 24A,24B) and βarrestin1/βarrestin2 hetero-oligomers and DAPI staining (FIGS. 24C,24D) (puncta). Results show that β-arrestin2 oligomerization mutants (ΔIP6C or ΔIP6N) significantly reduce βarrestin1 homo-oligomers (FIGS. 24A,24B) as well as βarrestin1/βarrestin2 hetero-oligomers (n=4, one-way ANOVA, post hoc Dunnett's, #P<0.0001). Cells subjected to 1 probe only or exclusion of primary antibody shows no red PLA puncta (negative controls).
Figure 24D:
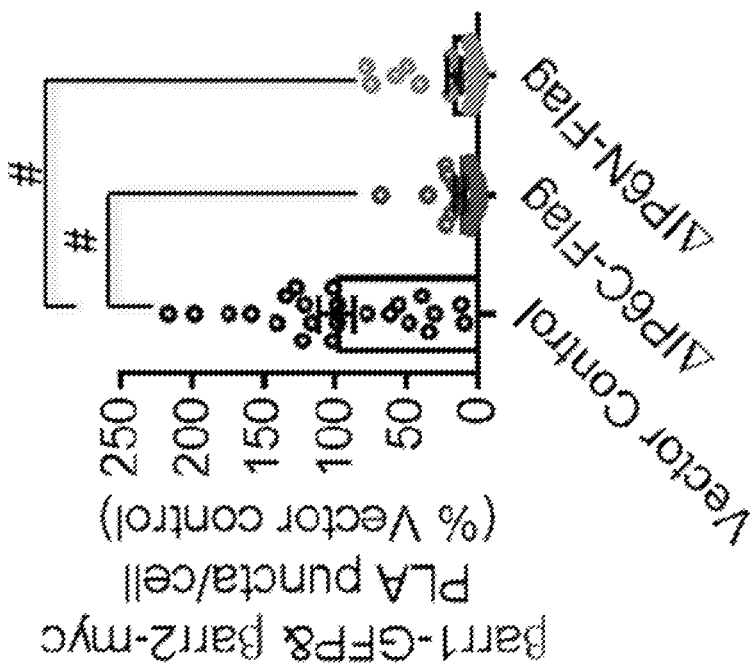
Figure 24B:
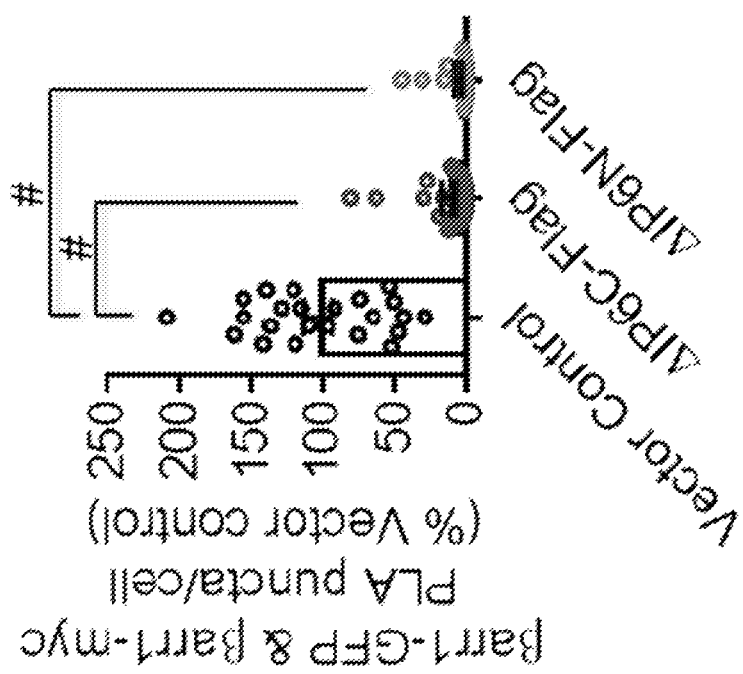

Multiple studies have shown that microtubule destabilization impairs autophagosome maturation and autophagy-mediated protein degradation (Fass, E., et al. J Biol Chem (2006) 281:36303-36316; Aplin, A., et al. J Cell Physiol (1992) 152:458-466), as microtubule-based transport is needed for the delivery of autophagosomes to lysosomes (Farfel-Becker, T. et al. Cell Rep (2019) 28:51-64 e54; Boecker, C. A. & Holzbaur, E. L. Curr Opin Neurobiol (2019) 57:94-101). To clear misfolded proteins through autophagy, autophagy cargo receptors such as p62/SQSTM1 must first sequester the cargo and link the polyubiquitinated cargo to LC3+ autophagosomes, after which they are collectively delivered to lysosomes for fusion and degradation (Katsuragi, Y., et al. FEBS J (2015) 282:4672-4678; Pankiv, S. et al. J Biol Chem (2007) 282:24131-24145). As β-arrestin1 displaced tau from microtubules, destabilized microtubules, and increased tau stability, it was initially hypothesized that β-arrestin1-mediated destabilization of microtubules could disrupt the delivery of p62 to LC3+ autophagosomes, thereby increasing tau stability. Hela-V5-tau cells were transfected with GFP-p62 together with control vector or β-arrestin1 and subjected cells to treatment with vehicle or nocodazole for 30 minutes. In control vector transfected cells, GFP-p62 puncta (green) of varying sizes were present, while endogenous LC3 (magenta) was observed as small punctate staining (FIG. 18E). GFP-p62 often colocalized (white puncta) with LC3 (FIG. 18E). As expected, nocodazole treatment dramatically decreased GFP-p62 colocalization with endogenous LC3 positive puncta in vector control transfected cells (FIGS. 18E,18F). However, β-arrestin1 overexpressing cells showed a surprisingly robust disruption GFP-p62 colocalization with LC3 at steady-state, an extent that was equivalent to nocodazole treatment (FIGS. 18E,18F). Hence, nocodazole treatment to β-arrestin1 expressing cells did not further disrupt GFP-p62/LC3 colocalization (FIGS. 18E,18F). This indicated that either β-arrestin1-mediated destabilization of microtubules is as severe as nocodazole treatment (unlikely) or other factors may be at play in such robust disruption of p62-LC3 colocalization. To examine LC3 and p62 in a different way, the effects β-arrestin1 on LC3 and GFP-p62 puncta was assessed with or without bafilomycin A1 treatment, a potent lysosome inhibitor known to promote the accumulation of both LC3 and p62 puncta (Yamamoto, A. et al. Cell Struct Funct (1998) 23:33-42; Mauvezin, C. & Neufeld, T. P. Autophagy (2015) 11:1437-1438; Yoshimori, T., et al. J Biol Chem (1991) 266:17707-17712). Overexpression of β-arrestin1 in Hela V5-tau cells not only reduced LC3 puncta at steady-state but also significantly blunted bafilomycin A1-induced increase in LC3 puncta (FIGS. 24A,24B), indicating that β-arrestin1 blocks autophagy at the level of LC3 or upstream. Likewise, overexpression of β-arrestin1 also reduced GFP-p62 puncta at steady-state and significantly blunted bafilomycin A1-induced increase in GFP-p62 puncta (FIGS. 18G,18H). Moreover, while bafilomycin A treatment significantly increased the colocalization of GFP-p62 with LC3 in vector control transfected cells, β-arrestin1 transfection significantly blunted the increase in GFP-p62/LC3 colocalization (FIGS. 18G,18I), collectively indicating that β-arrestin1 blocks autophagy at the level of p62 or upstream and likely not directly on LC3.

Figure 18J:
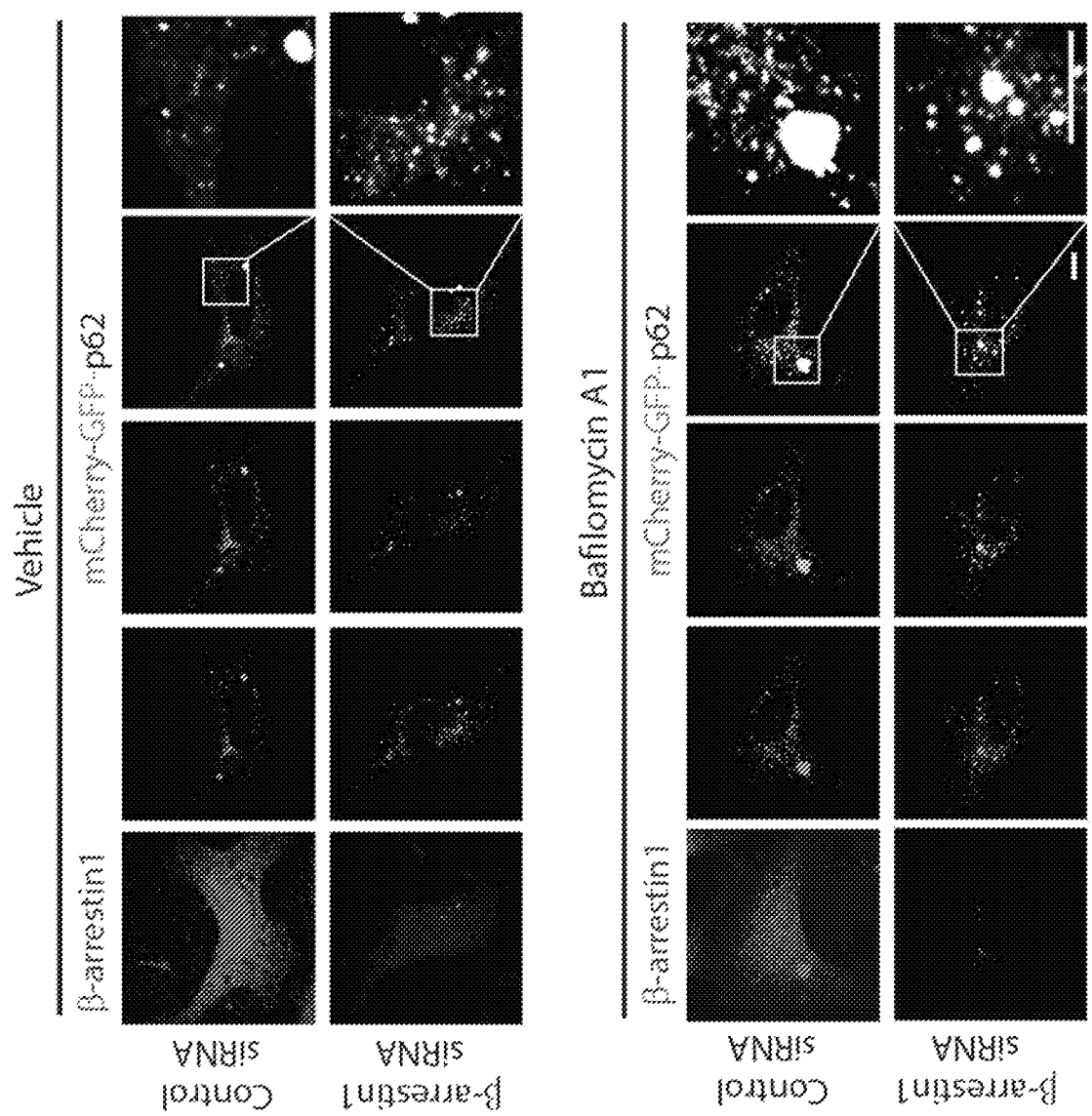
FIG. 18J contains confocal images of Hela-V5-tau cells transfected with mCherry-GFP-p62 with either control siRNA or β-arrestin1 siRNA and treated with vehicle or 100 nM of Bafilomycin A1 for 4 hours. Cells were fixed and immunostained for β-arrestin1 (Scale bar=10 μm). mCherry is pseudocolored to magenta. Representative images are shown.
Figure 18L:
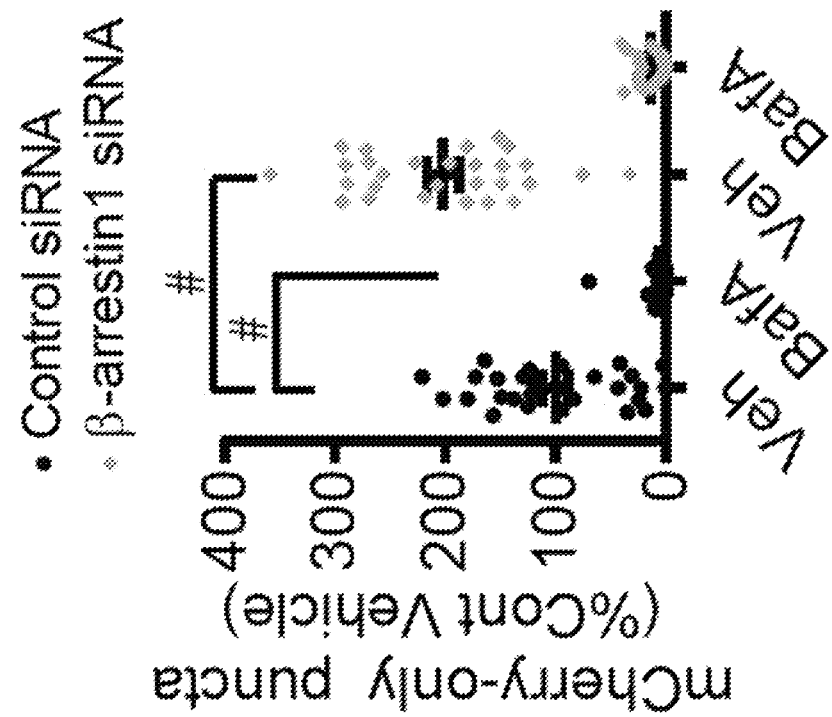
FIG. 18L shows quantification of mCherry-only (magenta) puncta normalized to control vehicle treatment. n=4 independent experiments. #p<0.0001. 1-way ANOVA with Dunnett's test.
Figure 18K:
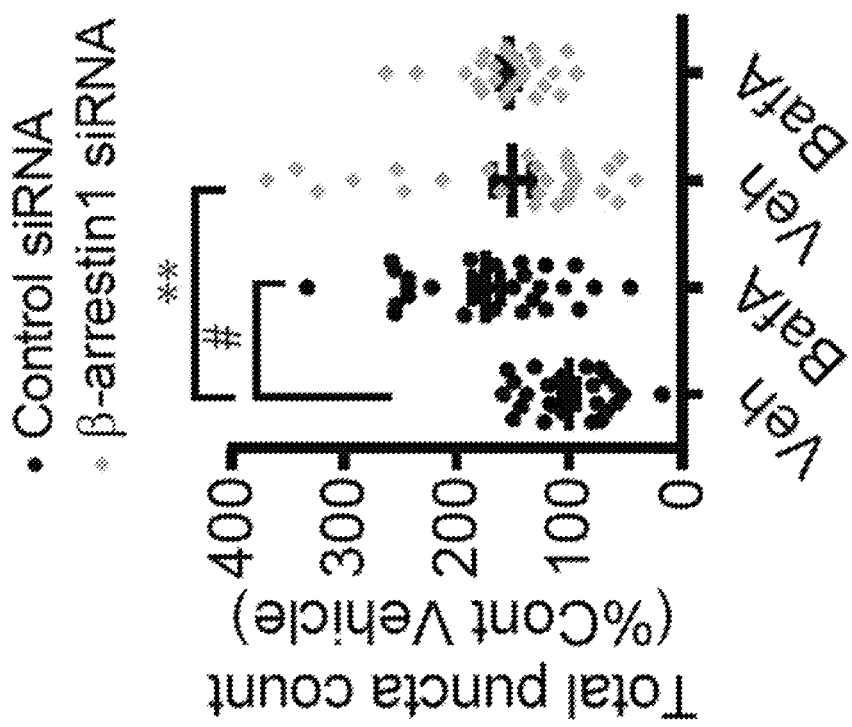
FIG. 18K shows quantification of total p62 puncta (mCherry+GFP) normalized to control vehicle treatment. n=4 independent experiments. #p<0.0001, p<0.005. 1-way ANOVA with Dunnett's test.
Figure 18N:
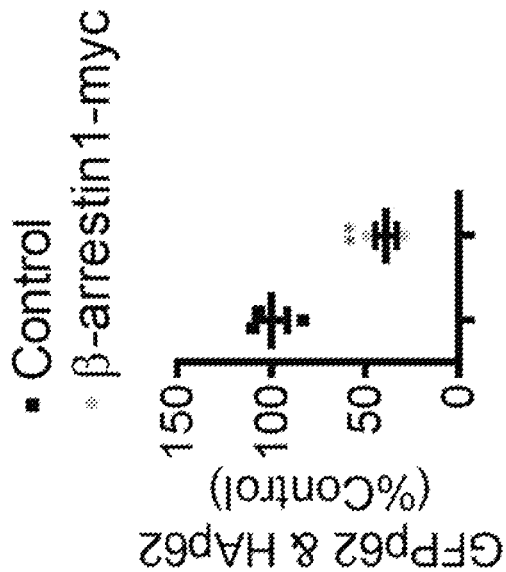
Figure 18M:
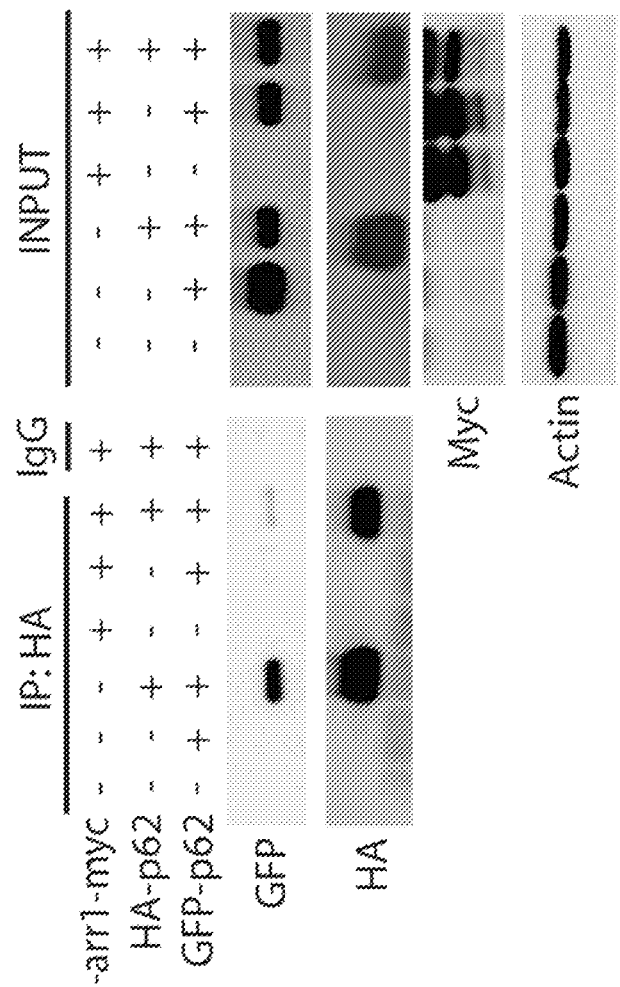
FIG. 18M shows Hela-V5-tau cells transiently transfected with control vector or β-arrestin1-myc together with either GFP-p62 and/or HA-p62 and subjected to co-immunoprecipitation for HA and immunoblotting for GFP, HA, myc, and actin. Representative blots are shown.
Figure 19:
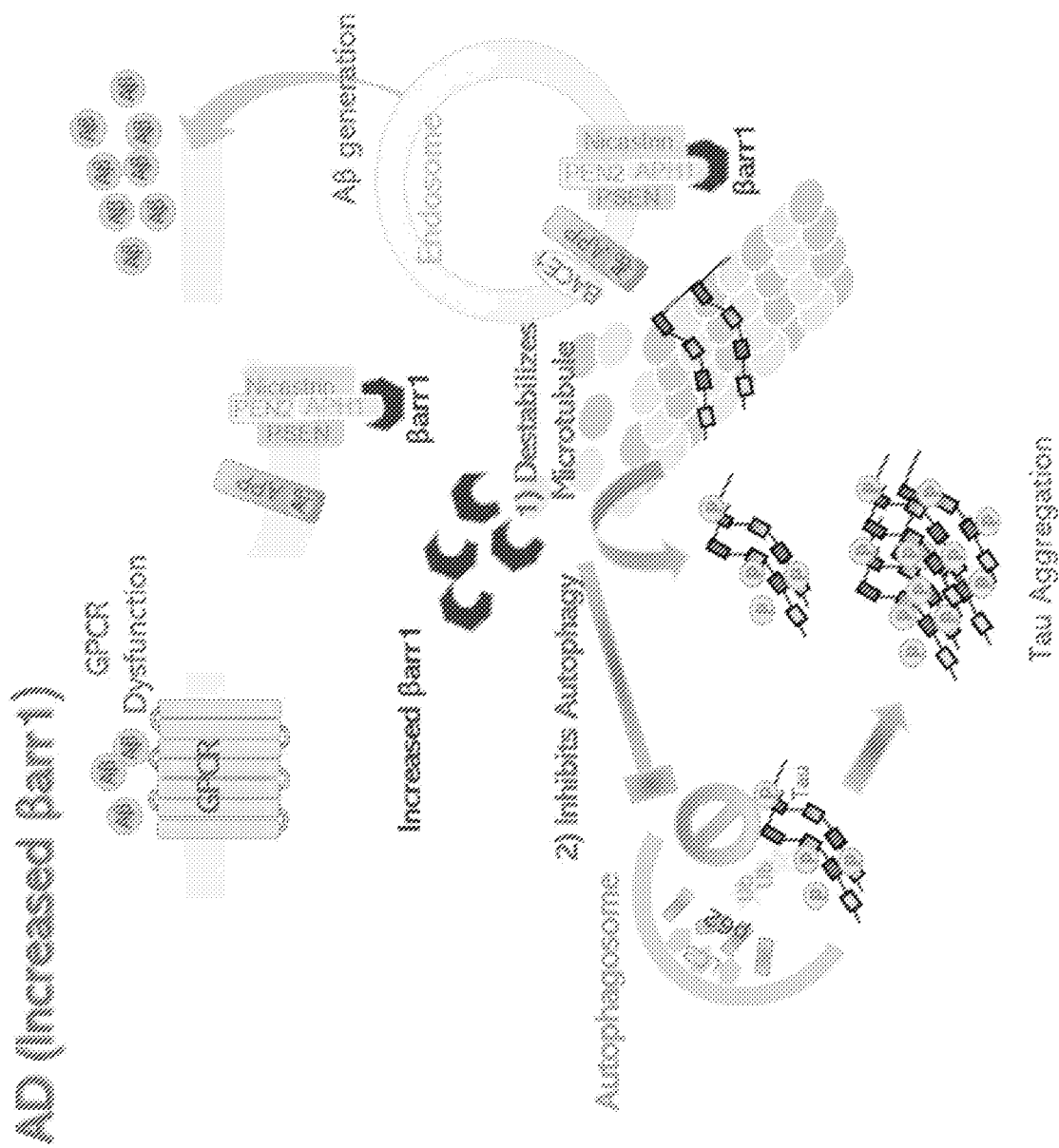
FIG. 19 is a schematic model of β-arrestin1 in promotion of tauopathy. In FTLD-tau and AD brains, β-arrestin1 is upregulated. Increased β-arrestin1 can interact with □-secretase to promotes Aβ generation. (1) Increased β-arrestin1 also binds to microtubules and promotes the dissociation of tau from microtubules, thereby disrupting microtubule stability and enabling tau missorting. (2) β-arrestin1 also physically interacts with p62 and inhibits p62 body formation, thereby impairing p62 flux and clearance of pathogenic tau. The combined effects of tau displacement, microtubule instability, and tau accumulation promote tauopathy.
Figures 20A, 20B:
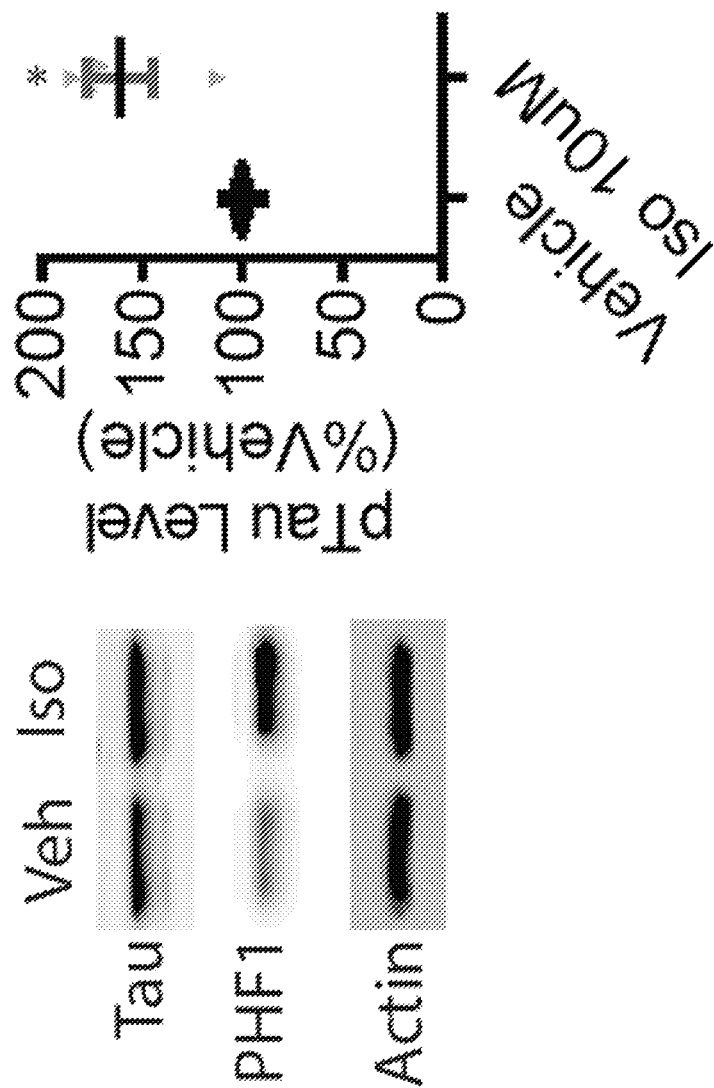
FIGS. 20A to 20E show β-arrestin is required mGluR2 and β2AR mediated tau accumulation and phosphorylation.
Figures 20C, 20D:
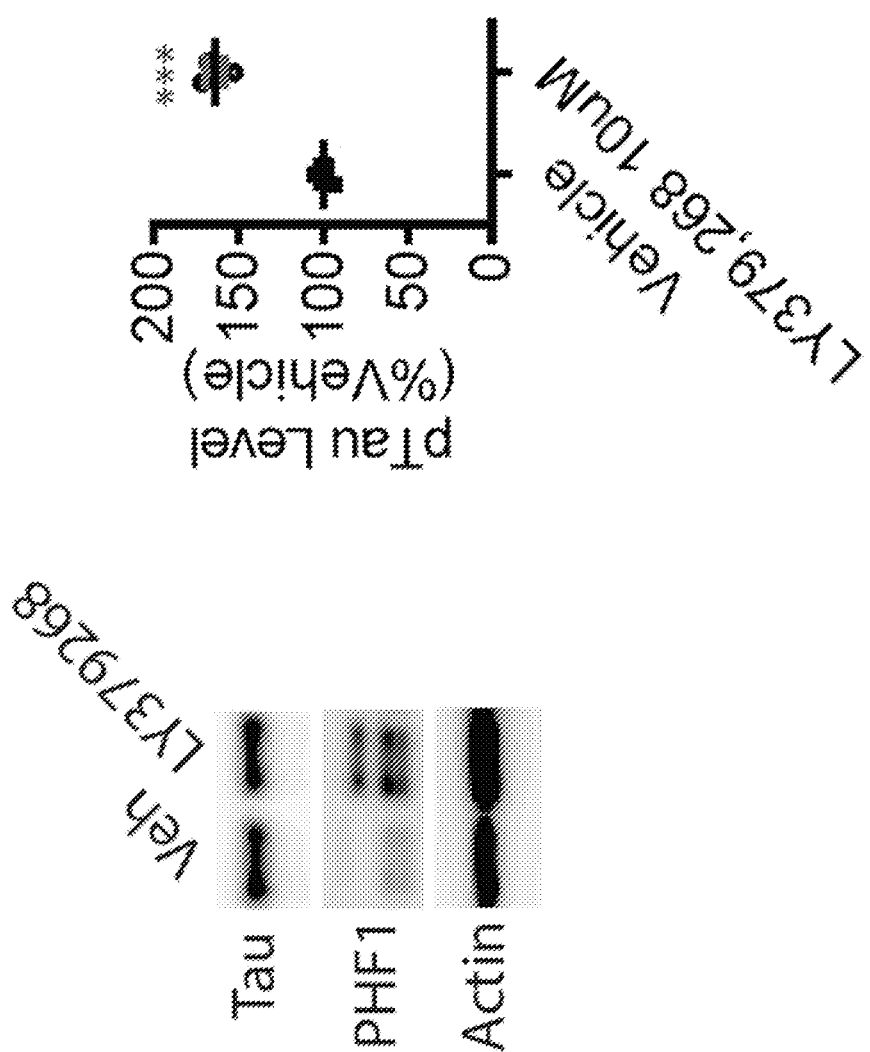
Figure 20E:
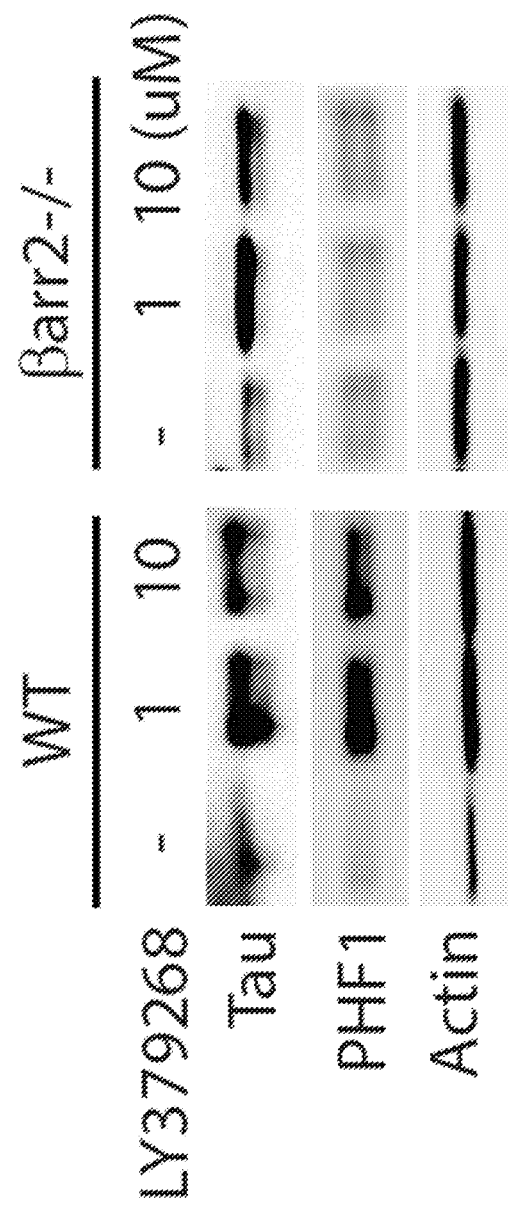
Figure 24C:
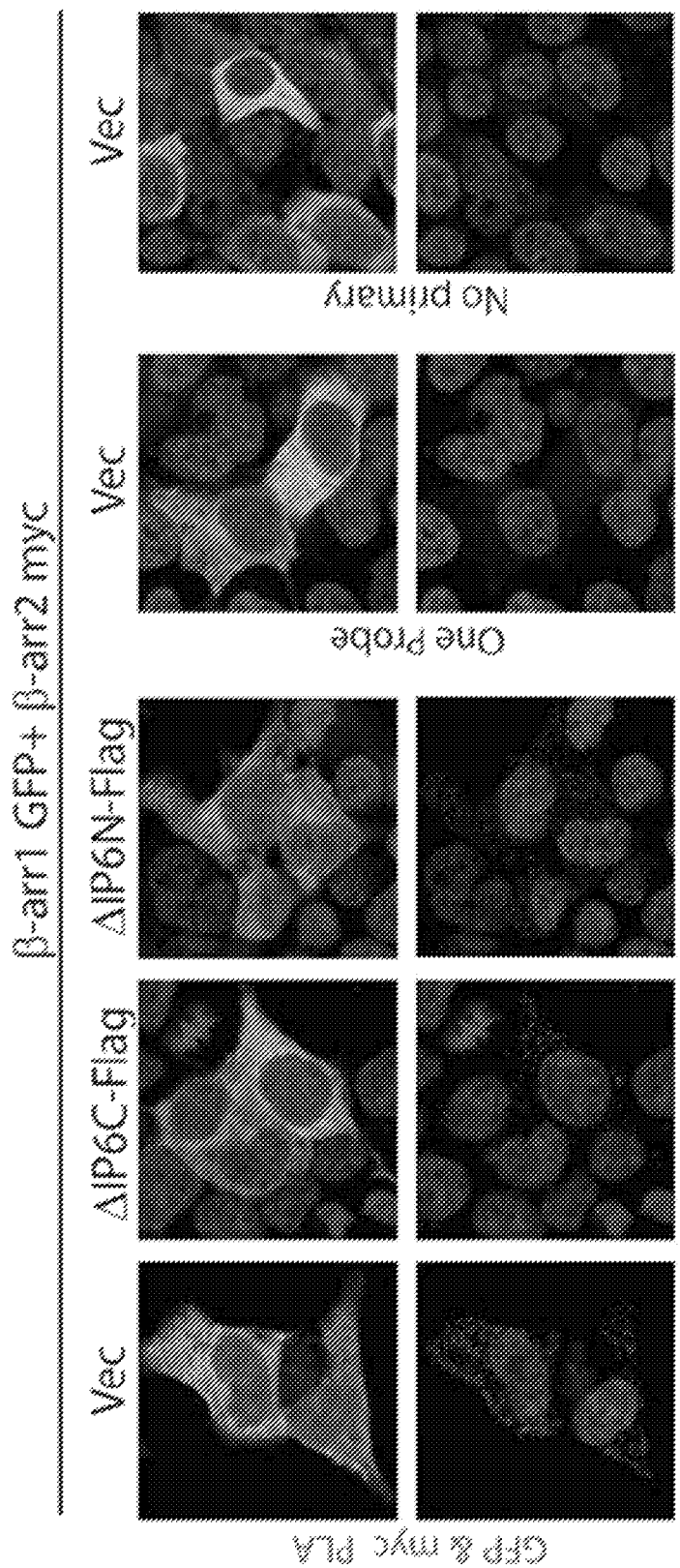

P62 is associated with neurofibrillary tangles (King, A. et al. Acta Neuropathol (2013) 125:303-310; Kuusisto, E., et al. Neuropathol Appl Neurobiol (2002) 28:228-237), and soluble cytoplasmic p62 levels are significantly reduced in AD brains (Caccamo, A., et al. Mol Psychiatry (2017) 22:865-873; Zheng, X. et al. Neural Regen Res (2012) 7:1304-1311). Increased p62 expression improves cognitive impairments in AD animal models by enhancing autophagy induction (Caccamo, A., et al. Mol Psychiatry (2017) 22:865-873; Zheng, X. et al. Neural Regen Res (2012) 7:1304-1311; Ramesh Babu, J. et al. J Neurochem (2008) 106:107-120). To further investigate β-arrestin1-induced changes in p62, p62 flux was assessed using the mCherry-GFP-p62 reporter. This reporter takes advantage of the sensitivity of GFP (green) and the insensitivity of mCherry (pseudocolored to magenta) to low pH, which allows the tracking of p62 flux to lysosomes (Pankiv, S. et al. J Biol Chem (2007) 282:24131-24145; Larsen, K. B. et al. Autophagy (2010) 6:784-793). Therefore, perfectly colocalized mCherry and GFP (white or light green) are indicative of non-lysosomal LC3. However, upon fusion with acidified lysosomes (autolysosomes), mCherry puncta persist while GFP puncta disappear (hence magenta only). Hela-V5-cells were co-transfected with mCherry-GFP-p62 with either control siRNA or β-arrestin1 siRNA and quantified total mCherry+GFP puncta (white/light green) and mCherry only (magenta) puncta. As expected, bafilomycin A treatment increased total mCherry+GFP puncta in vector control transfected cells (FIGS. 18J,18K). However, β-arrestin1 siRNA transfected cells showed significantly increased total mCherry+GFP puncta at steady-state, and bafilomycin A treatment did not significantly further increase this measure (FIGS. 18J,18K). The percentage of acidified mCherry-only (magenta) puncta out of total p62 puncta was increased by approximately 2-fold in β-arrestin1 siRNA versus control siRNA transfected cells, nearly all of which were abolished by 4 h bafilomycin A treatment, indicating that the loss of β-arrestin1 promotes p62 flux (FIGS. 18J,18L). β-arrestin1 formed a specific complex with HA-p62 in co-immunoprecipitation (co-IP) experiments from Hela-V5-tau cells (FIG. 24C), suggesting that β-arrestin1 might directly modify p62 activity by physical interaction. To query this possibility, the known ability of p62 to form particles by self-interaction via its N-terminal PB1 domain was taken advantage of, which allows the formation of p62 helical filaments arranged in a head to tail configuration (Ciuffa, R. et al. Cell Rep (2015) 11:748-758), a step that is essential for its cargo receptor activity (Wurzer, B. et al. Elife (2015) 4:e08941; Itakura, E. & Mizushima, N. J Cell Biol (2011) 192:17-27). Hence, whether β-arrestin1/p62 interaction alters the ability of p62 to form self-interacting complexes using HA-p62 and GFP-p62 constructs was tested. The specific presence of GFP-p62 in HA-p62 immune complexes was observed, which was significantly diminished by >60% by β-arrestin1 overexpression under conditions where similar amounts of HA-p62 were pulled down in HA immune complexes (FIGS. 18M, 18N). These results therefore show that increased β-arrestin1, as seen in brains of FTLD-tau and AD, strongly blocks the self-interaction of p62, an initial step required for p62-mediated clearance of cargo including misfolded tau (Caccamo, A., et al. Mol Psychiatry (2017) 22:865-873; Zheng, X. et al. Neural Regen Res (2012) 7:1304-1311; Ramesh Babu, J. et al. J Neurochem (2008) 106:107-120; Wurzer, B. et al. Elife (2015) 4:e08941; Itakura, E. & Mizushima, N. J Cell Biol (2011) 192:17-27).

Methods

Patients Samples

Frontal cortex tissue samples of pathologically confirmed FTLD-tau and age-matched nondemented controls were obtained from Emory ADRC (P50 AG025688).

Animal Models

The following mouse strains were used in this study: WT C57BL/6, tauP301S, and Arrb1$^{+/-}$, mice. C57BL/6J (Jackson Laboratory line 000664), tauP301S (Jackson Laboratory line 008169), and Arrb1$^{-/-}$ (Jackson Laboratory line 011131) were all obtained from Jackson laboratory. Arrb1$^{-/-}$ mice (AbdAlla, S. et al. J Biol Chem (2009) 284:6554-6565) and tauP301S (Yoshiyama, Y. et al. Neuron (2007) 53:337-351) mice have been characterized. Mice were housed under pathogen-free conditions, and all experiments involving mice were performed in accordance with approved protocols by the Institutional Animal Care and Use Committee (IACUC) at University of South Florida.

Primary Neuronal Cultures

Primary neurons were obtained from postnatal day 0 mice. Cortex and hippocampus were dissected in cold HBSS and digested with 0.25% trypsin. Neurons were plated on poly-D-lysine coated plates or coverslips and maintained in neurobasal media with Glutamax and B27 supplement as previously described (Woo, J. A. et al. Nat Commun (2017) 8:15558).

DNA Transfection, Constructs, and siRNA pcDNA3 β-arrestin 1-HA (addgene, 14693) (Luttrell, L. M. et al. Science (1999) 283:655-661), pcDNA3 β-arrestin1-Flag (addgene, 14687) (Luttrell, L. M. et al. Science (1999) 283:655-661), pMXs-puro GFP-p62 (Addgene, 38277) (Itakura, E. & Mizushima, N. J Cell Biol (2011) 192:17-27) were obtained from addgene. β-arrestin 1-GFP and β-arrestin 1-myc constructs were obtained. β-arrestin1 ON-TARGET plus SMART pool siRNA were purchased from Dharmacon. DNA constructs and siRNAs were transiently transfected with Lipofectamine 2000 and Opti-MEM.

Recombinant Proteins pFast-tau-his, pFast-β-arrestin1-his constructs were transformed into DH10Bac competent cells. After blue-white screening, DH10Bac strains were chosen to express recombinant Bacmids. Sf9 insect cells transfected with Bacmid were cultured for 3 days with Sf900 II SFM medium, then P1 generation virus in medium was collected and added to new Sf9 cells. After 2 days culture, Sf9 cells were harvested and lysed with lysis buffer (Tris 20 mM, pH7.4, NaCl 150 mM, Triton-X100 1%, 10 mM imidazole, with protease inhibitors). After centrifugation at 12,000 g for 15 minutes, supernatant was collected and shaken for 1 hour at 4° C. with GE Healthcare Ni Sepharose. Bound proteins on sepharose were washed 3 times with ice-cold lysis buffer, and recombinant proteins were eluted with ice-cold elution buffer (Tris 20 mM, NaCl 150 mM, 200 mM imidazole), after which proteins were dialyzed in dialysis buffer (Tris 20 mM, NaCl 150 mM, DTT 1 mM) at 4° C. overnight.

SDS-PAGE and Western Blotting

Mouse brain extracts or cells were lysed in RIPA buffer (1% NP-40, 0.1% sodium dodecyl sulfate, 50 mM Tris pH 7.4, 150 mM NaCl, 2 mM Ethylenediaminetetraacetic acid) with protease and phosphatase inhibitors. After equalizing protein concentration with BCA assay, lysates were mixed with 4×LDS sample buffer and loaded on SDS-PAGE gels. Membranes were blocked with 5% milk in TBS-T for 1 hour at room temperature. After blocking, membranes were probed with indicated primary antibodies for overnight at 4° C. and incubated with horseradish peroxidase-linked secondary antibodies for 2-4 hours at room temperature.

Immunoprecipitation

Cells were lysed with CHAPS buffer (30 mM Tris-Cl pH 7.5, 150 mM NaCl, 1% CHAPS) with protease and phosphatase inhibitors. After equalizing protein concentration, lysates were pre-incubated with IgG beads for 1 hour, and washed with CHAPS buffer. Lysates were incubated with indicated primary antibody with IgG beads for overnight at 4° C., and proteins were eluted with 4×LDS sample buffer with boiling for subsequent SDS-PAGE and Western blotting.

Sarkosyl Insoluble and Soluble Extraction

Sarkosyl extraction was performed as previously described (Woo, J. A. et al. Commun Biol (2019) 2:112). Briefly, brain homogenates were lysed with A68 buffer containing 10 mM Tris-HCl, pH 7.4, 0.8M NaCl, 10% Sucrose, 1 mM EGTA. Samples were centrifuged at 400 g for 20 min at 4° C. After a centrifugation, 1% sarkosyl was added to the supernatants. The samples were incubated for 1 hour and 30 min and centrifuged at 80,000 g for 30 min at room temperature. The pellets were resuspended in 100 ul of 50 mM Tris-HCl, pH 7.4 and subjected to SDS-PAGE.

Tubulin Polymerization Assay

Tubulin polymerization was measured by the absorbance readings at 340 nm using the tubulin polymerization assay kit (Cytoskeleton Inc., Denver, CO, USA). The concentration of tubulin was 3 mg/ml in 0.5 mM EGTA, 2 mM MgCl2, 1 mM GTP, 80 mM PIPES pH 6.9, and total polymerization volumes were 100 µl.

Microtubule Binding Assay

Microtubule-binding assay was performed by microtubule binding protein spin-down assay kit (Cytoskeleton Inc., Denver, CO, USA). Stable microtubules between 5-10 µm in length were used for the assay. After incubating stable microtubules with recombinant proteins, microtubule-associated proteins were pulled down at 100,000×g.

Immunofluorescence

Cells were washed with ice-cold PBS and fixed with 4% paraformaldehyde at room temperature. After fixation, cells were washed with 0.2% triton in TBS. Mice were perfused with PBS and fixed with 4% paraformaldehyde. 25 µm sections were washed with 0.2% triton in TBS. After washing, cells and tissue sections were blocked with 3% normal goat serum with 0.1% triton X-100 for 1 hour at room temperature and incubated with indicated primary antibodies for overnight at 4° C. After washing with PBS for 3 times, cells and tissue sections were incubated with secondary antibodies for 45 min at room temperature. Images were obtained with the Olympus FV10i confocal microscope (Tokyo, Japan) or Zeiss LSM880 confocal microscope (Germany). Immunoreactivities were quantified using the Image J software (National Institutes of Health, Bethesda, MD). All comparison images were acquired with identical laser intensity and exposure time. Investigators were blinded to experimental conditions during image acquisition and quantification.

Generation of β-Arrestin1 shRNA Lentivirus

β-arrestin1 shRNA plasmid was obtained from Abm (Richmond, BC, Canada). Lenti-virus vectors were co-transfected with pVSVG and Pax2 using polyethylenimine (PEI) in HEK293 cells for overnight. The media was removed and replaced with serum-free media the next day. After 72 hrs incubation, the media was collected and centrifuged to remove cell debris. Virus was filtered through a syringe filter (0.2-0.45 µm).

Electrophysiology

Electrophysiological recording was performed as described (Woo, J. A. et al. Hum Mol Genet (2017) 26:3973-3988; Woo, J. A. et al. Commun Biol (2019) 2:112; Woo, J. A., et al. Cell Death & Differentiation (2015) 2015 Feb. 20). Briefly, brain slices were prepared from 4-month-old WT, tauP301S, and tauP301S/Arrb1$^{+/-}$ mice. Input/output (IO) curve, paired pulse facilitation (PPF), and long-term potentiation (LTP) were measured.

Quantitative Real-Time RT-PCR

Quantitative real-time RT-PCR was performed using Roche LightCycler® 96 System (Life Science, San Francisco, CA, USA). After isolating total RNA using Trizol reagent (Invitrogen, CA, USA), total RNA was reverse transcribed and subjected to quantitative PCR analysis using Syber green master mix (Invitrogen, CA, USA). The comparative threshold cycle (Ct) value was used to calculate the amplification factor, and the relative amount of tau was normalized to GAPDH.

Statistical Analysis and Data Presentation

Statistical analyses were performed by the GraphPad Prism 7.0 software (GraphPad Software, San Diego, CA, USA) using paired or unpaired Student's t-tests, and one- or two-way ANOVA with indicated post hoc tests. Data are shown as representative experiments. Box and whisker plots represent all data points with mean±S.E.M. $P<0.05$ was considered statistically significant.

Discussion

Previous studies have implicated multiple GPCR pathways in AD pathogenesis (Ni, Y. et al. Nat Med (2006) 12:1390-1396; AbdAlla, S. et al. J Biol Chem (2009) 284: 6566-6574; AbdAlla, S. et al. J Biol Chem (2009) 284:6554-6565; Thathiah, A. et al. Science (2009) 323:946-951; Bakshi, P., et al. ACS Chem Biol (2008) 3:777-789; Alley, G. M. et al. J Neurosci Res (2010) 88:143-154; Minkeviciene, R., et al. J Pharmacol Exp Ther (2004) 311:677-682; Dobarro, M., et al. Int J Neuropsychopharmacol (2013) 16:2245-2257; Wisely, E. V., et al. Hum Mol Genet (2014) 23:4024-4034; Luong, K. & Nguyen, L. T. Am J Alzheimers Dis Other Demen (2013) 28:427-439; Lee, H. G. et al. Acta Neuropathol (2004) 107:365-371; Lee, H. G. et al. Brain Res (2009) 1249:244-250; Sun, L. et al. FEBS Lett (2005) 579:251-258), including pAR2 (Dobarro, M., et al. Int J Neuropsychopharmacol (2013) 16:2245-2257; Wisely, E. V., et al. Hum Mol Genet (2014) 23:4024-4034; Luong, K. & Nguyen, L. T. Am J Alzheimers Dis Other Demen (2013) 28:427-439; Kalaria, R. N. et al. J Neurochem (1989) 53:1772-1781; Kalaria, R. N. & Harik, S. I. Neurosci Lett (1989) 106:233-238) and mGluR2 (Lee, H. G. et al. Acta Neuropathol (2004) 107:365-371; Lee, H. G. et al. Brain Res (2009) 1249:244-250). However, it is unclear how different classes of GPCRs similarly act to impinge on AD pathogenesis.

As β-arrestin1 and β-arrestin2 were initially identified and named on the basis of its ability to terminate GPCR signaling through agonist-induced receptor internalization and desensitization (Lohse, M. J., et al. Science (1990) 248: 1547-1550; Wilden, U., et al. Proc Natl Acad Sci USA (1986) 83:1174-1178; Moore, C. A., et al. Annu Rev Physiol (2007) 69:451-482; Gurevich, V. V. & Gurevich, E. V. Pharmacol Ther (2006) 110:465-502), the first goal was to determine whether β-arrestin1 and/or β-arrestin2 represent a common point of convergence by which β2AR and mGluR2 agonism alter tau phosphorylation. The findings showed that the loss of β-arrestin1 or β-arrestin2 abrogates the ability of β2AR or mGluR2 agonism to increase phospho-tau, indicating that β-arrestin1/2 functions as an essential node of convergence for GPCR-mediated tau regulation. Although it remains to be determined whether other AD-implicated GPCRs (i.e. ADRBs, GPR3, AT2R, CXCR2, etc) (AbdAlla, S. et al. J Biol Chem (2009) 284:6566-6574; AbdAlla, S. et al. J Biol Chem (2009) 284:6554-6565; Thathiah, A. et al. Science (2009) 323:946-951; Bakshi, P., et al. ACS Chem Biol (2008) 3:777-789) require β-arrestin1 and/or β-arrestin2 for their pathogenic activities, these initial observations led us to examine brains of FTLD-tau patients for alterations in β-arrestin1 levels. Interestingly, previous studies had reported that β-arrestin1 (Liu, X. et al. Cell Res (2013) 23:351-365) and β-arrestin2 (Thathiah, A. et al. Nat Med (2013) 19:43-49) are significantly increased in brains of AD patients and that both β-arrestin1 and β-arrestin2 interact with the Aph-1 subunit of the □-secretase complex to increase Aβ production, thereby linking β-arrestin1/2 to Aβ pathogenesis. β-arrestin2 is significantly elevated in brains of FTLD-tau patients, and increased β-arrestin2 promotes tau aggregation in the absence of GPCR stimulation. As disclosed herein, β-arrestin1 levels are highly elevated in brains of FTLD-tau patients suggesting that both β-arrestin1 and β-arrestin2 are elevated in AD and FTD-patients brains. It has not been studied whether β-arrestin1 and/or β-arrestin2 levels are increased during aging. Furthermore, whether β-arrestin1 and β-arrestin2 contribute to progression of other neurodegenerative disorders such as Amyotrophic lateral sclerosis (ALS) and Parkinson's disease need to be exploited.

β-arrestin1 levels are also highly elevated in brains of FTLD-tau patients, a disease pathologically defined by tauopathy in the absence of Aβ deposits (Irwin, D. J. et al. Acta Neuropathol (2015) 129:469-491) suggests that tau but not Aβ component of AD pathology is required to elevate β-arrestin1 levels in brain. Moreover, the observation that insoluble tau levels are robustly correlated with insoluble β-arrestin1 levels and that AT8-positive phospho-tau aggregates are nearly perfectly colocalized with β-arrestin1 suggests a functional pathogenic relationship between β-arrestin1 and tau pathogenesis in FTLD-tau.

The above findings led us to hypothesize that increased β-arrestin1 levels promote tau accumulation and tauopathy, whereas reduced β-arrestin1 levels counteract such phenotypes in primary neurons and in vivo. Indeed, the hypothesis was confirmed in primary neurons by β-arrestin1 overexpression and RNAi-mediated silencing experiments. In vivo, genetic reduction of β-arrestin1 not only alleviated tauopathy in tauP301S transgenic mice but also functionally rescued the prominent deficits in synaptic plasticity (i.e. PPF & LTP) and synaptic integrity in tauP301S acute slices and neurons. These findings therefore indicate that pathogenic tau accumulation upregulates β-arrestin1 through as yet unknown mechanisms, which in turn, further drives tauopathy via increased β-arrestin1 in a maladaptive positive feed-back cycle of progressive pathogenesis. Hence, the observation that 50% reduction in β-arrestin1 ameliorates tauopathy and associated synaptic dysfunction demonstrates the proof-of-principle that β-arrestin1 represents a viable point of therapeutic interdiction to break this pathogenic feed-forward loop. As homozygous β-arrestin1 null mutants were not utilized in this study, however, it remains to be determined whether the complete absence of β-arrestin1 provides further benefits in the setting of tauopathy.

A major biological function of tau is ascribed to its ability to bind and stabilize microtubules as well as promote its assembly (Cleveland, D. W., et al. J Mol Biol (1977) 116:207-225). In AD and other tauopathies, however, tau dissociates from microtubules, leading to its missorting from the somatoaxonal to somatodendritic compartments (Ballatore, C., et al. Nat Rev Neurosci (2007) 8:663-672; Biernat, J. & Mandelkow, E. M. Mol Biol Cell (1999) 10:727-740; Hoover, B. R. et al. Neuron (2010) 68:1067-1081). This event occurs early in the disease process and is thought to be required for its hyperphosphorylation and self-assembly into aggregates (Wang, Y. & Mandelkow, E. Nat Rev Neurosci (2016) 17:5-21). As a significant pool of β-arrestin1 binds directly to microtubules (Hanson, S. M. et al. J Mol Biol (2007) 368:375-387; Gurevich, V. V. & Gurevich, E. V. Curr Protoc Pharmacol (2014) 67, Unit 2 10 11-19), β-arrestin1 binding to microtubules is shown to promote the dissociation of tau from microtubules in a dose-dependent manner, thereby potently inhibiting tau-mediated microtubule assembly in vitro and in transfected cells. Such actions of β-arrestin1 are highly reminiscent of the manner which the actin-binding protein cofilin displaces tau from microtubules, inhibits tau-induced microtubule assembly, and promotes tauopathy (Woo, J. A. et al. Commun Biol (2019) 2:112). Interestingly, β-arrestin1 and β-arrestin2 bind cofilin and scaffold the interaction with the cofilin activating phosphatase chronophin to enhance cofilin activation (Zoudilova, M. et al. J Biol Chem (2007) 282:20634-20646; Zoudilova, M. et al. J Biol Chem (2010) 285:14318-14329). β-arrestin2 interaction with cofilin also plays an important role in the translocation of activated cofilin to dendritic spines to regulate spine morphology (Pontrello, C. G. et al. Proc Natl Acad Sci USA (2012) 109:E442-451). However, β-arrestin1 inhibited tau microtubule binding and tau-induced microtubule assembly in the setting of purified recombinant proteins where cofilin was absent. Hence, such inhibitory actions of β-arrestin1 do not require cofilin per se and support the notion that the capacity of β-arrestin1 to displace tau from microtubules (with or without cofilin) contributes to tau mislocalization and subsequent propensity to self-assemble into aggregates.

Microtubule dynamics and autophagy machinery are intricately linked in cells and particularly in neurons, as autophagosomes formed in distal neurites or axons must come together with mature lysosomes that are relatively enriched in the soma (Lee, S., et al. J Neurosci (2011) 31:7817-7830; Maday, S., et al. J Cell Biol (2012) 196:407-417; Cheng, X. T., et al. Autophagy (2015) 11:1434-1436; Wang, T. et al. J Neurosci (2015) 35: 6179-6194). Such spatial disparity therefore necessitates microtubule-based transport of autophagosomes and lysosomes over relatively long distances. Indeed, impaired microtubule dynamics disrupts autophagic clearance (Fass, E., et al. J Biol Chem (2006) 281:36303-36316; Aplin, A., et al. J Cell Physiol (1992) 152:458-466; Farfel-Becker, T. et al. Cell Rep (2019) 28:51-64 e54; Boecker, C. A. & Holzbaur, E. L. Curr Opin Neurobiol (2019) 57:94-101), and defects in autophagy contribute to AD pathogenesis (Nixon, R. A. et al. J Neuropathol Exp Neurol (2005) 64:113-122; Yang, D. S. et al. Am J Pathol (2008) 173:665-681; Sanchez-Varo, R. et al. Acta Neuropathol (2012) 123:53-70) by promoting the accumulation of Aβ and tau (Caccamo, A., et al. Mol Psychiatry (2017) 22:865-873; Zheng, X. et al. Neural Regen Res (2012) 7:1304-1311; Ramesh Babu, J. et al. J Neurochem (2008) 106:107-120; Xu, Y., et al. Autophagy (2019) 15:583-598). Having observed that β-arrestin1 does not alter tau mRNA but increases tau protein stability, the initial focus was on the p62-LC3 autophagy machinery, because microtubule-based transport facilitates the coming together of p62-bound cargo with LC3+ autophagosomes (Lee, S., et al. J Neurosci (2011) 31:7817-7830; Maday, S., et al. J Cell Biol (2012) 196:407-417; Cheng, X. T., et al. Autophagy (2015) 11:1434-1436; Wang, T. et al. J Neurosci (2015) 35: 6179-6194). Moreover, β-arrestin2 disrupts p62-mediated tau clearance. Thus, it was hypothesized that β-arrestin1 could inhibit p62-mediated tau clearance as they share multiple biological functions with 78% sequence identity.

p62/SQSTM1 knockout mice display severe neurodegeneration as well as hyperphosphorylated tau and neurofibrillary tangles (Ramesh Babu, J. et al. J Neurochem (2008) 106:107-120), and p62 overexpression strongly reduces pathogenic tau in transfected cells and in vivo (Xu, Y., et al. Autophagy (2019) 15:583-598). β-arrestin1 overexpression alone is as effective as nocodazole treatment (potent microtubule destabilizing agent) in disrupting p62-LC3 colocalization at steady-state, which suggests that either β-arrestin1 is as effective as nocodazole in destabilizing microtubules (which is unlikely) or other mechanisms might also contribute to such robust disruption. Indeed, the finding that β-arrestin1 reduces both LC3 and p62 puncta and significantly blunts bafilomycin-induced accumulation of both LC3 and p62 puncta indicates that β-arrestin1 inhibits autophagy at the level of p62 per se or upstream. P62 flux and co-IP experiments confirmed that β-arrestin1 acts to inhibit autophagy at the level of p62, as β-arrestin1 not only impedes p62 flux but also binds to p62 and interferes with p62 self-association, an essential step for the formation of p62 bodies (Ciuffa, R. et al. Cell Rep (2015) 11:748-758). Such self-association of p62 via its N-terminal PB1 domain is essential for its cargo receptor activity by enabling stronger connection (multiple binding) to its ubiquitinated cargo as well as simultaneous binding to multiple LC3 proteins (Wurzer, B. et al. Elife (2015) 4:e08941; Itakura, E. & Mizushima, N. J Cell Biol (2011) 192:17-27), which helps to account for the loss of p62 puncta seen by β-arrestin1 overexpression. Moreover, cargo-bound p62 acts to promote autophagosome formation by enhancing the conversion of LC3 to its active lipidated form LC3-II (Cha-Molstad, H. et al. Nat Commun (2017) 8:102), which likely accounts for the observation that β-arrestin1 overexpression also decreases LC3 puncta and reduces p62-LC3 colocalization. Such mechanisms of β-arrestin1 in binding to p62 and interfering with p62 self-oligomerization, together with destabilization of microtubules, are consistent with the observed role of β-arrestin1 in impeding p62 flux and impairing the clearance of misfolded tau.

To date, no previous study has implicated β-arrestin1 in tauopathy, microtubule dynamics, or p62-mediated autophagy. These findings collectively implicate β-arrestin1 in destabilization of microtubules, promoting tau mislocalization, and inhibition of p62-mediated tau clearance. In addition to these activities uncovered in this study, β-arrestin1 also promotes Aβ production and deposition in vivo (Liu, X. et al. Cell Res (2013) 23:351-365). Hence, targeting β-arrestin1 represents a promising point of therapeutic intervention that can simultaneously mitigate Aβ and tau pathogenesis. Although β-arrestin1$^{-/-}$ mice exhibit impaired desensitization to β-adrenergic receptor stimulation in the heart, they are grossly normal, fertile, and do not display any physical or behavioral abnormalities (Conner, D. A. et al. Circ Res (1997) 81:1021-1026). Therefore, reducing β-arrestin1 level or activity could be beneficial strategies to mitigate tauopathic disorders including AD.

Example 3: Pharmacological Inhibitors

β-arrestin1 and β-arrestin2 form homo- and hetero-oligomers, and inositol hexakisphosphate (IP6) promotes these oligomers. Therefore, in some embodiments, the β-arrestin oligomerization inhibitor is a molecule, such as a peptide, that blocks IP6 binding, thereby reducing oligomerization of β-arrestin2. In some embodiments, the oligomerization inhibitor is a β-arrestin mutant that acts as dominant negative for homo-hetero oligomerization of β-arrestin1 and/or β-arrestin2.

The provided data also indicated that pharmacological inhibitors for β-arrestin oligomerization can represent a promising therapeutic strategy that can alleviate AD and tauopathies. Therefore, molecular docking screening was performed with FTMap analysis to screen millions of compounds that block the interface between β-arrestin2 and β-arrestin2. Approximately 30 predicted inhibitory compounds were tested using cell-based assays, resulting in a few small molecule compounds and their analogs that reduce pathogenic tau. Next, we tested whether these inhibitors that reduced pathogenic tau also abolish the oligomerization of β-arrestin2. The co-immunoprecipitation, fluorescence resonance energy transfer (FRET), and proximity ligation assay (PLA) data indicate that these compounds indeed block the oligomerization of β-arrestin2.

FIGS. 24A to 24D show β-arrestin2 oligomerization mutants impair β-arrestin1 homo-oligomers and β-arrestin1/β-arrestin2 hetero-oligomers. HeLa-V5-tau cells were co-transfected with vector control or β-arrestin2 oligomerization mutants (ΔIP6C or ΔIP6N) together with βarrestin1-GFP+βarrestin1-myc or βarrestin2-myc. Cells were then subjected to proximity ligation assay (PLA) using antibodies against GFP and mycto detect βarrestin1 homo-oligomers (FIGS. 24A,24B) and βarrestin1/βarrestin2 hetero-oligomers and DAPI staining (FIGS. 24C,24D) (puncta). Results show that β-arrestin2 oligomerization mutants (ΔIP6C or ΔIP6N) significantly reduce βarrestin1 homo-oligomers (FIGS. 24A,24B) as well as βarrestin1/βarrestin2 hetero-oligomers (n=4, one-way ANOVA, post hoc Dunnett's, #P<0.0001). Cells subjected to 1 probe only or exclusion of primary antibody shows no red PLA puncta (negative controls).

Figure 25:
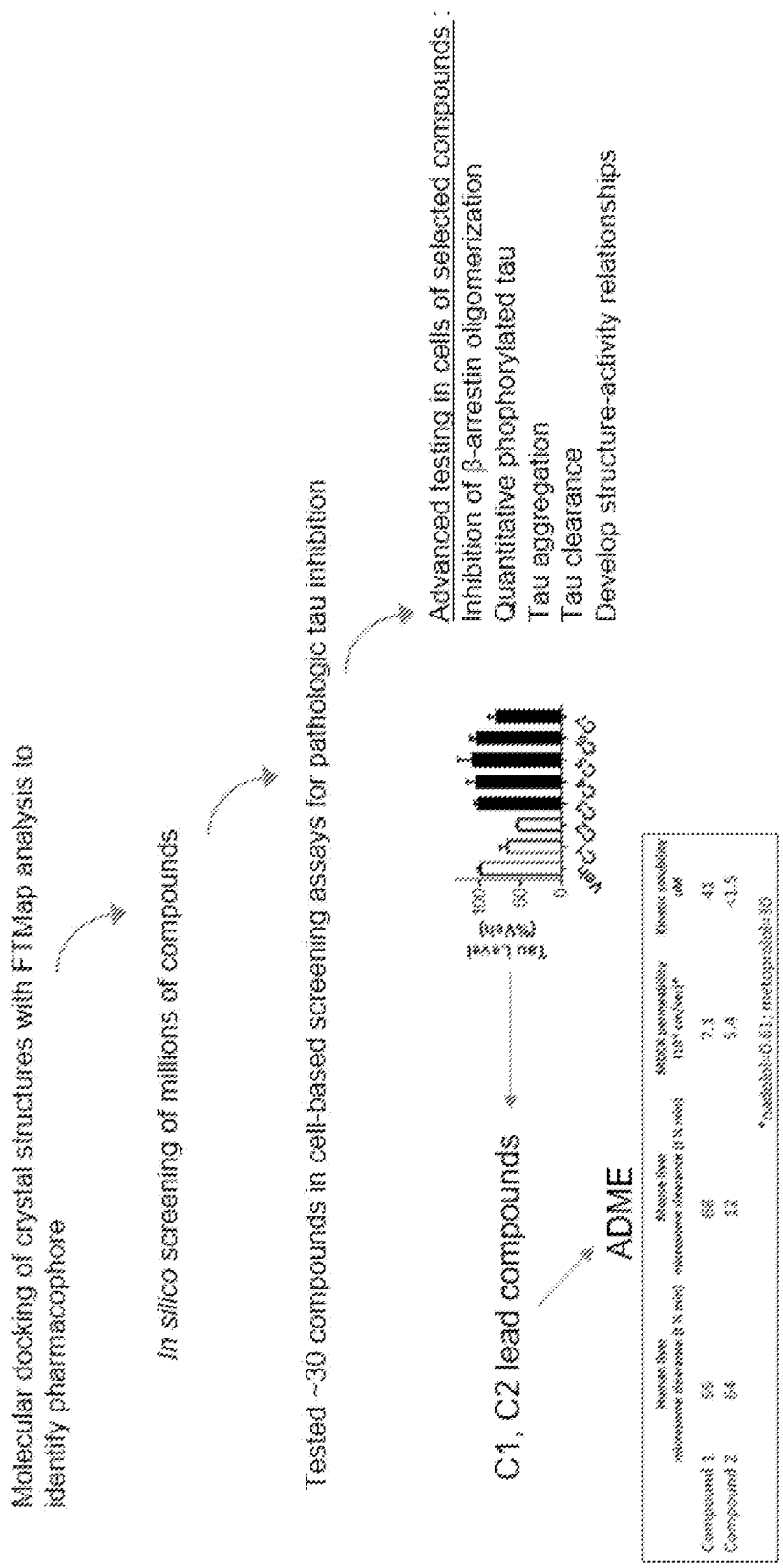
FIG. 25 shows workflow used to screen for compounds that block β-arrestinoligomization and reduce pathological tau. Based on the crystal structure of β-arrestin2, we performed in silico computational screening of millions of compounds that can dock onto the trimer binding interface of β-arrestin2. The top 30 compounds were then tested for their capacity to reduce pathological tau. Those that reduced tau were then tested for their capacity to block β-arrestin2 oligomerization.

FIG. 25 shows workflow used to screen for compounds that block β-arrestin oligomerization and reduce pathological tau. Based on the crystal structure of β-arrestin2, we performed in silico computational screening of millions of compounds that can dock onto the trimer binding interface of β-arrestin2. The top 30 compounds were then tested for their capacity to reduce pathological tau. The compounds provided in the table below (Synthesized by MolPort) that reduced tau were then tested for their capacity to block β-arrestin2 oligomerization:

| | |
|---|---|
| C1 | 2-[(2,3-dihydro-1H-inden-5-yl)formamido]-N-({imidazo[1,2-a]pyridin-2-yl}methyl)acetamide |
| C2 | N-{2-[(6-methylpyridazin-3-yl)amino]ethyl}-3-phenyl-1,2-oxazole-5-carboxamide |
| C1A | 2-[(2,4-difluorophenyl)formamido]-N-({imidazo[1,2-a]pyridin-2-yl}methyl)acetamide |
| C1B | (2S)-N-({imidazo[1,2-a]pyridin-2-yl}methyl)-3-methyl-2-[(3-methylphenyl)formamido]butanamide |
| C1C | 2-[(3-bromophenyl)formamido]-N-({imidazo[1,2-a]pyridin-2-yl}methyl)acetamide |
| C1D | N-({imidazo[1,2-a]pyridin-2-yl}methyl)-3-[(piperidin-4-yl)methyl]benzamide |
| C1E | 2-[(3-chlorophenyl)formamido]-N-({imidazo[1,2-a]pyridin-2-yl}methyl)acetamide |
| C2A | N-{2-[(3-methylpyridin-4-yl)amino]ethyl}-3-phenyl-1,2-oxazole-5-carboxamide |
| C2B | 1-(4-fluorophenyl)-4-[3-(4-fluorophenyl)-1,2-oxazole-5-carbonyl]piperazine |
| C2C | 2-{[3-(4-methylphenyl)-1,2-oxazol-5-yl]formamido}-N-(2,4,6-trimethylphenyl)acetamide |
| C2D | N-(2-bromophenyl)-2-{[3-(4-methylphenyl)-1,2-oxazol-5-yl]formamido}acetamide |
| C2E | 3-phenyl-N-(propan-2-yl)-1,2-oxazole-5-carboxamide |

Figure 26:
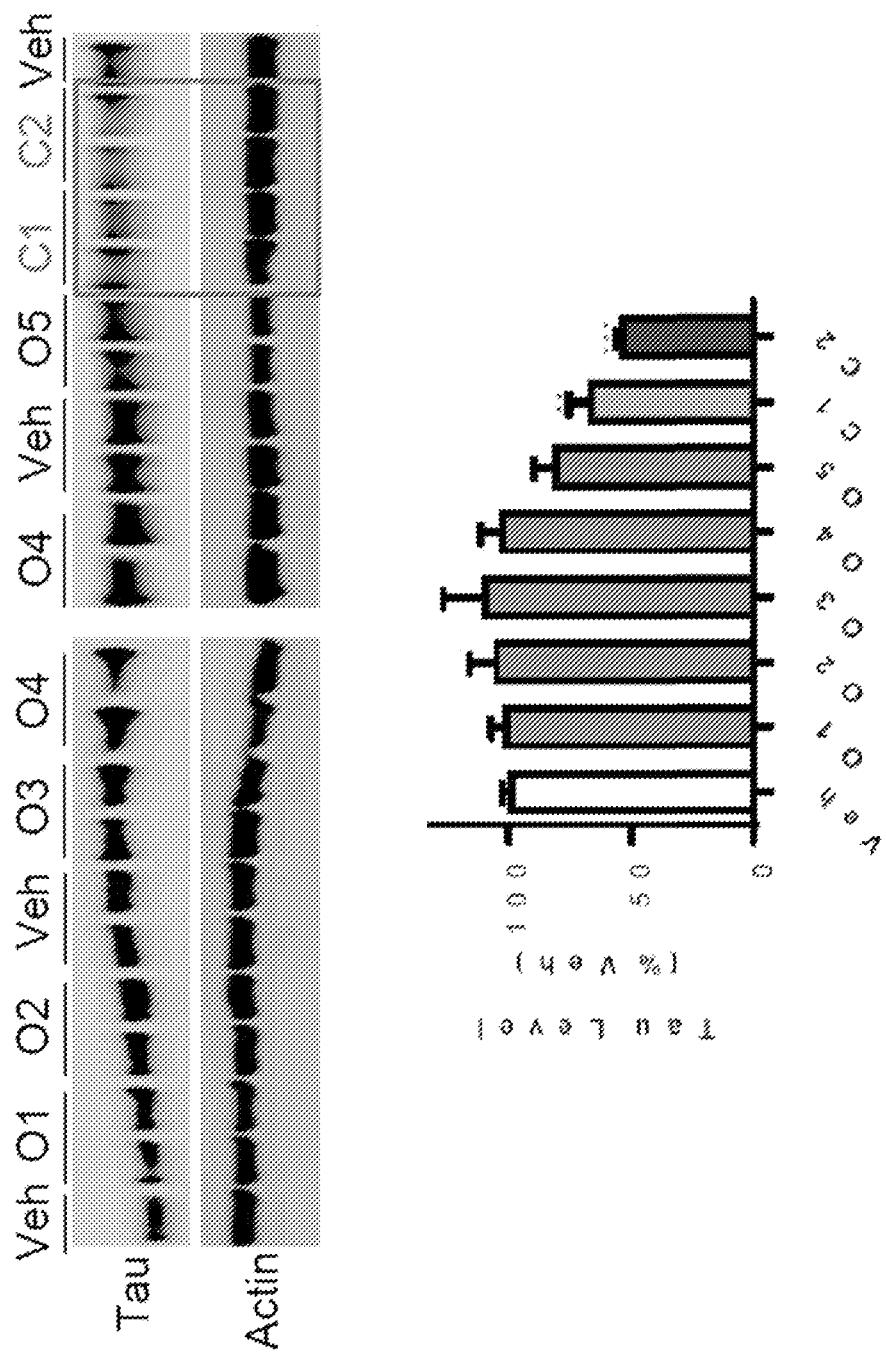
FIG. 26 shows C1 and C2 compounds reduce tau levels HeLa-V5-tau cells were treated with 10 μM of potential β-arrestin2 oligomerization inhibitors for 6 hours and subjected to western blotting. C1 and C2 significantly decreased total tau levels in HeLa-V5-tau cells. (n=4, one-way ANOVA, post hoc Dunnett's, P<0.005, *P<0.0005).

FIG. 26 shows C1 and C2 compounds reduce tau levels HeLa-V5-tau cells were treated with 10 μM of potential β-arrestin2 oligomerization inhibitors for 6 hours and subjected to western blotting. C1 and C2 significantly decreased total tau levels in HeLa-V5-tau cells. (n=4, one-way ANOVA, post hoc Dunnett's, P<0.005, *P<0.0005).

Figure 27A:
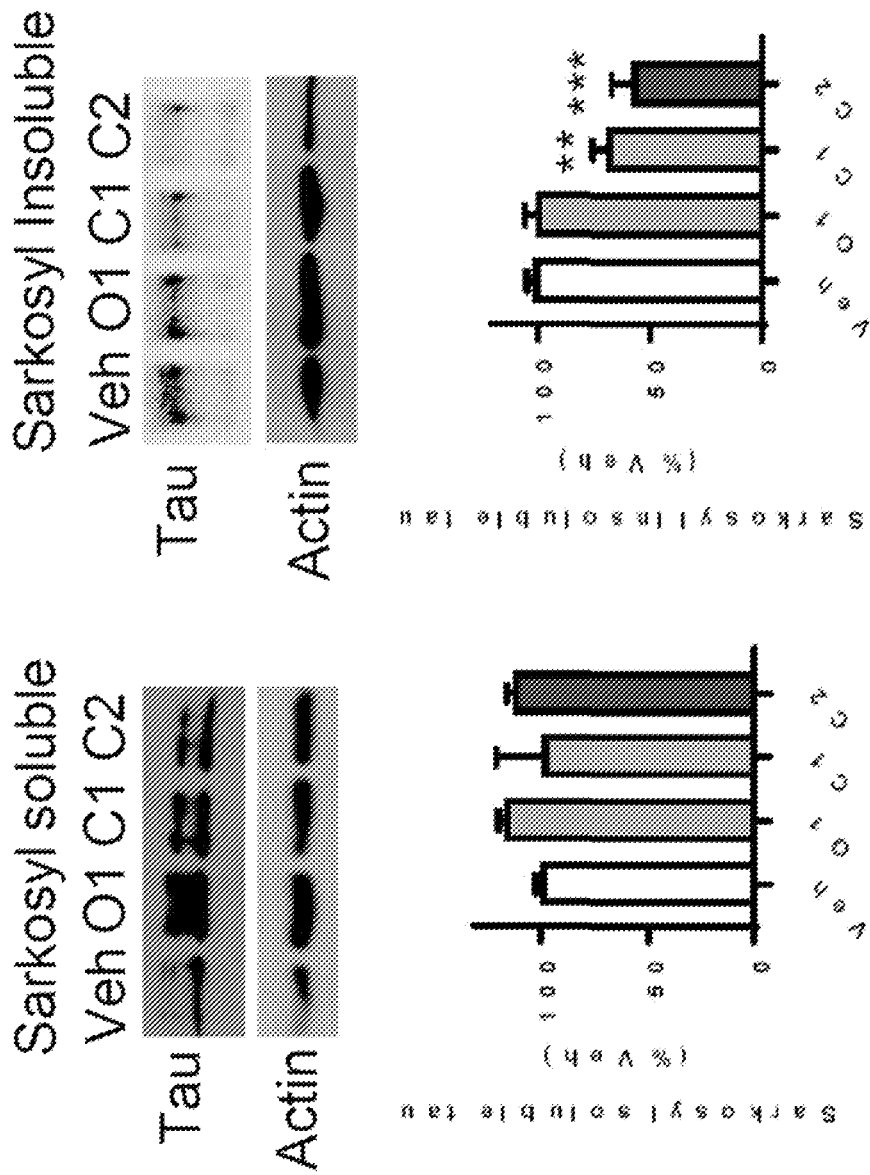
FIGS. 27A and 27B show C1 and C2 compounds reduce pathogenic tau.
Figure 27B:
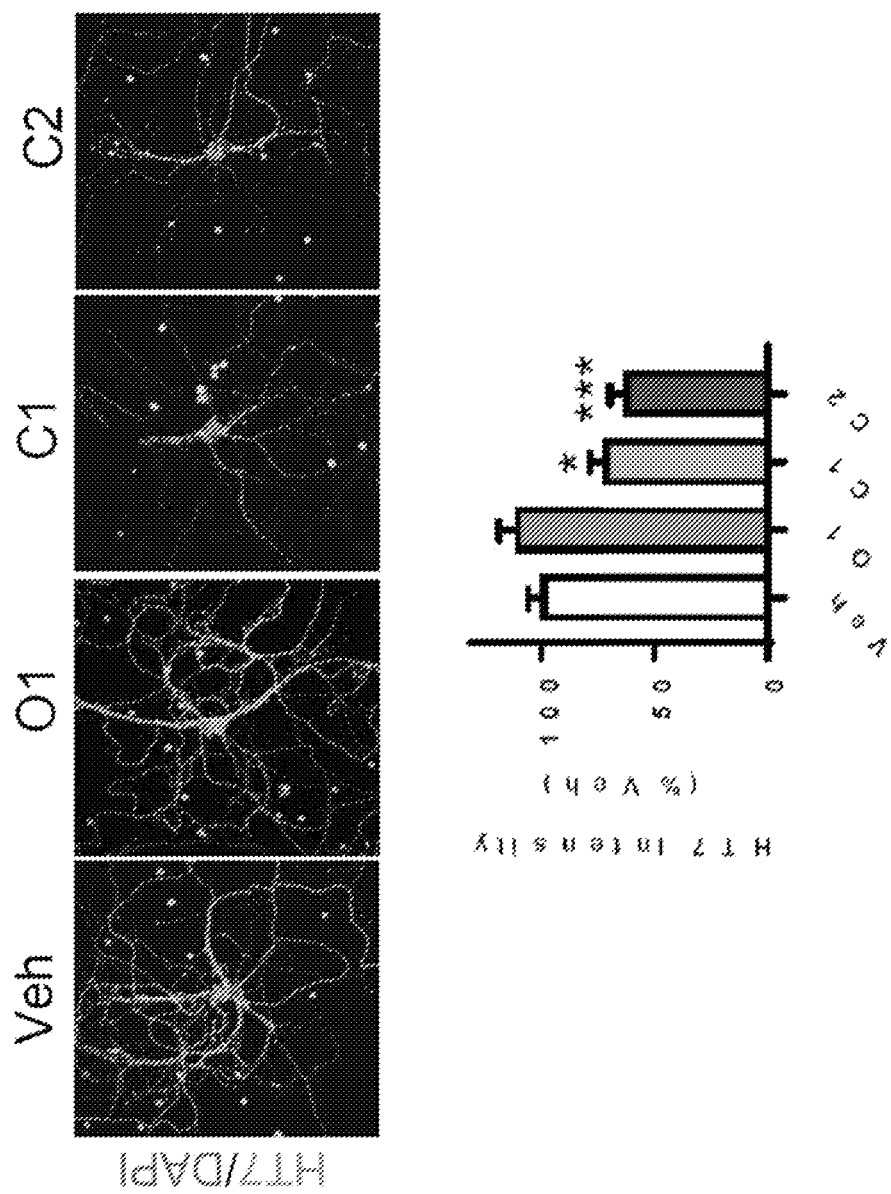

FIGS. 27A and 27B show C1 and C2 compounds reduce pathogenic tau. FIG. 27A shows HeLa-V5-tau cells treated with 20 μM of 01, C1, or C2 compounds for 6 hours, and subjected to sarkosylsoluble and insoluble fractionation. C1 and C2 significantly decreased sarkosyl-insoluble tau levels in HeLa-V5-tau cells. (n=4, one-way ANOVA, post hoc Dunnett's, P<0.005, *P<0.0005). FIG. 27B shows DIV21 hippocampal primary neurons derived from Tau-P301S mice treated with 20 μM of 01, C1, or C2 compounds for 6 hours, and stained for HT 7 (total human tau). C1 and C2 significantly decreased HT7 immunoreactivity (n=3, one-way ANOVA, post hoc Dunnett's, *P<0.05, ***P<0.0005.

Figure 28A:
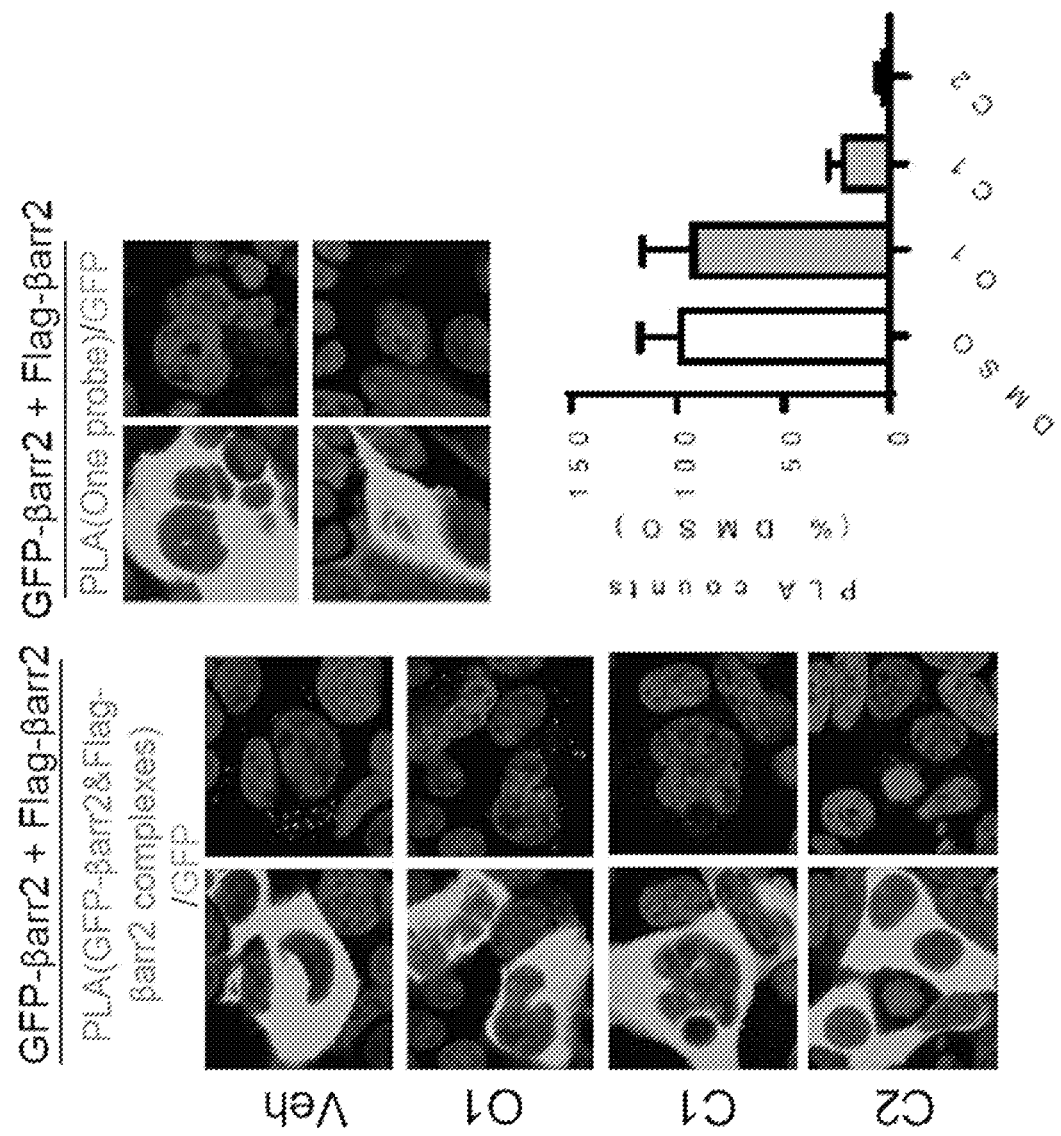
FIGS. 28A and 28B show compounds C2 and C2 inhibit β-arrestin2 oligomerization. Hela-V5-tau cells were transfected with GFP-βarrestin2 and Flag-βarrestin2 and treated with 20 μM of 01, C1, or C2 for 6 hours.
Figure 28B:
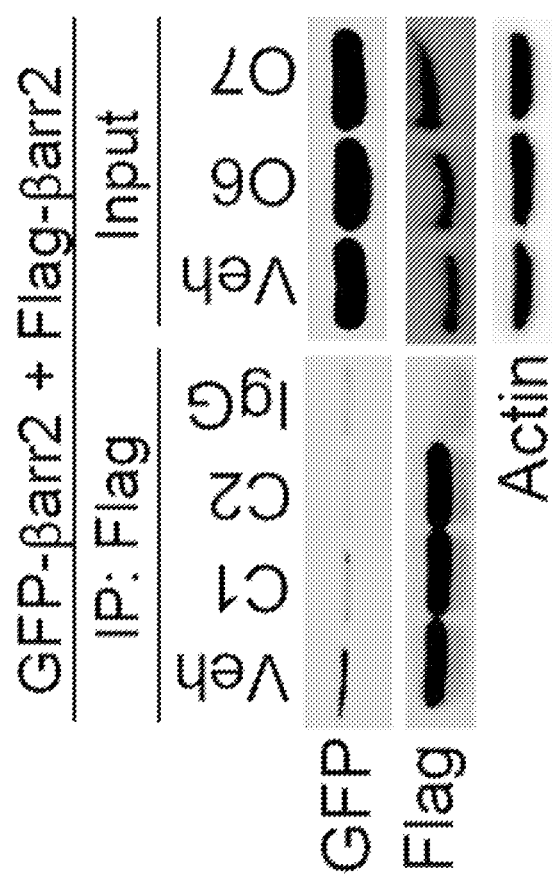

FIGS. 28A and 28B show compounds C2 and C2 inhibit β-arrestin2 oligomerization. Hela-V5-tau cells were transfected with GFP-βarrestin2 and Flag-βarrestin2 and treated with 20 μM of 01, C1, or C2 for 6 hours. FIG. 28A shows proximity ligation assay (PLA) using antibodies against GFP and Flag (M2) to detect GFP-βarrestin2/Flag-βarrestin2 complexes show significant reduction in βarrestin2 oligomerization (n=3, one-way ANOVA, post hoc Dunnett's, *P<0.05, ***P<0.0005). Inclusion of only 1 PLA probe as negative control shows no PLA red puncta. FIG. 28B shows cells subjected to lysis and co-immunoprecipitation (co-IP) for GFP-βarrestin2/Flag-βarrestin2 complexes, demonstrating that C1 and C2 compounds reduce βarrestin2 self-interaction to background levels similar to anti-mouse IgG beads alone.

Figure 29:
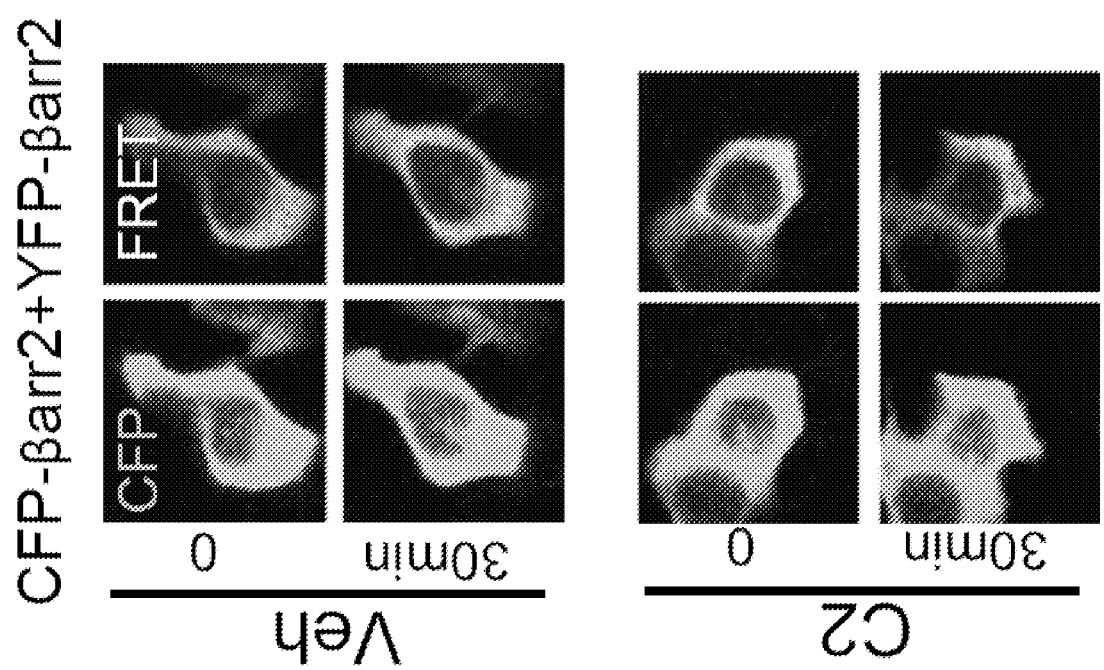
FIG. 29 shows compound C2 inhibits βarrestin2 oligomerization. Hela-V5-tau cells were transfected with CFP-βarrestin2 and YFP-βarrestin2 and treated with vehicle or 20 μM C2 for 30 min. β-arrestin2 oligomerization was detected by FRET assay, showing that the C2 compound but not the vehicle reduces CFP to YFP FRET signal.

FIG. 29 shows compound C2 inhibits βarrestin2 oligomerization. Hela-V5-tau cells were transfected with CFP-βarrestin2 and YFP-βarrestin2 and treated with vehicle or 20 μM C2 for 30 min. β-arrestin2 oligomerization was detected by FRET assay, showing that the C2 compound but not the vehicle reduces CFP to YFP FRET signal.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating a tauopathy in a subject, the method comprising administering to the human subject a therapeutically effective amount of a β-arrestin oligomerization inhibitor, wherein the inhibitor is a compound having a structure or a pharmaceutically-acceptable salt thereof selected from the group consisting of:

(a)
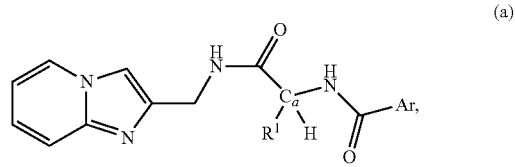

wherein $R^1$ is hydrogen or an alkyl group;
wherein Ar is an aryl group; and
wherein when $R^1$ is an alkyl group, the stereochemistry at $C_a$ is racemic, substantially R, or substantially S;

(b)
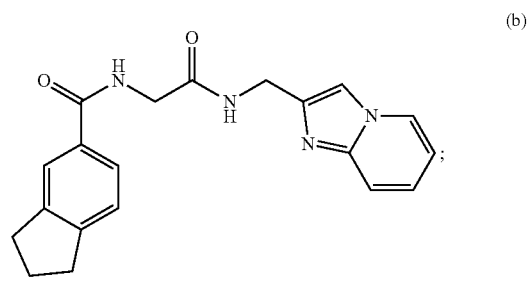

-continued
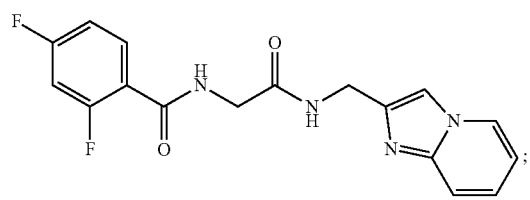
(c)
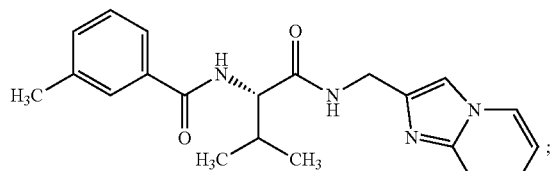
(d)
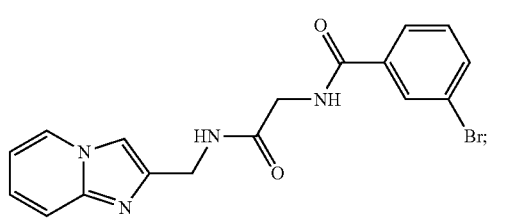
(e)
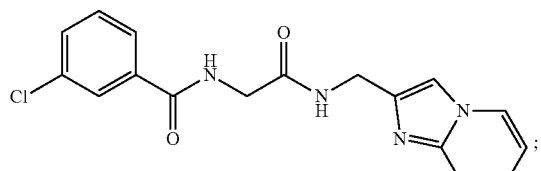
(f)
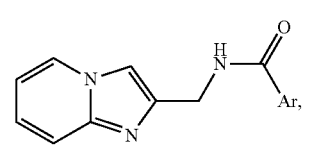
(g)
wherein Ar is an aryl group;
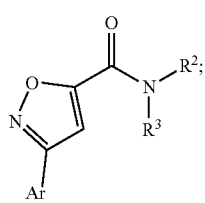
(i)
wherein $R^2$ and $R^3$ are, independently, hydrogen or an alkyl group; and Ar is an aryl group;
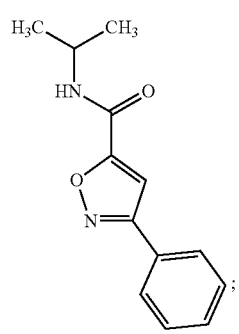
(j)
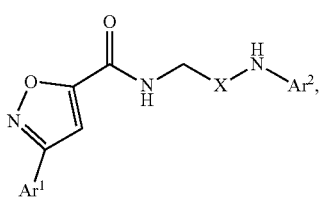
(k)
wherein $Ar^1$ and $Ar^2$ are, independently, an aryl group; and
wherein X is $CH_2$ or C=O;
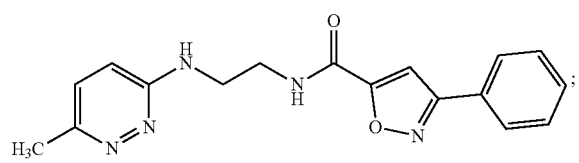
(l)
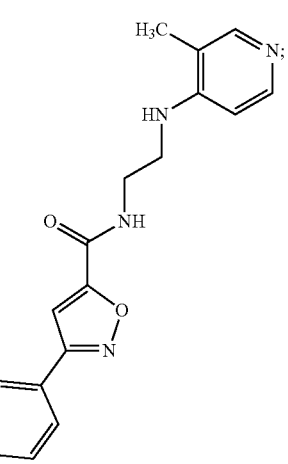
(m)
(h)

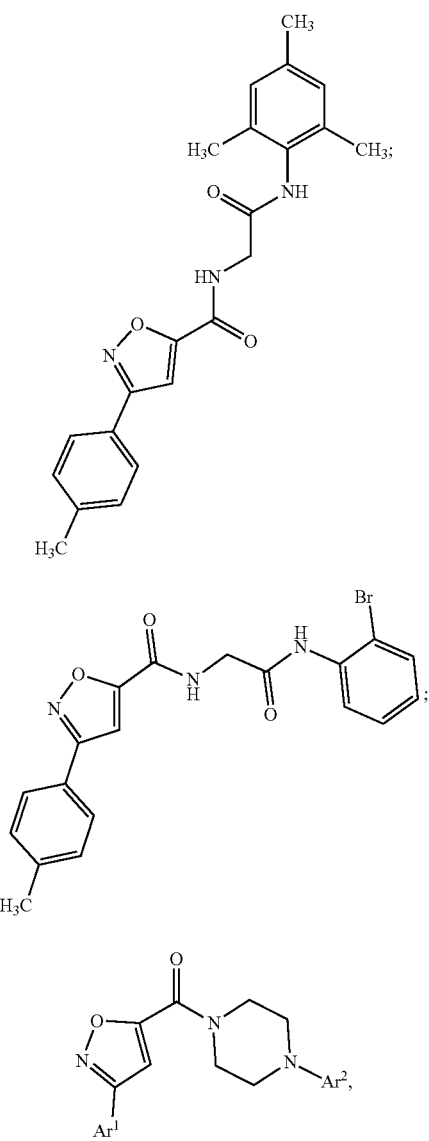

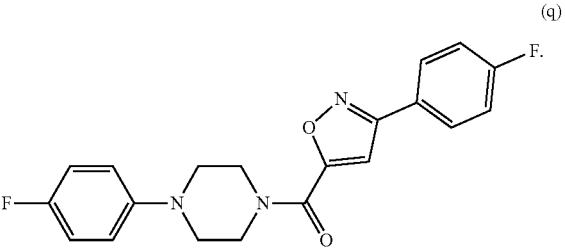

wherein Ar¹ and Ar² are, independently, an aryl group; and

2. The method of claim 1, wherein R¹ is hydrogen.

3. The method of claim 1, wherein when the compound or pharmaceutically-acceptable salt thereof is (a), Ar is an unsubstituted or substituted phenyl group.

4. The method of claim 1, wherein when the compound or pharmaceutically-acceptable salt thereof is (a), Ar is a phenyl group substituted with one or more halogen atoms.

5. The method of claim 1, wherein R¹ is a $C_1$ to $C_{10}$ alkyl group.

6. The method of claim 1, wherein the tauopathy is selected from the group consisting of Alzheimer's disease, Pick's disease, Frontotemporal dementia, Frontotemporal dementia with Parkinsonism linked to chromosome 17, progressive supranuclear palsy, Corticobasal degeneration, subacute sclerosing panencephalitis, amyotrophic lateral sclerosis/parkinsonism-dementia complex, argyrophilic grain dementia, British type amyloid angiopathy, cerebral amyloid angiopathy, Creutzfeldt-Jakob disease, dementia pugilistica, diffuse neurofibrillary tangles with calcification, Down's syndrome, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, postencephalitic parkinsonism, prion protein cerebral amyloid angiopathy, progressive subcortical gliosis, Tangle only dementia, multi-infarct dementia, ischemic stroke, chronic traumatic encephalopathy, traumatic brain injury, and stroke.

7. The method of claim 1, wherein the tauopathy is frontotemporal lobar degeneration.

* * * * *